United States Patent
Ushirogochi et al.

(10) Patent No.: US 10,329,263 B2
(45) Date of Patent: *Jun. 25, 2019

(54) DISUBSTITUTED 1, 2, 4-TRIAZINE COMPOUND

(71) Applicant: MITSUBISHI TANABE PHARMA CORPORATION, Osaka-shi, Osaka (JP)

(72) Inventors: Hideki Ushirogochi, Osaka (JP); Wataru Sasaki, Osaka (JP); Yuichi Onda, Osaka (JP); Ryo Sakakibara, Osaka (JP); Fumihiko Akahoshi, Osaka (JP)

(73) Assignee: MITSUBISHI TANABE PHARMA CORPORATION, Osaka-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/016,053

(22) Filed: Jun. 22, 2018

(65) Prior Publication Data

US 2018/0305326 A1 Oct. 25, 2018

Related U.S. Application Data

(63) Continuation of application No. 15/305,587, filed as application No. PCT/JP2015/062440 on Apr. 23, 2015, now Pat. No. 10,029,993.

(30) Foreign Application Priority Data

Apr. 24, 2014 (JP) .................................. 2014-090754

(51) Int. Cl.
C07D 253/07 (2006.01)
C07D 401/04 (2006.01)
(Continued)

(52) U.S. Cl.
CPC ............ *C07D 253/07* (2013.01); *A61K 31/53* (2013.01); *A61K 31/5377* (2013.01); *A61K 31/541* (2013.01); *A61K 31/553* (2013.01); *A61P 9/04* (2018.01); *A61P 13/12* (2018.01); *C07D 253/06* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/04* (2013.01); *C07D 405/12* (2013.01); *C07D 405/14* (2013.01); *C07D 409/04* (2013.01); *C07D 409/12* (2013.01); *C07D 413/12* (2013.01); *C07D 413/14* (2013.01); *C07D 417/04* (2013.01); *C07D 451/02* (2013.01); *C07D 453/02* (2013.01); *C07D 471/04* (2013.01); *C07D 471/08* (2013.01); *C07D 498/08* (2013.01); *C07D 498/10* (2013.01)

(58) Field of Classification Search
CPC .............. C07D 253/065; C07D 403/04; C07D 403/14; C07D 411/04; C07D 411/14; A61K 31/53
USPC ........................ 544/182, 112; 514/242, 231.5
See application file for complete search history.

(56) References Cited

U.S. PATENT DOCUMENTS 10,029,993 B2 * 7/2018 Ushirogochi et al. ...................... C07D 253/07 544/182
2007/0207985 A1 9/2007 Li et al.

FOREIGN PATENT DOCUMENTS

EP 1 970 373 A1 9/2008
WO WO 91/13885 A1 9/1991
(Continued)

OTHER PUBLICATIONS

Amar et al., "Aldosterone Synthase Inhibition with LCI699 A Proof-of-Concept Study in Patients with Primary Aldosteronism", Hypertension, vol. 56 (2010) pp. 831-838.
(Continued)

*Primary Examiner* — Venkataraman Balasubramanian
(74) *Attorney, Agent, or Firm* — Birch, Stewart, Kolasch & Birch, LLP

(57) ABSTRACT

This invention provides a novel disubstituted 1,2,4-triazine compound or a pharmaceutically acceptable salt thereof, which has an aldosterone synthetase inhibitory activity and is useful for preventing and/or treating various diseases or conditions associated with aldosterone; a method for preparing it; use of it; as well as a pharmaceutical composition comprising it as an active ingredient. A compound of the general formula [I]:

[I]

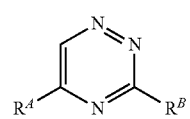

wherein $R^A$ is, for example, a group of the following formula (A-1):

(A-1)

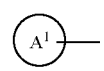

wherein ring $A^1$ is, for example, a cycloalkyl group which may be substituted,
and $R^B$ is, for example, a monocyclic cycloalkyl group, or a pharmaceutically acceptable salt thereof.

14 Claims, No Drawings

(51) Int. Cl.

| | | |
|---|---|---|
| *C07D 401/14* | (2006.01) | |
| *C07D 403/04* | (2006.01) | |
| *C07D 403/14* | (2006.01) | |
| *C07D 405/14* | (2006.01) | |
| *A61K 31/53* | (2006.01) | |
| *A61P 9/04* | (2006.01) | |
| *A61P 13/12* | (2006.01) | |
| *C07D 403/12* | (2006.01) | |
| *C07D 413/14* | (2006.01) | |
| *A61K 31/5377* | (2006.01) | |
| *A61K 31/541* | (2006.01) | |
| *A61K 31/553* | (2006.01) | |
| *C07D 401/12* | (2006.01) | |
| *C07D 405/04* | (2006.01) | |
| *C07D 405/12* | (2006.01) | |
| *C07D 409/04* | (2006.01) | |
| *C07D 409/12* | (2006.01) | |
| *C07D 413/12* | (2006.01) | |
| *C07D 417/04* | (2006.01) | |
| *C07D 453/02* | (2006.01) | |
| *C07D 471/04* | (2006.01) | |
| *C07D 471/08* | (2006.01) | |
| *C07D 253/06* | (2006.01) | |
| *C07D 498/08* | (2006.01) | |
| *C07D 498/10* | (2006.01) | |
| *C07D 451/02* | (2006.01) | |

(56) References Cited

FOREIGN PATENT DOCUMENTS

| WO | WO 02/083667 A2 | 10/2002 |
|---|---|---|
| WO | WO 2006/081230 A2 | 8/2006 |
| WO | WO 2009/156462 A2 | 12/2009 |
| WO | WO 2010/130796 A1 | 11/2010 |
| WO | WO 2011/131593 A1 | 10/2011 |
| WO | WO 2012/012478 A1 | 1/2012 |
| WO | WO 2013/037779 A1 | 3/2013 |
| WO | WO 2013/079452 A1 | 6/2013 |
| WO | WO 2013/104597 A1 | 7/2013 |

OTHER PUBLICATIONS

Andersen, K., "Aldosterone Synthase Inhibition in Hypertension," Curr Hypertens Rep, 2013, vol. 15, pp. 484-488.

Cerny, M.A., "Progress Towards Clincally Useful Aldosterone Synthase Inhibitors," Current Topics in Medicinal Chemistry, 2013, vol. 13, pp. 1385-1401.

English translation of International Search Report for Appl. No. PCT/JP2015/062440 dated Jul. 28, 2015.

English translation of Written Opinion of the International Searching Authority for Appl. No. PCT/JP2015/062440 dated Jul. 28, 2015.

Hakki, T. et al., "The development of a whole-cell based medium throughput screening system for the discovery of human aldosterone synthase (CYP1162) inhibitors: Old drugs disclose new applications for the therapy of congestive heart failure, myocardial fibrosis and hypertension," Journal of Steroid Biochemistry & Molecular Biology, 2011, vol. 125, pp. 120-128.

Hargovan et al., "Aldosterone Synthase Inhibitors in Hypertension: Current Status and Future Possibilities", Journal of the Royal Society of Medicine Cardiovascular Disease, (2014) 1-9.

Heilman et al., "Synthesis and Anti-Inflammatory Evaluation of 3-Methylthio-1,2,4-triazines, 3-Alkoxy-1,2,4-triazines, and 3-Aryloxy-1,2,4-triazines", Journal of Pharmaceutical Sciences, vol. 69, No. 3 (1980) pp. 282-287.

Office Action dated Apr. 10, 2017 in Australian Patent Application No. 2015251030 (5 pages).

Pitt, B., M.D. et al., "The Effect of Spironolactone on Morbidity and Mortality in Patients with Severe Heart Failure," The New England Journal of Medicine, Sep. 2, 1999, vol. 341, No. 10, pp. 709-717.

Pitt, B., M.D., et al., "Eplerenone, a Selective Aldosterone Blocker, in Patients with Left Ventricular Dysfuncyion after Myocardial Infarction," N Engl J Med, Apr. 3, 2003, vol. 348, No. 14, pp. 1309-1321.

PubChem, Compound Search 1-1, Create Date Mar. 29, 2017.

PubChem, Compound Search 6, Create Date Mar. 29, 2017.

PubChem, Compound Summary for CID 25373218; NIH U.S. National Library of Medicine; National Center for Biotechnology Information; Create Date May 27, 2009.

PubChem, Compound Summary for CID 26397087; NIH U.S. National Library of Medicine; National Center for Biotechnology Information; Create Date May 28, 2009.

PubChem, Compound Summary for CID 42242165; NIH U.S. National Library of Medicine; National Center for Biotechnology Information; Create Date May 30, 2009.

Russian Office Action issued in Russian Patent Application No. 2016145737/04 dated Jan. 29, 2018, with English translation.

Supplementary European Search Report issued in European Patent Application No. 15782458.2 dated Feb. 19, 2018.

Wang et al., "Efficacy and Safety of LCI699 for Hypertension: a Meta-Analysis of Randomized Controlled Trials and Systematic Review", European Review for Medical and Pharmacological Sciences; vol. 19 (2015) pp. 296-304.

\* cited by examiner

DISUBSTITUTED 1, 2, 4-TRIAZINE COMPOUND

CROSS-REFERENCE TO RELATED APPLICATIONS

This application is a Continuation of copending application Ser. No. 15/305,587, filed on Oct. 20, 2016, which is the National Phase under 35 U.S.C. § 371 of International Application No. PCT/JP2015/062440, filed on Apr. 23, 2015, which claims the benefit under 35 U.S.C. § 119(a) to Patent Application No. 2014-090754, filed in JAPAN on Apr. 24, 2104, all of which are hereby expressly incorporated by reference into the present application.

TECHNICAL FIELD

This invention relates to a novel disubstituted 1,2,4-triazine compound which has an aldosterone synthetase (hereinafter also referred to as Cyp11B2) inhibitory effect and is useful for preventing and/or treating various diseases or conditions associated with aldosterone.

BACKGROUND ART

Aldosterone is a specific ligand for a mineral corticoid receptor (hereinafter also referred to as MR) and one of mediators for renin-angiotensin-aldosterone system (RAAS). Aldosterone is mainly produced in an adrenal gland and has been considered as a mineral corticoid hormone which regulates metabolism of sodium and water by affecting a distal tubule of a kidney. In a recent study, it has been shown that aldosterone is produced in various tissues such as a heart, blood vessels and a brain, and that the MR is widely distributed to tissues such as cardiovascular tissues. Therefore, aldosterone is recognized as a risk hormone which exerts various deleterious effects on cardiovascular tissues (e.g., heart fibrosis and necrosis; enhanced effect of catecholamine, and decrease of a baroreceptor reaction), in addition to, as an exacerbation factor for hypertension.

A means of blocking an effect of aldosterone is an effective method for treating, for example, cardiovascular diseases associated with said aldosterone and a receptor thereof. An MR antagonist (e.g., eplerenone or spironolactone), which has an affinity for MR and blocks its receptor function, has already been used for treating hypertension. In large clinical tests (RALES and EPHESUS), it was confirmed that, by combined administration of the MR antagonist and a conventional therapeutic agent such as an ACE inhibitor, a hospitalization rate, and a mortality rate caused by cardiac diseases in patients with severe heart failure were significantly decreased, and that prognosis of patients with acute myocardial infarction was significantly improved (non-patent documents 1 and 2).

On the other hand, the MR antagonist (e.g., spironolactone or eplerenone) has specific serious adverse effects (e.g., hyperkalemia). In addition, use of spironolactone is often associated with gynecomastia, menstrual disorders, erectile dysfunction, and the like. Accordingly, it is desired to develop a compound for treating a disease associated with aldosterone which has no such adverse effect and has higher safety. An aldosterone synthetase (Cyp11B2) inhibitor has been proposed as an alternative approach from the point of view above (i.e., another approach for blocking or reducing an effect of aldosterone).

Cyp11B2 is a cytochrome P450 enzyme and is known as an enzyme which catalyzes a series of reactions leading from 11-deoxycorticosterone (i.e., an aldosterone precursor) to aldosterone. Cyp11B2 is mainly expressed in an adrenal cortex spherical layer and a level of plasma aldosterone is regulated by enzymic activity of Cyp11B2 present in an adrenal gland. In addition, it has been confirmed that aldosterone was expressed in some tissues other than adrenal glands such as a cardiovascular system, a kidney, adipose tissues and a brain, as well as, it has drawn attention that organ disorders were associated with aldosterone, which was locally produced in each organ. It has been reported that an inhibitor of Cyp11B2 inhibited production of aldosterone through studies using the enzyme and cells in culture, and that the inhibitor had a suppressive effect against production of aldosterone and any therapeutic effect through studies using various experimental animal models. Further, it has been confirmed that a Cyp11B2 inhibitor showed a plasma aldosterone level-lowering effect and a urine aldosterone level-lowering effect as well as an antihypertensive effect in hypertensive patients and primary aldosteronism patients (non-patent documents 3 and 4). A highly feasible approach for establishing an effective therapy for various diseases associated with aldosterone is to find a means for inhibiting a biosynthesis route of aldosterone.

Previously, although aryl pyridine compounds (patent document 1), benzimidazol substituted pyridine compounds (patent document 2), and the like are known as a compound having an aldosterone synthetase (Cyp11B2) inhibitory activity, it has not been reported that a 1,2,4-triazine compound such as a compound of the present invention had an aldosterone synthetase inhibitory activity. In addition, 1,2,4-triazine compounds of the following formulae (a), (b) and (c):

[Chemical formula 1]

(a)

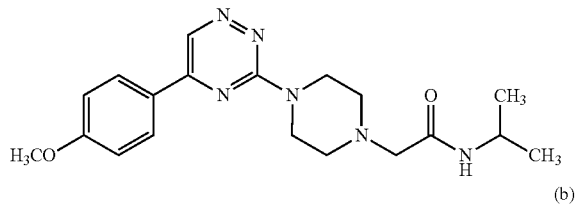

(b)

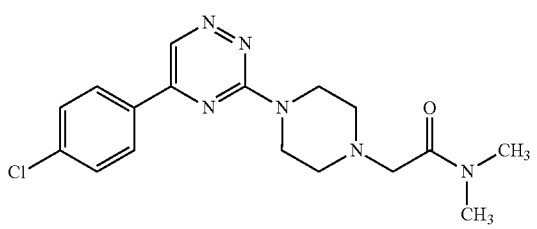

(c)

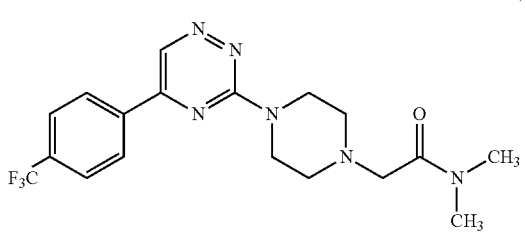

are listed in a commercial compound database (Registry) as Accession Nos: 1070398-58-1, 1069628-74-5, 1060824-77-2. However, it is not clarified what kind of physiological activity these compounds have.

PRIOR ART DOCUMENT(S)

Patent Document(s)

[Patent document 1] WO2010/130796
[Patent document 2] WO2012/012478

NON-PATENT DOCUMENT(S)

[Non-patent document 1] New England Journal of Medicine, 1999; 341: p. 709-717
[Non-patent document 2] New England Journal of Medicine, 2003; 348: p. 1309-1321
[Non-patent document 3] Current Topics in Medicinal Chemistry, 2013; 313: p. 1385-1401
[Non-patent document 4] Current Hypertension Reports, 2013; 15: p. 484-488

DISCLOSURE OF INVENTION

Problem to be Solved by the Invention

The present invention relates to a novel disubstituted 1,2,4-triazine compound or a pharmaceutically acceptable salt thereof which has an aldosterone synthetase (Cyp11B2) inhibitory effect. The compound of the present invention is useful for preventing and/or treating various diseases or conditions associated with aldosterone.

Means for Solving Problem

Particularly, the present invention is as follows:
The present invention relates to a compound of the following formula [I]:

[Chemical formula 2]

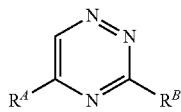

[I]

wherein
$R^A$ is
(a) a group of the following formula (A-1):

[Chemical formula 3]

(A-1)

wherein ring $A^1$ represents (1) a cycloalkyl group which may be substituted, (2) an aryl group which may be partially hydrogenated and may be substituted, or (3) a heteroaryl group which may be partially hydrogenated and may be substituted, or
(b) a group of the following formula (A-2):

[Chemical formula 4]

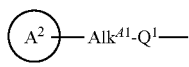

(A-2)

wherein ring $A^2$ represents a cycloalkyl group which may be substituted or an aryl group which may be substituted, $Alk^{41}$ represents a straight or branched chain alkylene group, or a straight or branched chain alkenylene group, and $Q^1$ represents a single bond, an oxygen atom or —$N(R^{a1})$—, wherein $R^{a1}$ represents a hydrogen atom or an alkyl group;
$R^B$ is
(a) a monocyclic cycloalkyl group,
(b) an isoindolinyl group,
(c) a group of the following formula (B-1):

[Chemical formula 5]

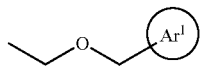

(B-1)

wherein ring $Ar^1$ represents an aryl group which may be substituted,
(d) a group of the following formula (B-2):

[Chemical formula 6]

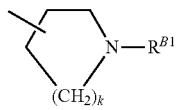

(B-2)

wherein $R^{B1}$ represents an alkoxycarbonyl group or a heteroaryl group, k represents an integer of 1-2,
(e) a group of the formula: —$N(R^{B2})(R^{B3})$
wherein $R^{B}2$ represents an alkylsulfonyl group which may be substituted and $R^{B3}$ represents an alkyl group which may be substituted; or
$R^{B2}$ represents a hydrogen atom or an alkyl group, and $R^{B3}$ represents an alkyl group substituted with an alkylsulfonyl group,
(f) an aliphatic heterocyclic group of the following formula (B-3):

[Chemical formula 7]

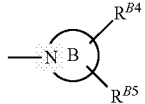

(B-3)

wherein ring B represents an aliphatic heterocyclic group which may further contain one heteroatom selected from the group consisting of a sulfur atom, an oxygen atom, and a nitrogen atom, in addition to the nitrogen atom shown in the formula (B-3); $R^{B4}$ represents a cyano group, an alkyl group substituted with an alkylsulfonyl group, an alkyl group substituted with an alkanoylamino group, a heteroaryl-O— group, or an alkoxy group substituted with a carbamoyl group which may be substituted with 1-2 alkyl groups; and $R^{B5}$ represents a hydrogen atom,
(g) a group of the following formula (B-4):

[Chemical formula 8]

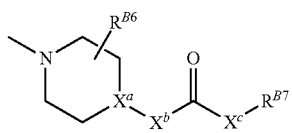

(B-4)

wherein $X^a$ represents $CR^{3a}$ or N,
(i) when $X^a$ represents $CR^{3a}$,
$X^b$ represents $CHR^{3b}$, $X^c$ represents O or $NR^{4c}$,
$X^b$ represents O, $X^c$ represents $NR^{4c}$, or
$X^b$ represents $NR^{4b}$, $X^c$ represents O, $NR^{4c}$, or $CHR^{3c}$, (ii) when $X^a$ represents N,
$X^b$ represents $CHR^{3b}$ or C(=O), $X^c$ represents $NR^{4c}$, or
$X^b$ represents $NR^{4b}$, $X^c$ represents $CHR^{3c}$;
$R^{3a}$ represents a hydrogen atom, a hydroxyl group, an alkyl group, or an amino group,
each of $R^{3b}$ and $R^{3c}$ represents a group selected independently from the group consisting of a hydrogen atom, a hydroxyl group, and an alkyl group,
each of $R^{4b}$ and $R^{4c}$ represents a group selected independently from the group consisting of a hydrogen atom, an alkyl group, and a cycloalkyl group;
$R^{B6}$ represents a hydrogen atom or an alkyl group;
$R^{B7}$ represents
(i) an alkyl group which may be substituted,
(ii) a cycloalkyl group which may be substituted,
(iii) an aliphatic heterocyclic group which may be substituted,
(iv) a heteroaryl group which may be partially hydrogenated and may be substituted, or
(v) a hydrogen atom, or,
when $X^c$ represents $NR^{4c}$, $R^{B7}$ and $R^{4c}$ are bound to each other at their terminus to form an aliphatic heterocyclic group, which may be substituted with an alkyl group which may be substituted, together with a nitrogen atom to which they are bound,
(h) a spirocyclic group of the following formula (B-5):

[Chemical formula 9]

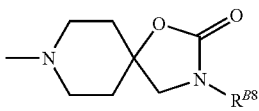

(B-5)

wherein $R^{B8}$ represents a hydrogen atom or an alkyl group, or
(i) a group of the following formula (B-6):

[Chemical formula 10]

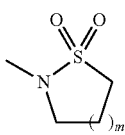

(B-6)

wherein m represents 1 or 2,
or a pharmaceutically acceptable salt thereof
provided that the following formulae (a), (b) and (c):

[Chemical formula 11]

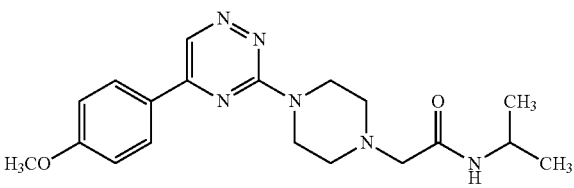

(a)

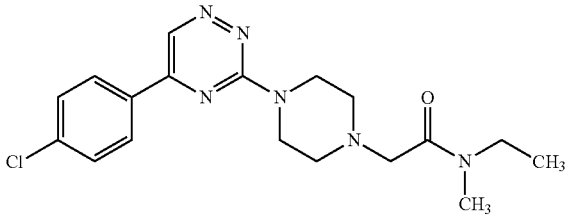

(b)

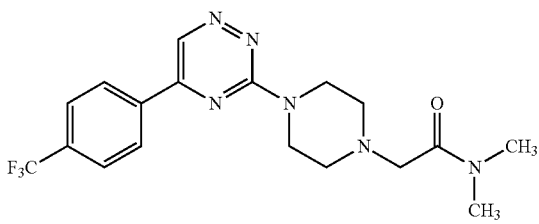

(c)

are excluded.

In addition, the present invention relates to a method for preventing or treating various diseases or conditions associated with aldosterone, comprising administering a therapeutically effective amount of a compound of the above formula [I] or a pharmacologically acceptable salt thereof. Additionally, the present invention relates to a pharmaceutical composition comprising the above compound [I] or a pharmaceutically acceptable salt thereof as an active ingredient as well as to use of the compound [I] for manufacturing the composition. Furthermore, the present invention relates to the above compound [I] or a pharmaceutically acceptable salt thereof, and a pharmaceutical composition comprising said compound or a salt thereof as an active ingredient, for use in prevention or treatment of various diseases or conditions associated with aldosterone. Furthermore, the present invention relates to a method for preparing the above compound [I] or a pharmaceutically acceptable salt thereof.

Effect of Invention

A compound [I] of the present invention or a pharmaceutically acceptable salt thereof has an excellent inhibitory activity against aldosterone synthetase (Cyp11B2), and therefore, it is useful for preventing or treating various diseases and/or disease states evoked by an increased level of aldosterone and/or overproduction of aldosterone, such as hypertension, primary aldosteronism, or for improving prognosis of these diseases.

BEST MODE FOR CARRYING OUT THE INVENTION

The definitions of each group can be freely combined unless otherwise stated.

In the present invention, alkyl refers to a straight or branched chain saturated hydrocarbon group containing 1-6 carbons ($C_{1-6}$). Particularly, an alkyl group containing 1-4 carbons ($C_{1-4}$) is preferable. In particular, alkyl includes methyl, ethyl, n-propyl, i-propyl, n-butyl, t-butyl, i-amyl, n-pentyl, and n-hexyl. Particularly, methyl, ethyl, i-propyl, or t-butyl is preferable.

Cycloalkyl refers to a monocyclic saturated hydrocarbon group containing 3-8 carbons ($C_{3-8}$) and adamantyl. In addition, cycloalkyl also includes a group wherein the ring-constituting two carbon atoms are cross-linked by an alkylene group to form a bicyclo ring. Particularly, cycloalkyl includes cyclopropyl, cyclobutyl, cyclopentyl, cyclohexyl, cycloheptyl, bicyclo[2.2.2]octyl, adamantyl, and the like.

Cycloalkenyl refers to a cyclic group containing 3-7 carbons ($C_{3-7}$) having at least one double bond. Particularly, cycloalkenyl includes cyclopropenyl, cyclobutenyl, cyclopentenyl, and cyclohexenyl.

Alkoxy refers to a monovalent group wherein the above alkyl is bound to oxygen. Alkoxy includes a straight or branched chain alkyl-O— containing 1-6 carbons ($C_{1-6}$). Alkyl-O— containing 1-4 carbons ($C_{1-4}$) is preferable. Particularly, alkoxy includes methoxy, ethoxy, n-propoxy, i-propoxy, n-butoxy, t-butoxy, and the like.

Alkylene refers to a straight or branched chain divalent group containing 1-6 carbons ($C_{1-6}$). Alkylene containing 1-4 carbons ($C_{1-4}$) is preferable. Particularly, alkylene includes methylene, ethylene, trimethylene, and tetramethylene.

Alkenylene refers to a straight or branched chain divalent group containing 2-6 carbons ($C_{2-6}$) having at least one double bond. Alkenylene containing 2-4 carbons ($C_{2-4}$) is preferable. Particularly, alkenylene includes vinylene, and propenylene.

Alkylenedioxy refers to a divalent group wherein both terminus of alkylene are bound to oxygen. Particularly, alkylenedioxy includes —O-alkylene-O— containing 1-6 carbons ($C_{1-6}$). "—O-Alkylene-O—" containing 1-4 carbons ($C_{1-4}$) is preferable. For example, a group wherein a phenyl group is substituted with aklylenedioxy includes the following structures.

[Chemical formula 12]

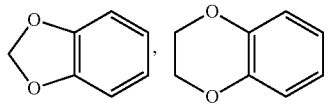

In addition, a structure wherein two substituents on the same carbon atom in a cycloalkyl group are bound to each other at the terminus thereof to form an alkylene group (wherein the alkylene group may contain 1-2 heteroatoms in the alkylene chain, which are selected independently from a nitrogen atom, an oxygen atom, or a sulfur atom) refers to, for example, the following structures.

[Chemical formula 13]

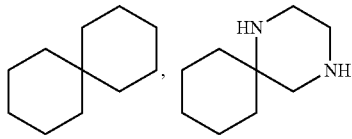

Furthermore, a structure wherein two substituents on the same carbon atom in a cycloalkyl group are bound to each other at the terminus thereof to form an alkylene group substituted with 1-3 groups selected independently from the group consisting of an alkyl group, and an oxo group (wherein the alkylene group may contain 1-3 heteroatoms in the alkylene chain, which are selected independently from a nitrogen atom, an oxygen atom, or a sulfur atom) refers to, for example, the following structures.

[Chemical formula 14]

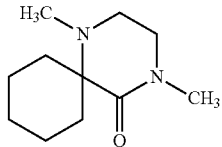

Halogen or halo refers to fluorine, chlorine, bromine or iodine. Fluorine and chlorine are preferable.

Haloalkyl means the above alkyl substituted with 1-3 halogen atoms, and is preferably trifluoromethyl.

Alkoxyalkyl means the above alkyl substituted with 1-2 alkoxy groups, and is preferably methoxymethyl, methoxyethyl, methoxypropyl, and the like.

Alkanoyl refers to a monovalent group wherein a carbonyl group is bound to the above alkyl. Alkanoyl includes a straight or branched chain alkyl-CO— containing 1-6 carbons ($C_{1-6}$). Alkyl-CO— containing 1-4 carbons ($C_{1-4}$) is preferable. Particularly, alkanoyl includes acetyl, propionyl, pivaloyl, butanoyl, pentanoyl, hexanoyl, and heptanoyl.

Aryl refers to a 6- to 10-membered aromatic hydrocarbon group, and a monocyclic or bicyclic aryl is preferable. Particularly, aryl includes phenyl, and naphthyl, and especially, phenyl is preferable.

Partially hydrogenated aryl refers to the above aryl which is partially hydrogenated, and includes, for example, a cyclic group formed by condensation between a phenyl group and a cycloalkyl group as well as a cyclic group formed by condensation between a phenyl group and a cycloalkenyl group. Particularly, includes dihydrophenyl, cyclohexenyl, indanyl, tetrahydronaphthyl, and the like.

Preferably, aryl which may be partially hydrogenated is phenyl, naphthyl, tetrahydronaphthyl, and cyclohexenyl.

Heteroaryl refers to a 5- to 10-membered aromatic heterocyclic group having 1-4 heteroatoms selected independently from the group consisting of a sulfur atom, an oxygen atom, and a nitrogen atom, and a monocyclic or bicyclic heteroaryl is preferable. More preferably, heteroaryl is a 5- to 10-membered monocyclic or bicyclic heteroaryl having 1-2 heteroatoms selected independently from the group consisting of a sulfur atom, an oxygen atom, and a nitrogen atom.

In addition, other preferable heteroaryl is a 5- to 10-membered monocyclic or bicyclic heteroaryl which contains at least 1 nitrogen atom, and additionally may contain 1 heteroatom selected from the group consisting of a sulfur atom, an oxygen atom, and a nitrogen atom. Particularly, heteroaryl includes pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, benzopyranyl, and the like.

Partially hydrogenated heteroaryl refers to the above heteroaryl which is partially hydrogenated, and includes, for example, a cyclic group formed by condensation between a phenyl group and an aliphatic heterocyclic group. Particularly, partially hydrogenated heteroaryl includes imidazolinyl, dihydrobenzofuranyl, dihydrobenzopyranyl, tetrahydroimidazopyridyl, isoindolinyl, and the like.

Heteroaryl which may be partially hydrogenated includes pyrrolyl, furanyl, thienyl, imidazolyl, imidazolinyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, isoindolinyl, indazolyl, benzimidazolyl, benzothiazolyl, benzofuranyl, dihydrobenzofuranyl, quinolyl, isoquinolyl, imidazopyridyl, tetrahydroimidazopyridyl, benzopyranyl, dihydrobenzopyranyl, and the like. Thienyl, pyridyl, indolyl, indazolyl, isoquinolyl, dihydrobenzofuranyl, dihydrobenzopyranyl, and benzothiazolyl are preferable. For example, heteroaryl which may be partially hydrogenated represented by $R^A$ in the above general formula [I] includes pyrrolyl, furanyl, thienyl, imidazolyl, imidazolinyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, isoindolinyl, indazolyl, benzimidazolyl, benzothiazolyl, benzofuranyl, dihydrobenzofuranyl, quinolyl, isoquinolyl, benzopyranyl, dihydrobenzopyranyl, and the like. Thienyl, pyridyl, indolyl, indazolyl, isoquinolyl, dihydrobenzofuranyl, dihydrobenzopyranyl, and benzothiazolyl are preferable.

Further, in another preferable example, heteroaryl which may be partially hydrogenated includes isoindolinyl. For example, heteroaryl which may be partially hydrogenated represented by $R^B$ in the above general formula [I] includes isoindolinyl.

An aliphatic heterocyclic ring refers to a 4- to 9-membered cyclic group having 1-3 heteroatoms selected independently from the group consisting of a sulfur atom, an oxygen atom, and a nitrogen atom. In addition, an aliphatic heterocyclic ring also includes a group wherein the ring-constituting two carbon atoms are cross-linked by an alkylene group to form a bicyclo ring. Particularly, azetidinyl, oxetanyl, pyrrolidinyl, tetrahydrothiophenyl, tetrahydrofuranyl, piperidinyl, piperazinyl, morpholinyl, thiomorpholinyl, homomorpholinyl, tetrahydrothiopyranyl, tetrahydropyranyl, azabicyclo[2.2.2]octyl(quinuclidinyl), azabicyclo[3.2.1]octyl, oxabicyclo[3.3.1]nonyl, diazabicyclo[2.2.1]heptyl, oxo-9-azabicyclo[3.3.1]nonyl, and the like, are preferable.

In addition, another preferable example of the aliphatic heterocyclic ring is a 4- to 9-membered aliphatic heterocyclic ring which contains at least 1 nitrogen atom, and additionally may contain 1 heteroatom selected from the group consisting of a sulfur atom, an oxygen atom, and a nitrogen atom. Particularly, the aliphatic heterocyclic ring includes azetidinyl, pyrrolidinyl, piperidinyl, piperazinyl, morpholinyl, thiomorpholinyl, homomorpholinyl, azabicyclo[2.2.2]octyl(quinuclidinyl), azabicyclo[3.2.1]octyl, diazabicyclo[2.2.1]heptyl, and the like.

In yet another preferable example, the aliphatic heterocyclic ring is a 4- to 9-membered aliphatic heterocyclic ring which contains 1-2 heteroatoms selected from an oxygen atom or a nitrogen atom. Particularly, the aliphatic heterocyclic ring includes oxetanyl, tetrahydrofuranyl, tetrahydropyranyl, pyrrolidinyl, piperidinyl, and homopiperidinyl.

Aliphatic heterocyclic carbonyl refers to a group wherein a carbonyl group is bound to the above aliphatic heterocyclic ring, and a 4- to 9-membered aliphatic heterocyclic ring-(CO)— which contains 1-3 heteroatoms selected independently from the group consisting of a sulfur atom, an oxygen atom, and a nitrogen atom.

Especially, a 5- or 6-membered aliphatic heterocyclic ring-(CO)— which contains 1-2 heteroatoms selected independently from the group consisting of a sulfur atom and an oxygen atom.

As one embodiment, the present invention comprises a compound of the above general formula [I]:
wherein
(A) in $R^A$,
  a substituent of (1) a cycloalkyl group which may be substituted, (2) an aryl group which may be partially hydrogenated and may be substituted, and (3) a heteroaryl group which may be partially hydrogenated and may be substituted, represented by ring $A^1$ in the above formula (A-1) is 1-3 groups selected independently from the group consisting of a halogen atom, a cyano group, an alkyl group, a haloalkyl group, an alkoxyalkyl group, an alkoxy group, and an alkylenedioxy group which may be substituted with 1-2 halogen atoms,
  an aryl moiety in the aryl group which may be partially hydrogenated and may be substituted is 6- to 10-membered monocyclic or bicyclic aryl,
  a heteroaryl moiety in the heteroaryl group which may be partially hydrogenated and may be substituted is 5- to 10-membered monocyclic or bicyclic heteroaryl which contains 1-2 heteroatoms selected independently from the group consisting of a sulfur atom, an oxygen atom, and a nitrogen atom;
  ring $A^2$ in the above formula (A-2) is a 6- to 10-membered monocyclic or bicyclic aryl group which may be substituted with (a) a cycloalkyl group, or (b) a halogen atom,
  $Q^1$ is a single bond, an oxygen atom, or —NH—;
(B) $R^B$ is
  (a) a monocyclic cycloalkyl group,
  (b) an isoindolinyl group,
  (c) a group represented by the above formula (B-1):
    wherein ring $Ar^1$ is a 6- to 10-membered monocyclic or bicyclic aryl group,
  (d) a group represented by the above formula (B-2):
    wherein a heteroaryl group represented by $R^{B1}$ is a 5- to 10-membered monocyclic or bicyclic heteroaryl group which contains 1-2 heteroatoms selected independently from the group consisting of a sulfur atom, an oxygen atom, and a nitrogen atom,
  (e) a group represented by the above formula: —N($R^{B2}$)($R^{B3}$)
    wherein $R^{B2}$ represents an alkylsulfonyl group which may be substituted with a 6- to 10-membered monocyclic or bicyclic aryl group, and $R^{B3}$ represents an alkyl group which may be substituted with a 6- to 10-membered monocyclic or bicyclic aryl group or heteroaryl group (wherein heteroaryl is 5- to 10-membered monocyclic or bicyclic heteroaryl which contains 1-2 heteroatoms selected independently from the group consisting of a sulfur atom, an oxygen atom, and a nitrogen atom), or
    $R^{B2}$ represents a hydrogen atom or an alkyl group, and $R^{B3}$ represents an alkyl group substituted with an alkylsulfonyl group,
  (f) a group represented by the above formula (B-3):
    wherein ring B is a 4- to 9-membered aliphatic heterocyclic group which may further contain one heteroatom selected from the group consisting of a sulfur atom, an oxygen atom, and a nitrogen atom in addition to the nitrogen atom shown in the above formula (B-3);
    a heteroaryl moiety of the heteroaryl-O— group represented by $R^{B4}$ is 5- to 10-membered monocyclic or bicyclic heteroaryl which contains at least one nitrogen atom, and may further contain 1 heteroatom selected from the group consisting of a sulfur atom, an oxygen atom, and a nitrogen atom,
  (g) a group of the above formula (B-4):
    wherein a substituent of (i) the alkyl group which may be substituted, represented by $R^{B7}$, is 1-4 groups selected independently from the group consisting of a halogen atom; a hydroxyl group; an oxo group; an amino group which may be substituted with 1-2 groups selected independently from the group consisting of an alkyl group, an alkanoyl group, an alkoxycarbonyl group and an alkylsulfonyl group; a heteroaryl group which may be substituted with an alkyl group and may be partially hydrogenated; a cycloalkyl group which may be substituted with 1-2 groups selected independently from the group consisting of a hydroxyl group and an alkylsulfonyl group; an aryl group; a heteroaryl group which may be partially hydrogenated; an alkanoyl group which may be substituted with 1-3 groups selected independently from the group consisting of a halogen atom and a hydroxyl group; a cycloalkylcarbonyl group which may be substituted with a hydroxyl group; an aliphatic heterocyclic carbonyl group which may be substituted with an alkyl group; an amino group which may be substituted with 1-2 groups selected independently from the group consisting of an alkyl group which may be substituted with an alkylsulfonyl group, an alkanoyl group, and an alkoxycarbonyl group; a carbamoyl group which may be substituted with 1-2 alkyl groups; an alkylsulfonyl group; an alkoxy group which may be substituted with a carbamoyl group which may be substituted with 1-2 alkyl groups; and an aliphatic heterocyclic group which may be substituted with 1-3 groups selected independently from the group consisting of a hydroxyl group, an oxo group, an alkyl group, an alkanoyl group, and an alkylsulfonyl group, a substituent of (ii) the cycloalkyl group which may be substituted, (iii) the aliphatic heterocyclic group which may be substituted, and (iv) the heteroaryl group which may be partially hydrogenated and may be substituted represented by $R^{B7}$ is 1-4 groups selected independently from the group consisting of a halogen atom; a hydroxyl group; an oxo group; an alkyl group which may be substituted with 1-3 groups selected independently from the group consisting of a hydroxyl group, an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, an aliphatic heterocyclic carbonyl group, and a heteroaryl group which may be substituted with an alkyl group and may be partially hydrogenated; a cycloalkyl group which may be substituted with 1-2 groups selected independently from the group consisting of a hydroxyl group and an alkylsulfonyl group; an aryl group; a heteroaryl group which may be partially hydrogenated; an alkanoyl group which may be substituted with 1-3 groups selected independently from the group consisting of a halogen atom and a hydroxyl group; a cycloalkylcarbonyl group which may be substituted with a hydroxyl group; an aliphatic heterocyclic carbonyl group which may be substituted with an alkyl group; an amino group which may be substituted with 1-2 groups selected independently from the group consisting of an alkyl group which may be substituted with an alkylsulfonyl group, an alkanoyl group, and an alkoxycarbonyl group; a carbamoyl group which may be substituted with 1-2 alkyl groups; an alkylsulfonyl group; an alkoxy group which may be substituted with a carbamoyl group which may be substituted with 1-2 alkyl groups; and an aliphatic heterocyclic group which may be substituted with 1-3 groups selected independently from the group consisting of a hydroxyl group, an oxo group, an alkyl group, an alkanoyl group, and an alkylsulfonyl group, or when $R^{B7}$ is (ii) a cycloalkyl group which may be substituted, or (iii) an aliphatic heterocyclic group which may be substituted, two substituents on the same ring-constituting carbon atom may be bound to each other at the terminus thereof to form an alkylene group which may be substituted (wherein a substituent of the alkylene group is an oxo group or an alkyl group, and the alkylene group may contain 1-3 heteroatoms selected independently from a sulfur atom, an oxygen atom, and a nitrogen atom), in $R^{B7}$, aryl is 6- to 10-membered monocyclic or bicyclic aryl, heteroaryl is 5- to 10-membered monocyclic or bicyclic heteroaryl which contains 1-4 heteroatoms selected independently from the group consisting of a sulfur atom, an oxygen atom, and a nitrogen atom, an aliphatic heterocyclic ring is a 4- to 9-membered aliphatic heterocyclic ring which contains 1-2 heteroatoms selected independently from the group consisting of an oxygen atom or a nitrogen atom, or when $X^C$ is $NR^{4C}$, and $R^{B7}$ and $R^{4c}$ are bound to each other at their terminus to form an aliphatic heterocyclic group which may be substituted with an alkyl group which may be substituted, together with a nitrogen atom to which they are bound, a substituent of the alkyl group which may be substituted is a hydroxyl group, and the aliphatic heterocyclic group is a 4- to 9-membered aliphatic heterocyclic ring which may further contain one heteroatom selected independently from the group consisting of a sulfur atom, an oxygen atom or a nitrogen atom other than the nitrogen atom to which RB7 and R4c are bound, (h) a group represented by the above formula (B-5): wherein $R^{B8}$ is a hydrogen atom, or (i) a group represented by the above formula (B-6): wherein m is 2, or a pharmaceutically acceptable salt thereof
provided that the following formulae (a), (b) and (c):

[Chemical formula 15]

(a)

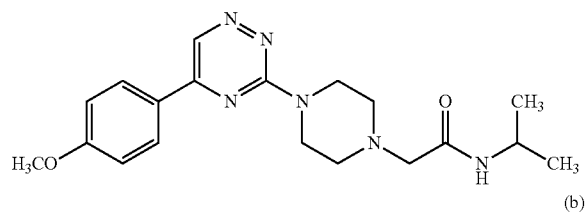

(b)

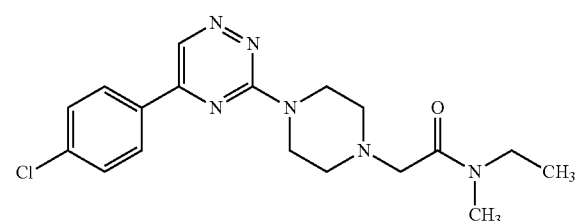

(c)

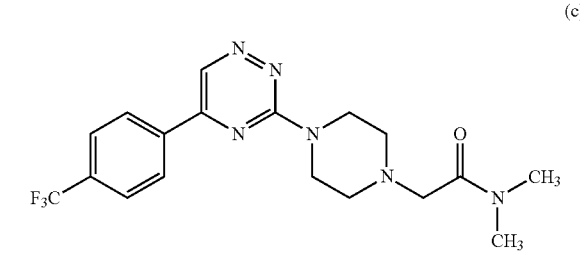

are excluded.

As another preferable embodiment, the present invention comprises a compound of the above general formula [I]:
wherein
in a group represented by the above formula [A-1], ring $A^1$ is
(1) a cycloalkyl group which may be substituted with an alkyl group, (2) an aryl group which may be partially hydrogenated and may be substituted, or (3) a heteroaryl group which may be partially hydrogenated and may be substituted, wherein a substituent of the aryl group which may be partially hydrogenated and may be substituted is 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, a substituent of the heteroaryl group which may be partially hydrogenated and may be substituted is 1-2 groups selected independently from the group consisting of a halogen atom, a cyano group, and an alkyl group, an aryl moiety of the aryl group which may be partially hydrogenated and may be substituted is phenyl or naphthyl, a heteroaryl moiety of the heteroaryl group which may be partially hydrogenated and may be substituted is thienyl, pyridyl, indazolyl, benzofuranyl, indolyl, benzothiazolyl, isoquinolinyl, or benzopyranyl;

in the above formula [A-2], ring $A^2$ is (a) a cycloalkyl group, or (b) a phenyl group which may be substituted with a halogen atom, $Alk^{A1}$ is a straight or branched chain alkylene group, or a straight or branched chain alkenylene group, $Q^1$ is a single bond, an oxygen atom, or —NH—;

in a group represented by the above formula [B-1], $Ar^1$ represents a phenyl group;

in a group represented by the above formula [B-2], a heteroaryl moiety in the heteroaryl group represented by $R^{B1}$ is pyrazinyl;

in a group represented by the above formula: —N($R^{B2}$)($R^{B3}$), $R^{B2}$ represents an alkylsulfonyl group which may be substituted with a phenyl group, and $R^{B3}$ represents an alkyl group which may be substituted with a phenyl group or a pyridyl group;

in a group of the above formula [B-3], ring B is pyrrolidinyl, piperidinyl, piperazinyl, morpholinyl, or 2,5-diazabicyclo[2.2.1]heptyl, $R^{B4}$ is a group selected from the group consisting of a cyano group; an alkyl group substituted with an alkylsulfonyl group; an alkyl group substituted with an alkanoylamino group; a heteroaryl-O— group (wherein heteroaryl is pyridyl); and an alkoxy group which may be substituted with a carbamoyl group which may be substituted with 1-2 alkyl groups;

in a group represented by the above formula [B-4], $R^{B7}$ is (i) an alkyl group which may be substituted, (ii) a cycloalkyl group which may be substituted, (iii) an aliphatic heterocyclic group which may be substituted, (iv) a heteroaryl group which may be partially hydrogenated and may be substituted, or (v) a hydrogen atom, or when $X^c$ is $NR^{4c}$, $R^{B7}$ and $R^{4c}$ may be bound to each other at their terminus to form an aliphatic heterocyclic group which may be substituted with an alkyl group which may be substituted with a hydroxyl group, together with a nitrogen atom to which they are bound, wherein (i) a substituent of the alkyl group which may be substituted is 1-4 groups selected independently from the group consisting of a halogen atom; a hydroxyl group; a cycloalkyl group which may be substituted with 1-2 groups selected independently from the group consisting of a hydroxyl group and an alkylsulfonyl group; a phenyl group; a heteroaryl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of a hydroxyl group, an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, an aliphatic heterocyclic carbonyl group, and a heteroaryl group which may be substituted with an alkyl group and may be partially hydrogenated; an alkanoyl group which may be substituted with 1-3 groups selected independently from the group consisting of a halogen atom and a hydroxyl group; a cycloalkylcarbonyl group which may be substituted with a hydroxyl group; an aliphatic heterocyclic carbonyl group which may be substituted with an alkyl group; an alkoxy group; a carbamoyl group which may be substituted with 1-2 alkyl groups; an aliphatic heterocyclic group which may be substituted with an oxo group; and a heteroaryl group, (iv) a substituent of the heteroaryl group which may be partially hydrogenated and may be substituted is 1-2 groups selected independently from the group consisting of an aliphatic heterocyclic group; and an alkyl group which may be substituted with 1-2 groups selected independently from the group consisting of a carbamoyl group which may be substituted with 1-2 alkyl groups, alkylsulfonyl group, and a heteroaryl group, in the above items (i)-(iv), the aliphatic heterocyclic ring is selected from azetidinyl, oxetanyl, pyrrolidinyl, tetrahydrothiophenyl, tetrahydrofuranyl, piperidinyl, piperazinyl, morpholinyl, thiomorpholinyl, homomorpholinyl, tetrahydrothiopyranyl, tetrahydropyranyl, 1-azabicyclo[2.2.2]octyl (quinuclidinyl), 8-azabicyclo[3.2.1]octyl, 3-oxabicyclo [3.3.1]nonyl, or 3-oxo-9-azabicyclo[3.3.1]nonyl, the aliphatic heterocyclic ring in the aliphatic heterocyclic carbonyl is selected from azetidinyl, oxetanyl, pyrrolidinyl, tetrahydrothiophenyl, tetrahydrofuranyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, the heteroaryl is selected from pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl, the heteroaryl group which may be partially hydrogenated is selected from a pyrrolyl group, a furanyl group, a thienyl group, an imidazolyl group, an imidazolinyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, or a dihydrobenzopyranyl group, or when $X^c$ is $NR^{4c}$, and $R^{B7}$ and $R^{4c}$ are bound to each other at their terminus to form an aliphatic heterocyclic group which may be substituted with an alkyl group which may be substituted with a hydroxyl group, together with a nitrogen atom to which they are bound, an aliphatic heterocyclic group is a group selected from azetidinyl, pyrrolidinyl, piperidinyl, piperazinyl, morpholinyl, thiomorpholinyl, or homomorpholinyl, or a pharmaceutically acceptable salt thereof.

As another preferable embodiment, the present invention comprises a compound of the above general formula [I]:
[wherein
(A) in $R^4$,
in a group represented by the above formula [A-1], ring $A^1$ is
(1) a cycloalkyl group which may be substituted with an alkyl group,
(2) an aryl group which may be partially hydrogenated and may be substituted, or
(3) a heteroaryl group which may be partially hydrogenated and may be substituted,
wherein
a substituent of the aryl group which may be partially hydrogenated and may be substituted is 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms,
a substituent of the heteroaryl group which may be partially hydrogenated and may be substituted is 1-2 groups selected independently from the group consisting of a halogen atom, a cyano group, and an alkyl group,
an aryl moiety of the aryl group which may be partially hydrogenated and may be substituted is phenyl or naphthyl,
a heteroaryl moiety of the heteroaryl group which may be partially hydrogenated and may be substituted is thienyl, pyridyl, indazolyl, benzofuranyl, indolyl, benzothiazolyl, isoquinolinyl, or benzopyranyl;

in the above formula [A-2], ring $A^2$ is (a) a cycloalkyl group, or (b) a phenyl group which may be substituted with a halogen atom,
$Alk^{A1}$ is a straight or branched chain alkylene group, or a straight or branched chain alkenylene group,
$Q^1$ is a single bond, an oxygen atom, or —NH—;
(B) a group represented by $R^B$ is
(b) an isoindolinyl group;
(c) a group represented by the above formula (B-1) wherein ring $Ar^1$ is a phenyl group;
(d) a group represented by the above formula (B-2) wherein a heteroaryl moiety of the heteroaryl group represented by $R^{B1}$ is pyrazinyl;
(e) a group represented by the formula: $-N(R^{B2})(R^{B3})$
wherein $R^{B2}$ represents an alkylsulfonyl group which may be substituted with a phenyl group, and $R^{B3}$ represents an alkyl group which may be substituted with a phenyl group or a pyridyl group, or
$R^{B2}$ represents a hydrogen atom or an alkyl group, and $R^{B3}$ represents an alkyl group substituted with an alkylsulfonyl group;
(f) an aliphatic heterocyclic group represented by the above formula (B-3):
wherein ring B is pyrrolidinyl, piperidinyl, piperazinyl, morpholinyl, or 2,5-diazabicyclo[2.2.1]heptyl,
$R^{B4}$ is a group selected from the group consisting of
an alkanoylamino group or an alkyl group substituted with an alkylsulfonyl group;
a cyano group;
an alkoxy group substituted with a carbamoyl group which may be substituted with 1-2 alkyl groups; and
a pyridyl-O— group,
$R^{B5}$ is a hydrogen atom;
(g) a group represented by the above formula (B-4):
(wherein
(i) when $X^a$ represents $CR^{3a}$,
$X^b$ represents $CHR^{3b}$, $X^c$ represents O or $NR^{4c}$,
$X^b$ represents O, $X^c$ represents $NR^{4c}$, or
$X^b$ represents $NR^{4b}$, $X^c$ represents O, $NR^{4c}$, or $CHR^{3c}$,
(ii) when $X^a$ represents N,
$X^b$ represents $CHR^{3b}$ or $C(=O)$, $X^c$ represents $NR^{4c}$, or
$X^b$ represents $NR^{4b}$, $X^c$ represents $CHR^{3c}$,
wherein $R^{3a}$ represents a hydrogen atom, a hydroxyl group, an alkyl group, or an amino group,
each of $R^{3b}$ and $R^{3c}$ represents a group selected independently from the group consisting of a hydrogen atom, a hydroxyl group, and an alkyl group,
each of $R^{4b}$ and $R^{4c}$ represents a group selected independently from the group consisting of a hydrogen atom, an alkyl group, and a cycloalkyl group;
$R^{B6}$ represents a hydrogen atom or an alkyl group;
$R^{B7}$ is (i) an alkyl group which may be substituted, (ii) a cycloalkyl group which may be substituted, (iii) an aliphatic heterocyclic group which may be substituted, (iv) a heteroaryl group which may be partially hydrogenated and may be substituted, or (v) a hydrogen atom, or,
when $X^c$ represents $NR^{4c}$, $R^{B7}$ and $R^{4c}$ may be bound to each other at their terminus to form an aliphatic heterocyclic group, which may be substituted with an alkyl group which may be substituted with a hydroxyl group, together with a nitrogen atom to which they are bound,
wherein
(i) a substituent of the alkyl group which may be substituted is 1-4 groups selected independently from the group consisting of a halogen atom; a hydroxyl group; a phenyl group; a heteroaryl group which may be partially hydrogenated; an amino group which may be substituted with 1-2 groups selected independently from the group consisting of an alkyl group, an alkanoyl group, an alkoxycarbonyl group, and an alkylsulfonyl group; an alkylsulfonyl group; an alkoxy group; and an aliphatic heterocyclic group which may be substituted with 1-3 groups selected independently from the group consisting of a hydroxyl group, an oxo group, an alkanoyl group, and an alkylsulfonyl group, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, or a sulfur atom), (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of a hydroxyl group, an alkoxy group, an alkylsulfonyl group, an amino group which may be substituted with 1-2 groups selected independently from the group consisting of an alkoxycarbonyl group, and an alkylsulfonylamino group, a carbamoyl group which may be substituted with 1-2 alkyl groups, a cycloalkyl group which may be substituted with a hydroxyl group, an aliphatic heterocyclic carbonyl group, an aryl group, and a heteroaryl group which may be substituted with an alkyl group and may be partially hydrogenated; an alkanoyl group which may be substituted with 1-2 groups selected independently from the group consisting of an aliphatic heterocyclic group which may be substituted with an alkyl group, a halogen atom, a hydroxyl group, and a cycloalkyl group which may be substituted with a hydroxyl group; an alkoxy group; a carbamoyl group which may be substituted with 1-2 alkyl groups; an aliphatic heterocyclic group which may be substituted with an oxo group; an alkylsulfonyl group; a heteroaryl group; and a phenyl group, (iv) a substituent of the heteroaryl group which may be partially hydrogenated and may be substituted is 1-2 groups selected independently from the group consisting of a carbamoyl group which may be substituted with 1-2 alkyl groups; an aliphatic heterocyclic group; and an alkyl group which may be substituted with 1-2 groups selected independently from the group consisting of a hydroxyl group, an alkoxy group, an amino group, a carbamoyl group which may be substituted with 1-2 alkyl groups, and an alkylsulfonyl group, in the above items (i)-(iv), an aliphatic heterocyclic ring is selected from azetidinyl, oxetanyl, pyrrolidinyl, thioranyl, piperidinyl, piperazinyl, morpholinyl, thiomorpholinyl, homomorpholinyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, the aliphatic heterocyclic ring in the aliphatic heterocyclic carbonyl is selected from azetidinyl, oxetanyl, pyrrolidinyl, thioranyl, piperidinyl, piperazinyl, morpholinyl, thiomorpholinyl, homomorpholinyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, the heteroaryl is selected from pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl, the heteroaryl group which may be partially hydrogenated is selected from a pyrrolyl group, a furanyl group, a thienyl group, an imidazolyl group, an imidazolinyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, or a dihydrobenzopyranyl group, or when $X^c$ is $NR^{4c}$, and $R^{B7}$ and $R^{4c}$ are bound to each other at their terminus to form an aliphatic heterocyclic group which may be substituted with an alkyl group which may be substituted with a hydroxyl group, together with a nitrogen atom to which they are bound, an aliphatic heterocyclic group is a group selected from azetidinyl, pyrrolidinyl, piperidinyl, piperazinyl, morpholinyl, thiomorpholinyl, or homomorpholinyl;

(h) a nitrogen-containing spiro heterocyclic group represented by the above formula (B-5):
wherein $R^{B8}$ is a hydrogen atom or an alkyl group; or (i) an aliphatic heterocyclic group represented by the above formula (B-6):
wherein m is 2,
or a pharmaceutically acceptable salt thereof.

The preferable compound of the present invention is a compound of the above general formula [I] wherein $R^4$ is phenyl which may be substituted, or a pharmaceutically acceptable salt thereof.

Further, the preferable compound of the present invention is a compound of the above general formula [I] wherein $R^B$ is a group represented by the above formula (B-4), or a pharmaceutically acceptable salt thereof.

The more preferable compound of the present invention is a compound of the above general formula [I] wherein $X^a$ in the above formula (B-4) is N, or a pharmaceutically acceptable salt thereof.

The more preferable compound of the present invention is a compound of the above general formula [I] wherein in the above formula (B-4),
$X^a$ is N,
$X^b$ is $CH_2$ and $X^c$ is NH; or $X^b$ is NH and $X^c$ is $CH_2$; and
$R^{B6}$ is a hydrogen atom,
or a pharmaceutically acceptable salt thereof.

Another more preferable compound of the present invention is a compound of the above general formula [I] wherein in the above formula (B-4), $X^a$ is N, $X^b$ is $CHR^{3b}$ or C(=O), and $X^c$ is $NR^{4c}$, $R^{3b}$ is a hydrogen atom or an alkyl group, $R^{4c}$ is a hydrogen atom, an alkyl group, or a cycloalkyl group, and $R^{B6}$ is a hydrogen atom or an alkyl group, or a pharmaceutically acceptable salt thereof.

The further more preferable compound of the present invention is a compound of the above general formula [I] wherein, in the above formula (B-4), $X^a$ is N, $X^b$ is CHR$^{3b}$ or C(=O), and $X^c$ is NR$^{4c}$, $R^{3b}$ is a hydrogen atom or an alkyl group, $R^{4c}$ is a hydrogen atom, an alkyl group, or a cycloalkyl group, and $R^{B6}$ is a hydrogen atom, or a pharmaceutically acceptable salt thereof.

In addition, the preferable compound of the present invention is a compound of the above general formula [I] wherein $R^A$ is a group represented by the above formula (A-1), and $R^B$ is a group represented by the above formula (B-4), or a pharmaceutically acceptable salt thereof.

Further, the preferable compound of the present invention is a compound of the above general formula [I] wherein $R^A$ is a phenyl group which may be substituted, and $R^B$ is a group represented by the above formula (B-4), or a pharmaceutically acceptable salt thereof.

The particularly preferable compound of the present invention is a compound of the above general formula [I] wherein $R^A$ is a phenyl group which may be substituted, $R^B$ is a group represented by the above formula (B-4) (wherein $X^a$ is N, $X^b$ is CHR$^{3b}$, $X^c$ is NR$^{4c}$, $R^{3b}$ is a hydrogen atom or an alkyl group, and $R^{4c}$ is a hydrogen atom, an alkyl group, or a cycloalkyl group), or a pharmaceutically acceptable salt thereof.

The more preferable compound of the present invention is a compound of the above general formula [I] wherein, in the above formula (B-4), $X^a$ is N, $X^b$ is CH$_2$, $X^c$ is NH, and $R^{B6}$ is a hydrogen atom, or a pharmaceutically acceptable salt thereof.

Another more preferable compound of the present invention is a compound of the above general formula [I] wherein $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, and $R^B$ is a group represented by the above formula (B-4) (wherein $X^a$ is N, $X^b$ is CH$_2$, $X^c$ is NH, and $R^{B6}$ is a hydrogen atom), or a pharmaceutically acceptable salt thereof.

Another more preferable compound of the present invention is a compound of the above general formula [I] wherein $R^{B7}$ is a cycloalkyl group which may be substituted, wherein a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and an cycloalkyl moiety of the above cycloalkyl group which may be substituted is cyclobutyl, cyclopentyl, cyclohexyl, bicyclo[2.2.2]octyl, or adamantyl, or a pharmaceutically acceptable salt thereof.

As another preferable embodiment, the present invention comprises a compound of the above general formula [I]: wherein (A) $R^A$ is (1) a cycloalkyl group which may be substituted with an alkyl group, (2) a cycloalkenyl group which may be substituted with an alkyl group, (3) a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, (4) a naphthyl group which may be partially hydrogenated and may be substituted with an alkyl group, (5) a heteroaryl group which may be partially hydrogenated and may be substituted with 1-2 groups selected independently from the group consisting of a cyano group, and an alkyl group, the heteroaryl moiety is pyridyl, indazolyl, thienyl, isoquinolyl, benzopyranyl, benzofuranyl, indolyl, or benzothiazolyl, (B) $R^B$ is a group of the above formula (B-4):

wherein (i) when $X^a$ represents CR$^{3a}$, $X^b$ represents CHR$^{3b}$, and $X^c$ represents O or NR$^{4c}$, $X^b$ represents O, and $X^c$ represents NR$^{4c}$, or $X^b$ represents NR$^{4b}$, and $X^c$ represents O, NR$^{4c}$, or CHR$^{3c}$, (ii) when $X^a$ represents N, $X^b$ represents CHR$^{3b}$ or C(=O), and $X^c$ represents NR$^{4c}$, or $X^b$ represents NR$^{4b}$, and $X^c$ represents CHR$^{3c}$, wherein $R^{3a}$ represents a hydrogen atom, a hydroxyl group, an alkyl group, or an amino group, each of $R^{3b}$ and $R^{3c}$ represents a group selected independently from the group consisting of a hydrogen atom, a hydroxyl group, and an alkyl group, each of $R^{4b}$ and $R^{4c}$ represents a group selected independently from the group consisting of a hydrogen atom, an alkyl group, and a cycloalkyl group;

$R^{B6}$ represents a hydrogen atom or an alkyl group;

$R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or, when $X^c$ is NR$^{4c}$, $R^{B7}$ and $R^{4c}$ are bound to each other at their terminus to form an aliphatic heterocyclic group, which may be substituted with an alkyl group (wherein the alkyl group may be substituted with a hydroxyl group), together with a nitrogen atom to which they are bound, wherein (i) a substituent of the alkyl group which may be substituted is 1-4 groups selected independently from the group consisting of a halogen atom; a hydroxyl group; a cycloalkyl group which may be substituted with 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group, wherein the aliphatic heterocyclic group is selected from tetrahydrothiophenyl, piperidinyl, piperazinyl, thiomorpholinyl, or morpholinyl, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (ii) the cycloalkyl group which may be substituted is cyclobutyl, cyclopentyl, cyclohexyl, bicyclo[2.2.2]octyl, or adamantyl, (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-3 groups selected independently from the group consisting of an a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein heteroaryl of (iv) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group which may be substituted with a hydroxyl group is piperazinyl or pyrrolidinyl (wherein the aliphatic heterocyclic group is formed from $R^{B7}$ and $R^{4c}$ being bound to each other at their terminus, together with a nitrogen atom to which they are bound, when $X^c$ is $NR^{4c}$)], or a pharmaceutically acceptable salt thereof.

As another preferable embodiment, the present invention comprises a compound of the above general formula [I]:
wherein
(A) $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms,
(B) $R^B$ is a group of the above formula (B-4):
wherein
(i) when $X^a$ represents $CR^{3a}$,
$X^b$ represents $CHR^{3b}$, and $X^c$ represents O or $NR^{4c}$,
$X^b$ represents O, and $X^c$ represents $NR^{4c}$, or
$X^b$ represents $NR^{4b}$, and $X^c$ represents O, $NR^{4c}$, or $CHR^{3c}$,
(ii) when $X^a$ represents N,
$X^b$ represents $CHR^{3b}$ or $C(=O)$, and $X^c$ represents $NR^{4c}$, or
$X^b$ represents $NR^{4b}$, and $X^c$ represents $CHR^{3c}$,
wherein $R^{3a}$ represents a hydrogen atom, a hydroxyl group, an alkyl group, or an amino group,
each of $R^{3b}$ and $R^{3c}$ represents a group selected independently from the group consisting of a hydrogen atom, a hydroxyl group, and an alkyl group,
each of $R^{4b}$ and $R^{4c}$ represents a group selected independently from the group consisting of a hydrogen atom, an alkyl group, and a cycloalkyl group;
$R^{B6}$ represents a hydrogen atom or an alkyl group;
$R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or,
when $X^c$ represents $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound,
wherein
(i) a substituent of the alkyl group which may be substituted is 1-4 groups selected independently from the group consisting of a halogen atom; a hydroxyl group; a cycloalkyl group which may be substituted with 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group,
wherein the aliphatic heterocyclic group is selected from tetrahydrothiophenyl, piperidinyl, piperazinyl, thiomorpholinyl, or morpholinyl,
(ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or
two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom),
wherein the aliphatic heterocyclic group is pyrrolidinyl, piperidinyl, piperazinyl, morpholinyl, or thiomorpholinyl, and
a cycloalkyl moiety of (ii) the cycloalkyl group which may be substituted is cyclobutyl, cyclopentyl, cyclohexyl, bicyclo[2.2.2]octyl, or adamantyl,
(iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-2 groups selected independently from the group consisting of an a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group,
wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl,
(iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, alkylsulfonyl group, and pyridazinyl group,
wherein a heteroaryl group of (iv) the heteroaryl group which may be partially hydrogenated and may be substituted is pyrazolyl, pyridyl, or imidazopyridinyl,
an aliphatic heterocyclic moiety of the aliphatic heterocyclic group which may be substituted with an alkyl group which may be substituted with a hydroxyl group is piperazinyl or pyrrolidinyl (wherein the aliphatic heterocyclic group is formed from $R^{B7}$ and $R^{4c}$ being bound to each other at their terminus, together with a nitrogen atom to which they are bound, when $X^c$ is $NR^{4c}$),
or a pharmaceutically acceptable salt thereof.

As another preferable embodiment, the present invention comprises a compound of the above general formula [I]:
wherein
(A) $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms,
(B) $R^B$ is a group of the above formula (B-4):
wherein
$X^a$ represents N,
$X^b$ represents $CHR^{3b}$ or $C(=O)$, and $X^c$ represents $NR^{4c}$, or
$X^b$ represents $NR^{4b}$, and $X^c$ represents $CHR^{3c}$,
wherein each of $R^{3b}$ and $R^{3c}$ represents a group selected independently from the group consisting of a hydrogen atom, a hydroxyl group, and an alkyl group,
each of $R^{4b}$ and $R^{4c}$ represents a group selected independently from the group consisting of a hydrogen atom, an alkyl group, and a cycloalkyl group,
$R^{B6}$ represents a hydrogen atom or an alkyl group,
$R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or,
when $X^c$ represents $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound, wherein (i) a substituent of the alkyl group which may be substituted is 1-4 groups selected independently from the group consisting of a halogen atom; a hydroxyl group; a cycloalkyl group which may be 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group, wherein the aliphatic heterocyclic group is selected from tetrahydrothiophenyl, piperidinyl, piperazinyl, thiomorpholinyl, or morpholinyl, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (ii) the cycloalkyl group which may be substituted is cyclobutyl, cyclopentyl, cyclohexyl, bicyclo[2.2.2]octyl, or adamantyl, (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-2 groups selected independently from the group consisting of an a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein a heteroaryl group of (iv) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group (wherein the alkyl may be substituted with a hydroxyl group) which is formed from $R^{B7}$ and $R^{4c}$ being bound to each other at their terminus, together with a nitrogen atom to which they are bound, when $X^c$ is $NR^{4c}$, is piperazinyl, or pyrrolidinyl, or a pharmaceutically acceptable salt thereof.

As another preferable embodiment, the present invention comprises a compound of the above general formula [I]:

wherein (A) $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, (B) $R^B$ is a group of the above formula (B-4):

wherein $X^a$ represents N, $X^b$ represents $CH_2$, and $X^c$ represents NH, $R^{B6}$ represents a hydrogen atom or an alkyl group, $R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or, when $X^c$ represents $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound, wherein (i) a substituent of the alkyl group which may be substituted is 1-4 groups selected independently from the group consisting of a halogen atom; a hydroxyl group; a cycloalkyl group which may be 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group, wherein the aliphatic heterocyclic group is selected from tetrahydrothiophenyl, piperidinyl, piperazinyl, thiomorpholinyl, or morpholinyl, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (ii) the cycloalkyl group which may be substituted is cyclobutyl, cyclopentyl, cyclohexyl, bicyclo[2.2.2]octyl, or adamantyl, (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-2 groups selected independently from the group consisting of an a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein a heteroaryl group of (iv) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group (which may be substituted with a hydroxyl group) is piperazinyl or pyrrolidinyl wherein the aliphatic heterocyclic group is formed from $R^{B7}$ and $R^{4c}$ being bound to each other at their terminus, together with a nitrogen atom to which they are bound, when $X^c$ is $NR^{4c}$, or a pharmaceutically acceptable salt thereof.

As another preferable embodiment, the present invention comprises a compound of the above general formula [I]: wherein (A) $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, (B) $R^B$ is a group of the above formula (B-4):
wherein
$X^a$ represents N,
$X^b$ represents $CH_2$, and $X^c$ represents NH,
$R^{B6}$ represents a hydrogen atom or an alkyl group,
$R^{B7}$ is a cycloalkyl group which may be substituted,
wherein a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and wherein a cycloalkyl moiety of the above cycloalkyl group which may be substituted is cyclobutyl, cyclopentyl, cyclohexyl, bicyclo[2.2.2]octyl, or adamantyl,
or a pharmaceutically acceptable salt thereof.

As another preferable embodiment, the present invention comprises a compound of the above general formula [I]:
wherein
(A) $R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms,
(B) $R^B$ is a group of the above formula (B-4):
    wherein
    $X^a$ represents N,
    $X^b$ represents $CH_2$, and $X^c$ represents NH,
    $R^{B6}$ represents a hydrogen atom,
    $R^{B7}$ is a cycloalkyl group which may be substituted,
    wherein a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or
    two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene may contain, in the alkylene chain, 1-2 heteroatoms selected independently from a nitrogen atom, an oxygen atom, and a sulfur atom),
    wherein the aliphatic heterocyclic group is pyrrolidinyl, piperidinyl, piperazinyl, morpholinyl, or thiomorpholinyl, and
    wherein a cycloalkyl moiety of the above cycloalkyl group which may be substituted is cyclobutyl, cyclopentyl, cyclohexyl, bicyclo[2.2.2]octyl, or adamantyl,
or a pharmaceutically acceptable salt thereof.

As another preferable embodiment, the present invention comprises a compound of the above general formula [I]:
wherein
(A) $R^A$ is a group represented by the above formula (A-1):
    wherein $R^A$ is
    (1) a cycloalkyl group which may be substituted with an alkyl group,
    (2) a cycloalkenyl group which may be substituted with an alkyl group,
    (3) a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms,
    (4) a naphthyl group which may be partially hydrogenated and may be substituted with an alkyl group,
    (5) a heteroaryl group which may be partially hydrogenated and may be substituted with 1-2 groups selected independently from the group consisting of a cyano group, and an alkyl group,
    wherein the heteroaryl moiety is pyridyl, indazolyl, thienyl, isoquinolyl, benzopyranyl, benzofuranyl, indolyl, or benzothiazolyl,
(B) $R^B$ is a group of the above formula (B-4):
    wherein
    $X^a$ is N, $X^b$ is $CHR^{3b}$ or $C(=O)$, $X^c$ is $NR^{4c}$, $R^{3b}$ is a hydrogen atom or an alkyl group, and $R^{4c}$ is a hydrogen atom, an alkyl group, or a cycloalkyl group,
    $R^{B6}$ is a hydrogen atom or an alkyl group,
    $R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or,
    when $X^c$ represents $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound, wherein
    (i) a substituent of the alkyl group which may be substituted is 1-4 groups selected independently from the group consisting of a halogen atom; a hydroxyl group; a cycloalkyl group which may be 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group,
    wherein the aliphatic heterocyclic group is selected from tetrahydrothiophenyl, piperidinyl, piperazinyl, thiomorpholinyl, or morpholinyl,
    (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or
    two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (ii) the cycloalkyl group which may be substituted is cyclobutyl, cyclopentyl, cyclohexyl, bicyclo[2.2.2]octyl, or adamantyl, (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-2 groups selected independently from the group consisting of a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein a heteroaryl group of (iv) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group (wherein the alkyl may be substituted with a hydroxyl group) which is formed from $R^{B7}$ and $R^{4c}$ being bound to each other at their terminus, together with a nitrogen atom to which they are bound, when $X^c$ is $NR^{4c}$, is piperazinyl, or pyrrolidinyl, or a pharmaceutically acceptable salt thereof.

As another preferable embodiment, the present invention comprises a compound of the above general formula [I]: wherein (A) $R^A$ is a group represented by the above formula (A-1): wherein $R^A$ is (1) a cycloalkyl group which may be substituted with an alkyl group, (2) a cycloalkenyl group which may be substituted with an alkyl group, (3) a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, (4) a naphthyl group which may be partially hydrogenated and may be substituted with an alkyl group, (5) a heteroaryl group which may be partially hydrogenated and may be substituted with 1-2 groups selected independently from the group consisting of a cyano group, and an alkyl group, wherein the heteroaryl moiety is pyridyl, indazolyl, thienyl, isoquinolyl, benzopyranyl, benzofuranyl, indolyl, or benzothiazolyl, (B) $R^B$ is a group of the above formula (B-4): wherein $X^a$ is N, $X^b$ is $CH_2$, and $X^c$ is NH, $R^{B6}$ is a hydrogen atom, $R^{B7}$ is (i) an alkyl group which may be substituted, (ii) a cycloalkyl group which may be substituted, (iii) an aliphatic heterocyclic group which may be substituted, or (iv) a heteroaryl group which may be partially hydrogenated and may be substituted, or, when $X^c$ represents $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound, wherein (i) a substituent of the alkyl group which may be substituted is 1-4 groups selected independently from the group consisting of a halogen atom; a hydroxyl group; a cycloalkyl group which may be 1-2 groups selected independently from the group consisting of a hydroxyl group and an alkylsulfonyl group; a phenyl group; a pyridyl group; an amino group which may be substituted with 1-2 groups selected independently from the group consisting of an alkyl group, an alkanoyl group, and an alkoxycarbonyl group; an alkylsulfonyl group; an alkoxy group; and an aliphatic heterocyclic group which may be substituted with 1-3 groups selected independently from the group consisting of a hydroxyl group, an oxo group, an alkyl group, an alkanoyl group, and an alkylsulfonyl group, wherein the aliphatic heterocyclic group is selected from tetrahydrothiophenyl, piperidinyl, piperazinyl, thiomorpholinyl, or morpholinyl, (ii) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (ii) the cycloalkyl group which may be substituted is cyclobutyl, cyclopentyl, cyclohexyl, bicyclo[2.2.2]octyl, or adamantyl, (iii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group, and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may partially hydrogenated is imidazolyl, imidazolinyl, oxazolyl, triazolyl, or pyridyl); an alkanoyl group which may be substituted with 1-2 groups selected independently from the group consisting of a halogen atom, and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (iii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iv) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein a heteroaryl group of (iv) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group (wherein the alkyl may be substituted with a hydroxyl group) which is formed from $R^{B7}$ and $R^{4c}$ being bound to each other at their terminus, together with a nitrogen atom to which they are bound, when $X^c$ is $NR^{4c}$, is piperazinyl, or pyrrolidinyl, or a pharmaceutically acceptable salt thereof.

As another preferable embodiment, the present invention comprises a compound of the above general formula [I]:
wherein (A) $R^A$ is (1) a 3- to 7-membered monocyclic cycloalkyl group which may be substituted with an alkyl group, (2) a 3- to 7-membered monocyclic cycloalkenyl group which may be substituted with an alkyl group, (3) a phenyl group which may be substituted with 1-3 groups selected independently from the group consisting of a halogen atom, an alkyl group, a haloalkyl group, an alkoxyalkyl group, an alkoxy group, and a methylenedioxy group which may be substituted with 1-2 halogen atoms, (4) a naphthyl group which may be substituted with an alkyl group, (5) a tetrahydronaphthyl group, (6) a heteroaryl group which may be substituted with a cyano group or an alkyl group (wherein the heteroaryl group is a pyridyl group, a thienyl group, an indazolyl group, an indolyl group, a benzothiazolyl group, or an isoquinolyl group), or (7) a dihydrobenzopyranyl group, (B) $R^B$ is a group of the above formula (B-4):
wherein (i) when $X^a$ is $CR^{3a}$,
$X^b$ is $CHR^{3b}$, and $X^c$ is O or $NR^{4c}$,
$X^b$ is O, and $X^c$ is $NR^{4c}$, or
$X^b$ is $NR^{4b}$, and $X^c$ is O, $NR^{4c}$, or $CHR^{3c}$, (ii) when $X^a$ is N,
$X^b$ is $CHR^{3b}$ or C(=O), and $X^c$ is $NR^{4c}$, or
$X^b$ is $NR^{4b}$, and $X^c$ is $CHR^{3c}$, wherein $R^{3a}$ is a hydrogen atom, a hydroxyl group, an alkyl group, or an amino group, each of $R^{3b}$ and $R^{3c}$ is a group selected independently from the group consisting of a hydrogen atom, a hydroxyl group, and an alkyl group, each of $R^{4b}$ and $R^{4c}$ is a group selected independently from the group consisting of a hydrogen atom, an alkyl group, and a cycloalkyl group, $R^{B6}$ is a hydrogen atom or an alkyl group, $R^{B7}$ is (i) an alkyl group which may be substituted, wherein a substituent of the alkyl group is an aliphatic heterocyclic group which may be substituted with 1-2 groups selected independently from the group consisting of an oxo group, an alkylsulfonyl group, a hydroxyl group, an alkyl group, and an alkanoyl group (wherein the aliphatic heterocyclic ring is morpholinyl, thiomorpholinyl, or piperidinyl), (ii) a cycloalkyl group which may be substituted (wherein the cycloalkyl group is a cyclopentyl group, a cyclohexyl group, a bicyclo[2.2.2]octyl group, or an adamantyl group), wherein a substituent of the cycloalkyl group is 1-2 groups selected independently from the group consisting of a hydroxyl group; an aliphatic heterocyclic group which may be substituted with 1-2 groups selected independently from the group consisting of a hydroxyl group and an oxo group (wherein the aliphatic heterocyclic group is selected from a thiomorpholinyl group, a piperidinyl group, a piperazinyl group, or a morpholinyl group); an amino group which may be substituted with 1-2 groups selected independently from the group consisting of an alkyl group and an alkanoyl group; an alkyl group which may be substituted with a hydroxyl group; an alkoxy group which may be substituted with a carbamoyl group which may be substituted with 1-2 alkyl groups; and an alkylsulfonyl group, (iii) an aliphatic heterocyclic group which may be substituted (wherein the aliphatic heterocyclic group is selected from an azetidinyl group, a tetrahydrofuranyl group, a pyrrolidinyl group, a tetrahydropyranyl group, a piperidinyl group, a tetrahydrothiopyranyl group, or 3-oxabicyclo [3.3.1]nonyl), wherein a substituent of the aliphatic heterocyclic group is 1-3 groups selected independently from the group consisting of a halogen atom; a hydroxyl group; an oxo group; an alkyl group which may be substituted with 1-3 groups selected independently from the group consisting of a hydroxyl group, a cycloalkyl group which may be substituted with a hydroxyl group, an alkoxy group, alkylsulfonyl group, an alkylsulfonylamino group, a carbamoyl group which may be substituted with 1-2 alkyl groups, morpholinylcarbonyl group, and a heteroaryl group which may be substituted with an alkyl group and may be partially hydrogenated (wherein the heteroaryl which may be partially hydrogenated is pyridyl, imidazolyl, imidazolinyl, oxazolyl, or triazolyl); an alkanoyl group which may be substituted with a hydroxyl group; a pyrimidinyl group; and a cycloalkylcarbonyl group which may be substituted with a hydroxyl group, or (iv) a pyrazolyl group which may be substituted with an alkyl group which may be substituted with a carbamoyl group which may be substituted with 1-2 alkyl groups, or a pharmaceutically acceptable salt thereof.

As another preferable embodiment, the present invention comprises a compound of the above general formula [I]:
wherein
(A) $R^A$ is
(1) a phenyl group which may be substituted with 1-3 groups selected independently from the group consisting of a halogen atom, an alkyl group, and a haloalkyl group,
(2) a pyridyl group which may be substituted with a cyano group, or
(3) a dihydrobenzopyranyl group,
(B) $R^B$ is a group of the above formula (B-4):
 wherein $X^a$ represents N,
 $X^b$ represents $CH_2$, and $X^c$ represents NH, or
 $X^b$ represents NH, and $X^c$ represents $CH_2$,
 $R^{B6}$ represents a hydrogen atom,
 $R^{B7}$ is
 (i) an alkyl group which may be substituted, wherein a substituent of the alkyl group is an aliphatic heterocyclic group which may be substituted with 1-2 groups selected independently from the group consisting of an oxo group, a hydroxyl group, an alkyl group, and an alkanoyl group (wherein the aliphatic heterocyclic ring is morpholinyl, thiomorpholinyl, or piperidinyl),
 (ii) a cyclohexyl group which may be substituted, wherein a substituent of the cyclohexyl group is 1-2 groups selected independently from the group consisting of a piperidinyl group which may be substituted with a hydroxyl group; an amino group which may be substituted with 1-2 groups selected independently from the group consisting of an alkyl group and an alkanoyl group; and an alkoxy group which may be substituted with a carbamoyl group which may be substituted with 1-2 alkyl groups,
 (iii) an aliphatic heterocyclic group which may be substituted (wherein the aliphatic heterocyclic group is selected from an azetidinyl group, a tetrahydrofuranyl group, a pyrrolidinyl group, a tetrahydropyranyl group, a piperidinyl group, a tetrahydrothiopyranyl group, or 3-oxabicyclo[3.3.1]nonyl), wherein a substituent of the aliphatic heterocyclic group is 1-3 groups selected independently from the group consisting of a hydroxyl group; an alkyl group which may be substituted with 1-3 groups selected independently from the group consisting of an amino group which may be substituted with an alkylsulfonyl group, a carbamoyl group which may be substituted with 1-2 alkyl groups, and an imidazolinyl group which may be substituted with an alkyl group; an alkanoyl group which may be substituted with a hydroxyl group; and a cycloalkylcarbonyl group which may be substituted with a hydroxyl group, or (iv) a pyrazolyl group which may be substituted with an alkyl group which may be substituted with a carbamoyl group which may be substituted with 1-2 alkyl groups, or a pharmaceutically acceptable salt thereof.

As another preferable embodiment, the present invention comprises a compound of the above general formula [I]:
wherein
$R^A$ is a phenyl group which may be substituted with an alkyl group or a haloalkyl group,
$R^B$ is a group of the above formula (B-4):
 wherein
 $X^a$ is $CR^{3a}$,
 $X^b$ is $CHR^{3b}$,
 $R^{3a}$ is a hydrogen atom,
 $R^{3b}$ is a hydrogen atom or a hydroxyl group,
 $X^c$ is $NR^{4c}$,
 $R^{4c}$ is a hydrogen atom or an alkyl group,
 $R^{B6}$ is a hydrogen atom,
 $R^{B7}$ is a cycloalkyl group which may be substituted with an alkyl group or an amino group which may be substituted with 1-2 alkyl groups, or a pharmaceutically acceptable salt thereof.

As another preferable embodiment, the present invention comprises a compound of the above general formula [I]:
wherein
$R^A$ is a phenyl group which may be substituted with a halogen atom,
$R^B$ is a group of the above formula (B-4):
 wherein
 $X^a$ is $CR^{3a}$,
 $X^b$ is $NR^{4b}$,
 $X^c$ is $NR^{4c}$,
 $R^{3a}$ is a hydrogen atom,
 $R^{4b}$ is a hydrogen atom or an alkyl group,
 $R^{4c}$ is a hydrogen atom or an alkyl group,
 $R^{B6}$ is a hydrogen atom,
 $R^{B7}$ is an alkyl group, or a pharmaceutically acceptable salt thereof.

The specific and non-limiting examples of the compounds which are included in the preferable embodiments of the present invention are those selected from the group consisting of:

3-[4-[(cis-3-hydroxytetrahydrofuran-4-yl)carbamoylmethyl]piperazin-1-yl]-5-(4-trifluoromethylphenyl)-1,2,4-triazine, 5-(4-fluorophenyl)-3-[4-[[trans-4-(N-methylcarbamoylmethyloxy)cyclohexyl]carbamoylmethyl]piperazin-1-yl]-1,2,4-triazine, 3-[4-[[(1-acetyl-4-hydroxypiperidin-4-yl)methyl]carbamoylmethyl]piperazin-1-yl]-5-(4-chlorophenyl)-1,2,4-triazine, 3-[4-[[(7-exo-9-endo)-9-hydroxy-3-oxabicyclo[3.3.1]nonan-7-yl]carbamoylmethyl]piperazin-1-yl]-5-(4-trifluoromethylphenyl)-1,2,4-triazine, 5-(4-fluorophenyl)-3-[4-[[1-[2-(methylsulfonylamino)ethyl]piperidin-4-yl]carbamoylmethyl]piperazin-1-yl]-1,2,4-triazine, 5-(2-cyano-5-pyridyl)-3-[4-[[1-[(1-hydroxycyclopropyl)carbonyl]piperidin-4-yl]carbamoylmethyl]piperazin-1-yl]-1,2,4-triazine, 5-(4-fluorophenyl)-3-[4-[[trans-4-(4-hydroxypiperidino)cyclohexyl]carbamoylmethyl]piperazin-1-yl]-1,2,4-triazine, 5-(4-fluorophenyl)-3-[4-[[1-((R)-2-hydroxybutanoyl)piperidin-4-yl]carbamoylmethyl]piperazin-1-yl]-1,2,4-triazine, 5-(4-fluorophenyl)-3-[4-[(3S)-1-[(1-hydroxycyclopropyl)carbonyl]pyrrolidin-3-yl]carbamoylmethyl]piperazin-1-yl]-1,2,4-triazine, 3-[4-[[cis-3-(dimethylamino)cyclohexyl]carbamoylmethyl]piperazin-1-yl]-5-(4-fluorophenyl)-1,2,4-triazine, 3-[4-[[1-[(4,5-dihydro-1H-imidazol-2-yl)methyl]piperidin-4-yl]carbamoylmethyl]piperazin-1-yl]-5-(4-fluorophenyl)-1,2,4-triazine, 3-[4-[[trans-4-(acetoamino)cyclohexyl]carbamoylmethyl]piperazin-1-yl]-5-(p-tolyl)-1,2,4-triazine, 3-[4-[[1-(N,N-dimethylcarbamoylmethyl)-1H-pyrazol-4-yl]carbamoylmethyl]piperazin-1-yl]-5-(4-fluorophenyl)-1,2,4-triazine, 5-(4-fluorophenyl)-3-[4-[1-[(1-hydroxycyclopropyl)carbonyl]azetidin-3-yl]carbamoylmethyl]piperazin-1-yl]-1,2,4-triazine, 3-[4-[[trans-4-(N-methylcarbamoylmethyloxy)cyclohexyl]carbamoylmethyl]piperazin-1-yl]-5-(4-trifluoromethylphenyl)-1,2,4-triazine, 3-[4-[[cis-3-(acetoamino)cyclohexyl]carbamoylmethyl]piperazin-1-yl]-5-(4-fluorophenyl)-1,2,4-triazine, 5-(4-chlorophenyl)-3-[(3S,4S)-4-[(cis-3-hydroxytetrahydropyran-4-yl)carbamoylmethyl]piperazin-1-yl]-1,2,4-triazine, 3-[4-[[1-(N,N-dimethylcarbamoylmethyl)-1H-pyrazol-4-yl]carbamoylmethyl]piperazin-1-yl]-5-(p-tolyl)-1,2,4-triazine, 5-(4-chlorophenyl)-3-[4-[[1-(N,N-dimethylcarbamoylmethyl)-1H-pyrazol-4-yl]carbamoylmethyl]piperazin-1-yl]-1,2,4-triazine, 5-(4-chlorophenyl)-3-[4-[(trans-3-hydroxytetrahydropyran-4-yl)carbamoylmethyl]piperazin-1-yl]-1,2,4-triazine, 3-[4-[[1-(N-methylcarbamoylmethyl)-1H-pyrazol-4-yl]carbamoylmethyl]piperazin-1-yl]-5-(p-tolyl)-1,2,4-triazine, 5-(4-fluorophenyl)-3-[4-[[1-(N-methylcarbamoylmethyl)-1H-pyrazol-4-yl]carbamoylmethyl]piperazin-1-yl]-1,2,4-triazine, 5-(4-chlorophenyl)-3-[4-[[1-(N-methylcarbamoylmethyl)-1H-pyrazol-4-yl]carbamoylmethyl]piperazin-1-yl]-1,2,4-triazine, 5-(4-chlorophenyl)-3-[4-[[(3-methylbutanoyl)amino]piperazin-1-yl]-1,2,4-triazine, 5-(4-fluorophenyl)-3-[4-[[((2R)-4-methylmorpholyn-2-yl)methyl]carbamoylmethyl]piperazin-1-yl]-1,2,4-triazine, 3-[4-[[1-(N-methylcarbamoylmethyl) piperidin-4-yl]carbamoylmethyl]piperazin-1-yl]-5-(p-tolyl)-1,2,4-triazine, 3-[4-[[2-(1,1-dioxothiomorpholino)ethyl]carbamoylmethyl]piperazin-1-yl]-5-(4-fluorophenyl)-1,2,4-triazine, 3-[4-[[trans-4-(dimethylamino)cyclohexyl]carbamoylmethyl]piperazin-1-yl]-5-(4-fluorophenyl)-1,2,4-triazine, 5-(4-fluorophenyl)-3-[4-[(piperazin-1-yl)carbamoylmethyl]piperazin-1-yl]-1,2,4-triazine, 5-(dihydrobenzopyran-5-yl)-3-[4-(isopropylcarbamoylmethyl) piperazin-1-yl]-1,2,4-triazine, 3-[4-(4-fluorophenyl) piperazin-1-yl]-5-(o-tolyl)-1,2,4-triazine, and 5-(2-cyano-5-pyridyl)-3-[4-(isopropylcarbamoylmethyl) piperazin-1-yl]-1,2,4-triazine, or a pharmaceutically acceptable salt thereof.

If a compound [I] of the present invention has chiral carbon atom(s) in the molecule, there can be multiple stereoisomers based on the chiral carbon atom(s) (i.e., diastereomers, or enantiomers). However, any one of the stereoisomers and any combination thereof are also included in the present invention.

A compound [I] of the present invention includes, for example, a radiolabeled compound (e.g., it is labeled with $^3H$, $^{13}C$, $^{14}C$, $^{15}N$, $^{18}F$, $^{32}P$, $^{35}S$, $^{125}I$, and the like) and a deuterium converter thereof.

A compound [I] of the present invention or a pharmaceutically acceptable salt thereof has an inhibitory effect against aldosterone synthetase, and therefore it is useful for preventing or treating various diseases and/or disease states evoked by an increased level of aldosterone and/or overproduction of aldosterone, or for improving prognosis of these diseases. These diseases includes, for example, primary aldosteronism (unilateral or bilateral adrenal adenomas, unilateral or bilateral adrenal hyperplasia, aldosterone-producing adrenal carcinoma, unilateral adrenal multiple nodules aldosteronism, glucocorticoid reactive aldosteronism, familial aldosteronism, or ectopic aldosterone-producing tumors, and the like), secondary aldosteronism (hypertension caused by an estrogen preparation, renal vascular hypertension, pregnancy hypertension, malignant hypertension, pheochromocytoma, congestive heart failure, pseudo-hypoaldosteronism, chronic liver disease associated with ascites (hepatic cirrhosis, and the like), inappropriate use of a medicament such as a laxative and a diuretic, or hyperaldosteronemia associated with nephrotic syndrome, Bartter's syndrome or Gitelman syndrome, and the like), hypertension (essential hypertension, secondary hypertension (renal vascular hypertension, renal parenchymal hypertension, primary aldosteronism, pheochromocytoma, sleep apnea syndrome, Cushing's syndrome, drug induced hypertension, aortostenosis, or hyperparathyroidism, and the like), treatment-resistant hypertension, mineralocorticoid-related hypertension, and the like), hart failure (congestive heart failure, left ventricular failure, right ventricular failure, systolic dysfunction, diastolic dysfunction, and the like), cardiomyopathy, cardiac hypertrophy (left ventricular hypertrophy, and the like), myocardial infarction, myocardial necrosis lesion, failure after myocardial ischemia, coronary artery disease, fibrosis or remodeling of myocardium or blood vessels (cardiovascular fibrosis and remodeling caused by hypertension and/or vascular endothelial function disorder, and the like), vascular restenosis, blood vessel wall thickening, arterial sclerosis, renal failure (chronic renal failure, and the like), acute renal disorder, chronic kidney disease, renal fibrosis, nephropathy (diabetic nephropathy, and the like), hypokalemia, obesity, metabolic syndrome, sleep apnea syndrome, retinopathy (diabetic retinopathy, and the like), hepatic disease, abnormal lipid metabolism, sympathetic hyperactivity, idiopathic and/or cyclic edema, headache, anxiety, depressive disorders, and the like In particular, a compound [I] of the present invention or a pharmaceutically acceptable salt thereof is useful for preventing or treating primary aldosteronism, secondary aldosteronism, hypertension, heart failure, arterial sclerosis, nephropathy, or retinopathy.

As described above, a compound [I] of the present invention or a pharmaceutically acceptable salt thereof has an excellent inhibitory activity against Cyp11B2, and as a result of studying the inhibitory activity against human Cyp1B2 according to an assay method described in Experimental example 1 below, each of the compounds of the compound [I] described in Examples of the present application has an $IC_{50}$ value of 100 nM or below. In addition, a compound [I] of the present invention includes a compound which exhibits high selectivity to CyP11B2.

For example, the $IC_{50}$ value (nM) of the compound described in Example 22 (that is, chemical name, 3-[4-[[trans-4-(dimethylamino)cyclohexyl]carbamoylmethyl] piperazin-1-yl]-5-(4-fluorophenyl)-1,2,4-triazine) against human Cyp1B2 is 500 times higher than those against human Cyp11B1 because of high selectivity to human Cyp11B2.

A compound [I] of the present invention can be applied for a medical use as both a free form and a pharmaceutically acceptable salt thereof. The pharmaceutically acceptable salt includes, for example, an inorganic salt such as hydrochloride, sulfate, phosphate or hydrobromide, an organic salt such as acetate, fumarate, oxalate, citrate, methanesulfonate, benzenesulfonate, tosylate salt or maleate.

A compound [I] of the present invention or a pharmaceutically acceptable salt thereof includes any of an inner salt and an adduct thereof, as well as a solvate or a hydrate thereof.

A compound [I] of the present invention or a pharmaceutically acceptable salt thereof can be orally or parenterally administered alone, or as a pharmaceutical composition comprising the compound and a pharmaceutically acceptable carrier. The pharmaceutically acceptable carrier may be a conventional carrier in the art, and includes, for example, a diluent, a binder (syrup, gum arabic, gelatin, sorbitol, tragacanth, polyvinylpyrrolidone, and the like), an excipient (lactose, sucrose, corn starch, potassium phosphate, sorbit, glycine, and the like), a lubricant (magnesium stearate, talc, polyethylene glycol, silica, and the like), a disintegrant (potato starch), and a wetting agent (sodium lauryl sulfate, and the like).

A dosage form for such a pharmaceutical composition is not limited to a particular one, and includes a conventional medicinal formulation such as, for example, a tablet, a granule, a capsule, a powder, an injection, an inhalant, and a suppository.

A dosage of a compound [I] of the present invention or a pharmaceutically acceptable salt thereof varies depending on a mode of administration, age, body weight, condition of a patient, and the like. In the case of parenteral administration, the dosage is generally 0.001-10 mg/kg/day, and preferably 0.01-10 mg/kg/day. In the case of oral administration, the dosage is generally 0.01-100 mg/kg/day, and preferably 0.1-10 mg/kg/day.

A compound [I] of the present invention or a pharmaceutically acceptable salt thereof can be used alone, or in combination with one or more other medicaments depending on, for example, a disease to be treated. Such a medicament includes, for example, one or two or more medicaments selected from the group consisting of (1) an antihypertensive drug such as an angiotensin converting enzyme inhibitor, an angiotensin II receptor antagonist, a calcium antagonist, a β-blocker, an α/β-blockers; (2) a diuretic such as a thiazide diuretic and a loop diuretic; (3) a therapeutic agent for heart failure such as nitroglycerin and a digitalis preparation; (4) an anti-arrhythmic agent such as Na channel blocker; (5) an antilipemic agent such as an HMG-CoA reductase inhibitor; (6) an antithrombogenic agent such as a blood coagulation inhibitor and a thrombolytic agent; (7) a therapeutic agent for diabetes/diabetes complications such as insulin, ac α-glucosidase inhibitor, an insulin resistance improving agent, an insulin secretion enhancer, and an aldose reductase inhibitor; (8) an anti-obesity agent; (9) a chemotherapeutic agent; and (10) an Immunomodulatory agent such as an immunosuppressant and an immunoenhancer.

A compound of the present invention or a pharmaceutically acceptable salt thereof can be prepared, for example, as follows.

Synthetic Process A1

[Chemical formula 16]

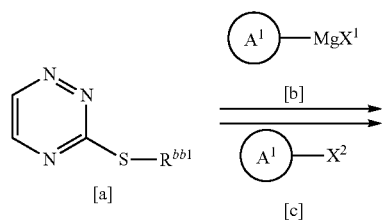

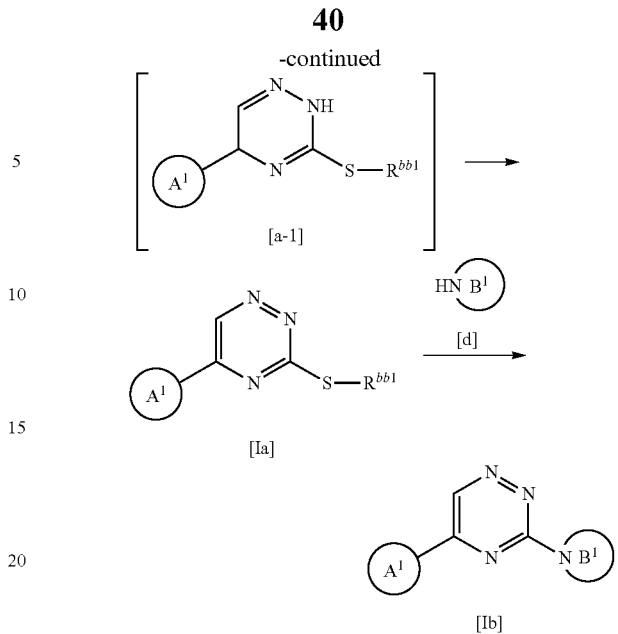

[wherein $R^{bb1}$ represents an alkyl group, $X^1$ represents a halogen atom, $X^2$ represents a hydrogen atom or a halogen atom, ring $B^1$ represents an isoindolinyl group, an aliphatic heterocyclic group of the above formula (B-3), a group of the above formula (B-4), or a spiro cyclic group of the above formula (B-5), and ring $A^1$ is the same as defined above.]

A compound of the general formula [Ib] which is one of the desired compounds [I] of the present invention can be prepared, for example, as follows.

Firstly, a compound of the general formula [Ia] is prepared by a nucleophilic addition reaction of a compound of the general formula [a] with a compound of the general formula [b], or with a compound of the general formula [c] in the presence of an organic lithium compound, and then, the resulting compound of the general formula [a-1] is oxidized. The resulting compound [Ia] is reacted with a compound of the general formula [d] or a salt thereof, and optionally a resulting product is converted to a pharmaceutically acceptable salt thereof to give the desired compound [Ib] or a pharmaceutically acceptable salt thereof.

The nucleophilic addition reaction between the compounds [a] and [b] can be carried out in an appropriate solvent according to a conventional method. The solvent, which does not interfere with the reaction, includes, for example, ethers such as tetrahydrofuran, aromatic hydrocarbons such as toluene, aliphatic hydrocarbons such as hexane, or a mixture thereof. An amount used of the compound [b] may be 1.0-1.5 equivalents, preferably 1.2 equivalents to the compound [a]. This reaction can be carried out at −78° C. to room temperature, preferably at 0° C. to room temperature.

The nucleophilic addition reaction between the compounds [a] and [c] can be carried out in an appropriate solvent in the presence of an organic lithium compound according to a conventional method. The solvent, which does not interfere with the reaction, includes, for example, ethers such as tetrahydrofuran, aromatic hydrocarbons such as toluene, aliphatic hydrocarbons such as hexane, or a mixture thereof. The organic lithium compound includes n-butyllithium, and s-butyllithium. An amount used of the compound [c] may be 1.0-2.0 equivalents, preferably 1.3-1.5 equivalents to the compound [a]. An amount used of the organic lithium compound may be 1.0-2.0 equivalents, preferably 1.2-1.4 equivalents to the compound [a]. This reaction can be carried out at −78° C. to room temperature, preferably at −78 to −40° C.

The oxidation reaction of the compounds [a-1] can be carried out in an appropriate solvent in the presence of an oxidizing agent according to a conventional method. The solvent, which does not interfere with the reaction, includes, for example, aromatic hydrocarbons such as toluene, ethers such as dioxane, halogenated aliphatic hydrocarbons such as chloroform, amides such as N-methylpyrrolidone, or a mixture thereof. The oxidizing agent includes, for example, 2,3-dichloro-5,6-dicyano-p-benzoquinone (DDQ), and manganese dioxide. An amount used of the oxidizing agent may be 1.0-1.5 equivalents, preferably 1.2 equivalents to the compound [a-1]. This reaction can be carried out at 0° C. to room temperature, preferably at room temperature.

A reaction of the compound [Ia] with the compound [d] or a salt thereof can be carried out, for example, in an appropriate solvent in the presence or absence of a base. A salt with an inorganic acid such as, for example, hydrochloride and sulfate can be used as a salt of the compound [d]. The solvent is required not to interfere with the reaction, and includes, for example, amides such as N-methylpyrrolidone, ethers such as tetrahydrofuran, alcohols such as methanol, dimethylsulfoxide, water, or a mixture thereof. It is preferable that the reaction is carried out in the presence of a base in order to accelerate the reaction. Such a base includes, for example, diisopropylethylamine, diazabicycloundecene, and sodium carbonate, and is preferably diisopropylethylamine. An amount used of the compound [d] or a salt thereof may be 1.0-10 equivalents, preferably 2.0-7.0 equivalents to the compound [Ia]. This reaction can be carried out at room temperature-250° C., preferably at 150-240° C.

Firstly, the compound [Ia] is oxidized to give a compound of the general formula [e]. This compound is reacted with the compound [d] or a salt thereof to give a compound, and optionally, the resulting compound is converted to a pharmaceutically acceptable salt thereof to give the desired compound [Ib] or a pharmaceutically acceptable salt thereof.

The oxidation reaction of the compound [Ia] can be carried out in an appropriate solvent in the presence of an oxidizing agent according to a conventional method. The solvent, which does not interfere with the reaction, includes, for example, halogenated aliphatic hydrocarbons such as dichloromethane. The oxidizing agent includes, for example, m-chloroperbenzoic acid (mCPBA), potassium permanganate, and oxone (Aldrich). An amount used of the oxidizing agent may be 2.0-3.0 equivalents, preferably 2.0 equivalents to the compound [Ia]. This reaction can be carried out at 0° C. to room temperature, preferably at room temperature.

The reaction of the compound [e] and the compound [d] or a salt thereof can be carried out, for example, in an appropriate solvent. The similar salt of the compound [d] as described in the above synthetic process A1 can be used as a salt of the compound [d]. The solvent, which does not interfere with the reaction, includes, for example, ethers such as tetrahydrofuran, halogenated aliphatic hydrocarbons such as chloroform, aromatic hydrocarbons such as toluene, amides such as dimethylformamide, acetonitrile, or a mixture thereof. It is preferable that the reaction is carried out in the presence of a base in order to accelerate the reaction. The base includes, for example, diisopropylethylamine, diazabicycloundecene, and sodium carbonate, and is preferably diisopropylethylamine. An amount used of the compound [d] or a salt thereof may be 1.0-10 equivalents, preferably 2.0-5.0 equivalents to the compound [e]. This reaction can be carried out at 0-100° C., preferably at room temperature.

Synthetic Process A2

Synthetic Process A3

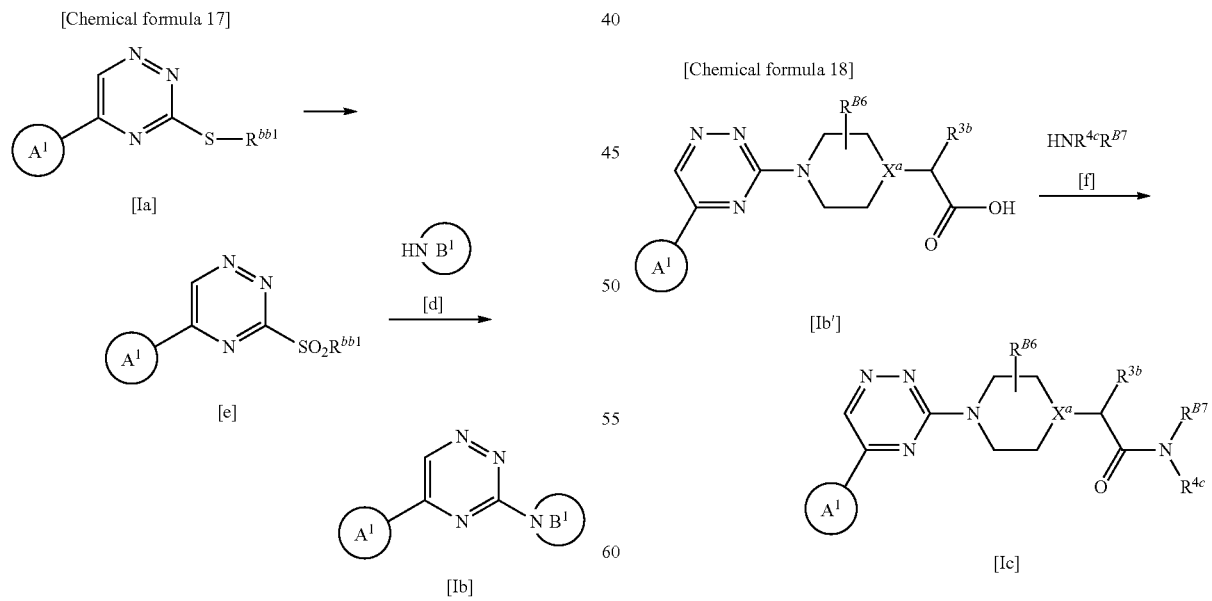

[Chemical formula 17]

[Chemical formula 18]

[wherein the symbols are the same as defined above.]

A conversion reaction from the compound [Ia] to the compound [Ib], can also be carried out, for example, as follows.

wherein the symbols are the same as defined above.

A desired compound [Ic] can be prepared by a condensation reaction between a compound of the general formula [Ib'] and a compound of the general formula [f] or a salt thereof.

The condensation reaction between a compound of the general formula [Ib'] and a compound of the general formula [f] or a salt thereof can be carried out, for example, in an appropriate solvent in the presence of a condensing agent and a base according to a conventional method. The similar salt of the compound [d] as described in the above synthetic process A1 can be used as a salt of the compound [f]. The solvent, which does not interfere with the reaction, includes, for example, amides such as dimethylformamide, ethers such as tetrahydrofuran, halogenated aliphatic hydrocarbons such as chloroform, and aromatic hydrocarbons such as toluene, acetonitrile, or a mixture thereof. The condensing agent includes, for example, o-(7-azabenzotriazol-1-yl)-N,N,N',N'-tetramethyluroniumhexafluorophosphate (HATU), and 1-ethyl-3-(3-dimethylaminopropyl)carbodiimide hydrochloride. The base includes, for example, amines such as diisopropylethylamine. An amount used of the condensing agent may be 1.0-5.0 equivalents, preferably 1.2-3.0 equivalents to the compound [Ib']. An amount used of the base may be 0-10 equivalents, preferably 2.0-6.0 equivalents to the compound [Ib']. This reaction can be carried out at 0-100° C., preferably at room temperature.

Synthetic Process B

[Chemical formula 19]

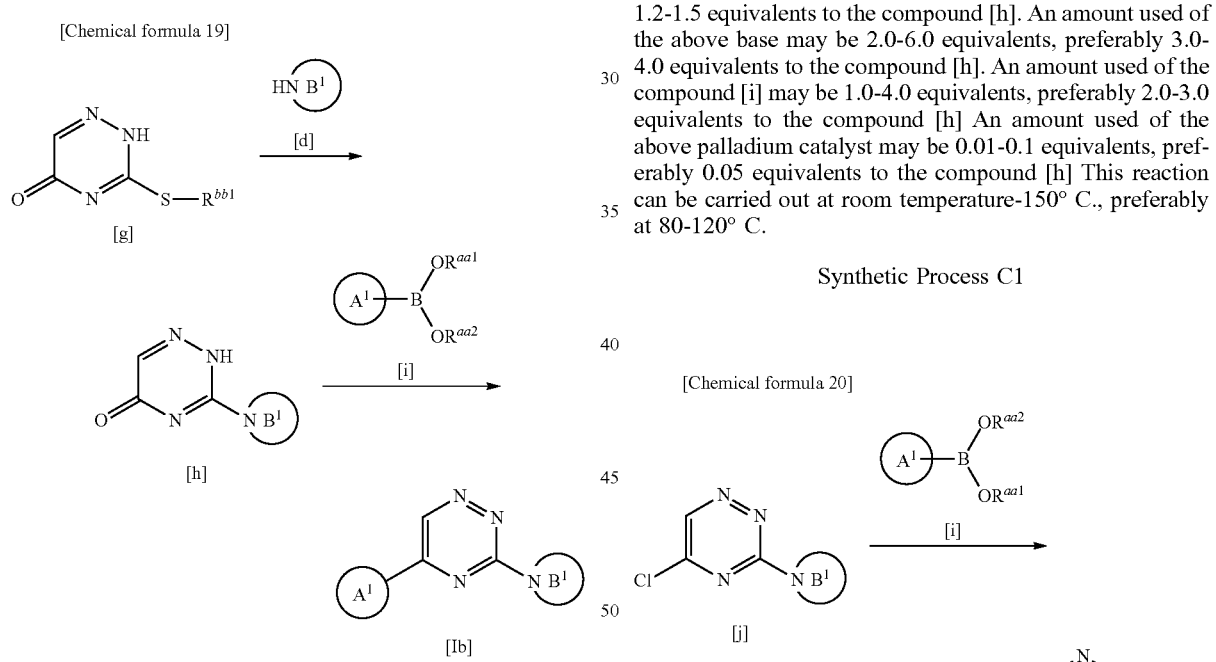

wherein $R^{aa1}$ and $R^{aa2}$ are the same or different and each represents a hydrogen atom or an alkyl group, or both are bound to each other at the terminus thereof to form a straight or branched chain alkylene group; and the other symbols are the same as defined above.

A desired compound [Ib] can also be prepared, for example, as follows.

Firstly, a compound of the general formula [g] is reacted with the compound [d] or a salt thereof to give a compound of the general formula [h]. The desired compound [Ib] can be prepared by subjecting this compound [h] to a coupling reaction with a compound of the general formula [i].

The reaction of the compound [g] and the compound [d] or a salt thereof can be carried out by the similar manner as that of the compound [Ia] and the compound [d] or a salt thereof. The similar salt of the compound [d] as described in the above synthetic process A1 can be used as a salt of the compound [d].

The coupling reaction between the compound [h] and the compound [i] can be carried out according to a conventional method in an appropriate solvent in the presence of a base, a phosphonium type condensing agent, a palladium catalyst, and water. The solvent, which does not interfere with the reaction, includes, for example, ethers such as dioxane, amides such as dimethylformamide, aromatic hydrocarbons such as toluene, or a mixture thereof.

The phosphonium type condensing agent includes, for example, bromotris(pyrrolidino)phosphonium hexafluorophosphate (PyBROP), and benzotriazol-1-yloxy-trisdimethylaminophosphonium (BOP). The base includes, for example, amines such as triethylamine, alkaline metal carbonates such as sodium carbonate, and potassium phosphate. The palladium catalyst includes, for example, bis(triphenylphosphine)palladium chloride, tetrakis(triphenylphosphine)dipalladium, palladium acetate, and 1,1'-bis(diphenylphosphino)ferrocenepalladium dichloride. The ligand includes, for example, tri-t-butylphosphine, triphenylphosphine, and 4,5-bis(diphenylphosphino)-9,9-dimethylxanthene(xantphos). An amount used of the above phosphonium type condensing agent may be 1.0-2.0 equivalents, preferably 1.2-1.5 equivalents to the compound [h]. An amount used of the above base may be 2.0-6.0 equivalents, preferably 3.0-4.0 equivalents to the compound [h]. An amount used of the compound [i] may be 1.0-4.0 equivalents, preferably 2.0-3.0 equivalents to the compound [h] An amount used of the above palladium catalyst may be 0.01-0.1 equivalents, preferably 0.05 equivalents to the compound [h] This reaction can be carried out at room temperature-150° C., preferably at 80-120° C.

Synthetic Process C1

[Chemical formula 20]

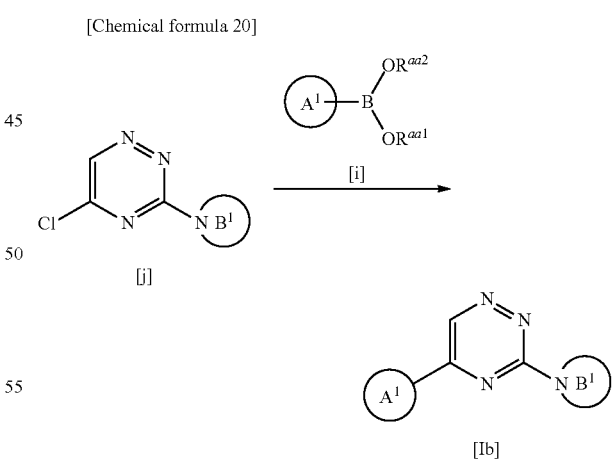

wherein the symbols are the same as defined above.

A desired compound [Ib] can also be prepared, for example, by a coupling reaction between a compound of the general formula [j] and the compound [i].

The coupling reaction between the compound [j] and the compound [i] can be carried out in an appropriate solvent in the presence of a palladium catalyst and a base in the presence or absence of a ligand according to a conventional method. The solvent, which does not interfere with the reaction, includes, for example, ethers such as tetrahydrofuran, aromatic hydrocarbons such as toluene, amides such as dimethylformamide, water, or a mixture thereof. The palladium catalyst includes, for example, tris(dibenzylideneacetone)dipalladium and bis(triphenylphosphine)palladium chloride. The base includes, for example, alkali metal carbonates such as cesium carbonate and potassium phosphate. The ligand includes, for example, tri(tert-butyl)phosphine, and tertiary phosphine such as triphenylphosphine. An amount used of the compound [i] may be 1.0-3.0 equivalents, preferably 1.1-1.5 equivalents to the compound [j]. An amount used of the palladium catalyst may be 0.01-0.1 equivalents, preferably 0.05 equivalents to the compound [j]. An amount used of the base may be 2.0-6.0 equivalents, preferably 3.0-4.0 equivalents to the compound [j]. An amount used of the ligand may be 0.02-0.2 equivalents, preferably 0.1 equivalents to the compound [j]. This reaction can be carried out at room temperature-200° C., preferably at 80-150° C.

Synthetic Process C2

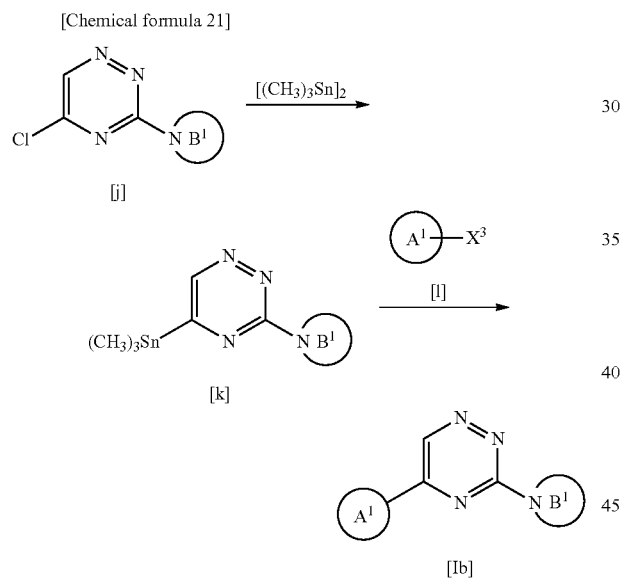

[Chemical formula 21]

wherein $X^3$ represents a halogen atom (e.g., a bromine atom), and the other symbols are the same as defined above.

A desired compound [Ib] can also be prepared, for example, as follows.

Firstly, the compound [j] is converted to a tin compound of the general formula [k]. Then, the desired compound [Ib] can be prepared by subjecting the compound [k] to a coupling reaction with a compound of the general formula [l].

The reaction for obtaining the compound [k] from the compound [j] can be carried out by reacting the compound [j] with bis(trimethyltin) in an appropriate solvent in the presence of a palladium catalyst according to a conventional method. The solvent, which does not interfere with the reaction, includes, for example, ethers such as dioxane, aromatic hydrocarbons such as toluene, amides such as dimethylformamide, or a mixture thereof. The palladium catalyst includes, for example, tetrakis(triphenylphosphine) dipalladium, and bis(triphenylphosphine)palladium chloride. An amount used of bis(trimethyltin) may be 1.0-3.0 equivalents, preferably 1.5-2.0 equivalents to the compound [j]. An amount used of a palladium catalyst may be 0.01-0.1 equivalents, preferably 0.03 equivalents to the compound [j]. This reaction can be carried out at room temperature-150° C., preferably at 80-120° C.

The coupling reaction between the compound [k] and the compound [l] can be carried out in an appropriate solvent in the presence of a palladium catalyst according to a conventional method. The solvent, which does not interfere with the reaction, includes, for example, ethers such as dioxane, aromatic hydrocarbons such as toluene, amides such as dimethylformamide, or a mixture thereof. The palladium catalyst includes, for example, tetrakis(triphenylphosphine) dipalladium, and bis(triphenylphosphine)palladium chloride. An amount used of the compound [l] may be 1.0-1.5 equivalents, preferably 1.0-1.2 equivalents to the compound [k]. An amount used of a palladium catalyst may be 0.01-0.1 equivalents, preferably 0.1 equivalents to the compound [k]. This reaction can be carried out at room temperature-150° C., preferably at 80-120° C.

Synthetic Process C3

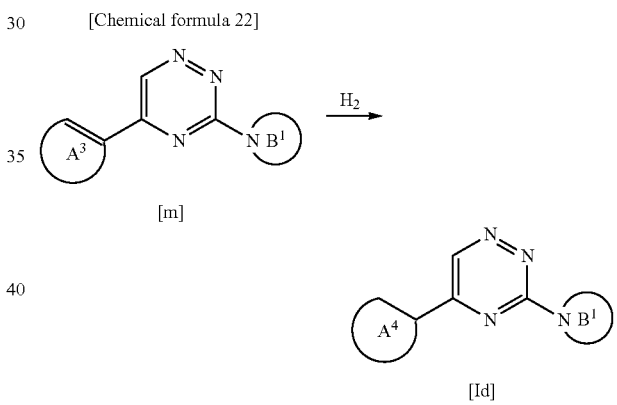

[Chemical formula 22]

wherein ring $A^3$ represents cycloalkenyl group which may be substituted, ring $A^4$ represents a cycloalkyl group which may be substituted, and the symbols are the same as defined above.

A desired compound [Id] can be prepared by subjecting a compound of the general formula [m] to catalytic reduction.

The catalytic reduction reaction of the compound [m] can be carried out in an appropriate solvent in the presence of a base and a catalyst under a hydrogen atmosphere according to a conventional method. The solvent, which does not interfere with the reaction, includes, for example, alcohols such as methanol, esters such as ethyl acetate, ethers such as tetrahydrofuran, or a mixture thereof. The catalyst includes, for example, a palladium/carbon catalyst. The base includes, for example, amines such as triethylamine. An amount used of the catalyst may be 0.3-1.0, preferably 0.3 in a weight ratio to the compound [m]. An amount used of the base may be 3-10, preferably 5 in a volume/weight ratio to the compound [m]. This reaction can be carried out at 0° C. to room temperature, preferably at room temperature.

Synthetic Process C4

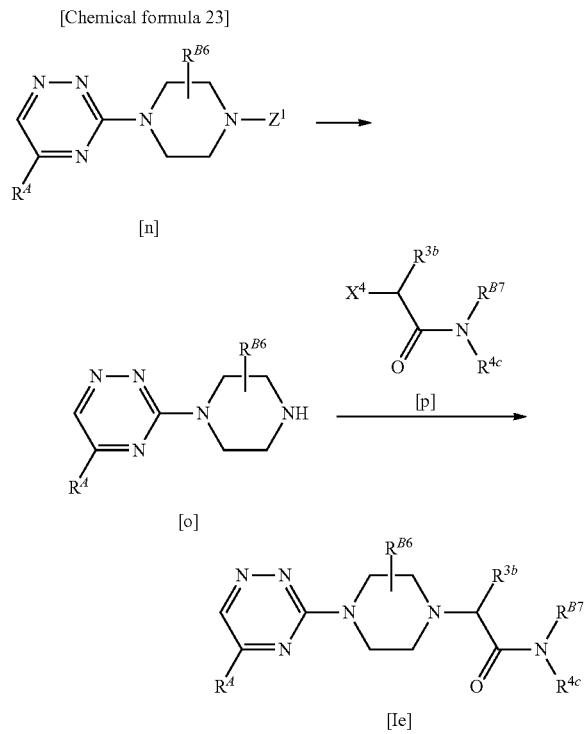

wherein $Z^1$ represents a protecting group of an amino group (e.g., an alkoxycarbonyl group such as tert-butoxycarbonyl group), $X^4$ represents a halogen atom (e.g., a chlorine atom, and a bromine atom), and the other symbols are the same as defined above.

A desired compound [Ie] can be prepared as follows.

Firstly, a compound of the general formula [n] is deprotected to give a compound of the general formula [o]. The desired compound [Ie] can be prepared by subjecting the compound [o] to a substitution reaction with a compound of the general formula [p].

A deprotection reaction of the compound [n] for obtaining the compound [o] can be carried out by removing a protecting group using a conventional method depending on a type of said protecting group $Z^1$. For example, when $Z^1$ is a tert-butoxycarbonyl group, said protecting group can be removed by treating the compound [n] with an acid in an appropriate solvent according to a conventional method. The solvent, which does not interfere with the reaction, includes, for example, esters such as ethyl acetate, halogenated aliphatic hydrocarbons such as chloroform, alcohols such as methanol, or a mixture thereof. The acid includes, for example, hydrochloric acid, and trifluoroacetic acid.

The substitution reaction of the compound [o] and the compound [p] can be carried out in an appropriate solvent in the presence of a base according to a conventional method. The solvent, which does not interfere with the reaction, includes, for example, nitriles such as acetonitrile, halogenated aliphatic hydrocarbons such as chloroform, amides such as dimethylformamide, or a mixture thereof. The base includes, for example, alkali metal carbonates such as sodium carbonate, organic amines such as triethylamine. An amount used of the compound [p] may be 1.0-3.0 equivalents, preferably 2.0 equivalents to the compound [o]. An amount used of the base may be 1.0-3.0 equivalents, preferably 2.0 equivalents to the compound [o]. This reaction can be carried out at room temperature-100° C., preferably at 50-60° C.

Synthetic Process C5

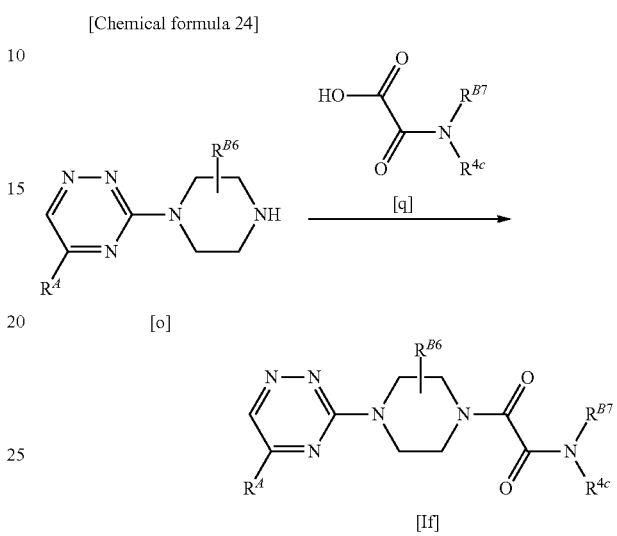

wherein the symbols are the same as defined above.

A desired compound [If] can be prepared by a condensation reaction between the compound [o] and the compound [q].

The condensation can be carried out in an appropriate solvent in the presence of a condensing agent and a base according to a conventional method. The solvent, the condensing agent, the base, the reaction temperature, and the like can be used under the similar conditions as Synthetic process A3.

Synthetic Process D

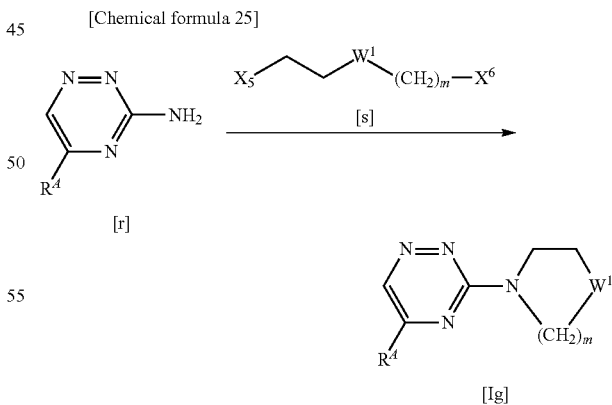

wherein $W^1$ represents an oxygen atom or a sulfur atom, each of $X^5$ and $X^6$ represents a leaving group (e.g., p-toluenesulfonyloxy group), m represents an integer of 2 or 3, and the other symbols are the same as defined above.

A desired compound [Ig] can be prepared by reacting a compound of the general formula [r] with a compound of the general formula [s].

The reaction of the compound [r] and the compound [s] can be carried out, for example, in an appropriate solvent in the presence of a base. The solvent, which does not interfere with the reaction, includes, for example, amides such as dimethylformamide, ethers such as tetrahydrofuran, or a mixture thereof. The base includes, for example, alkali metal hydrides such as sodium hydride. An amount used of the compound [s] may be 1.0-1.2 equivalents, preferably 1.0 equivalent to the compound [r]. An amount used of the base may be 2.0-3.0 equivalents, preferably 2.0-2.5 equivalents to the compound [r]. This reaction can be carried out at room temperature-100° C., preferably at 80-100° C.

Synthetic Process E

[Chemical formula 26]

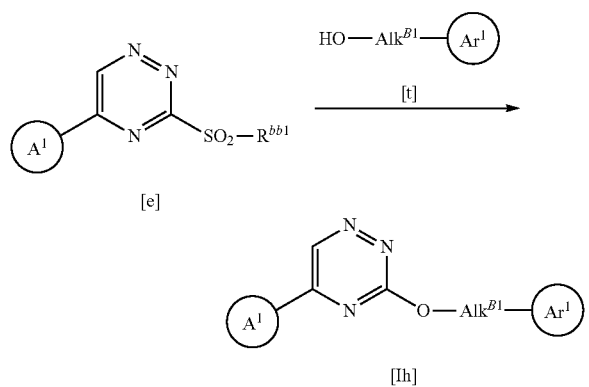

wherein $Alk^{B1}$ represents a methylene group, and the other symbols are the same as defined above.

A desired compound [Ih] can be prepared by reacting the compound [e] with a compound of the general formula [t].

The reaction of the compound [e] and the compound [t] can be carried out, for example, in an appropriate solvent in the presence of a base. The solvent, which does not interfere with the reaction, includes, for example, ethers such as tetrahydrofuran, amides such as dimethylformamide, or a mixture thereof. The base includes, for example, alkali metal hydrides such as sodium hydride, and n-butyllithium. An amount used of the compound [t] may be 1.0-3.0 equivalents, preferably 1.1-2.0 equivalents to the compound [e]. An amount used of the base may be 1.0-2.0 equivalents, preferably 1.1-1.5 equivalents to the compound [e]. This reaction can be carried out at 0° C. to room temperature, preferably at room temperature.

Synthetic Process F1

[Chemical formula 27]

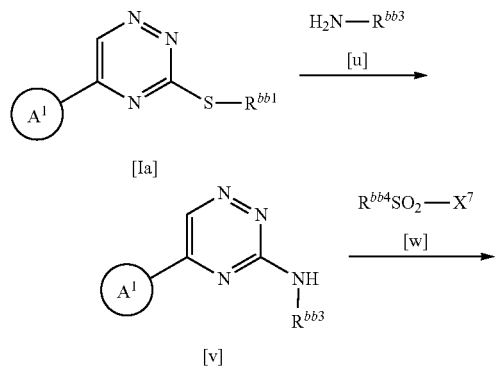

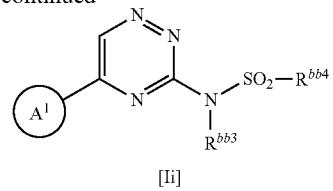

wherein $R^{bb3}$ represents an alkyl group which may be substituted, $R^{bb4}$ represents an alkyl group, $X^7$ represents a reactive residue (e.g., a halogen atom such as a chlorine atom), and the other symbols are the same as defined above.

A desired compound [Ii] can be prepared as follows.

Firstly, the compound [Ia] is reacted with a compound of the general formula [u] to give a compound of the general formula [v]. The desired compound [Ii] can be prepared by subjecting the compound [v] to a sulfonation reaction with a compound of the general formula [w].

The reaction of the compound [Ia] and the compound [u] or a salt thereof can be carried out, for example, in an appropriate solvent in the presence or absence of a base. A salt with an inorganic acid such as hydrochloride and hydrosulfate can be used as a salt of the compound [u]. The solvent, which does not interfere with the reaction, includes, for example, amides such as N-methylpyrrolidone, ethers such as tetrahydrofuran, alcohols such as methanol, dimethylsulfoxide, water, or a mixture thereof. It is preferable that the reaction is carried out in the presence of a base in order to accelerate the reaction. Such a base includes diisopropylethylamine, diazabicycloundecene, and sodium carbonate, and is preferably diisopropylethylamine. An amount used of the compound [u] or a salt thereof may be 1.0-10 equivalents, preferably 2.0-7.0 equivalents to the compound [Ia]. This reaction can be carried out at room temperature-250° C., preferably at 150-240° C.

The reaction of the compound [v] and the compound [w] can be carried out, for example, in an appropriate solvent in the presence of a base. The solvent, which does not interfere with the reaction, includes, for example, ethers such as tetrahydrofuran, amides such as dimethylformamide, or a mixture thereof. The base includes, for example, alkali metal hydrides such as sodium hydride, n-butyllithium, and lithiumdiisopropylamide. An amount used of the compound [w] may be 1.0-3.0 equivalents, preferably 2.0 equivalents to the compound [v]. An amount used of the base may be 1.0-2.0 equivalents, preferably 1.5 equivalents to the compound [v]. This reaction can be carried out at 0° C. to room temperature, preferably at room temperature.

Synthetic Process F2

[Chemical formula 28]

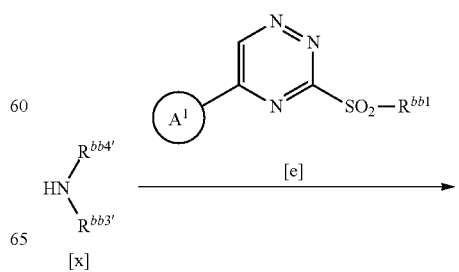

-continued

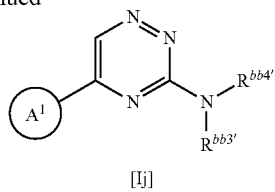

[Ij]

wherein $R^{bb3'}$ represents an alkylsulfonyl group which may be substituted, and $R^{bb4'}$ represents an alkyl group which may be substituted, or $R^{bb3'}$ represents an alkyl group substituted with alkylsulfonyl group, and $R^{bb4'}$ represents a hydrogen atom or an alkyl group, and the other symbols are the same as defined above.

A desired compound [Ij] can be prepared by reacting the compound [e] with a compound of the general formula [x].

The reaction of the compound [e] and the compound [x] can be carried out, for example, in an appropriate solvent in the presence of a base. The conversion reaction can be carried out by the similar manner as that of from the compound [v] to the desired compound [Ii].

Synthetic Process G1

[Chemical formula 29]

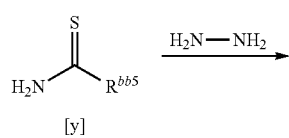

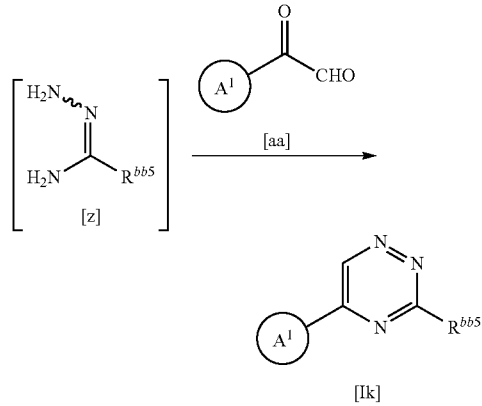

[Ik]

wherein $R^{bb5}$ is
(1) a monocyclic cycloalkyl group,
(2) a group of the following formula:

[Chemical formula 30]

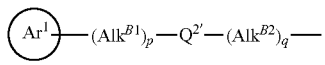

wherein ring $Ar^1$ represents an aryl group which may be substituted, $Alk^{B1}$ and $Alk^{B2}$ are the same or different and each represents methylene group, $Q^{2'}$ represents an oxygen atom or a single bond, each of p and q represents independently 0 or 1, and p+q is 1 or 2 or (3) a group of the following formula:

[Chemical formula 31]

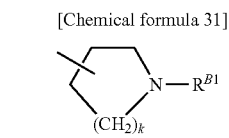

and the other symbols are the same as defined above.

A desired compound [Ik] can be prepared as follows.

Firstly, a compound of the general formula [y] is reacted with hydrazine or a hydrate thereof to give a compound of the general formula [z]. Then, this compound is reacted with a compound of the general formula [aa] to give the desired compound [Ik].

The reaction of the compound [y] and hydrazine or a hydrate thereof can be carried out in an appropriate solvent according to a conventional method. The solvent, which does not interfere with the reaction, includes, for example, alcohols such as methanol and ethanol, ethers such as tetrahydrofuran, or a mixture thereof. An amount used of the hydrazine may be 1.0-1.1 equivalents, preferably 1.0 equivalent to the compound [y]. This reaction can be carried out at 0° C. to room temperature, preferably at room temperature.

The reaction of the compound [z] and the compound [aa] can be carried out, for example, in an appropriate solvent. The solvent, which does not interfere with the reaction, includes, for example, alcohols such as ethanol, ethers such as tetrahydrofuran, amides such as dimethylformamide, or a mixture thereof. An amount used of the compound [aa] may be 1.0-1.1 equivalents, preferably 1.0 equivalent to the compound [z]. This reaction can be carried out at 0-100° C., preferably at 60° C.

Synthetic Process G2

[Chemical formula 32]

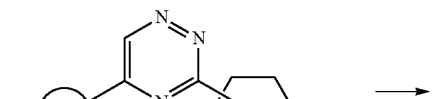

[ab]

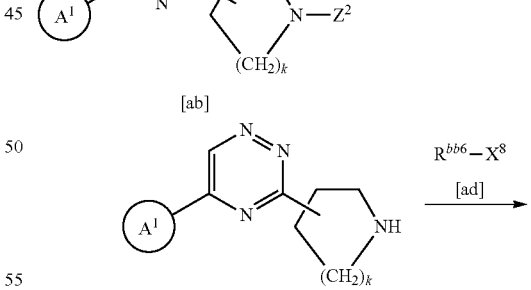

[ac]

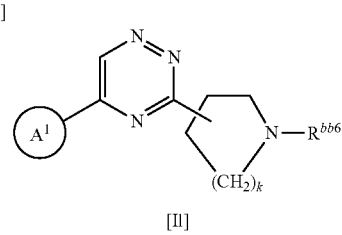

[Il]

wherein $R^{bb6}$ represents a heteroaryl group, $Z^2$ represents a protecting group of an amino group (e.g., an alkoxycarbonyl group such as a tert-butoxycarbonyl group), $X^8$ represents a halogen atom, and the other symbols are the same as defined above.

A desired compound [II] can be prepared as follows.

Firstly, a compound of the general formula [ab] is deprotected to give a compound of the general formula [ac]. Then, the desired compound [II] can be obtained by subjecting the resulting compound [ac] to a coupling reaction with a compound of the general formula [ad].

The deprotection of the compound [ab] can be carried out by the similar manner as that of the compound [n]

The coupling reaction between the compound [ac] and the compound [ad] can be carried out in an appropriate solvent in the presence of a palladium catalyst and a base in the presence or absence of a ligand according to a conventional method. The solvent, which does not interfere with the reaction, includes, for example, aromatic hydrocarbons such as toluene, alcohols such as t-butanol, ethers such as tetrahydrofuran, amides such as dimethylformamide, or a mixture thereof. The palladium catalyst includes, for example, tris(dibenzylideneacetone)dipalladium and palladium acetate. The base includes, for example, alkali metal alkoxydes such as tert-butoxysodium, cesium carbonate, and potassium phosphate. The ligand includes, for example, 4,5-bis(diphenylphosphino)-9,9-dimethylxanthene(xantphos) and 2,2'-bis(diphenylphosphino)-1,1'-binaphthyl. An amount used of the compound [ac] may be 1.0-3.0 equivalents, preferably 1.4 equivalents to the compound [ab]. An amount used of the palladium catalyst may be 0.01-0.05 equivalents, preferably 0.04 equivalents to the compound [ab]. An amount used of the base may be 1.5-3.0 equivalents, preferably 1.5 equivalents to the compound [ab]. An amount used of the ligand may be 0.03-0.3 equivalents, preferably 0.12 equivalents to the compound [ab]. This reaction can be carried out at room temperature-150° C., preferably at 80-120° C.

A starting compound for preparing a compound of the present invention can be prepared by a known method or the following methods.

Method for Preparation of Starting Compound (a)

[Chemical formula 33]

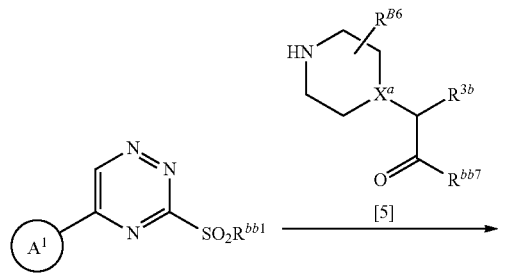

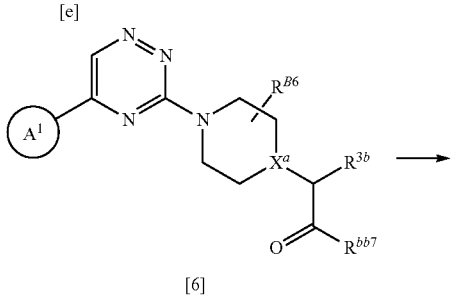

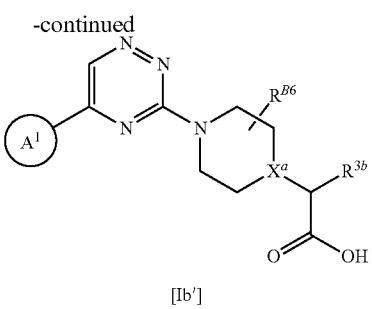

wherein $R^{bb7}$ represents alkoxy group, and the other symbols are the same as defined above.

The compound [Ib'] used in the above synthetic process A3 can be prepared, for example, as follows.

Firstly, the compound [6] is obtained by subjecting the compound [e] to a substitution reaction with the compound [5]. Then, the compound [Ib'] can be obtained by hydrolysis of this compound.

The substitution reaction of the compound [e] and the compound [5] can be carried out in an appropriate solvent according to a conventional method. The solvent, which does not interfere with the reaction, includes, for example, amides such as dimethylformamide, ethers such as tetrahydrofuran, halogenated aliphatic hydrocarbons such as chloroform, aromatic hydrocarbons such as toluene, acetonitrile, or a mixture thereof. This reaction can be carried out at 0° C. to room temperature, preferably at room temperature. An amount used of the compound [5] may be to the compound [e] 2.0-4.0 equivalents, preferably 2.5 equivalents.

The hydrolysis of the compound [6] for obtaining the compound [Ib'] can be carried out in an appropriate solvent in the presence of a base and water according to a conventional method. The solvent, which does not interfere with the reaction, includes, for example, alcohols such as ethanol, and ethers such as tetrahydrofuran. The base includes, for example, alkali metal hydroxides such as sodium hydroxide. This reaction can be carried out at 0° C. to room temperature, preferably at room temperature. An amount used of the base may be 1.0-3.0 equivalents, preferably 2.0 equivalents to the compound [6].

Method for Preparation of Starting Compound (b)

[Chemical formula 34]

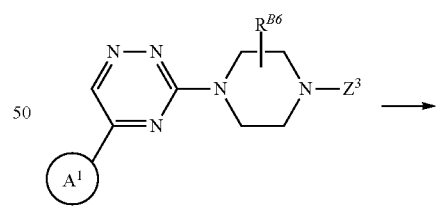

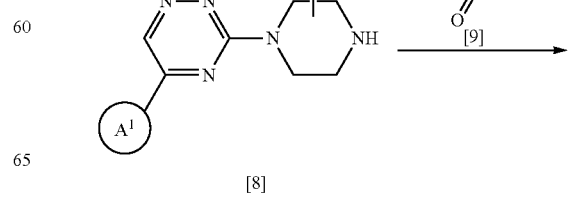

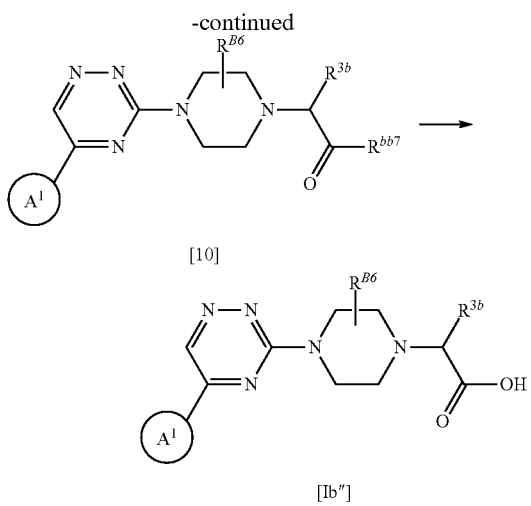

[10]

[Ib"]

wherein $Z^3$ represents a protecting group of an amino group (e.g., an alkoxycarbonyl group such as a tert-butoxycarbonyl group), $X^{10}$ represents a halogen atom (e.g., a chlorine atom and a bromine atom), and the other symbols are the same as defined above.

The compound [Ib"] can be prepared, for example, as follows.

Firstly, a protecting group is removed from the compound [7] to give the compound [8]. Then, this compound is subjected to a substitution reaction with the compound [9] to give the compound [10]. Then, the compound [Ib"] can be obtained by subjecting the compound [10] to a hydrolyzsis.

The removal of the protecting group ($Z^3$) from the compound [7] can be carried out, for example, by the similar manner as that of the protecting group from the compound [n].

The substitution reaction of the compound [8] and the compound [9] can be carried out in an appropriate solvent in the presence of a base according to a conventional method. The solvent, which does not interfere with the reaction, includes, for example, nitriles such as acetonitrile, ethers such as tetrahydrofuran, amides such as dimethylformamide, or a mixture thereof. The base includes, for example, alkaline metal carbonates such as sodium carbonate and organic amines such as diisopropylethylamine. An amount used of the compound [9] may be 1.0-2.0 equivalents, preferably 1.5 equivalents to the compound [8]. An amount used of the base may be 2.0-4.0 equivalents, preferably 2.0 equivalents to the compound [8]. This reaction can be carried out at room temperature –100° C., preferably at room temperature –60° C. The hydrolysis of the compound [10] for obtaining the compound [Ib"] can be carried out by the similar manner as that of the compound [6] for obtaining the compound [Ib'].

Method for Preparation of Starting Compound (c)

[Chemical formula 35]

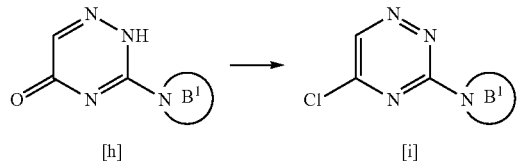

[h]    [i]

wherein the symbols are the same as defined above.

The compound [j] used in the above synthetic processes C1 and C2 can be prepared, for example, by chlorinating the compound [h].

The chlorination reaction of the compound [h] for obtaining the compound [j] can be carried out, for example, by reacting the compound [h] with a chlorine donner in an appropriate solvent in the presence or absence of a ligand. The solvent, which does not interfere with the reaction, includes, for example, ethers such as dioxane, halogenated aliphatic hydrocarbons such as dichloromethane, or a mixture thereof. The chlorine donner includes, for example, N-chlorosuccinimide (NCS) and phosphorus oxychloride. The ligand includes, for example, tertiary phosphine such as triphenylphosphine. An amount used of the chlorine donner may be 2.0-10 equivalents, preferably 3.0-5.0 equivalents to the compound [h]. An amount used of the ligand may be 2.0-10 equivalents, preferably 3.0-5.0 equivalents to the compound [h]. This reaction can be carried out at room temperature-150° C., preferably at 100° C.

Method for Preparation of Starting Compound (d)

[Chemical formula 36]

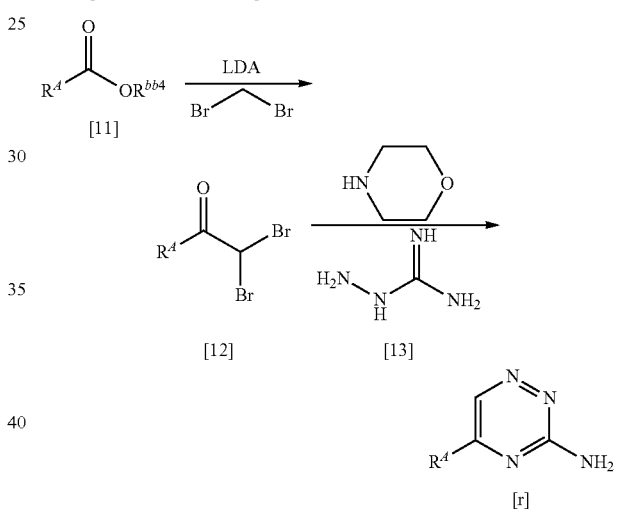

wherein the symbols are the same as defined above.

The compound [r] used in the above synthetic process D can be prepared, for example, as follows.

Firstly, the compound [11] is reacted with methylene bromide to give the compound [12]. The compound [r] can be obtained by reacting the resulting compound [12] with morpholine and the compound [13] or a hydrate thereof.

The reaction of the compound [11] and methylene bromide can be carried out, for example, in an appropriate solvent in the presence of a base. The solvent, which does not interfere with the reaction, includes, for example, ethers such as tetrahydrofuran, aromatic hydrocarbons such as toluene, or a mixture thereof. The base includes, for example, lithium diisopropylamide. This reaction can be carried out at –78--50° C., preferably at –78° C.

The reaction of the compound [12] with morpholine and the compound [13] can be carried out in an appropriate solvent in the presence of an acid. The solvent is required not to interfere with the reaction, and includes, for example, ethers such as tetrahydrofuran, alcohols such as methanol, or a mixture thereof.

The acid includes, for example, acetic acid. An amount used of the morpholine may be 4.0-10 equivalents, preferably 4.2 equivalents to the compound [12]. An amount used of the compound [13] may be 1.0-1.2 equivalents, preferably 1.0 equivalent to the compound [12]. An amount used of the acid may be 3.0-4.0 equivalents, preferably 3.0 equivalents to the compound [12]. This reaction can be carried out at room temperature-100° C., preferably at 70° C.

In the present specification, THF means tetrahydrofuran, and DMF means dimethylformamide.

EXAMPLES

Example 1 (Method A)

[Chemical formula 37]

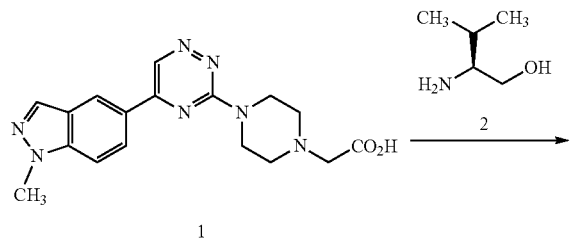

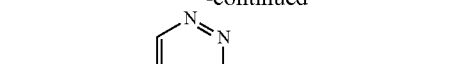

The compound 1 (200 mg) and the compound 2 (117 mg) were suspended in DMF (2 mL). Diisopropylethylamine (197 μL) and O-(7-azabenzotriazol-1-yl)-N,N,N',N'-tetramethyluroniumhexafluorophosphate (323 mg) were added to the suspension, and the reaction mixture was stirred for 4 days at room temperature. The reaction mixture was diluted with water, and extracted 3 times with ethyl acetate. The organic layer was washed with brine, and dried over anhydrous magnesium sulfate. The solvent was evaporated under reduced pressure, and the resulting residue was purified by silica gel column chromatography (eluent: chloroform-methanol; gradient: 100:0-95:5). The resulting crystalline residue was suspended and washed in a mixed solvent of ethyl acetate-hexane, taken by filtration, and dried to give 3-[4-[((S)-1-hydroxy-3-methylbutane-2-yl)carbamoylmethyl]piperazin-1-yl]-5-(1-methyl-1H-indazol-5-yl)-1,2,4-triazine (158 mg) as a yellow solid.

MS (APCI) 439 [M+H]$^+$

Example 2 (Method B)

[Chemical formula 38]

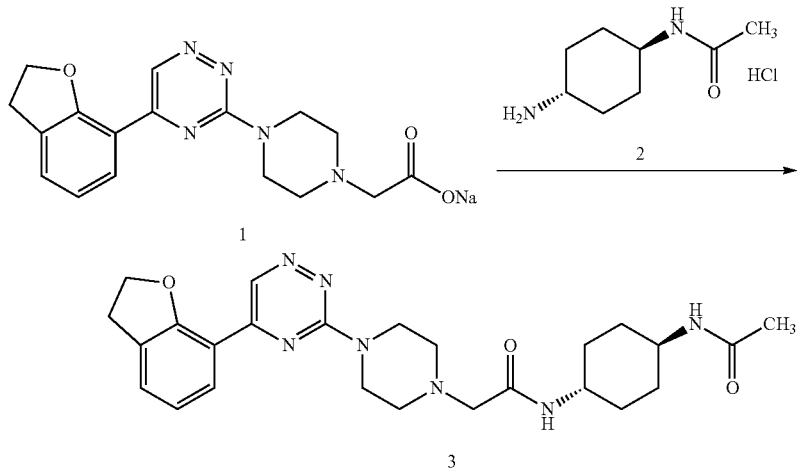

The compound 1 (100 mg) and the compound 2 (80 mg) were suspended in DMF (3 mL). Diisopropylethylamine (193 μL) and O-(7-azabenzotriazol-1-yl)-N,N,N',N'-tetramethyluroniumhexafluorophosphate (125 mg) were added to the suspension, and the reaction mixture was stirred for 4 hours at room temperature. The reaction mixture was diluted with water, and the precipitation was taken by filtration. The resulting crude crystals were suspended and washed in ethyl acetate, taken by filtration, and dried to give 3-[4-[[trans-4-(acetoamino)cyclohexyl]carbamoylmethyl]piperazin-1-yl]-5-(dihydrobenzopyran-7-yl)-1,2,4-triazine (53 mg) as a yellow solid.

MS (ESI) 480 [M+H]$^+$

Example 3-121

The corresponding starting compound was treated in a similar manner as described in the above Example 1 or 2 to give the compounds described in the following Tables 1-12.

However, "*" attached to the Example numbers means that the compound of said Example was prepared in a similar manner as described in Example 1. No "*" means that the compound was prepared in a similar manner as described in Example 2.

TABLE 1

[Chemical formula 39]

| Example | R[1] | R[2] | Ms | Salt |
|---|---|---|---|---|
| 3 | 2,3-dihydro-7-methylbenzofuran-yl | 1-(N-methylcarbamoylmethyl)-4-(methylamino)piperidinyl | 495 [M + H]+ APCI | |
| 4* | 4-chloro-2,6-difluoro-3-methylphenyl | 4-(4-(methylamino)cyclohexyl)piperazin-2-one | 549/551 [M + H]+ APCI | |
| 5 | 2,6-difluoro-3-methylphenyl | 4-(dimethylamino)cyclohexyl(methyl)amino | 478 [M + H]+ APCI | |
| 6 | 2,2-difluoro-5-methylbenzo[d][1,3]dioxol-yl | (S)-1-(methylamino)propan-2-ol | 437 [M + H]+ ESI | |
| 7* | 6-methylnaphthalen-2-yl | (S)-2-(methylamino)propan-1-ol | 407 [M + H]+ APCI | HCl |
| 8* | 2-methylphenyl | trans-4-methoxy-N-methylcyclohexan-1-amine | 425 [M + H]+ APCI | |
| 9* | 2-methylphenyl | 1-(methylamino)-3,3,3-trifluoropropan-2-ol | 425 [M + H]+ APCI | |
| 10* | 2-methylphenyl | (S)-3-methyl-2-(methylamino)butan-1-ol | 399 [M + H]+ APCI | |

TABLE 1-continued
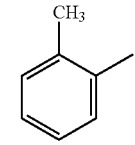
[Chemical formula 39]
| Example | R¹ | R² | Ms | Salt |
|---|---|---|---|---|
| 11* | 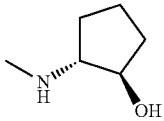 | 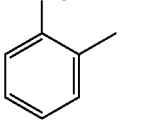 | 397 [M + H]+ | APCl |
TABLE 2
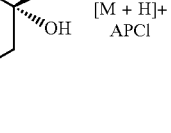
[Chemical formula 40]
| Example | R¹ | R² | Ms |
|---|---|---|---|
| 12* | 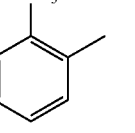 | 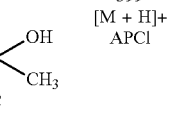 | 425 [M + H]+ APCl |
| 13* | 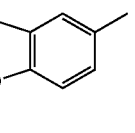 | 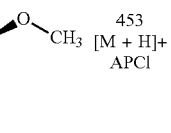 | 399 [M + H]+ APCl |
| 14 | 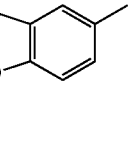 | 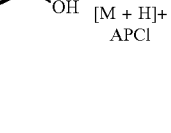 | 453 [M + H]+ APCl |
| 15 | 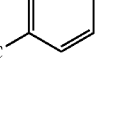 | 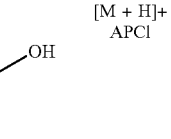 | 453 [M + H]+ APCl |
| 16 | 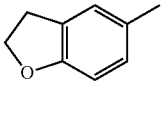 | 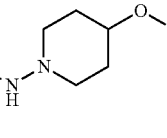 | 463 [M + H]+ APCl |
| 17 | 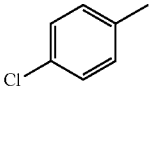 | 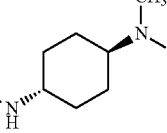 | 454 [M + H]+ APCl |
| 18 | 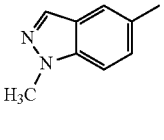 | 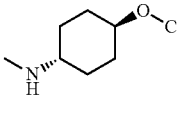 | 458/460 [M + H]+ APCl |
| 19* | 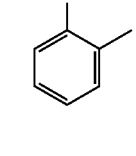 | 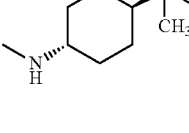 | 465 [M + H]+ APCl |
| 20* | 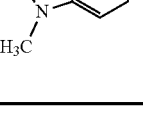 | 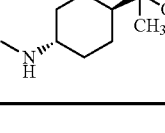 | 469 [M + H]+ APCl |
| 21* | 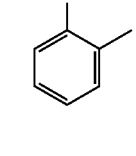 | 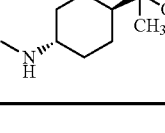 | 493 [M + H]+ APCl |

TABLE 3
[Chemical formula 41]
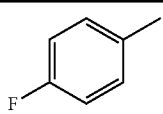
| Example | R¹ | R² | Ms | Salt |
|---|---|---|---|---|
| 22 | 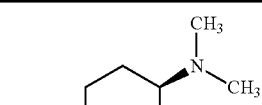 | 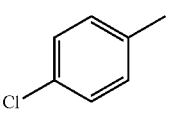 | 442 [M + H]+ APCl | |
| 23 | 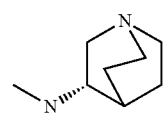 | 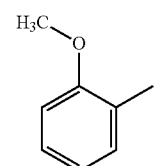 | 442/444 [M + H]+ ESI | |
| 24* | 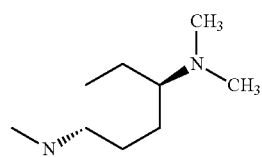 | 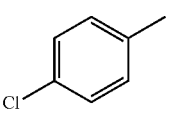 | 454 [M + H]+ APCl | |
| 25 |  | 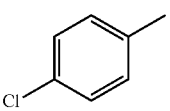 | 456/458 [M + H]+ APCl | 3HCl |
| 26 | 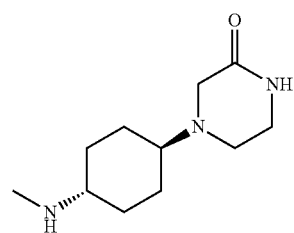 | 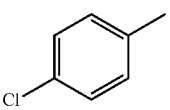 | 513/515 [M + H]+ APCl | |
| 27 | 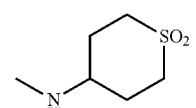 | 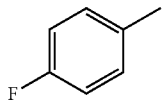 | 465/467 [M + H]+ APCl | |
| 28 | 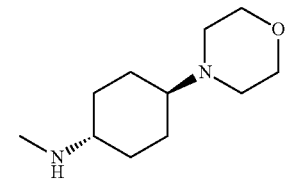 | 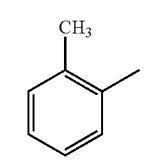 | 484 [M + H]+ APCl | |
| 29* | 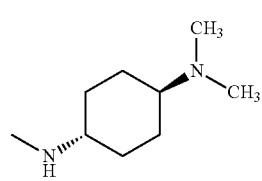 | | 438 [M + H]+ ESI | |

TABLE 3-continued

[Chemical formula 41]

| Example | R¹ | R² | Ms | Salt |
|---|---|---|---|---|
| 30* | 4-(methoxymethyl)phenyl (H₃C-O-CH₂-C₆H₄-) | 4-(dimethylamino)cyclohexyl-N(H)- (trans, with N,N-diMe) | 468 [M + H]+ APCl | |
| 31 | 5-methyl-2,3-dihydrobenzofuran-yl | 4-(1-hydroxycyclopropyl)cyclohexyl-N(H)- | 479 [M + H]+ APCl | |

TABLE 4

[Chemical formula 42]

| Example | R¹ | R² | Ms |
|---|---|---|---|
| 32 | 4-fluorophenyl | 1-(2-methoxyethyl)piperidin-4-yl-N(H)- | 458 [M + H]+ APCl |
| 33 | 4-fluorophenyl | 4-(2-hydroxypropan-2-yl)cyclohexyl-N(H)- | 457 [M + H]+ APCl |
| 34 | 4-chlorophenyl | 1-(N,N-dimethylcarbamoylmethyl)piperidin-4-yl-N(H)- | 501/503 [M + H]+ APCl |
| 35* | 2,3-dichlorophenyl | 4-(3-oxopiperazin-1-yl)cyclohexyl-N(H)- | 547/549 [M + H]+ APCl |

TABLE 4-continued
[Chemical formula 42]
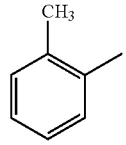
| Example | R¹ | R² | Ms |
|---|---|---|---|
| 36* | 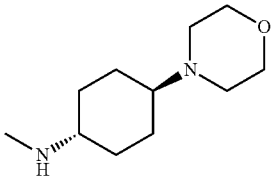 | 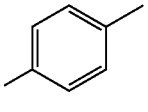 | 480 [M + H]+ APCl |
| 37 | 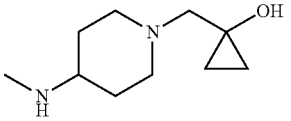 | 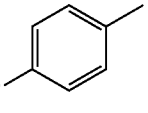 | 470 [M + H]+ APCl |
| 38 | 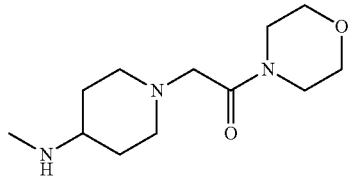 | 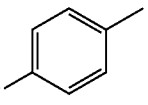 | 527 [M + H]+ ESI |
| 39 | 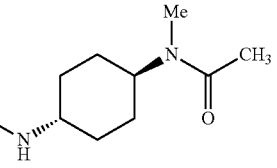 | 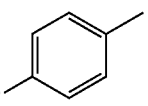 | 470 [M + H]+ APCl |
| 40 | 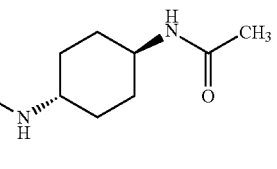 | 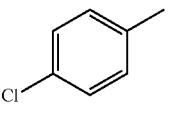 | 456 [M + H]+ ESI |
| 41 | 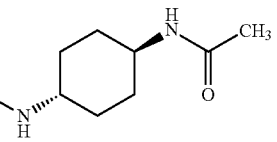 |  | 472/474 [M + H]+ ESI |

TABLE 5

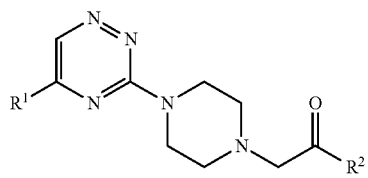

[Chemical formula 43]

| Example | R¹ | R² | Ms | Salt |
|---|---|---|---|---|
| 42 | 4-F-phenyl | cyclohexyl-N(thiomorpholine-SO₂)-NHCH₃ | 532 [M + H]+ ESI | |
| 43 | 4-F-phenyl | CH₃NH-propyl-N(thiomorpholine-SO₂) | 492 [M + H]+ APCI | |
| 44 | 4-F-phenyl | 4-(methylamino)piperidinyl-CH₂C(O)NHCH₃ | 471 [M + H]+ ESI | |
| 45 | 4-Cl-phenyl | 4-(methylamino)piperidinyl-CH₂C(O)NHCH₃ | 487/489 [M + H]+ ESI | |
| 46 | 4-F-phenyl | CH₃NH-CH₂-(1-SO₂CH₃-piperidin-4-yl) | 492 [M + H]+ ESI | |
| 47 | 4-F-phenyl | CH₃NH-ethyl-N(thiomorpholine-SO₂) | 478 [M + H]+ APCI | |
| 48 | 4-CH₃-phenyl | cyclohexyl-NHC(O)CH₃-NHCH₃ | 452 [M + H]+ APCI | |
| 49 | 4-F-phenyl | cyclohexyl-SO₂CH₃-NHCH₃ | 477 [M + H]+ APCI | |

TABLE 5-continued

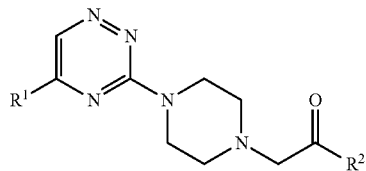

[Chemical formula 43]

| Example | R¹ | R² | Ms | Salt |
|---|---|---|---|---|
| 50 | 4-methylphenyl (H₃C-C₆H₄-) | trans-4-(methylamino)cyclohexyl-SO₂CH₃ | 473 [M + H]+ APCI | |
| 51 | 4-fluorophenyl (F-C₆H₄-) | 4-(methylamino)piperidin-1-yl-CH₂CH₂-SO₂CH₃ | 506 [M + H]+ APCI | |

TABLE 6

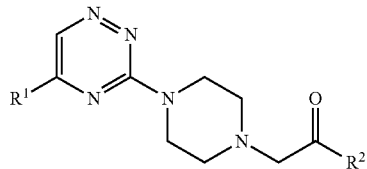

[Chemical formula 44]

| Example | R¹ | R² | Ms | Salt |
|---|---|---|---|---|
| 52 | 4-chlorophenyl (Cl-C₆H₄-) | 4-[2-(methylamino)ethyl]-1-acetylpiperazinyl | 487/489 [M + H]+ APCI | |
| 53 | 4-fluorophenyl (F-C₆H₄-) | 4-[2-(methylamino)ethyl]-1-(methylsulfonyl)piperazinyl | 507 [M + H]+ APCI | |
| 54 | 4-chlorophenyl (Cl-C₆H₄-) | (4-methylamino)-1-methyl-2-oxopiperidin-4-yl | 444/446 [M + H]+ APCI | |
| 55 | 4-fluorophenyl (F-C₆H₄-) | trans-4-(methylamino)cyclohexyloxy-CH₂-C(O)NHCH₃ | 486 [M + H]+ ESI | |

TABLE 6-continued

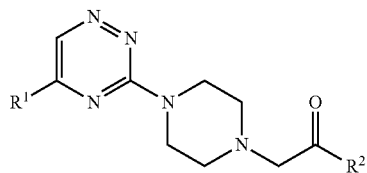

[Chemical formula 44]

| Example | R¹ | R² | Ms | Salt |
|---|---|---|---|---|
| 56 | 4-Cl-phenyl | 1-methyl-4-(methylamino)pyrazole | 413/415 [M + H]+ APCI | |
| 57 | 4-F-phenyl | trans-4-(methylamino)cyclohexyl-(3-hydroxypyrrolidin-1-yl) | 484 [M + H]+ APCI | 2HCl |
| 58 | 4-Cl-phenyl | trans-4-(methylamino)cyclohexyloxy-N,N-dimethylacetamide | 516/518 [M + H]+ APCI | |
| 59 | 4-Cl-phenyl | 1-acetyl-4-hydroxy-4-(methylaminomethyl)piperidine | 488/490 [M + H]+ APCI | |
| 60 | 4-Cl-phenyl | 1-methanesulfonyl-4-hydroxy-4-(methylaminomethyl)piperidine | 524/526 [M + H]+ APCI | |
| 61* | 2-methylphenyl | trans-4-(methylamino)cyclohexyl-methanol | 425 [M + H]+ APCI | |

TABLE 7
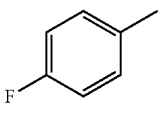
[Chemical formula 45]
| Example | R¹ | R² | Ms | Salt |
|---|---|---|---|---|
| 62 | 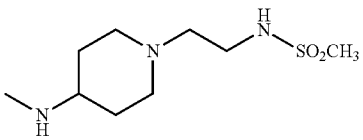 | 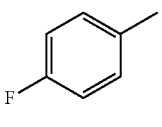 | 521 [M + H]+ APCI | |
| 63 | 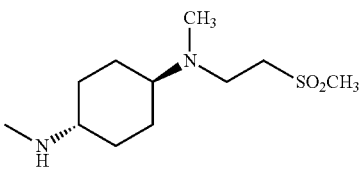 | 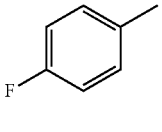 | 534 [M + H]+ ESI | |
| 64 | 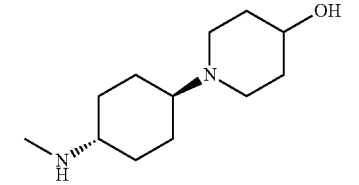 | 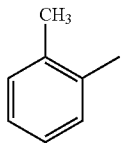 | 498 [M + H]+ APCI | 2 HCl |
| 65* | 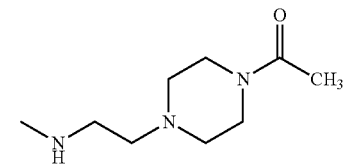 | 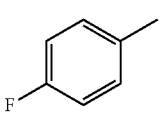 | 467 [M + H]+ ESI | |
| 66 | 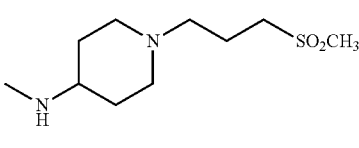 | 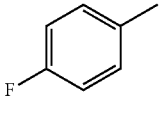 | 520 [M + H]+ APCI | |
| 67 | 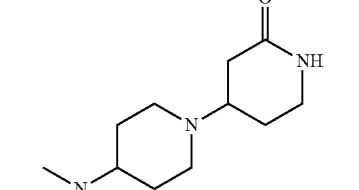 | 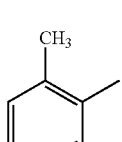 | 497 [M + H]+ APCI | |
| 68* | 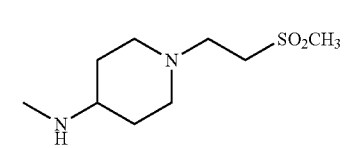 | 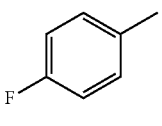 | 502 [M + H]+ APCI | |
| 69 | 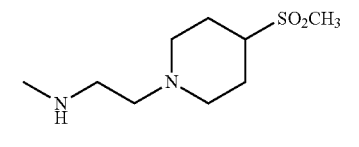 | | 506 [M + H]+ ESI | |

TABLE 7-continued

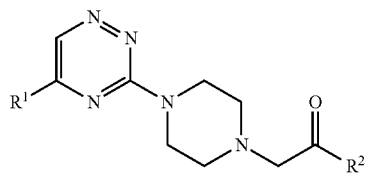

[Chemical formula 45]

| Example | R¹ | R² | Ms | Salt |
|---|---|---|---|---|
| 70 | 2-F, 4-CH₃-phenyl | N-(piperidin-4-yl)-N-methyl, N-acetyl | 470 [M + H]+ ESI | |
| 71 | 4-F-phenyl | 4-(methylamino)-1H-pyrazol-1-yl-CH₂-C(O)-NMe₂ | 468 [M + H]+ APCI | |

TABLE 8

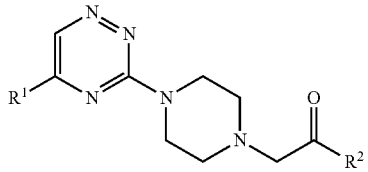

[Chemical formula 46]

| Example | R¹ | R² | Ms |
|---|---|---|---|
| 72 | 4-F-phenyl | 4-(methylamino)-1-(tetrahydro-2H-pyran-4-yl)-1H-pyrazol-... | 467 [M + H]+ APCI |
| 73 | 4-F-phenyl | 4-(methylamino)-1-(2-(ethylsulfonyl)ethyl)-1H-pyrazol-... -SO₂C₂H₅ | 503 [M + H]+ APCI |
| 74 | 4-CF₃-phenyl | trans-4-(methylamino)cyclohexyloxy-CH₂-C(O)-NHCH₃ | 536 [M + H]+ APCI |
| 75 | 4-CH₃-phenyl | 4-(methylamino)-1H-pyrazol-1-yl-CH₂-C(O)-N(CH₃)₂ | 464 [M + H]+ APCI |

TABLE 8-continued

[Chemical formula 46]

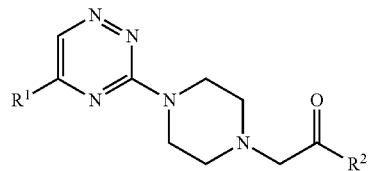

| Example | R¹ | R² | Ms |
|---|---|---|---|
| 76 | 4-Cl-phenyl | 1-(N,N-dimethylcarbamoylmethyl)-4-(methylamino)pyrazol-1-yl | 484 [M + H]+ APCI |
| 77 | 4-CF₃-phenyl | 1-(N,N-dimethylcarbamoylmethyl)-4-(methylamino)pyrazol-1-yl | 518 [M + H]+ APCI |
| 78 | 4-F-phenyl | 9-(methylamino)-1,4-dimethyl-1,4-diazaspiro[5.5]undecan-5-one | 511 [M + H]+ APCI |
| 79 | 4-CH₃-phenyl | 1-(N-methylcarbamoylmethyl)-4-(methylamino)pyrazol-1-yl | 450 [M + H]+ APCI |
| 80 | 4-F-phenyl | 1-(N-methylcarbamoylmethyl)-4-(methylamino)pyrazol-1-yl | 454 [M + H]+ APCI |
| 81 | 4-Cl-phenyl | 1-(N-methylcarbamoylmethyl)-4-(methylamino)pyrazol-1-yl | 470/472 [M + H]+ APCI |

TABLE 9
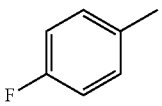
| Example | R¹ | R² | Ms |
|---|---|---|---|
| 82 | 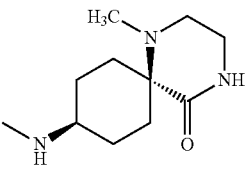 | 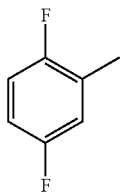 | 497 [M + H]+ APCI |
| 83* | 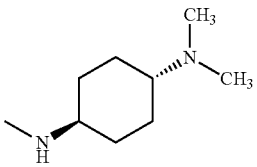 | 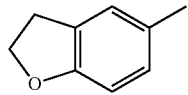 | 460 [M + H]+ ESI |
| 84 | 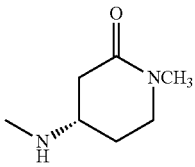 | 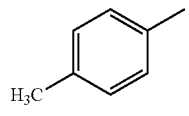 | 452 [M + H]+ APCI |
| 85 | 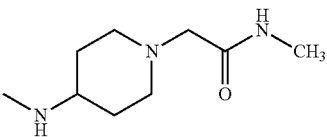 | 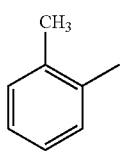 | 467 [M + H]+ APCI |
| 86* | 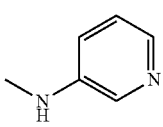 | 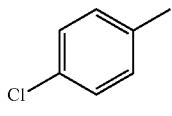 | 398 [M + H]+ APCI |
| 87 | 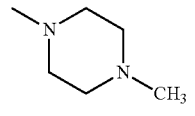 | 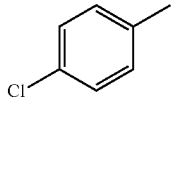 | 416/418 [M + H]+ APCI |
| 88 | 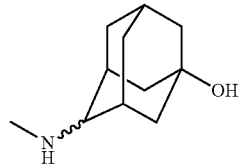 | 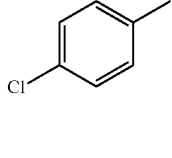 | 483/485 [M + H]+ APCI |
| 89 | 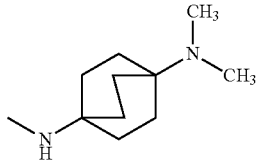 | | 484/486 [M + H]+ ESI |

TABLE 9-continued

[Chemical formula 47]

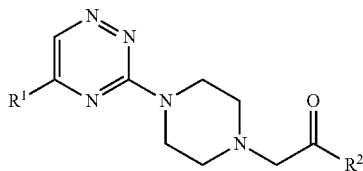

| Example | R¹ | R² | Ms |
|---|---|---|---|
| 90 | 4-Cl-phenyl | methyl-amino-methoxy-bicyclic | 487/489 [M + H]+ APCI |
| 91 | 4-F-phenyl | methyl-amino-acetyl-oxazepane | 458 [M + H]+ APCI |

TABLE 10

[Chemical formula 48]

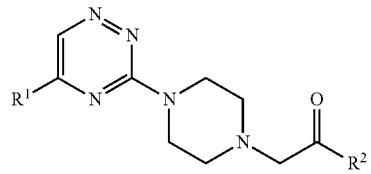

| Example | R¹ | R² | Ms | Salt |
|---|---|---|---|---|
| 92 | 4-F-phenyl | (1-methylpyrrolidin-2-yl)methanol | 401 [M + H]+ APCI | |
| 93 | 4-CH₃-phenyl | methylamino-tetrahydrothiopyran-SO₂ | 445 [M + H]+ APCI | |
| 94 | 4-F₃C-phenyl | methylamino-hydroxy-tetrahydrothiophene-SO₂ | 501 [M + H]+ APCI | |
| 95* | 2-CH₃-phenyl | N(CH₃)₂ | 341 [M + H]+ APCI | |
| 96 | 4-F-phenyl | NH-C(CH₃)₂-CH₃ | 373 [M + H]+ APCI | HCl |

TABLE 10-continued
[Chemical formula 48]
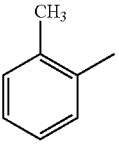
| Example | R¹ | R² | Ms | Salt |
|---|---|---|---|---|
| 97* | 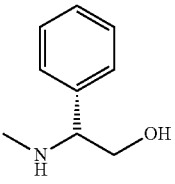 | 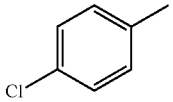 | 433 [M + H]+ APCI | |
| 98 | 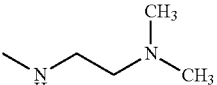 | 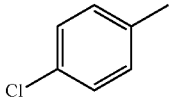 | 404/406 [M + H]+ APCI | 3HCl |
| 99 | 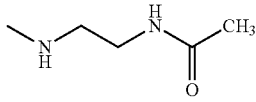 | 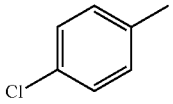 | 416/420 [M + H]+ ESI | |
| 100 | 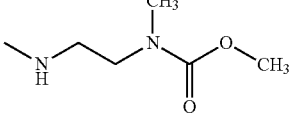 | 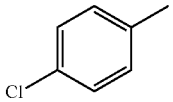 | 448/450 [M + H]+ ESI | 2HCl |
| 101 | 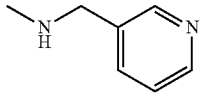 | 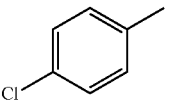 | 424/426 [M + H]+ APCI | |
TABLE 11
[Chemical formula 49]
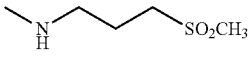
| Example | R¹ | R² | Ms | Salt |
|---|---|---|---|---|
| 102 | 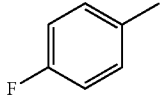 | 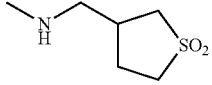 | 453/455 [M + H]+ APCI | |
| 103 | | | 449 [M + H]+ APCI | |

TABLE 11-continued

[Chemical formula 49]

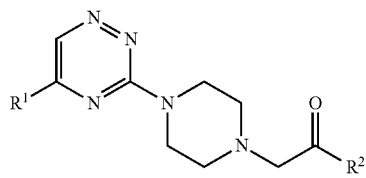

| Example | R¹ | R² | Ms | Salt |
|---|---|---|---|---|
| 104 | 4-F-phenyl | N-methyl-N-(2-(4-acetylpiperazin-1-yl)ethyl)amino | 471 [M + H]+ APCI | |
| 105 | 4-F-phenyl | N-methyl-(1-methylpiperidin-4-yl)amino | 414 [M + H]+ APCI | |
| 106 | 4-Cl-phenyl | N-cyclopropyl-(1-methylpiperidin-4-yl)amino | 470/472 [M + H]+ APCI | 3HCl |
| 107 | 4-Cl-phenyl | N-methyl-(1-(pyrimidin-2-yl)piperidin-4-yl)amino | 494/496 [M + H]+ APCI | |
| 108 | 4-F-phenyl | N-methyl-(1-(tetrahydro-2H-pyran-4-yl)piperidin-4-yl)amino | 484 [M + H]+ APCI | |
| 109 | 4-F-phenyl | N-methyl-(1-(tert-butylcarbamoyl)piperidin-4-yl)amino | 499 [M + H]+ APCI | |
| 110 | 4-F-phenyl | N-methyl-(trans-4-((3-hydroxypyrrolidin-1-yl))cyclohexyl)amino | 484 [M + H]+ APCI | 2HCl |

TABLE 11-continued

[Chemical formula 49]

(structure: R¹-triazine-piperazine-CH₂-C(=O)-R²)

| Example | R¹ | R² | Ms | Salt |
|---|---|---|---|---|
| 111 | 4-F-C₆H₄- | cyclohexyl(NHMe)-N-pyrrolidin-3-ol (OH wedge) | 464 [M + H]+ APCI | 2HCl |

TABLE 12

[Chemical formula 50]

(structure: R¹-triazine-piperazine-CH₂-C(=O)-R²)

| Example | R¹ | R² | Ms | Salt |
|---|---|---|---|---|
| 112 | 4-F-C₆H₄- | MeNH-CH₂CH₂-N(piperidin-4-ol) | 444 [M + H]+ ESI | |
| 113 | 4-F-C₆H₄- | MeNH-CH₂-C(OH)(cyclohexyl-SO₂CH₃) | 507 [M + H]+ APCI | |
| 114* | 2-CH₃-C₆H₄- | adamantyl-NHMe | 447 [M + H]+ APCI | |
| 115 | 4-F-C₆H₄- | MeNH-N-pyrrolidine | 386 [M + H]+ APCI | |
| 116* | 2-CH₃-C₆H₄- | MeNH-cyclobutyl-OH | 383 [M + H]+ APCI | |
| 117 | 4-Cl-C₆H₄- | MeNH-azetidin-N-CH₃ | 402/404 [M + H]+ APCI | |

TABLE 12-continued
[Chemical formula 50]
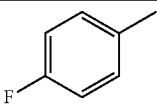
| Example | R¹ | R² | Ms | Salt |
|---|---|---|---|---|
| 118 | 4-F-C₆H₄ | (3R,4S)-1-methyl-4-(methylamino)-3-hydroxypyrrolidine | 416 [M + H]+ ESI | |
| 119* | 2-methylphenyl | NHCH₂CH₂CH₂OCH₃ (with N-CH₃) | 385 [M + H]+ APCI | |
| 120* | 2-methylphenyl | NHCH₂CH(OH)CH₃ (with N-CH₃) | 371 [M + H]+ APCI | |
| 121* | 2-methylphenyl | NHCH₂CH(OH)CF₃ (with N-CH₃) | 425 [M + H]+ APCI | HCl |
Example 122
[Chemical formula 51]
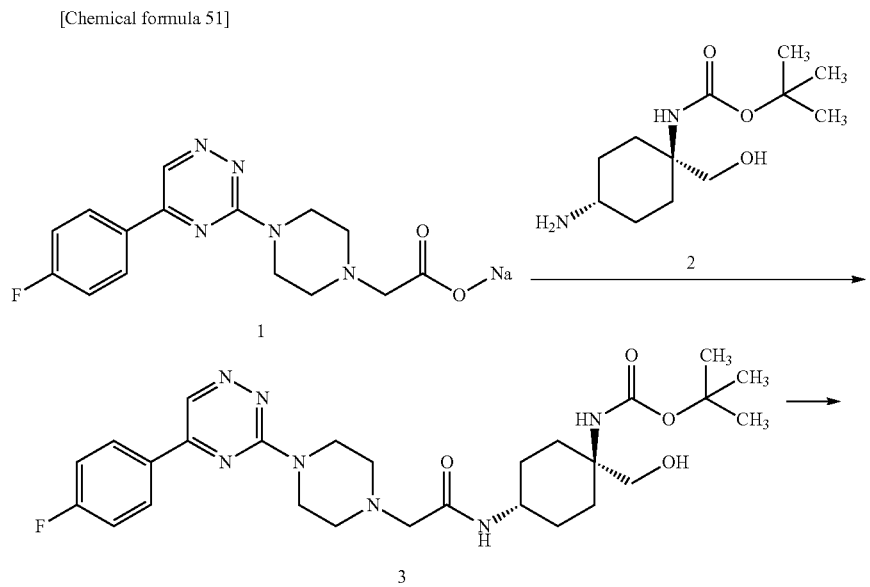

-continued

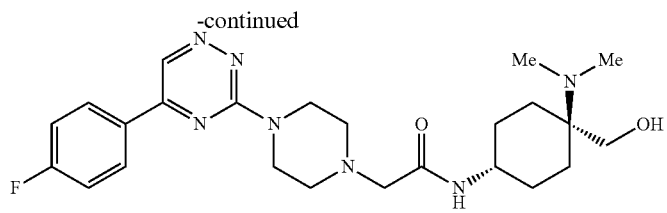

(1) The compound 1 (121.0 mg) was suspended in acetonitrile (3.5 mL). The compound 2 (101.0 mg), which was synthesized according to a method described in International Publication No. WO 2002/030891, and O-(7-azabenzotriazol-1-yl)-N,N,N',N'-tetramethyluroniumhexafluorophosphate (270.7 mg) were added to the suspension, and the reaction mixture was stirred for 20 hours. To the reaction mixture was added water, the reaction mixture was extracted with chloroform, and then the organic layer was dried over anhydrous sodium sulfate, followed by evaporation of the solvent. The resulting residue was purified by silica gel column chromatography (eluent: ethyl acetate-methanol; gradient: 100:0-92:8) to give the compound 3 (88.1 mg) as a yellow solid. MS (APCI) 544 [M+H]$^+$ (2) The compound 3 (80.0 mg) was dissolved in chloroform (1 mL). Trifluoroacetic acid (1 mL) was added to the solution, and the reaction mixture was stirred for 1.5 hours at room temperature. To the reaction mixture was added methanol (2 mL), and the reaction mixture was treated with a strong cation exchange resin column (Waters, PoraPak Rxn Cx, eluent: 1 mol/L ammonia in methanol solution), followed by evaporation of the solvent in the eluate. The resulting residue was dissolved in chloroform (1.5 mL), and then acetic acid (10 µL), 35% formalin (60 µL), sodium triacetoxyborohydride (95.5 mg) were added to the reaction mixture, and the reaction mixture was stirred for 23 hours at room temperature. To the reaction mixture was added a saturated aqueous solution of sodium bicarbonate, and the reaction mixture was stirred for 5 minutes. The mixture was extracted with chloroform, and the organic layer was dried over anhydrous sodium sulfate, and then the solvent was evaporated. The resulting residue was purified by NH-silica gel column chromatography (eluent: ethyl acetate-methanol; gradient: 100:0-90:10). The resulting fraction was concentrated under reduced pressure, and the residue was dissolved in a mixed solvent of ethyl acetate and diethylether, and then the solution was treated with a 4 mol/L solution of HCl in ethyl acetate, and the supernatant was removed by centrifugation. The precipitate was suspended and washed in diethyl ether, and the supernatant was removed by centrifugation to give 3-[4-[[trans-4-dimethylamino-4-(hydroxymethyl)cyclohexyl]carbamoylmethyl]piperazin-1-yl]-5-(4-fluorophenyl)-1,2,4-triazine (30.4 mg, pale yellow powder) as dihydrochloride.

MS(APCI) 472 [M+H]$^+$

Example 123

[Chemical formula 52]

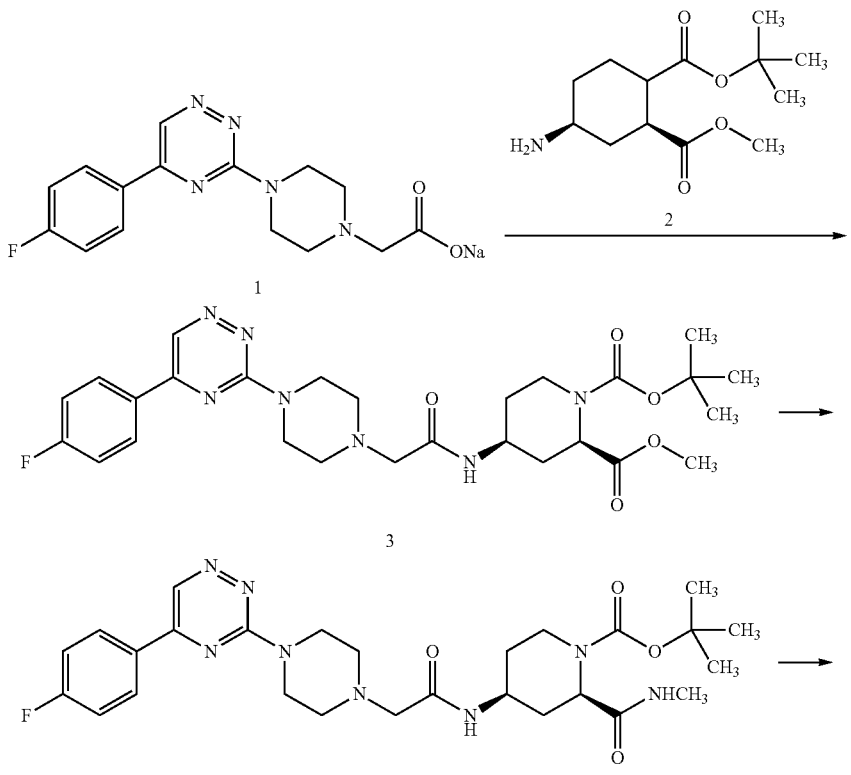

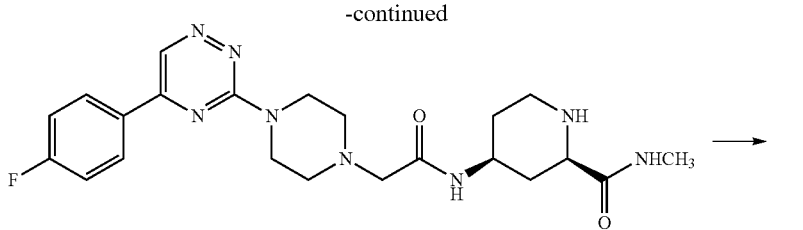

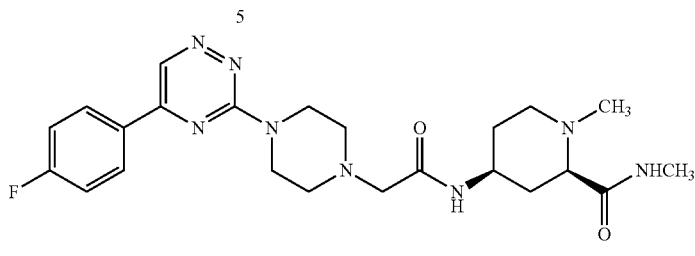

(1) The compound 1 (76 mg) and the compound 2 (70 mg) were suspended in DMF (2.5 mL). Diisopropylethylamine (78 μL) and O-(7-azabenzotriazol-1-yl)-N,N,N',N'-tetramethyluroniumhexafluorophosphate (86 mg) were added to the suspension, and the reaction mixture was stirred for 1 hour at room temperature.

To the reaction mixture were added water and a saturated aqueous solution of potassium hydroxide, and then the reaction mixture was extracted with chloroform. The organic layer was dried over anhydrous sodium sulfate, and then the solvent was evaporated under reduced pressure. The resulting residue was suspended and washed in hexane, taken by filtration, and dried to give the compound 3 (125 mg) as a yellow solid.

MS (ESI) 558 [M+H]$^+$ (2) The compound 3 (70 mg) was dissolved in ethanol (1 mL)-THF (1 mL). An aqueous solution of 1 mol/L of sodium hydroxide (220 μL) was added to the solution, and the reaction mixture was stirred for 2 hours at room temperature. The reaction mixture was concentrated under reduced pressure, and then the residue was suspended in DMF (1 mL), a solution of 2 mol/L methylamine in THF (110 μL), diisopropylethylamine (38 μL), and O-(7-azabenzotriazol-1-yl)-N,N,N',N'-tetramethyluroniumhexafluorophosphate (63 mg) were added to the suspension, and the reaction mixture was stirred for 17 hours at room temperature. To the reaction mixture were added water and a saturated aqueous solution of potassium carbonate, and then the reaction mixture was extracted with chloroform. The organic layer was dried over anhydrous sodium sulfate, and then the solvent was evaporated under reduced pressure. The resulting residue was purified by silica gel column chromatography (eluent: hexane-ethyl acetate; gradient: 20:80-0:100) to give the compound 4 (35 mg) as a yellow solid.

MS (ESI) 558 [M+H]$^+$ (3) The compound 4 (545 mg) was dissolved in chloroform (1 mL). Trifluoroacetic acid (700 μL) was added to the solution, and the reaction mixture was stirred for 3 hours at room temperature. The reaction mixture was diluted with methanol, and then treated with packed strong cation exchange resin (PoraPak Rxn Cx, eluent: a solution of 1 mol/L NH$_3$ in methanol), and the eluate was concentrated under reduced pressure to give the compound 5 (23 mg) as a yellow solid.

MS (ESI) 458 [M+H]$^+$ (4) The compound 5 (19 mg) was dissolved in chloroform (1 mL). 37% Formalin (100 μL), acetic acid (2.5 μL), and sodium triacetoxyborohydride (27 mg) were added to the solution, and the reaction mixture was stirred for 2 hours at room temperature. To the reaction mixture were added water and a saturated aqueous solution of sodium bicarbonate, and then the reaction mixture was extracted with ethyl acetate. The organic layer was dried over anhydrous sodium sulfate, and then the solvent was evaporated under reduced pressure. The resulting residue was suspended and washed in a mixed solvent of ethyl acetate/hexane, taken by filtration, and dried to give 5-(4-fluorophenyl)-3-[4-[[(2R,4S)-1-methyl-2-(N-methylcarbamoyl)piperidin-4-yl]carbamoylmethyl]piperazin-1-yl]-1,2,4-triazine (14 mg) as a yellow solid.

MS (ESI) 471 [M+H]$^+$

Example 124

[Chemical formula 53]

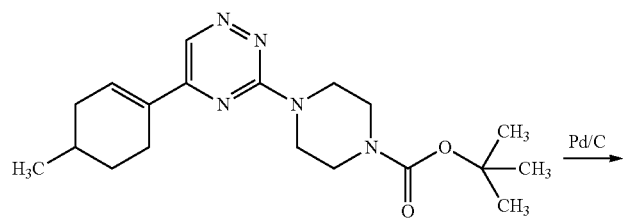

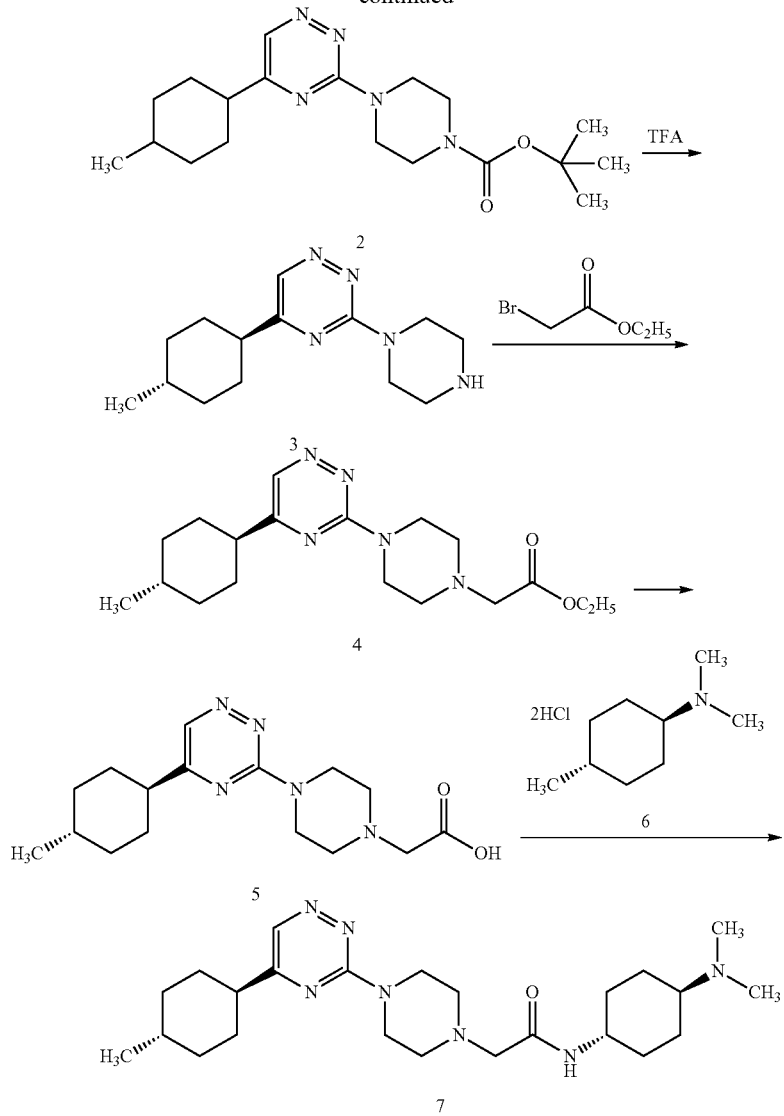

(1) To a solution of the compound 1 (1200 mg) in methanol (40 mL)-triethylamine (5 mL) was added wet 10% palladium on carbon (360 mg), and the reaction mixture was stirred under hydrogen atmosphere for 4.5 hours. The palladium on carbon was removed by filtration, and then washed with methanol. The filtrate was concentrated under reduced pressure to give the compound 2 (960 mg) as a yellow viscous substance of a mixture of cis:trans=7:3.

MS (ESI) 362 [M+H]$^+$ (2) To a solution of the compound 2 (960 mg) in DMF (9 mL) was added trifluoroacetic acid (9 mL). The reaction mixture was stirred for 2.5 hours at room temperature, and then stirred for additional 2 days at 50° C. The reaction mixture was cooled to room temperature, and the solvent was evaporated under reduced pressure. An aqueous solution of potassium carbonate was added under ice-cooling, and the reaction mixture was extracted twice with chloroform.

The resulting organic layer was dried over potassium carbonate, and the solvent was concentrated under reduced pressure to give the compound 3 (750 mg) as a yellow viscous substance of a mixture of cis:trans=1:9.

MS (ESI) 262 [M+H]$^+$ (3) The compound 3 (690 mg) was dissolved in acetonitrile (30 mL). Bromoethyl acetate (354 μL) and sodium carbonate (564 mg) were added to the solution, and the reaction mixture was stirred for 18 hours at room temperature. The reaction mixture was diluted with ethyl acetate, washed with water and brine, and dried over anhydrous sodium sulfate. The solvent was evaporated under reduced pressure, and the resulting residue was purified by NH-silica gel column chromatography (eluent: hexane-ethyl acetate; gradient: 80:20-60:40), and then isolated by HPLC (Chiralpak IA, hexane/2-propanol/diethylamine=80/20/0.1, flow rate: 20 mL/min) to give the compound 4 (470 mg) as a brown viscous substance.

MS (ESI) 348 [M+H]$^+$ (4) The compound 4 (470 mg) was dissolved in ethanol (8 mL)-THF (8 mL). An aqueous solution of 1 mol/L of sodium hydroxide (2.7 mL) was added to the solution, and the reaction mixture was stirred for 2 hours at room temperature. The reaction mixture was concentrated, and the resulting residue was dissolved in water, and then 1 mol/L hydrochloric acid (2.7 mL) was added to the solution for adjusting a pH of the solution to 4. The solvent was evaporated, the resulting residue was suspended and washed in water, taken by filtration, and dried to give the compound 5 (135 mg) as a pale yellow solid.

MS (ESI) 320 [M+H]$^+$ (5) The compound 5 (133 mg) and the compound 6 (180 mg) were suspended in DMF (4 mL). Diisopropylethylamine (296 μL) and O-(7-azabenzotriazol-1-yl)-N,N,N',N'-tetramethyluroniumhexafluorophosphate (316 mg) were added to the suspension, and the reaction mixture was stirred for 3.5 hours at room temperature. To the reaction mixture was added an aqueous solution of potassium carbonate, the solution was extracted twice with chloroform, and the resulting organic layer was dried over anhydrous sodium sulfate. The solvent was evaporated under reduced pressure, and the resulting residue was purified by NH-silica gel column chromatography (eluent: ethyl acetate-methanol; gradient: 100:0-95:5), and then isolated by HPLC (Chiralpak IA, ethanol/THF/diethylamine=95/5/0.5, flow rate: 20 mL/min) to give 3-[4-[[trans-4-(dimethylamino)cyclohexyl]carbamoylmethyl]piperazin-1-yl]-5-(trans-4-methylcyclohexyl)-1,2,4-triazine (65 mg) as a pale yellow solid.

MS (ESI) 444 [M+H]$^+$

Example 125

[Chemical formula 54]

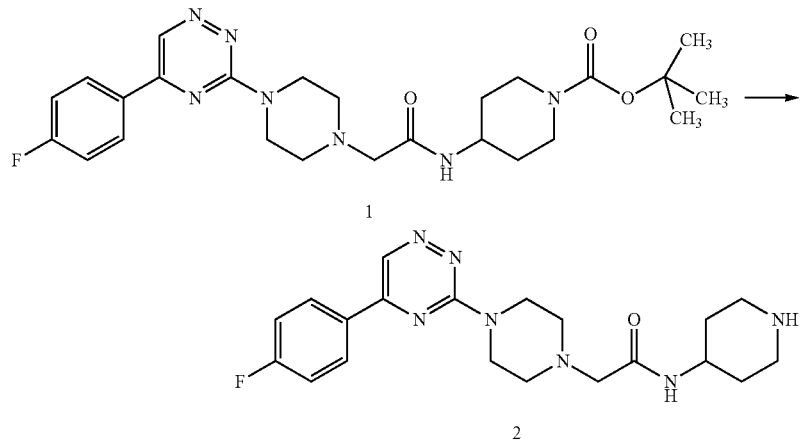

To a solution of the compound 1 (5.3 g) in chloroform (22 mL) was added trifluoroacetic acid (11 mL), and the reaction mixture was stirred for 2.1 hours at room temperature. The reaction mixture was concentrated under reduced pressure, and a saturated aqueous solution of sodium bicarbonate and an aqueous solution of 2 mol/L of sodium hydroxide were added thereto, and the reaction mixture was extracted 4 times with chloroform. The resulting organic layer was washed with brine, and then dried over anhydorous sodium sulfate, and the solvent was evaporated under reduced pressure. The resulting residue was purified by NH-silica gel column chromatography (eluent: chloroform-methanol; gradient: 100:0-95:5) to give 5-(4-fluorophenyl)-3-[4-[(piperidin-4-yl)carbamoylmethyl]piperazin-1-yl]-1,2,4-triazine (3.2 g) as a yellow solid.

MS (APCI) 400[M+H]$^+$

Example 126-130

The corresponding starting compound was treated in a similar manner as described in the above Example 125 to give the compounds described in the following Table 13.

TABLE 13

[Chemical formula 55]

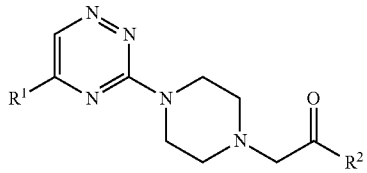

| Example | R$^1$ | R$^2$ | Ms | Salt |
|---|---|---|---|---|
| 126 | 4-Cl-phenyl | 4-(methylamino)piperidin-NH | 415/418 [M + H]+ APCI | 3HCl |

TABLE 13-continued
[Chemical formula 55]
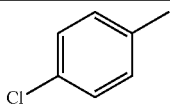
| Example | R¹ | R² | Ms | Salt |
|---|---|---|---|---|
| 127 | 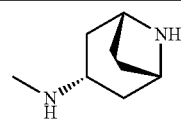 | 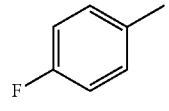 | 442/444 [M + H]+ APCI | 3HCl |
| 128 | 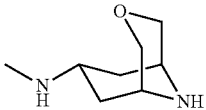 | 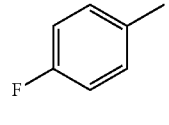 | 442 [M + H]+ APCI | |
| 129 | 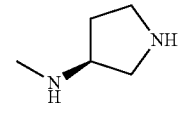 | 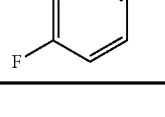 | 386 [M + H]+ APCI | |
| 130 | 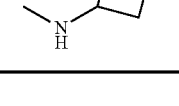 | | 372 [M + H]+ APCI | |
Example 131
[Chemical formula 56]
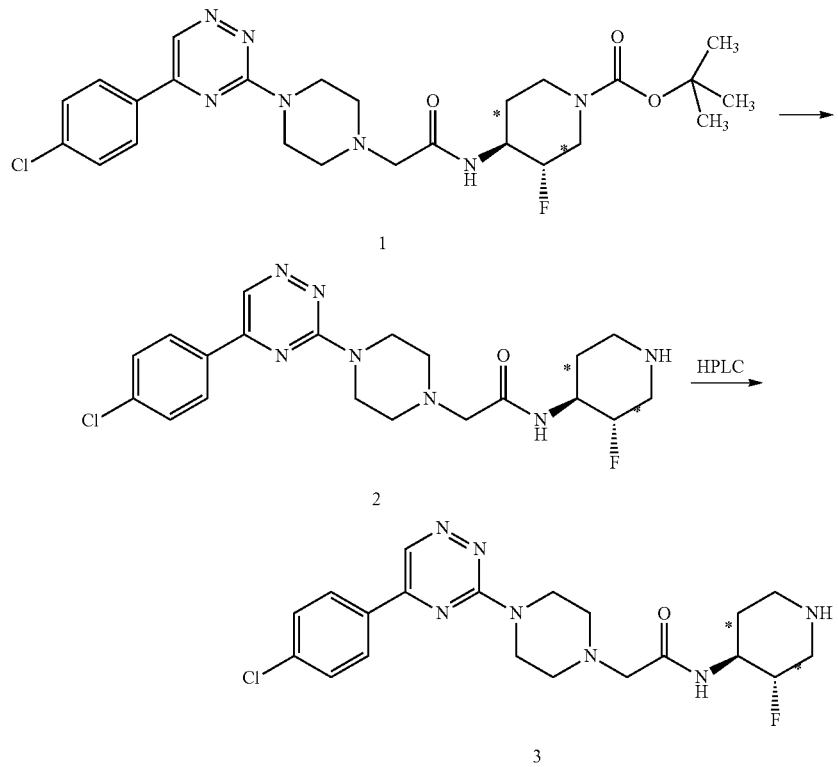

(wherein the stereochemistry for a substituent of the carbon atom labelled by "*" means trans configuration, and does not specify their absolute configuration.)

To a solution of the compound 1 (85 mg) in dichloromethane (1 mL) was added trifluoroacetic acid (1 mL), and the reaction mixture was stirred for 22 hours at room temperature. The reaction mixture was diluted with methanol, the solution was treated with packed strong cation exchange resin (PoraPak Rxn Cx, eluent: a solution of 1 mol/L $NH_3$ in methanol), and the eluate was concentrated under reduced pressure to give the racemic compound 2 (57 mg) as a yellow solid.

MS (APCI) 434/436 $[M+H]^+$

An optical isomer of the racemic compound 2 (45 mg) was isolated by recycle HPLC (Chiralpak IA (30×250), ethanol/THF/diethylamine=90/10/0.1, flow rate: 20 mL/min), and a fraction containing each isomer was concentrated under reduced pressure to give 5-(4-chlorophenyl)-3-[4-[(trans-3-fluoropiperidin-4-yl)carbamoylmethyl]piperazin-1-yl]-1,2,4-triazine (21 mg) as a yellow solid.

Example 131a

Retention time: 7.21 minutes (Chiralpak IA-3 (4.6×150), ethanol/THF/diethylamine=90/10/0.1, flow rate 0.5 mL/min)
Optical purity 100% ee
MS (APCI) 434/436 [M+H]

Example 131b (Enantiomer of Example 131a)

Retention time: 10.12 minutes

Example 132-134

The corresponding starting compound was treated in a similar manner as described in the above Example 131 to give the compound described in the following Table 14. However, the stereochemistry for a substituent of the carbon atom labelled by "*" means trans or cis configuration, and does not specify their absolute configuration.

TABLE 14

[Chemical formula 57]

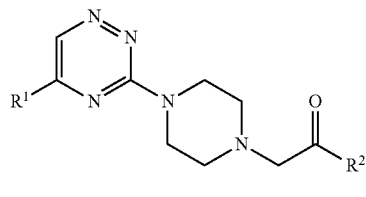

| Example | R¹ | R² | Ms | Salt | Retention Time HPLC (min) | Conditions |
|---|---|---|---|---|---|---|
| 132a | 4-chlorophenyl | N-methyl-3-methoxy-piperidin-4-yl (trans *,*) | 446/448 [M + H]+ APCI | | 8.69 | CHIRALPAK IA-3 THF/Ethanol/Methanol/Diethylamine = 5/47.5/47.5/0.1 Flow Rate 0.5 mL/min |
| 132b | (Enantiomer of 132a) | | | | 10.41 | |
| 133a | 4-chlorophenyl | N-methyl-3-hydroxy-piperidin-4-yl (trans *,*) | 432/434 [M + H]+ APCI | | 15.17 | CHIRALPAK IA-3 2-Propanol/THF/Diethylamine = 90/10/0.1 Flow Rate 0.5 mL/min |
| 133b | (Enantiomer of 133a) | | | | 9.44 | |
| 134a | 4-fluorophenyl | N-methyl-3-fluoro-piperidin-4-yl (trans *,*) | 418 [M + H]+ APCI | 2HCl | 9.31 | CHIRALPAK IA-3 Hexane/Ethanol/THF/Diethylamine = 70/20/10/0.1 Flow Rate 0.5 mL/min |
| 134b | (Enantiomer of 134a) | | | | 10.79 | |

Example 135

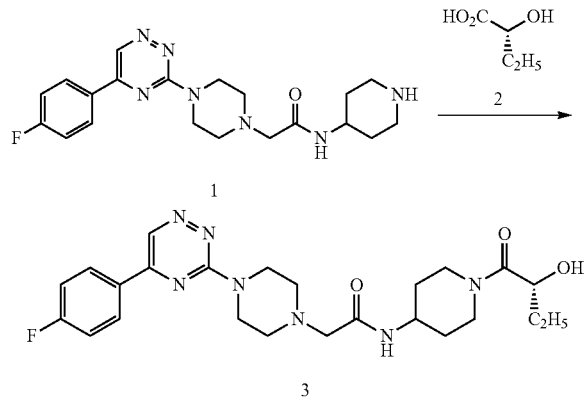

The compound 1 (107 mg) described in Example 125 and the compound 2 (42 mg) were dissolved in DMF (3 mL). Diisopropylethylamine (94 µL), 1-hydroxybenzotriazole (54 mg) and 1-(3-dimethylaminopropyl)-3-ethylcarbodiimide hydrochloride (77 mg) were added to the solution, and the reaction mixture was stirred for 18 hours at room temperature. The reaction mixture was diluted with a saturated aqueous solution of sodium bicarbonate, and extracted twice with ethyl acetate. The organic layer was washed with brine, and dried over anhydrous magnesium sulfate. The solvent was evaporated under reduced pressure, and the resulting residue was purified by silica gel column chromatography (eluent: chloroform-methanol; gradient: 100:0-95:5), treated with a solution of 4 mol/L of HCl in ethyl acetate. The precipitate was taken by filtration, and dried to give 5-(4-fluorophenyl)-3-[4-[[1-((R)-2-hydroxybutanoyl)piperidin-4-yl]carbamoylmethyl]piperazin-1-yl]-1,2,4-triazine 2 hydrochloride (53 mg) as an orange power.

MS (APCI) 486 [M+H]$^+$

Example 136-145

The corresponding starting compound was treated in a similar manner as described in the above Example 135 to give the compounds described in the following Table 15.

TABLE 15

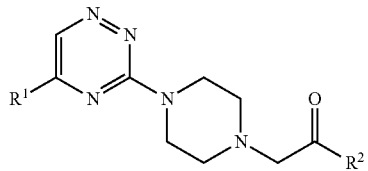

| Example | R$^1$ | R$^2$ | Ms | Salt |
|---|---|---|---|---|
| 136 | 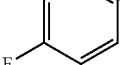 | 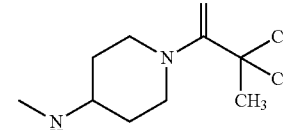 | 486 [M + H]+ APCI | 2HCl |
| 137 | 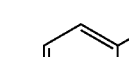 | 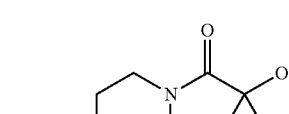 | 484 [M + H]+ APCI | 2HCl |
| 138 | 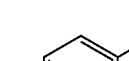 | 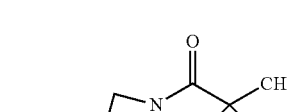 | 470 [M + H]+ APCI | |
| 139 |  | 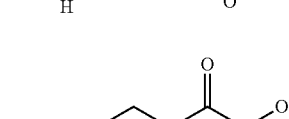 | 486 [M + H]+ APCI | 2HCl |

TABLE 15-continued
[Chemical formula 59]
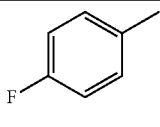
| Example | R¹ | R² | Ms | Salt |
|---|---|---|---|---|
| 140 | 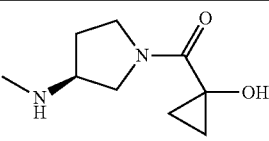 | 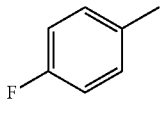 | 470 [M + H]+ APCI | 2HCl |
| 141 | 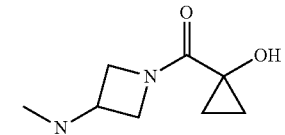 | 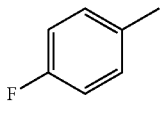 | 456 [M + H]+ APCI | |
| 142 | 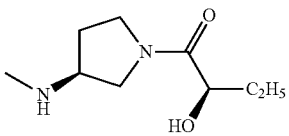 | 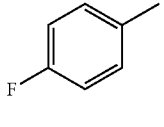 | 472 [M + H]+ APCI | 2HCl |
| 143 | 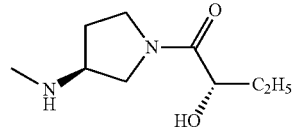 | 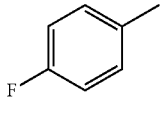 | 472 [M + H]+ APCI | 2HCl |
| 144 | 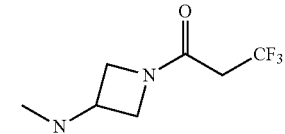 | 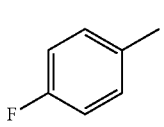 | 482 [M + H]+ APCI | |
| 145 | 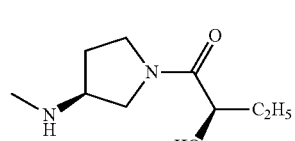 | 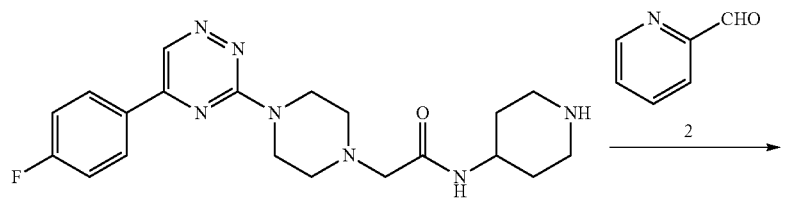 | 458 [M + H]+ APCI | 2HCl |
Example 146
[Chemical formula 60]
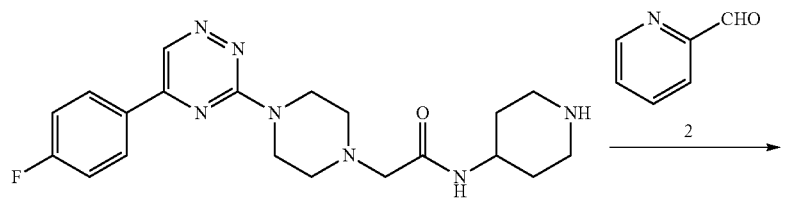

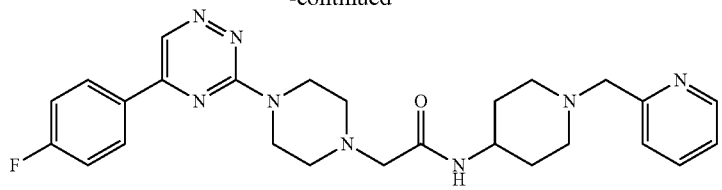

3

To a solution of the compound obtained in Example 125 (the compound 1, 151 mg) in chloroform (5 mL) were added the compound 2 (61 mg), acetic acid (22 μL), and sodium triacetoxyborohydride (160 mg), the reaction mixture was stirred for 14 hours at room temperature. The reaction mixture was diluted with a saturated aqueous solution of sodium bicarbonate, and then extracted twice with chloroform. The resulting organic layer was washed with brine, and then dried over sodium sulfate, followed by evaporation of the solvent. The resulting residue was dissolved in ethyl acetate, the solution was stand for 2 days to give crystals, the crystals were taken by filtration, and dried to give 5-(4-fluorophenyl)-3-[4-[[1-(2-pyridylmethyl) piperidin-4-yl]carbamoylmethyl]piperazin-1-yl]-1,2,4-triazine (87 mg) as a yellow solid.

MS (APCI) 491 [M+H]$^+$

Example 147

The corresponding starting compound was treated in a similar manner as described in the above Example 146 to give the compound described in the following Table 16.

TABLE 16

[Chemical formula 61]

| Example | R$^1$ | R$^2$ | Ms | Salt |
|---|---|---|---|---|
| 147 | 4-F-C$_6$H$_4$ | (1-(2-methyl-1H-imidazol-4-ylmethyl)piperidin-4-yl)(methyl)amino | 494 [M + H]+ APCI | 3HCl |

Example 148

[Chemical formula 62]

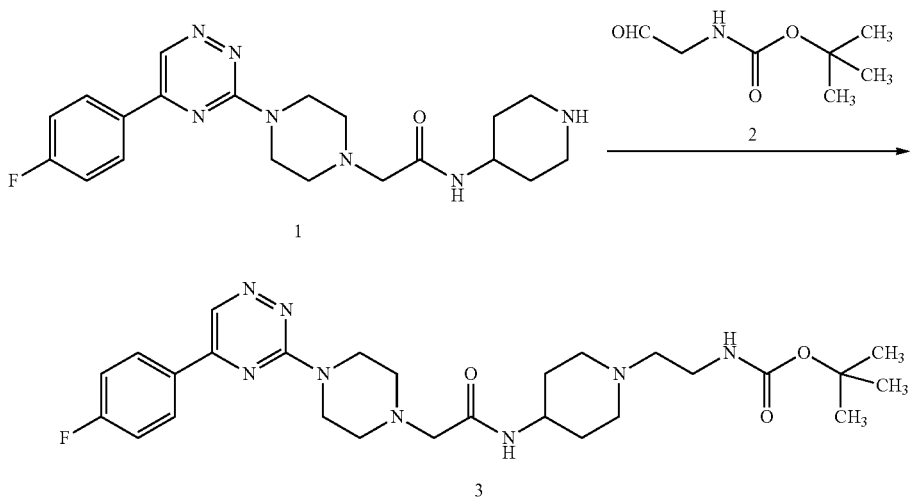

To a solution of the compound 2 (398 mg) in chloroform (5 mL) were added the compound obtained in Example 125 (the compound 1, 1.0 g) and sodium triacetoxyborohydride (795 mg) under ice-cooling, and the reaction mixture was stirred for 30 minutes. The reaction mixture was diluted with a saturated aqueous solution of sodium bicarbonate, and then extracted 3 times with chloroform. The resulting organic layer was dried over anhydrous sodium sulfate, and the solvent was evaporated under reduced pressure. The resulting residue was purified by NH-silica gel column chromatography (eluent: hexane-ethyl acetate; gradient: 30:70-0:100), and dried to give 3-[4-[[1-[2-(tert-butyloxycarbonylamino)ethyl]piperidin-4-yl]carbamoylmethyl]piperazin-1-yl]-5-(4-fluorophenyl)-1,2,4-triazine (1.02 g) as a yellow solid.

MS (APCI) 543 [M+H]$^+$

Example 149

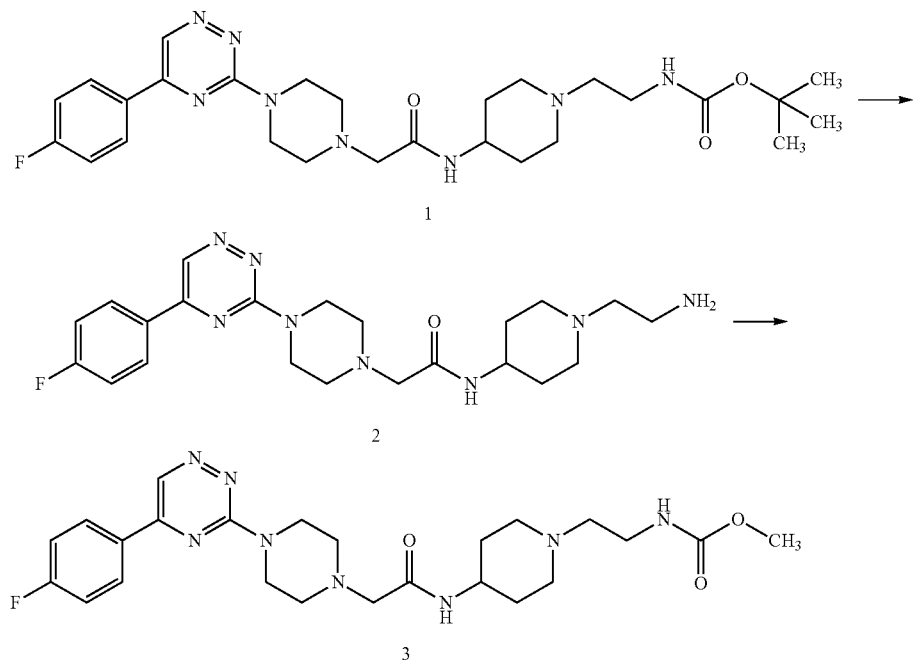

To a solution of the compound described in Example 148 (the compound 1, 200 mg) in chloroform (2 mL) was added trifluoroacetic acid (1 mL) under ice-cooling, and the reaction mixture was stirred for 30 minutes at room temperature.

The reaction mixture was diluted with methanol, the solution was treated with packed strong cation exchange resin (PoraPak Rxn Cx, eluent: a solution of 1 mol/L NH$_3$ in methanol), and the eluate was concentrated under reduced pressure. To a solution of the resulting residue in chloroform (2 mL) were added triethylamine (153 µL) and methyl chloroformate (57 µL) under argon atmosphere and ice-cooling, and the reaction mixture was stirred for 5 hours at room temperature. The reaction mixture was diluted with a saturated aqueous solution of sodium bicarbonate, and then extracted 4 times with chloroform. The resulting organic layer was dried over anhydrous sodium sulfate, and the solvent was evaporated under reduced pressure. The resulting residue was purified by silica gel column chromatography (eluent: chloroform-methanol; gradient: 100:0-95:5) to give 5-(4-fluorophenyl)-3-[4-[[1-[2-(methoxycarbonylamino)ethyl]piperidin-4-yl]carbamoylmethyl]piperazin-1-yl]-1,2,4-triazine (126 mg) as a yellow solid.

MS (APCI) 501 [M+H]$^+$

Example 150

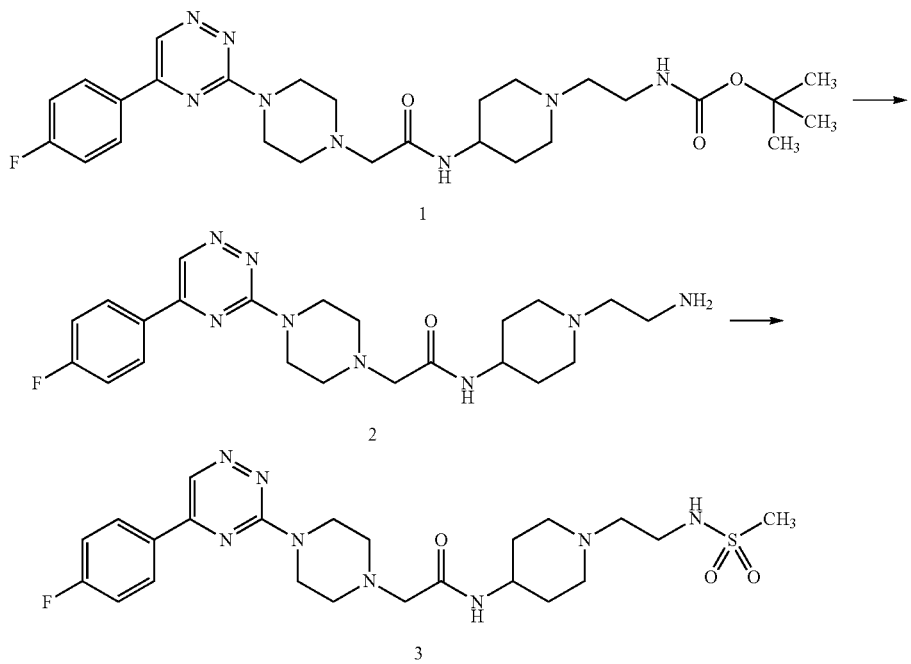

To a solution of the compound described in Example 148 (the compound 1, 200 mg) in chloroform (2 mL) was added trifluoroacetic acid (1 mL) under ice-cooling, and the reaction mixture was stirred for 30 minutes at room temperature.

The reaction mixture was diluted with methanol, the solution was treated with packed strong cation exchange resin (PoraPak Rxn Cx, eluent: a solution of 1 mol/L $NH_3$ in methanol), and the eluate was concentrated under reduced pressure. To a solution of the resulting residue in chloroform (2 mL) were added triethylamine (153 μL) and mesyl chloride (57 μL) under argon atmosphere and ice-cooling, and the reaction mixture was stirred for 5 hours at room temperature.

The reaction mixture was diluted with a saturated aqueous solution of sodium bicarbonate, and then extracted 4 times with chloroform. The resulting organic layer was dried over anhydrous sodium sulfate, and the solvent was evaporated under reduced pressure. The resulting residue was purified by silica gel column chromatography (eluent: chloroform-methanol; gradient: 100:0-95:5) to give 5-(4-fluorophenyl)-3-[4-[[1-[2-(methylsulfonylamino)ethyl]piperidin-4-yl]carbamoylmethyl]piperazin-1-yl]-1,2,4-triazine (85 mg) as a yellow solid.

MS (APCI) 521 [M+H]$^+$

Example 151

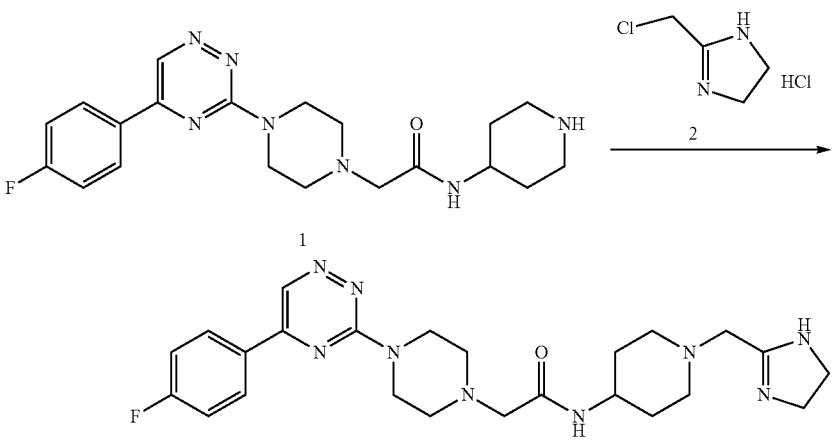

The compound described in Example 125 (the compound 1, 300 mg) and the compound 2 (151 mg) were suspended in DMF (6 mL).
Diisopropylethylamine (392 µL) was added to the suspension, and the reaction mixture was stirred for 13.5 hours at room temperature. The reaction mixture was diluted with a saturated aqueous solution of sodium bicarbonate, and extracted 3 times with chloroform. The organic layer was dried, and the solvent was evaporated under reduced pressure. The resulting residue was purified by silica gel column chromatography (eluent: chloroform-methanol-10% conc. ammonia water=90:9:1), and the resulting crystalline residue was precipitated from a mixed solution of ethanol-ethyl acetate, the crystals were taken by filtration, and dried to give 3-[4-[[1-[(4,5-dihydro-1H-imidazol-2-yl)methyl]piperidin-4-yl]carbamoylmethyl]piperazin-1-yl]-5-(4-fluorophenyl)-1,2,4-triazine (91 mg) as a yellow solid.

MS (APCI) 482 [M+H]$^+$

Example 152-156

The corresponding starting compound was treated in a similar manner as described in the above Example 151 to give the compounds described in the following Table 17.

TABLE 17

[Chemical formula 66]

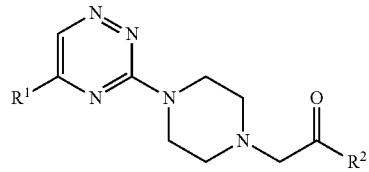

| Example | R$^1$ | R$^2$ | Ms | Salt |
|---|---|---|---|---|
| 152 | 4-F-phenyl | piperidine-N-CH$_2$-oxazole with NHCH$_3$ | 481 [M + H]+ APCI | |
| 153 | 4-F-phenyl | piperidine-N-CH$_2$-(4-CH$_3$-imidazole) with NHCH$_3$ | 494 [M + H]+ APCI | 3HCl |
| 154 | 4-Cl-phenyl | piperidine-N-CH$_2$-(4-CH$_3$-imidazole) with NHCH$_3$ | 510/512 [M + H]+ APCI | 2HCl |
| 155 | 4-F-phenyl | piperidine-N-CH$_2$-(1-CH$_3$-triazole) with NHCH$_3$ | 495 [M + H]+ APCI | |
| 156 | 4-F-phenyl | piperidine-N-CH$_2$-C(=O)NH$_2$ with NHCH$_3$ | 457 [M + H]+ APCI | |

Example 157a, Example 157b

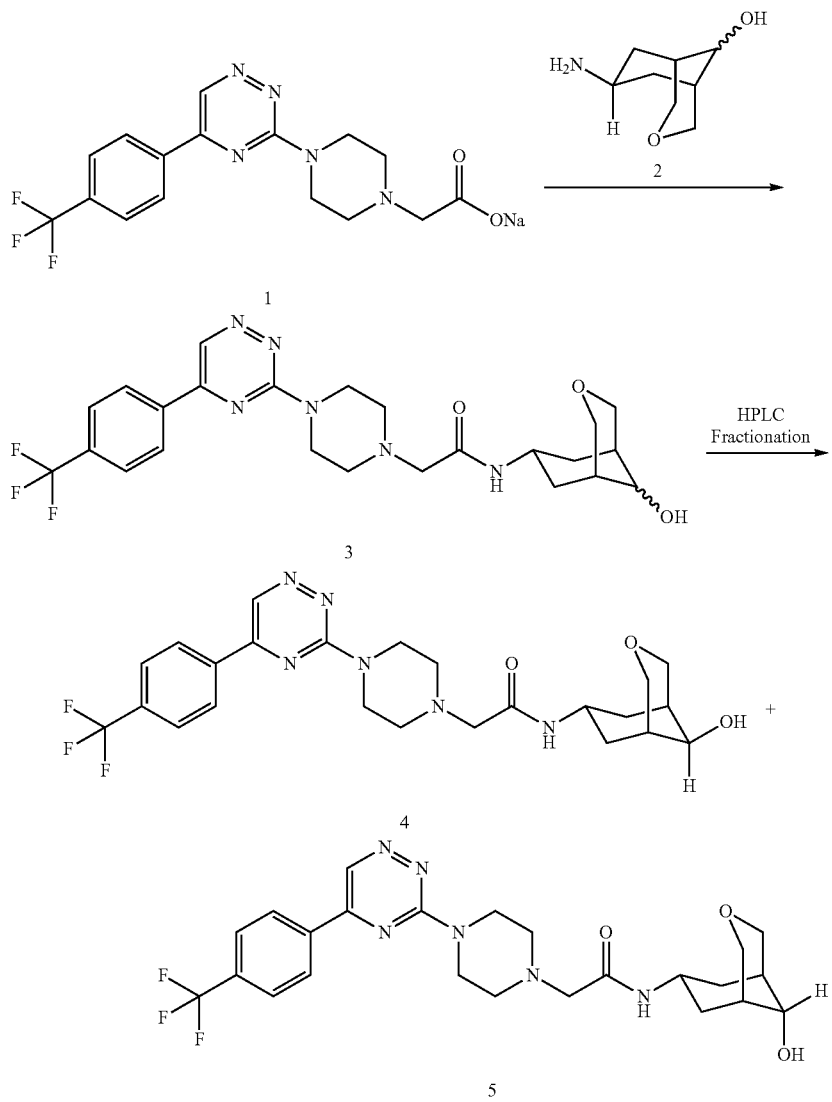

The compound 1 (297 mg) and the compound 2 (180 mg) were suspended in DMF (8 mL). Diisopropylethylamine (265 μL) and O-(7-azabenzotriazol-1-yl)-N,N,N',N'-tetramethyluroniumhexafluorophosphate (347 mg) were added to the suspension, and the reaction mixture was stirred for 30 minutes at room temperature. To the reaction mixture was added water and a saturated aqueous solution of sodium bicarbonate, and then the reaction mixture was extracted with chloroform. The organic layer was dried over anhydrous sodium sulfate, and then the solvent was evaporated under reduced pressure. The resulting residue was suspended and washed in a mixed solvent of ethyl acetate/hexane, taken by filtration, and dried. The resulting residue was isolated by recycle HPLC (Chiralpak IF (30×250), 2-propanol/THF/diethylamine=75/25/0.1, flow rate: 20 mL/min), and then the resulting fraction was concentrated under reduced pressure to give 3-[4-[[(7-exo-9-endo)-9-hydroxy-3-oxabicyclo[3.3.1]nonan-7-yl]carbamoylmethyl]piperazin-1-yl]-5-(4-trifluoromethylphenyl)-1,2,4-triazine (Example 157a, yellow solid, 83 mg), and 3-[4-[[(7-exo-9-exo)-9-hydroxy-3-oxabicyclo[3.3.1]nonan-7-yl]carbamoylmethyl]piperazin-1-yl]-5-(4-trifluoromethylphenyl)-1,2,4-triazine (Example 157b, yellow solid, 82 mg).

Example 157a

Retention time: 5.41 minutes (Chiralpak IF-3 (4.6×150), 2-propanol/THF/diethylamine=75/25/0.1, flow rate 0.5 mL/min)

MS (ESI) 507 [M+H]

Example 157b

Retention time: 8.48 minutes (Chiralpak IF-3 (4.6×150), 2-propanol/THF/diethylamine=75/25/0.1, flow rate 0.5 mL/min)

MS (APCI) 507 [M+H]

Example 158

The corresponding starting compound was treated in a similar manner as described in the above Example 157 to give the compounds described in the following Table 18.

TABLE 18

[Chemical formula 68]

| Example | R¹ | R² | Ms | Retention Time (min) | HPLC Conditions |
|---|---|---|---|---|---|
| 158a | | | 457 [M + H]+ APCI | 6.16 | CHIRALPAK IA-3 Hexane/2-Propanol/ THF/Diethylamine = 40/30/30/0.1 Flow Rate 0.5 mL/min |
| 158b | (Cis-form of 158a) | | | 7.28 | |

Example 159a, Example 159b

[Chemical formula 69]

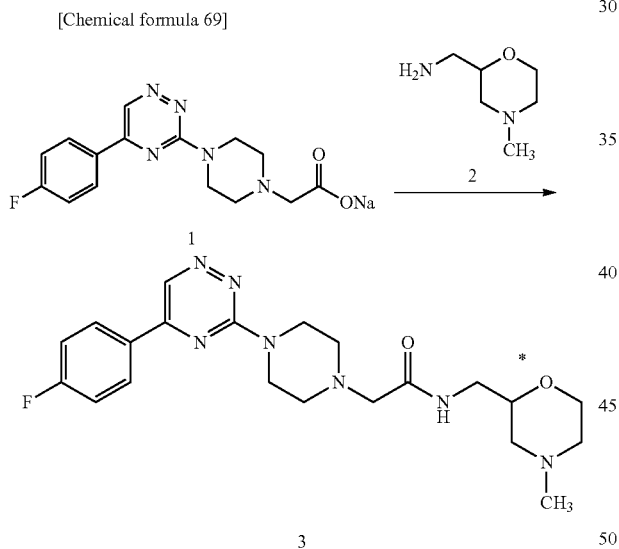

The compound 1 (250 mg) and the compound 2 (144 mg) were dissolved in DMF (7.5 mL). O-(7-azabenzotriazol-1-yl)-N,N,N',N'-tetramethyluroniumhexafluorophosphate (430 mg) was added to the solution, and the reaction mixture was stirred for 2 hours at room temperature. The reaction mixture was concentrated, and then the concentrate was diluted with water, and a saturated aqueous solution of potassium carbonate was added to the solution, and the reaction mixture was extracted 3 times with chloroform. The organic layer was dried over anhydrous sodium sulfate, and the solvent was evaporated under reduced pressure. The resulting residue was purified by NH-silica gel column chromatography (eluent: hexane-ethyl acetate; gradient: 50:50-0:100) to give a racemate of 5-(4-fluorophenyl)-3-[4-[[(4-methylmorpholyn-2-yl)methyl]carbamoylmethyl]piperazin-1-yl]-1,2,4-triazine (300 mg) as a yellow solid.

Then, two isomers having different steric configuration at a carbon atom labelled by "*" in the above formula of the racemate were isolated by recycle HPLC (Chiralpak IA (30×250), ethanol/diethylamine=100/0.1, flow rate: 20 mL/min). The obtained fraction containing each of the isomers was concentrated under reduced pressure, and the concentrate was treated with a solution of 4 mol/L HCl in ethyl acetate, followed by centrifugation to remove the supernatant. The precipitate was suspended, washed in diethyl ether, and the supernatant was removed by centrifugation, and dried to give two stereoisomers of 5-(4-fluorophenyl)-3-[4-[[(4-methylmorpholyn-2-yl)methyl]carbamoylmethyl]piperazin-1-yl]-1,2,4-triazine as a 2HCl salt (Example 159a, pale yellow powder, 150 mg and Example 159b, pale yellow powder, 134 mg).

Example 159a

Retention time: 10.60 minutes (Chiralpak IA-3 (4.6×150), ethanol/diethylamine=100/0.1, flow rate 0.5 mL/min)
Optical purity >99.8% ee
Absolute configuration R
MS (APCI) 430 [M+H]⁺

Example 159b

Retention time: 12.63 分 (Chiralpak IA-3 (4.6×150), ethanol/diethylamine=100/0.1, flow rate 0.5 mL/min)
Optical purity 97.2% ee
Absolute configuration S
MS (APCI) 430 [M+H]⁺

Example 160-168

The corresponding starting compound was treated in a similar manner as that of the above Example 159 to give the compounds described in the following Tables 19 and 20. However, the stereochemistry for a substituent of the carbon atom labelled by "*" does not specify their absolute configuration.

TABLE 19

[Chemical formula 70]

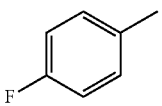

| Example | R¹ | R² | Ms | Salt | Retention Time (min) | HPLC Conditions |
|---|---|---|---|---|---|---|
| 160a | 4-F-phenyl | cyclohexyl with *NH-CH₃ and *N(CH₃)₂ | 442 [M + H]+ APCI | 2HCl | 15.14 | CHIRALPAK IC-3 2-Propanol/ Acetonitrile/ Diethylamine = 50/50/0.5 Flow Rate 0.5 mL/min |
| 160b | (Enantiomer of 160a) | | | | 11.49 | |
| 161a | 4-Cl-phenyl | tetrahydropyran with *NH-CH₃ and *OH | 433/435 [M + H]+ APCI | | 10.11 | CHIRALPAK IA-3 Methanol/THF/ Diethylamine = 90/10/0.1 Flow Rate 0.5 mL/min |
| 161b | (Enantiomer of 161a) | | | | 11.31 | |
| 162 | 4-CF₃-phenyl | tetrahydrofuran with *NH-CH₃ and *OH | 453 [M + H]+ APCI | | 10.24 | CHIRALPAK IC-3 Methanol/THF/ Diethylamine = 95/5/0.1 Flow Rate 0.5 mL/min |
| 163 | 4-CF₃-phenyl | tetrahydrofuran with *NH-CH₃ and *OH | 453 [M + H]+ APCI | | 11.70 | CHIRALPAK IC-3 Methanol/THF/ Diethylamine = 95/5/0.1 Flow Rate 0.5 mL/min |
| 164a | 4-CF₃-phenyl | tetrahydrofuran with *NH-CH₃ and *OH | 453 [M + H]+ APCI | | 9.79 | CHIRALPAK IC-3 Methanol/THF/ Diethylamine = 95/5/0.1 Flow Rate 0.5 mL/min |
| 164b | (Enantiomer of 164a) | | | | 12.25 | |

TABLE 20

[Chemical formula 71]

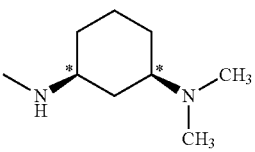

| Example | R¹ | R² | Ms | Salt | Retention Time (min) | HPLC Conditions |
|---|---|---|---|---|---|---|
| 165a | 4-F-phenyl | cyclohexyl with *NH-CH₃ and *SO₂CH₃ | 477 [M + H]+ APCI | | 7.61 | CHIRALPAK IA-3 Methanol/THF/ Diethylamine = 95/5/0.1 Flow Rate 0.5 mL/min |

TABLE 20-continued

[Chemical formula 71]

| Example | R¹ | R² | Ms | Salt | Retention Time (min) | HPLC Conditions |
|---|---|---|---|---|---|---|
| 165b | (Enantiomer of 165a) | | | | 9.63 | |
| 166a | 4-chlorophenyl | (methylamino)(hydroxy)tetrahydropyran | 433/435 [M + H]+ APCI | | 6.89 | CHIRALPAK IC-3 Methanol/THF/ Diethylamine = 90/10/0.1 Flow Rate 0.5 mL/min |
| 166b | (Enantiomer of 166a) | | | | 8.98 | |
| 167a | 4-fluorophenyl | (methylamino)(acetamido)cyclohexane | 456 [M + H]+ APCI | | 4.82 | CHIRALCEL OJ-3 Methanol/ Diethylamine = 100/0.1 Flow Rate 0.5 mL/min |
| 167b | (Enantiomer of 167a) | | | | 5.98 | |
| 168a | 4-fluorophenyl | (methylamino)tetrahydroimidazopyridine | 437 [M + H]+ APCI | | 9.74 | CHIRALPAK IC-3 Methanol/THF/ Diethylamine = 85/15/0.1 Flow Rate 0.5 mL/min |
| 168b | (Enantiomer of 168a) | | | | 11.0 | |
| 169a | 4-methylphenyl | (methylamino)(hydroxy)tetrahydropyran | 413 [M + H]+ ESI | | 11.1 | CHIRALPAK IC-3 Methanol/Acetonitrile/ Diethylamine = 80/20/0.1 Flow Rate 0.5 mL/min |
| 169b | (Enantiomer of 169a) | | | | 13.3 | |

Example 170

[Chemical formula 72]

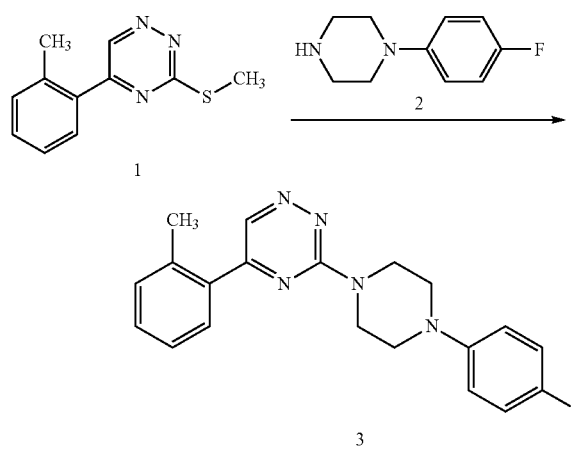

The compound 1 (2 g) and the compound 2 (11.6 g) were suspended in N-methylpyrrolidone (3.5 mL), and the suspension was stirred for 1.5 hours at 235° C. in a microwave reactor (Initiator, Biotage). The reaction mixture was cooled to room temperature, diluted with ethyl acetate, and then the solution was washed with water and brine, and dried. The solvent was evaporated under reduced pressure, and the resulting residue was purified by silica gel column chromatography (eluent: hexane-ethyl acetate; gradient: 80:20-65:35). The resulting crystalline residue was suspended and washed in a mixed solvent of ethyl acetate-hexane (1:5), taken by filtration, and dried to give 3-[4-(4-fluorophenyl)piperazin-1-yl]-5-(o-tolyl)-1,2,4-triazine (2.6 g) as a yellow solid.

MS (APCI) 350 [M+H]⁺

Example 171-173

The corresponding starting compound was treated in a similar manner as that of the above Example 170 to give the compounds described in the following Table 21.

TABLE 21

[Chemical formula 73]

| Example | R¹ | R² | MS [M + H]⁺ |
|---|---|---|---|
| 171 | CH₃ (o-tolyl) | N-methylpiperazinyl-benzimidazole | 372 (ESI) |
| 172 | CH₃ (o-tolyl) | N-methylisoindolinyl | 289 (ESI) |
| 173 | 2,3-dimethylthienyl | 4-methylmorpholinyl | 263 (ESI) |

Example 174

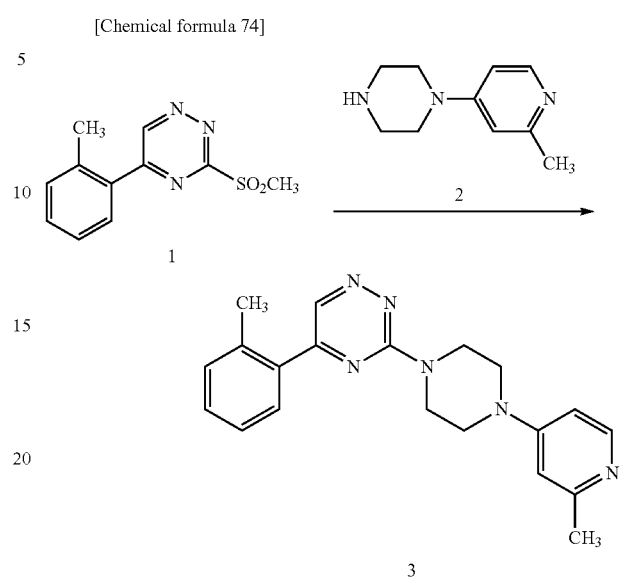

To a solution of the compound 1 (142 mg) in anhydrous THF (2 mL) was added the compound 2 (100 mg), and the reaction mixture was stirred for 6.5 hours at room temperature under argon atmosphere. The reaction mixture was diluted with ethyl acetate, and then the solution was washed with water and brine, and dried. The solvent was evaporated under reduced pressure, and the resulting residue was purified by NH-silica gel column chromatography (eluent: hexane-ethyl acetate; gradient: 30:70-0:100) to give 3-[4-(2-methyl-4-pyridyl) piperazin-1-yl]-5-(o-tolyl)-1,2,4-triazine (76 mg) as a yellow solid.

MS (APCI) 347 [M+H]⁺

Example 175-208

The corresponding starting compound was treated in a similar manner as described in the above Example 174 to give the compounds described in the following Tables 22-25.

TABLE 22

[Chemical formula 75]

| Example | R¹ | R² | Ms | Salt |
|---|---|---|---|---|
| 175 | CH₃ (o-tolyl) | N-methylpiperazinyl-acetyl | 298 [M + H]+ APCI |  |
| 176 | CH₃ (o-tolyl) | N-methylpiperazinyl-(1-methylpyrazol-4-yl) | 336 [M + H]+ APCI |  |

TABLE 22-continued
[Chemical formula 75]
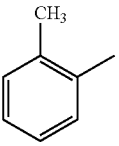
| Example | R¹ | R² | Ms | Salt |
|---|---|---|---|---|
| 177 | 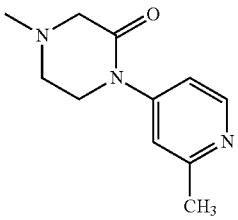 | 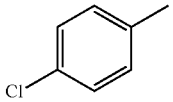 | 361 [M + H]+ APCI | |
| 178 | 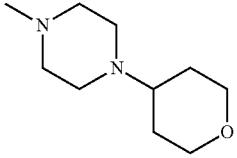 | 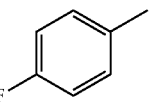 | 360/362 [M + H]+ APCI | |
| 179 | 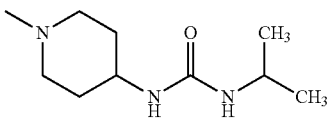 | 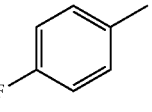 | 359 [M + H]+ APCI | |
| 180 | 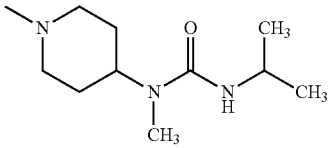 | 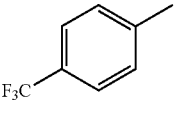 | 373 [M + H]+ ESI | HCl |
| 181 | 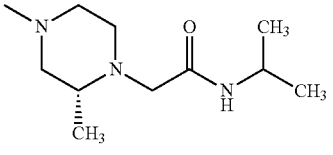 | 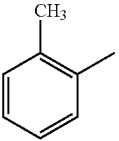 | 423 [M + H]+ APCI | |
| 182 | 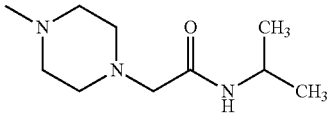 | 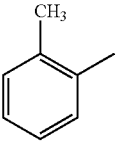 | 355 [M + H]+ APCI | 2HCl |
TABLE 23
[Chemical formula 76]
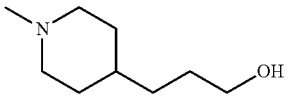
| Example | R¹ | R² | Ms | Salt |
|---|---|---|---|---|
| 183 | CH₃ (o-tolyl) | N-methylpiperidin-4-yl-propanol | 313 [M + H]+ APCI | |

TABLE 23-continued
[Chemical formula 76]
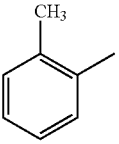
| Example | R¹ | R² | Ms | Salt |
|---|---|---|---|---|
| 184 | 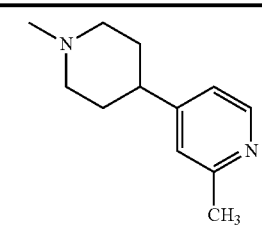 | 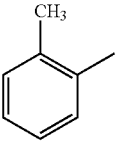 | 346 [M + H]+ APCI | |
| 185 | 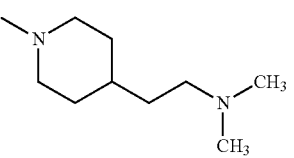 | 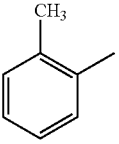 | 326 [M + H]+ APCI | |
| 186 | 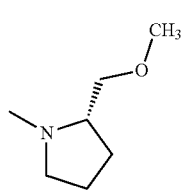 | 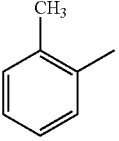 | 285 [M + H]+ APCI | |
| 187 | 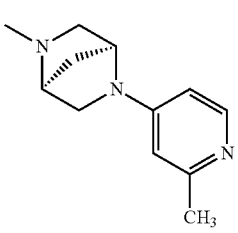 | 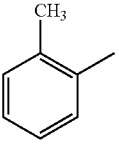 | 359 [M + H]+ APCI | 2HCl |
| 188 | 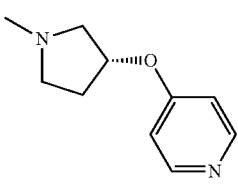 | 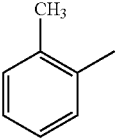 | 334 [M + H]+ APCI | |
| 189 | 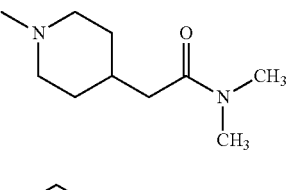 | 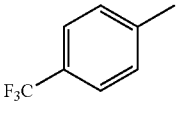 | 340 [M + H]+ APCI | |
| 190 | 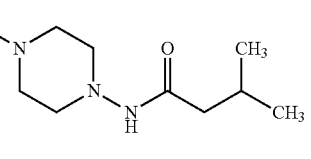 | 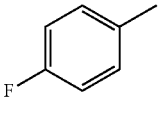 | 409 [M + H]+ APCI | |
| 191 | 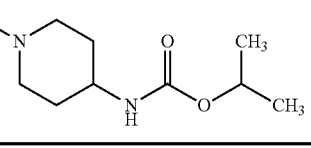 | | 360 [M + H]+ APCI | |

TABLE 24

[Chemical formula 77]

| Example | R¹ | R² | Ms |
|---------|----|----|-----|
| 192 | 2-naphthyl | -N(CH₃)CH₂CH₂CH₂SO₂CH₃ | 357 [M + H]+ APCI |
| 193 | 2-naphthyl | -NH-CH₂-(4-cyanophenyl) | 338 [M + H]+ APCI |
| 194 | 2-naphthyl | -N(CH₃)CH₂CH₂O-(4-fluorophenyl) | 375 [M + H]+ APCI |
| 195 | 2-naphthyl | -NH-CH₂-(4-(2-hydroxypropan-2-yl)cyclohexyl) | 377 [M + H]+ APCI |
| 196 | 2-naphthyl | -NH-CH₂-(1-acetylpiperidin-4-yl) | 362 [M + H]+ APCI |
| 197 | 2-naphthyl | (3)-1-methyl-3-methoxypiperidinyl | 321 [M + H]+ APCI |
| 198 | 2-naphthyl | 1-methyl-4-(acetamido)piperidinyl | 348 [M + H]+ APCI |
| 199 | 2-naphthyl | 8-methyl-1-oxa-3,8-diazaspiro[4.5]decan-2-one | 362 [M + H]+ APCI |
| 200 | 2-naphthyl | 1-methyl-4-(2-oxopyrrolidin-1-yl)piperidinyl | 374 [M + H]+ APCI |
| 201 | 2-naphthyl | 1-methyl-4-(2-oxopiperidin-1-yl)piperidinyl | 388 [M + H]+ APCI |

TABLE 25

[Chemical formula 78]

| Example | R¹ | R² | Ms | Salt |
|---|---|---|---|---|
| 202 | 2-naphthyl | 1-methylpiperidin-4-yl-CH₂-SO₂CH₃ | 383 [M + H]+ APCI | |
| 203 | 2-naphthyl | 1-methyl-4-cyanopiperidin-4-yl | 316 [M + H]+ APCI | HCl |
| 204 | 2-naphthyl | 1-methylpiperidin-4-yl-O-CH₂-C(O)N(CH₃)₂ | 392 [M + H]+ APCI | |
| 205 | 2-naphthyl | (3S)-1-methylpiperidin-3-yl-CH₂-NHC(O)CH₃ | 362 [M + H]+ APCI | |
| 206 | 4-fluorophenyl | 1-methyl-4-hydroxypiperidin-4-yl | 275 [M + H]+ APCI | |
| 207 | 4-fluorophenyl | 1-methylpiperidin-4-yl-NHC(O)OC(CH₃)₃ | 374 [M + H]+ APCI | |
| 208 | 4-fluorophenyl | 1-methylpiperidin-4-yl-CH(OH)C(O)OCH₃ | 347 [M + H]+ APCI | |

Example 209

[Chemical formula 79]

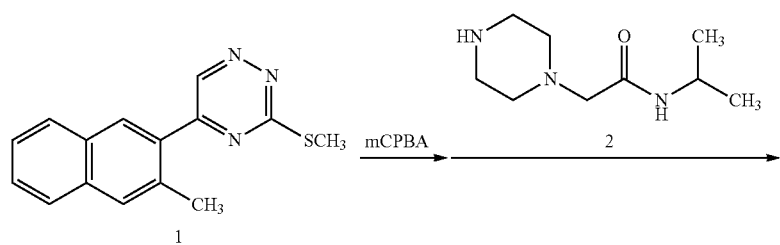

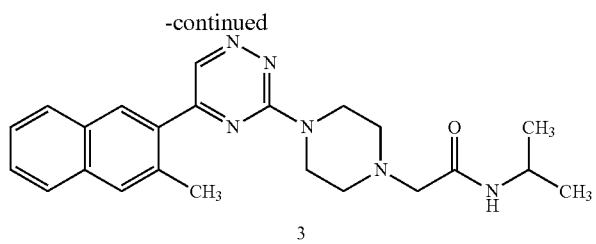

3

To a solution of the compound 1 (100 mg) in dichloromethane (4 mL) was added hydrous 25% m-chloroperbenzoic acid (202 mg), and the reaction mixture was stirred for 15.5 hours at room temperature. The reaction mixture was treated with an aqueous solution of sodium thiosulfate, and then extracted with ethyl acetate. The organic layer was washed with a saturated aqueous solution of sodium bicarbonate, and then dried over anhydrous sodium sulfate, and the solvent was evaporated under reduced pressure. The resulting residue was suspended in acetonitrile (2 mL), and the compound 2 (106 mg) and diisopropylethylamine (98 µL) were added to the suspension. The reaction mixture was stirred for 30 minutes at room temperature, and then stirred for additional 3 hours at 60° C. under argon atmosphere. The reaction mixture was cooled to room temperature, and then diluted with water, and extracted twice with chloroform. The resulting organic layer was dried over anhydrous sodium sulfate, and the solvent was evaporated under reduced pressure. The resulting residue was purified by NH-silica gel column chromatography (eluent: hexane-ethyl acetate; gradient: 90:10-60:40) to give 5-(3-methyl-2-naphthyl)-3-[4-(isopropylcarbamoylmethyl) piperazin-1-yl]-1,2,4-triazine (123 mg) as a yellow viscous substance.

MS (APCI) 405 [M+H]$^+$

Example 210

[Chemical formula 80]

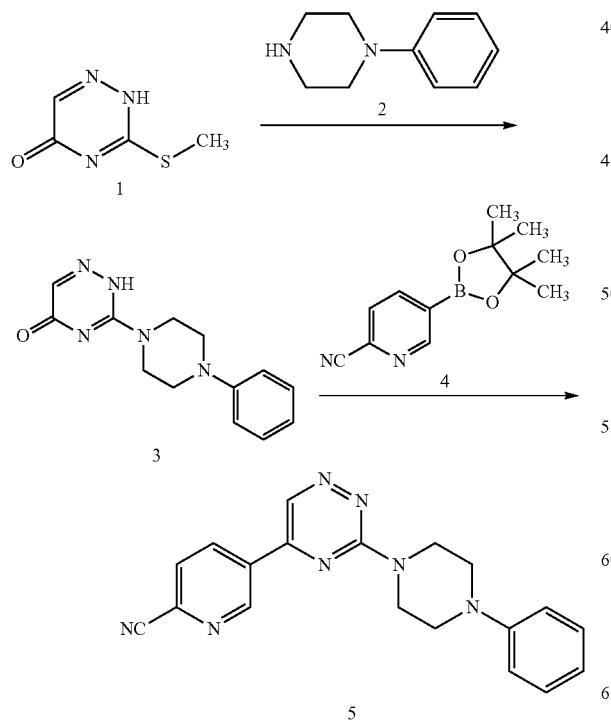

(1) The compound 1 (1 g) and the compound 2 (3.4 g) were suspended in THF (30 mL, and the suspension was stirred for 1 day under argon atmosphere with heating to reflux. The reaction mixture was cooled to room temperature, the precipitate was taken by filtration, washed with ethyl acetate, and dried to give the compound 3 (1.3 g) as colorless solid.

MS (APCI) 258 [M+H]$^+$ (2) The compound 3 (100 mg) and 1H-benzotriazol-1-yloxytripyrrolidinophosphoniumhexafluorophosphate (217 mg) were suspended in dioxane (4 mL). Triethylamine (163 µL) was added to the suspension, and the reaction mixture was stirred for 2 hours at room temperature under argon atmosphere. To the reaction mixture was added dichlorobis (triphenylphosphine) palladium (14 mg). The compound 4 (179 mg) and sodium carbonate (206 mg) were added to the reaction mixture, and water (1 mL) was further added thereto, and the reaction mixture was stirred for 4 hours at 100° C. The reaction mixture was cooled to room temperature, diluted with ethyl acetate, and then washed with a saturated aqueous solution of sodium bicarbonate and brine, and dried. The solvent was evaporated under reduced pressure, and the resulting residue was purified by silica gel column chromatography (eluent: hexane-ethyl acetate; gradient: 65:35-50:50) to give 5-(2-cyano-5-pyridyl)-3-(4-phenylpiperazin-1-yl)-1,2,4-triazine (22 mg) as a yellow solid.

MS (APCI) 344 [M+H]$^+$

Example 211

[Chemical formula 81]

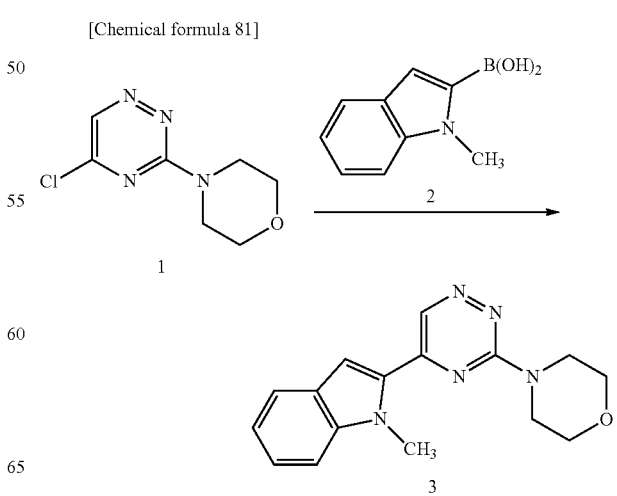

To a mixed solution of the compound 1 (60 mg), the compound 2 (63 mg), and dichlorobis(triphenylphosphine) palladium (10 mg) in dioxane (2 mL) was added an aqueous solution of 2 mol/L sodium carbonate (1.0 mL). The reaction mixture was stirred for 15 minutes at 150° C. in a microwave reactor (Initiator, Biotage). The reaction mixture was cooled to room temperature, diluted with ethyl acetate, and then the solution was washed with water and brine, and dried.

The solvent was evaporated under reduced pressure, then the resulting crystalline residue was suspended and washed in a mixed solvent of hexane-ethyl acetate (2:1), taken by filtration, and dried to give 5-(1-methyl-1H-indol-2-yl)-3-morpholino-1,2,4-triazine (50 mg) as a yellow solid.

MS (APCI) 296 [M+H]$^+$

Example 212-213

The corresponding starting compound was treated in a similar manner as that of the above Example 211 to give the compounds described in the following Table 26.

TABLE 26

[Chemical formula 82]

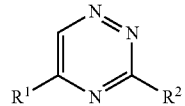

| Example | R$^1$ | R$^2$ | MS [M + H]$^+$ |
|---|---|---|---|
| 212 | 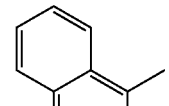 | 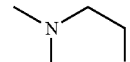 | 307 (APCI) |
| 213 |  | 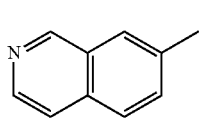 | 294 (APCI) |

Example 214

[Chemical formula 83]

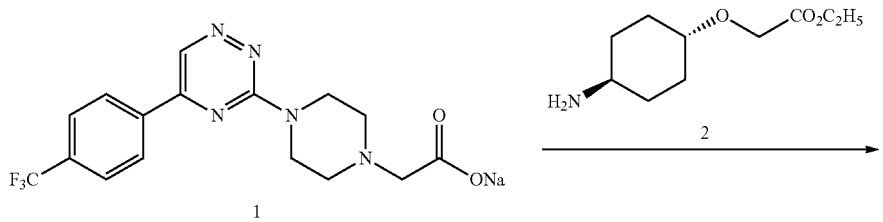

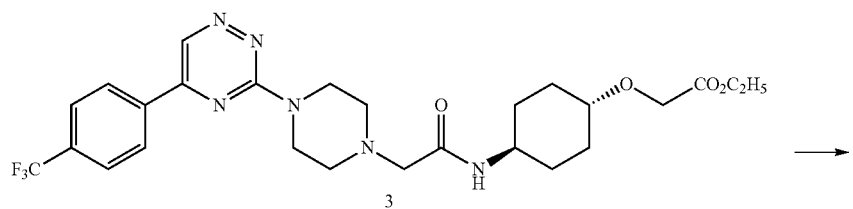

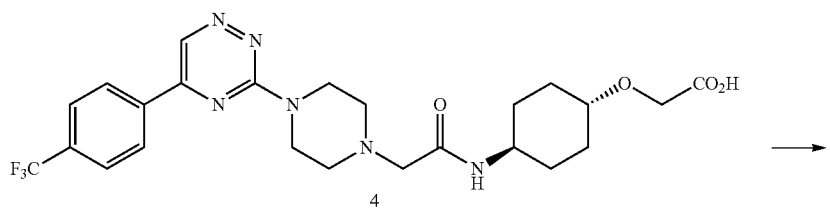

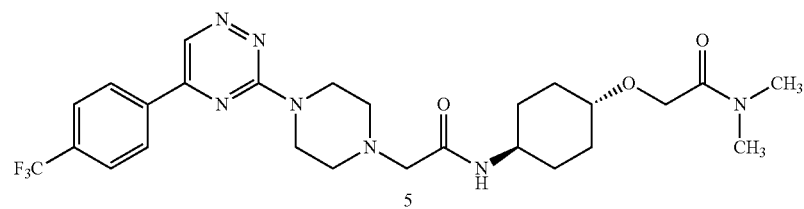

(1) The compound 1 (400 mg) was dissolved in DMF (10 mL). The compound 2 (70 mg), diisopropylethylamine (360 µL) and O-(7-azabenzotriazol-1-yl)-N,N,N',N'-tetramethyluroniumhexafluorophosphate (781 mg) were added to the solution, and the reaction mixture was stirred for 1.5 hours at room temperature. To the reaction mixture was added water, and then the reaction mixture was extracted with chloroform. The organic layer was dried over anhydrous sodium sulfate, and then the solvent was evaporated under reduced pressure. The resulting residue was purified by NH-silica gel column chromatography (eluent: hexane-ethyl acetate; gradient: 50:50-0:100) to give the compound 3 (443 mg) as a yellow solid.

MS (APCI) 551 [M+H]$^+$ (2) The compound 3 (430 mg) was dissolved in ethanol (8 mL)-THF (2 mL). An aqueous solution of 1 mol/L of sodium hydroxide (8 mL) was added to the solution, and the reaction mixture was stirred for 20 hours at room temperature. The reaction mixture was concentrated under reduced pressure, and the residue was dissolved in water. A pH of the solution was adjusted to pH 4-5 by adding an aqueous solution of 1 mol/L hydrochloric acid, and then the reaction mixture was extracted with chloroform. The organic layer was dried over anhydrous sodium sulfate, and then the solvent was evaporated under reduced pressure to give the compound 4 (349 mg) as a yellow solid.

MS (APCI) 523 [M+H]$^+$ (3) The compound 4 (100 mg) was dissolved in DMF (1.9 mL). A solution of 1 mol/L dimethylamine in THF (190 µL), diisopropylethylamine (70 µL) and O-(7-azabenzotriazol-1-yl)-N,N,N',N'-tetramethyluroniumhexafluorophosphate (95 mg) were added to the solution, and the reaction mixture was stirred for 1 hour at room temperature. To the reaction mixture was added water, and then the reaction mixture was extracted with chloroform. The organic layer was dried over anhydrous sodium sulfate, and then the solvent was evaporated under reduced pressure. The resulting residue was purified by silica gel column chromatography (eluent: chloroform-methanol; gradient: 100:0-95:5), treated with a solution of 4 mol/L HCl in ethyl acetate, and the supernatant was removed by centrifugation, and then the precipitate was dried to give 5-(4-trifluoromethylphenyl)-3-[4-[[trans-4-(N,N-dimethylcarbamoylmethyloxy)cyclohexyl]carbamoylmethyl]piperazin-1-yl]-1,2,4-triazine (yellow powder, 83 mg) as a HCl salt.

MS (APCI) 550 [M+H]$^+$

Example 215

[Chemical formula 84]

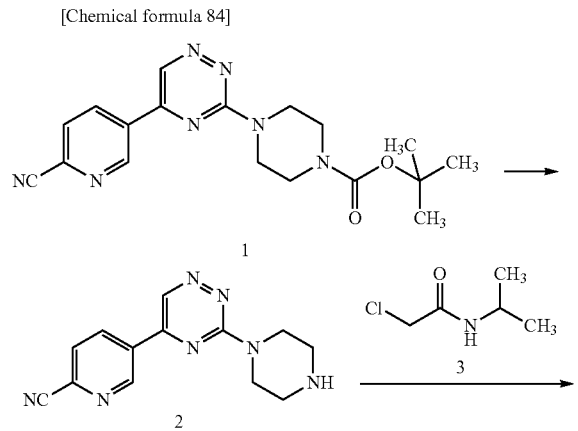

(1) To a solution of the compound 1 (152 mg) in dichloromethane (2 mL) was added trifluoroacetic acid (2 mL), and the reaction mixture was stirred for 30 minutes at room temperature. The reaction mixture was concentrated under reduced pressure, and the resulting residue was dissolved in ethyl acetate, and then the solution was treated with an aqueous solution of 40% potassium carbonate. The aqueous layer was saturated with potassium carbonate, and then extracted 3 times with a mixed solvent of ethyl acetate-THF. The organic layer was dried over anhydrous magnesium sulfate, and the solvent was evaporated under reduced pressure. The resulting crystalline residue was suspended and washed in a mixed solvent of ethyl acetate-hexane, taken by filtration, and dried to give the compound 2 (102 mg) as a yellow solid.

MS (APCI) 268 [M+H]$^+$ (2) The compound 2 (30 mg), the compound 3 (30 mg) and sodium carbonate (24 mg) were suspended in acetonitrile (3 mL), and the suspension was stirred for 14 hours at 60° C. under argon atmosphere. The reaction mixture was cooled to room temperature, diluted with ethyl acetate, and then the solution was washed with water and brine, and dried over anhydrous magnesium sulfate. The solvent was evaporated under reduced pressure, and the resulting residue was purified by silica gel column chromatography (eluent: ethyl acetate-methanol; gradient: 100:0-95:5) to give 5-(2-cyano-5-pyridyl)-3-[4-(isopropylcarbamoylmethyl) piperazin-1-yl]-1,2,4-triazine (20 mg) as a yellow solid.

MS (APCI) 367 [M+H]$^+$

Example 216-227

The corresponding starting compound was treated in a similar manner as that of the above Example 215 to give the compounds described in the following Table 27.

TABLE 27

[Chemical formula 85]

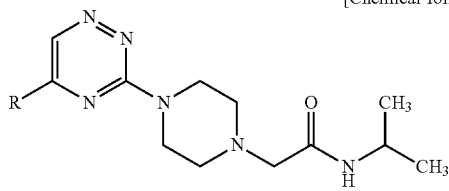

| Example | R | Ms | Salt |
|---------|---|----|----|
| 216 | 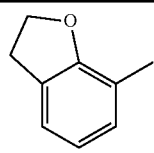 | 383 [M + H]+ APCI | |

TABLE 27-continued

[Chemical formula 85]

| Example | R | Ms | Salt |
|---|---|---|---|
| 217 | 6-methylisochroman | 397 [M + H]+ APCI | 2HCl |
| 218 | 8-methylisochroman | 397 [M + H]+ APCI | 2HCl |
| 219 | 5-methyl-2,3-dihydrobenzofuran | 383 [M + H]+ APCI | |
| 220 | 6-methylbenzothiazole | 398 [M + H]+ APCI | |
| 221 | 4-(trifluoromethyl)phenyl | 409 [M + H]+ APCI | |
| 222 | 1-methyl-5-yl-1H-indazole | 395 [M + H]+ APCI | |

TABLE 27-continued

[Chemical formula 85]

| Example | R | Ms | Salt |
|---|---|---|---|
| 223 | 1,7-dimethyl-1H-indazole | 395 [M + H]+ APCI | |
| 224 | 3-chlorophenyl | 375/377 [M + H]+ APCI | |
| 225 | 2,3,6-trifluoro-methylphenyl | 395 [M + H]+ APCI | |
| 226 | 4-methylcyclohex-1-en-1-yl (with H₃C) | 359 [M + H]+ APCI | |
| 227 | 3,4-difluorophenyl | 377 [M + H]+ APCI | |

Example 228

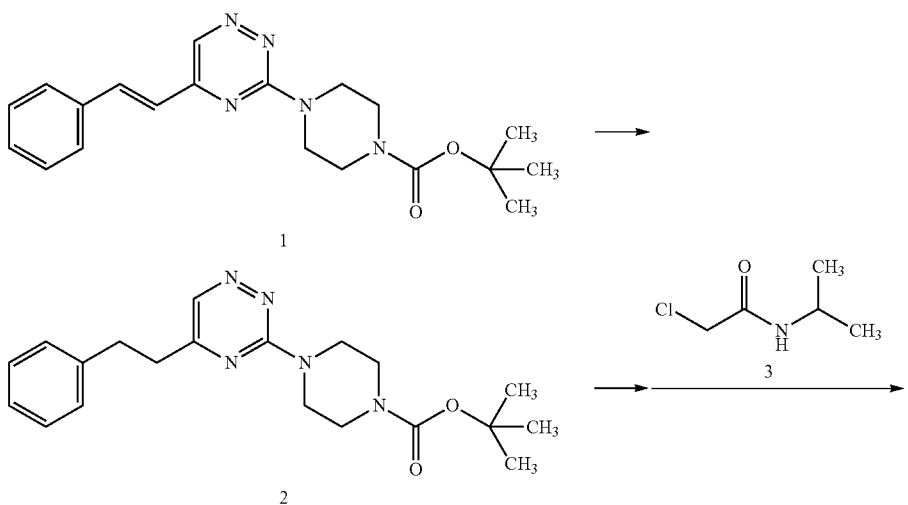

-continued

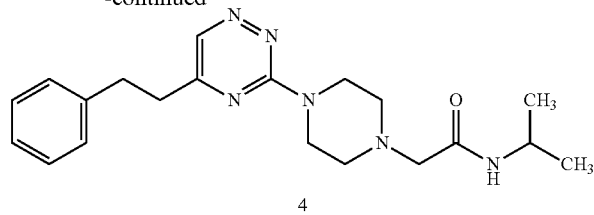

4

(1) To a solution of the compound 1 (177 mg) in methanol (7 mL)-triethylamine (1.2 mL) was added wet 10% palladium on carbon (53 mg), and the reaction mixture was stirred for 1 hour under hydrogen atmosphere. The palladium on carbon was removed by filtration, and then washed with methanol. The filtrate was concentrated under reduced pressure, and the resulting residue was purified by silica gel column chromatography (eluent: hexane-chloroform; gradient: 70:30-40:60) to give the compound 2 (87 mg) as a yellow solid.

MS (ESI) 370 [M+H]+

(2) To a solution of the compound 2 (112 mg) in dichloromethane (2 mL) was added trifluoroacetic acid (2 mL), and the reaction mixture was stirred for 1 hour at room temperature. The reaction mixture was diluted with methanol, then the solution was treated with packed strong cation exchange resin (PoraPak Rxn Cx, eluent: a solution of 1 mol/L NH3 in methanol), and the eluate was concentrated under reduced pressure. The resulting residue, the compound 3 (82 mg) and sodium carbonate (64 mg) were suspended in acetonitrile (3 mL), and the suspension was stirred for 19 hours at 65° C. under argon atmosphere. The reaction mixture was cooled to room temperature, diluted with chloroform, and then washed with water, and dried over anhydrous sodium sulfate. The solvent was evaporated under reduced pressure, and the resulting residue was purified by silica gel column chromatography (eluent: hexane-ethyl acetate; gradient: 80:20-50:50) to give 3-[4-(isopropylcarbamoylmethyl) piperazin-1-yl]-5-phenethyl-1,2,4-triazine (101 mg) as a yellow viscous substance.

MS (APCI) 369 [M+H]+

[Chemical formula 88]

Example 229-230

The corresponding starting compound was treated in a similar manner as that of the above Example 228 to give the compounds described in the following Table 28.

TABLE 28

[Chemical formula 87]

| Example | R | Ms |
|---|---|---|
| 229 | (2-methyl-tetralinyl) | 395 [M + H]+ APCI |
| 230 | (trans-4-methylcyclohexyl) | 361 [M + H]+ APCI |

Example 231

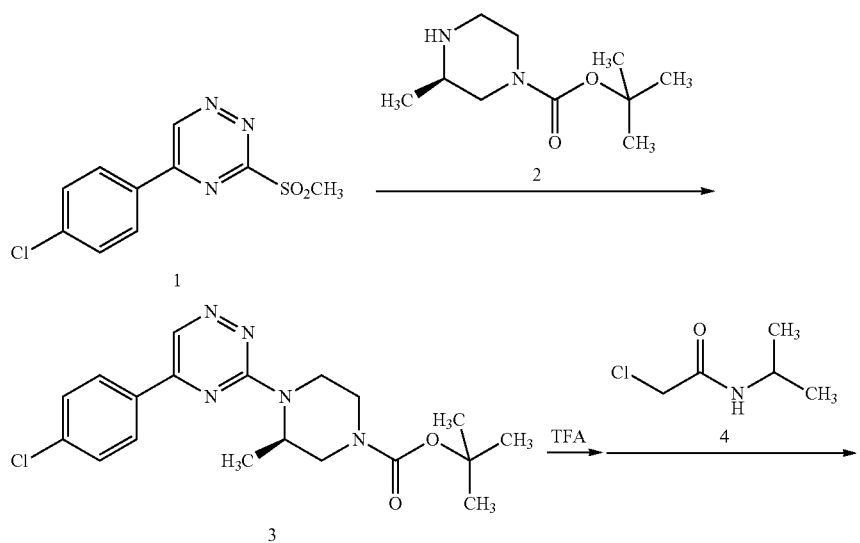

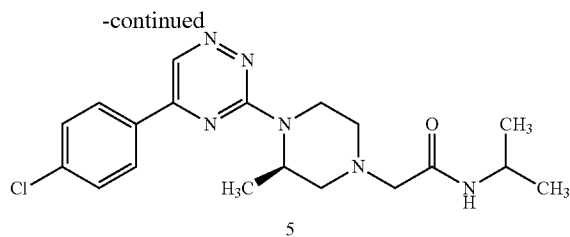
5

(1) To a solution of the compound 1 (500 mg) in anhydrous DMF (3.7 mL) was added the compound 2 (1100 mg), and the reaction mixture was stirred for 5 hours at room temperature under argon atmosphere, and then stirred for 3 hours at 60° C. The reaction mixture was cooled to room temperature, diluted with water, and then extracted 3 times with chloroform. The organic layer was dried over anhydrous sodium sulfate, and the solvent was evaporated under reduced pressure. The resulting residue was purified by NH-silica gel column chromatography (eluent: hexane-ethyl acetate; gradient: 85:15-60:40) to give the compound 3 (85 mg) as a yellow viscous substance.

MS (APCI) 390/392 [M+H]+

(2) To a solution of the compound 2 (80 mg) in chloroform (1 mL) was added trifluoroacetic acid (1 mL), and the reaction mixture was stirred for 15 hours at room temperature. The reaction mixture was diluted with methanol, the solution was treated with packed strong cation exchange sresin (PoraPak Rxn Cx, eluent: a solution of 1 mol/L NH3 in methanol), and the eluate was concentrated under reduced pressure. The resulting residue, the compound 4 (57 mg), and sodium carbonate (45 mg) were suspended in acetonitrile (1.5 mL), and the suspension was stirred for 15 hours at 60° C. under argon atmosphere. The reaction mixture was cooled to room temperature, diluted with water, and then extracted twice with chloroform, and dried over anhydrous sodium sulfate. The solvent was evaporated under reduced pressure, and the resulting residue was purified by NH-silica gel column chromatography (eluent: hexane-ethyl acetate; gradient: 90:10-60:40) to give 5-(4-chlorophenyl)-3-[(R)-4-(isopropylcarbamoylmethyl)-2-methylpiperazin-1-yl]-1,2,4-triazine (57 mg) as an orange viscous substance.

MS (APCI) 389/391 [M+H]+

Example 232

[Chemical formula 89]

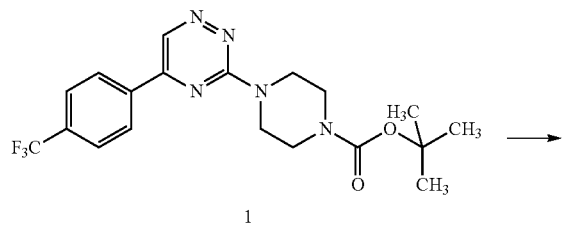
1

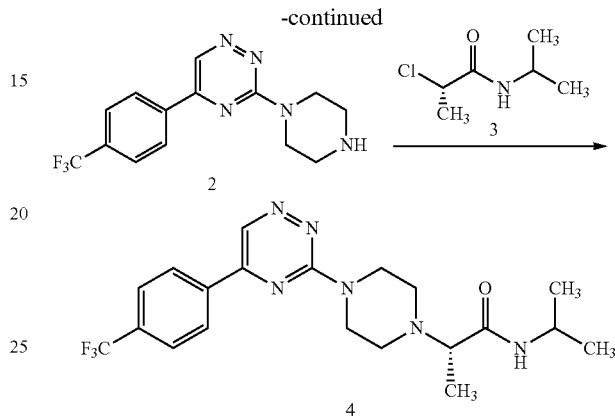

(1) To a solution of the compound 1 (407 mg) in dichloromethane (2.5 mL) was added trifluoroacetic acid (1 mL), and the reaction mixture was stirred for 3 hours at room temperature. The reaction mixture was diluted with methanol, and then the solution was treated with packed strong cation exchange resin (PoraPak Rxn Cx, eluent: a solution of 1 mol/L NH3 in methanol). The eluate was concentrated under reduced pressure to give the compound 2 (258 mg) as a yellow solid.

MS (APCI) 310 [M+H]+

(2) The compound 2 (79 mg), the compound 3 (104 mg) and sodium carbonate (56 mg) were suspended in acetonitrile (3 mL), and the suspension was stirred for 3.5 hours at 75° C. under argon atmosphere. To the reaction mixture was further added the compound 3 (3 mg), and the reaction mixture was stirred for additional 18 hours at the same temperature. The reaction mixture was cooled to room temperature, diluted with a saturated aqueous solution of sodium bicarbonate, and then extracted twice with ethyl acetate. The resulting organic layer was washed with brine, and dried over anhydrous sodium sulfate. The solvent was evaporated under reduced pressure, and the resulting residue was purified by silica gel column chromatography (eluent: chloroform-methanol 90:10). Then, the resulting crystalline residue was dissolved in ethyl acetate, the solution was treated with 4 mol/L HCl/ethyl acetate. The solvent was evaporated under reduced pressure, the residue was suspended and washed in diethylether, taken by filtration, and dried to give 3-[4-[(S)-1-(isopropylcarbamoyl)ethyl]piperazin-1-yl]-5-(4-trifluoromethylphenyl)-1,2,4-triazine hydrochloride (27 mg) as a yellow solid.

MS (APCI) 423 [M+H]+

Example 233

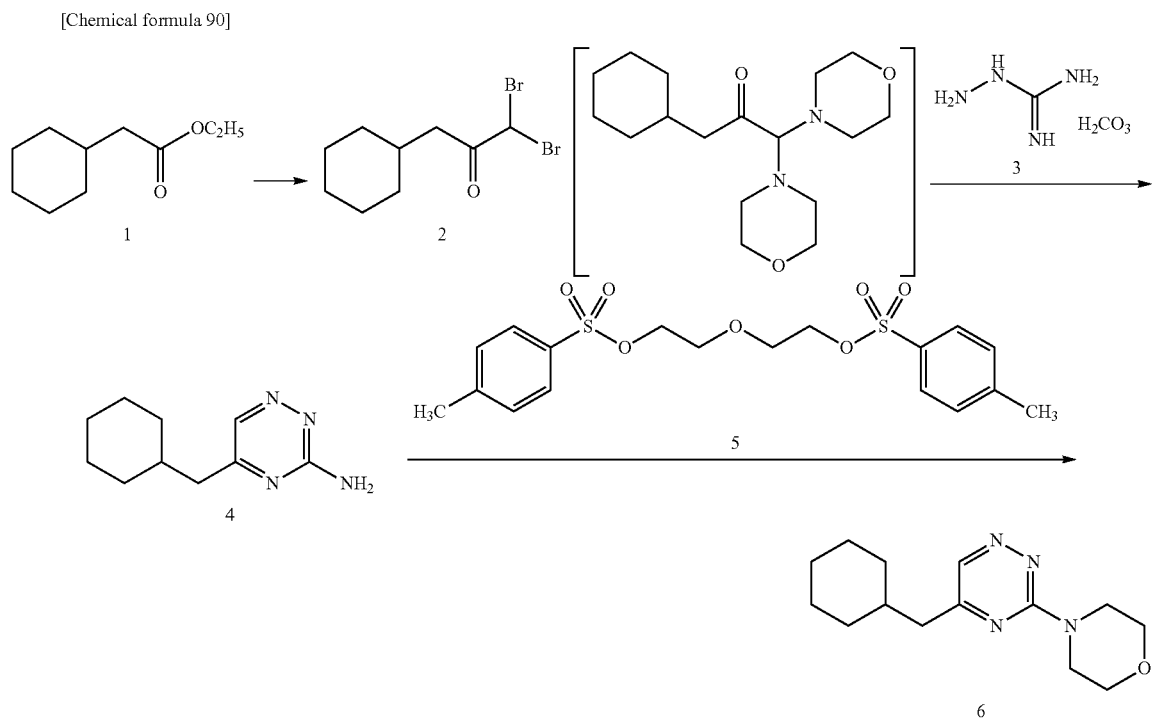

(1) A solution of diisopropylamine (6.5 mL) in anhydrous THF (40 mL) was cooled to −78° C. under argon atmosphere. A solution of 1.59 mol/L n-butyllithium in hexane (26.6 mL) was added dropwise to the solution, and then the reaction mixture was stirred for 30 minutes at −10° C. Then, the reaction mixture was added dropwise to a solution of the compound 1 (3.6 g) and methylene bromide (7.4 g) in anhydrous THF (40 mL) at −78° C. over 7 minutes, and stirred for 30 minutes at the same temperature under argon atmosphere. A solution of 6 mol/L hydrochloric acid (20 mL) was slowly added to the solution for quenching the reaction, a temperature of the reaction mixture was raised to room temperature, and the reaction mixture was diluted with ethyl acetate. The organic layer was washed with water and brine, and dried over anhydrous magnesium sulfate. The solvent was evaporated under reduced pressure to give the compound 2 (4.1 g) as a pale yellow solution.

MS (ESI) 295/297 [M−H]$^-$ (2) To a solution of the compound 2 (4.0 g) in THF (20 mL) was added morpholine (5.1 mL), and the reaction mixture was stirred for 30 hours at 50° C. under argon atmosphere. The reaction mixture was cooled to room temperature, the precipitate was removed by filtration, washed with THF, and the filtrate was concentrated under reduced pressure. The resulting residue was dissolved in methanol (20 mL), and the compound 3 (1.8 g) was added to the solution. To the reaction mixture was added dropwise acetic acid (2.3 mL) over 5 minutes, and the reaction mixture was stirred for 4 hours at room temperature, and then stirred for additional 19 hours with heating to reflux. The reaction mixture was cooled to room temperature, concentrated under reduced pressure, and then the concentrate was diluted with ethyl acetate, and washed with an aqueous solution of 20% potassium carbonate. The organic layer was dried over anhydrous magnesium sulfate, and the solvent was evaporated under reduced pressure, and the resulting residue was purified by silica gel column chromatography (eluent: chloroform-methanol; gradient: 99:1-92:8) to give the compound 4 (317 mg) as a pale yellow solid.

MS (APCI) 193 [M+H]$^+$ (3) To a solution of the compound 4 (80 mg) in anhydrous DMF (3 mL) was added sodium hydride (42 mg) under argon atmosphere, and the mixture was stirred for 30 minutes at room temperature. To the reaction mixture was added the compound 5 (173 mg), and the reaction mixture was stirred for 1 day at room temperature, and then stirred for additional 1 day at 100° C. The reaction mixture was cooled to room temperature, and water was slowly added to the reaction mixture. The reaction mixture was diluted with ethyl acetate, and then washed with water and brine, and dried. The solvent was evaporated under reduced pressure, and the resulting residue was purified by silica gel column chromatography (eluent: hexane-ethyl acetate; gradient: 70:30-50:50) to give 5-cyclohexylmethyl-3-morpholino-1,2,4-triazine (16 mg) as a yellow solid.

MS (APCI) 263 [M+H]$^+$

Example 234

[Chemical formula 91]

The corresponding starting compound was treated in a similar manner as that of the above Example 233 to give 3-morpholino-5-phenethyl-1,2,4-triazine.

MS (APCI) 271 [M+H]$^+$

Example 235

[Chemical formula 92]

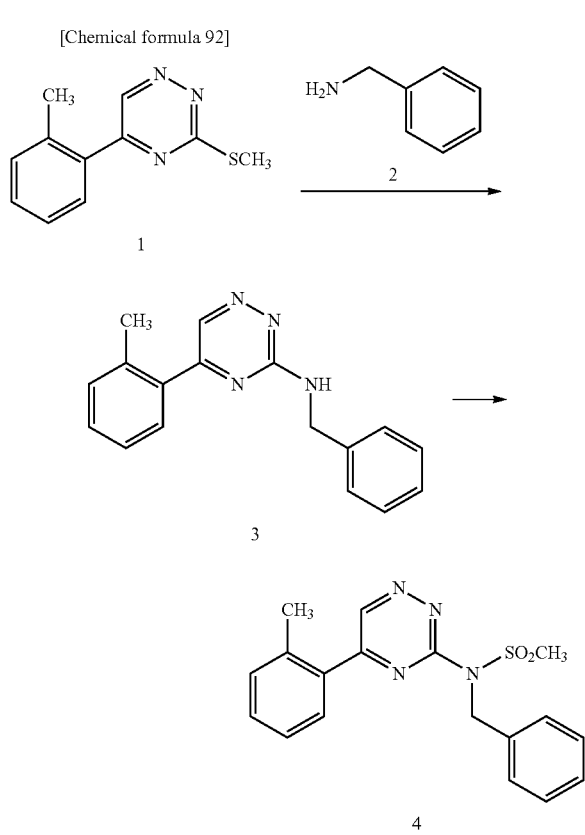

(1) To a solution of the compound 1 (400 mg) in N-methylpyrrolidone (1 mL) was added the compound 2 (2 mL), and the reaction mixture was stirred for 1 hour at 200° C. in a microwave reactor (Initiator, Biotage). The reaction mixture was cooled to room temperature, diluted with ethyl acetate, and then the solution was washed with water and brine, and dried. The solvent was evaporated under reduced pressure, and the resulting residue was purified by NH-silica gel column chromatography (eluent: hexane-ethyl acetate; gradient: 70:30-50:50) to give the compound 3 (436 mg) as a yellow solid.

MS (APCI) 277 [M+H]$^+$ (2) To a solution of the compound 3 (50 mg) in anhydrous THF (3 mL) was added sodium hydride (13 mg) under argon atmosphere, and the reaction mixture was stirred for 40 minutes at room temperature. To the reaction mixture was added methanesulfonic acid chloride (34 µL), and the reaction mixture was stirred for 6 hours at room temperature. To the reaction mixture was slowly added water, the reaction mixture was diluted with ethyl acetate, and then the solution was washed with water and brine, and dried. The solvent was evaporated under reduced pressure, and the resulting residue was purified by silica gel column chromatography (eluent: chloroform-ethyl acetate 95:5) to give 3-[N-benzyl-N-(methylsulfonyl)amino]-5-(o-tolyl)-1,2,4-triazine (56 mg) as a pale yellow viscous substance.

MS (APCI) 355 [M+H]$^+$

Example 236

[Chemical formula 93]

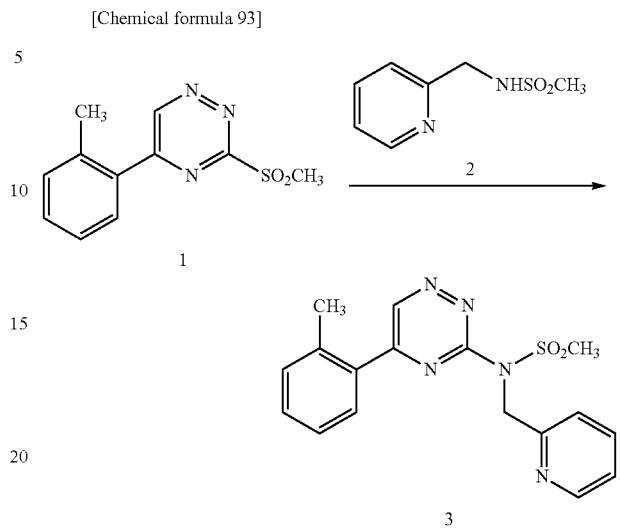

To a solution of the compound 2 (66 mg) in anhydrous DMF (1.5 mL) was added sodium hydride (15 mg) under argon atmosphere, and the reaction mixture was stirred for 30 minutes at room temperature. To the reaction mixture was added the compound 1 (80 mg), and the reaction mixture was stirred for 30 minutes at room temperature. To the reaction mixture was slowly added water, and the reaction mixture was diluted with ethyl acetate, and then the solution was washed with water and brine, and dried. The solvent was evaporated under reduced pressure, and the resulting residue was purified by silica gel column chromatography (eluent: hexane-ethyl acetate; gradient: 65:35-45:55) to give 3-[N-(methylsulfonyl)-N-(2-pyridylmethyl)amino]-5-(o-tolyl)-1,2,4-triazine (112 mg) as a pale yellow viscous substance.

MS (APCI) 356 [M+H]$^+$

Example 237-238

The corresponding starting compound was treated in a similar manner as that of the above Example 235 or 236 to give the compounds described in the following Table 29.

TABLE 29

[Chemical formula 94]

| Example | R$^1$ | R$^2$ | MS [M+H]+ | Method |
|---|---|---|---|---|
| 237 | 2-methylphenyl | N(CH$_3$)SO$_2$CH$_2$Ph | 355 (APCI) | Similar manner as Example 235 |
| 238 | 2-methylphenyl | N(CH$_3$)-cyclic sulfonyl (thiazinane 1,1-dioxide) | 305 (APCI) | Similar manner as Example 236 |

Example 239

[Chemical formula 95]

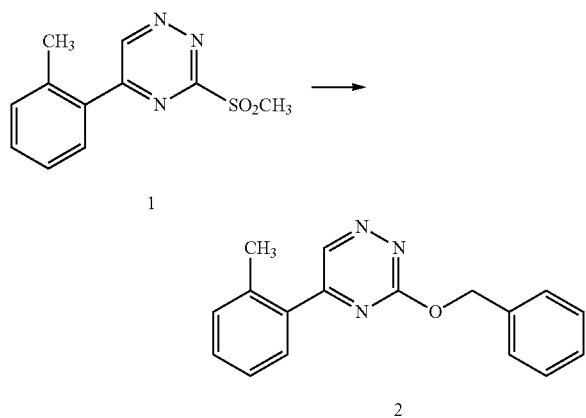

To a solution of benzyl alcohol (83 µL) in anhydrous THF (2 mL) was added sodium hydride (24 mg) under argon atmosphere, and the reaction mixture was stirred for 30 minutes at room temperature. To the reaction mixture was added the compound 1 (100 mg), and the reaction mixture was stirred for 15 hours at room temperature. To the reaction mixture was slowly added water, and the reaction mixture was diluted with ethyl acetate, and then the solution was washed with water and brine, and dried. The solvent was evaporated under reduced pressure, and the resulting residue was purified by silica gel column chromatography (eluent: chloroform-ethyl acetate 95:5) to give 3-benzyloxy-5-(o-tolyl)-1,2,4-triazine (67 mg) as a colorless solid.

MS (APCI) 278 [M+H]$^+$

Example 240

[Chemical formula 96]

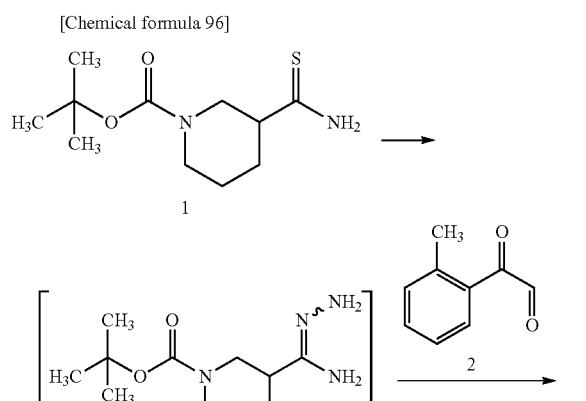

A solution of the compound 1 (2.4 g) and hydrazine hydrate (510 µL) in ethanol (20 mL) was stirred for 7 hours at room temperature. Then, to the reaction mixture was added the compound 2 (1.6 g), and the reaction mixture was stirred for 15.5 hours at room temperature, and then stirred for additional 1 hour at 70° C. The reaction mixture was cooled to room temperature, diluted with a saturated aqueous solution of sodium bicarbonate, and extracted with ethyl acetate. The organic layer was washed with brine, and dried over anhydrous sodium sulfate. The solvent was evaporated under reduced pressure, and the resulting residue was purified by silica gel column chromatography (eluent: hexane-ethyl acetate; gradient: 80:20-60:40) to give 3-[1-(tert-butyloxycarbonyl)-piperidin-3-yl]-5-(o-tolyl)-1,2,4-triazine (1.1 g) as an orange solid.

MS (APCI) 355 [M+H]$^+$

Example 241-243

The corresponding starting compound was treated in a similar manner as that of the above Example 240 to give the compounds described in the following Table 30.

TABLE 30

[Chemical formula 97]

| Example | R$^1$ | R$^2$ | MS [M + H]$^+$ |
|---|---|---|---|
| 241 | 2-methylphenyl (CH$_3$) | benzyl | 262 (APCI) |
| 242 | 4-fluorophenyl (F) | 4-methylpiperidin-1-yl C(O)O-C(CH$_3$)$_3$ | 359 (APCI) |
| 243 | 2-methylphenyl (CH$_3$) | cyclopropyl | 212 |

Example 244

[Chemical formula 98]

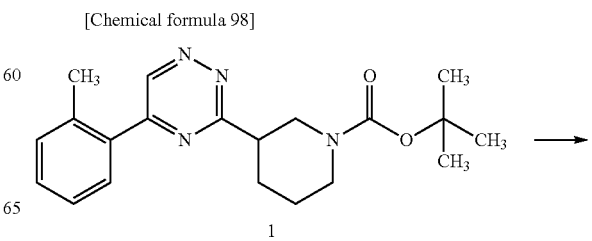

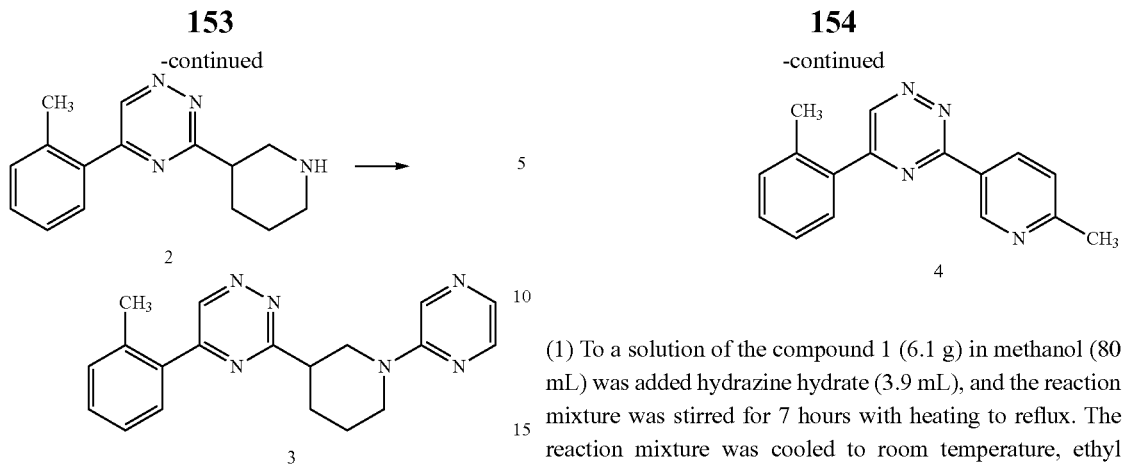

(1) To the compound 1 (1.1 g) was added a solution of 4 mol/L HCl in ethyl acetate (4 mL), and the reaction mixture was stirred for 4 hours at room temperature. To the reaction mixture was added a saturated aqueous solution of sodium bicarbonate, the reaction mixture was extracted with chloroform, and the organic layer was dried over anhydrous sodium sulfate. The solvent was evaporated under reduced pressure, and the resulting residue was purified by silica gel column chromatography (eluent: chloroform-methanol; gradient: 100:0-90:10) to give the compound 2 (752 mg) as a pale brown solid.

MS (APCI) 255 [M+H]+

(2) The compound 2 (100 mg), 2-iodopyrazine (111 mg), xantphos (27 mg), and sodium t-butoxide (57 mg) were suspended in toluene (2 mL), and the suspension was degassed under reduced pressure, and then back-filled with argon. To the reaction mixture was added tris(dibenzylideneacetone) dipalladium (14 mg), and the reaction mixture was stirred for 50 minutes at 120° C. The reaction mixture was cooled to room temperature, diluted with water, and then extracted with ethyl acetate. The organic layer was washed with brine, dried over anhydrous sodium sulfate, and then the solvent was evaporated, and the resulting residue was purified by silica gel column chromatography (eluent: hexane-ethyl acetate; gradient: 80:20-60:40) to give 3-[1-(pyrimidine-2-yl)-piperidin-3-yl]-5-(o-tolyl)-1,2,4-triazine (49 mg) as a pale brown viscous substance.

MS (APCI) 333 [M+H]+

Example 245

[Chemical formula 99]

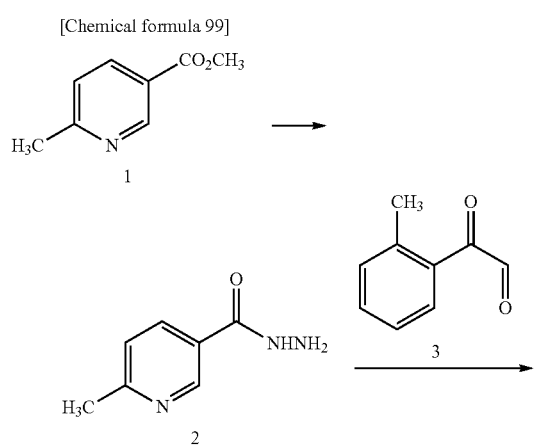

(1) To a solution of the compound 1 (6.1 g) in methanol (80 mL) was added hydrazine hydrate (3.9 mL), and the reaction mixture was stirred for 7 hours with heating to reflux. The reaction mixture was cooled to room temperature, ethyl acetate was added thereto, and the reaction mixture was stirred for 1 hour. The precipitate was taken by filtration, washed with ethyl acetate, and dried to give the compound 2 (4.2 g) as a slightly brown solid.

MS (APCI) 152 [M+H]+

(2) A solution of the compound 2 (290 mg) and the compound 3 (330 mg) in ethanol (3 mL) was stirred for 2 hours at room temperature. Then, to the reaction mixture was added ammonium acetate (745 mg), and the reaction mixture was stirred for 30 minutes at 150° C. in a microwave reactor (Initiator, Biotage). The reaction mixture was cooled to room temperature, washed with a saturated aqueous solution of sodium bicarbonate, and then extracted with ethyl acetate. The organic layer was washed with brine, and dried over anhydrous sodium sulfate. The solvent was evaporated under reduced pressure, and the resulting residue was purified by silica gel column chromatography (eluent: hexane-ethyl acetate; gradient: 70:30-50:50). The resulting residue was suspended and washed in a mixed solvent of hexane-diethyl ether (1:1), taken by filtration, and dried to give 3-(2-methyl-5-pyridyl)-5-(o-tolyl)-1,2,4-triazine (21 mg) as a pale yellow solid.

MS (APCI) 263 [M+H]+

Example 246

[Chemical Formula 100]

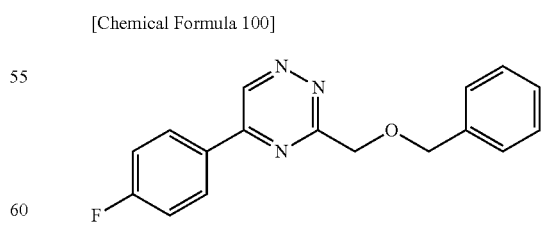

The corresponding starting compound was treated in a similar manner as that of the above Example 245 to give 3-benzyloxymethyl-5-(4-fluorophenyl)-1,2,4-triazine.

MS (APCI) 296 [M+H]+

Example 247

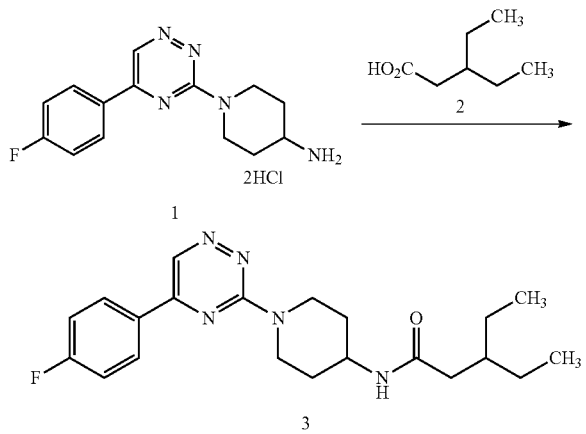

The compound 1 (200 mg) and the compound 2 (168 mg) were dissolved in DMF (4 mL). Diisopropylethylamine (676 µL) and O-(7-azabenzotriazol-1-yl)-N,N,N',N'-tetramethyl-uroniumhexafluorophosphate (491 mg) were added to the solution, and the reaction mixture was stirred for 21 hours at room temperature. The reaction mixture was diluted with ethyl acetate, the solution was washed with water and brine, and dried over anhydrous sodium sulfate. The solvent was evaporated under reduced pressure, and the resulting residue was purified by silica gel column chromatography (eluent: chloroform-ethyl acetate; gradient: 95:5-50:50) to give 3-[4-[(3-ethylpentanoyl)amino]piperidino]-5-(4-fluorophenyl)-1,2,4-triazine (224 mg) as a yellow solid.

MS (APCI) 386 [M+H]$^+$

Example 248

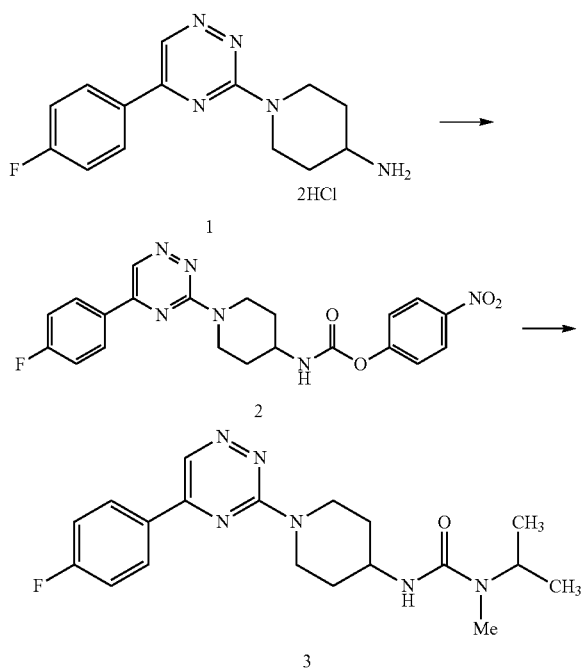

(1) To a solution of the compound 1 (400 mg) and diisopropylethylamine (676 µL) in chloroform (12 mL) was added 4-nitrophenyl chloroformate (281 mg), and the reaction mixture was stirred for 30 minutes at room temperature. The reaction mixture was diluted with water, and extracted twice with chloroform. The organic layer was dried over anhydrous sodium sulfate, and the solvent was evaporated under reduced pressure. The resulting residue was suspended and washed in ethyl acetate, taken by filtration, and dried to give the compound 2 (356 mg) as a yellow solid.

MS (APCI) 439 [M+H]$^+$ (2) To a solution of the compound 2 (100 mg) and diisopropylethylamine (340 µL) in chloroform (3 mL) was added isopropylmethylamine (85 mg), and the reaction mixture was stirred for 1 hour at room temperature. The reaction mixture was diluted with an aqueous solution of potassium carbonate, and extracted twice with chloroform. The organic layer was dried over anhydrous sodium sulfate, and the solvent was evaporated under reduced pressure. The resulting residue was suspended and washed in diisopropyl ether, taken by filtration, and dried to give 5-(4-fluorophenyl)-3-[4-(N-isopropyl-N-methylureido) piperidino]-1,2,4-triazine (66 mg) as a yellow solid.

MS (ESI) 373 [M+H]$^+$

Example 249

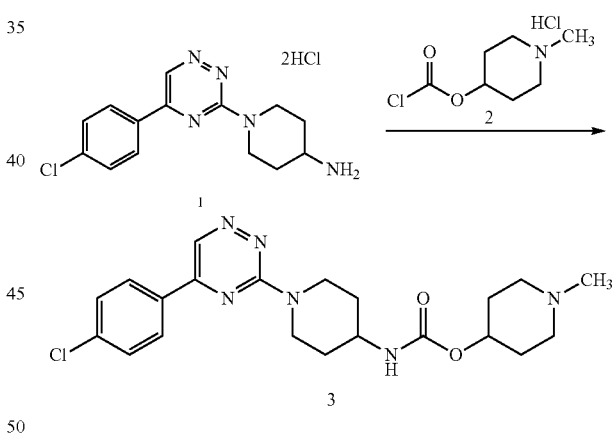

The compound 1 (100 mg) and the compound 2 (89 mg) were suspended in acetonitrile (3 mL). Diisopropylethylamine (240 µL) was added to the suspension, and the reaction mixture was stirred at room temperature for 5 hours. The reaction mixture was diluted with water, and a saturated aqueous solution of potassium carbonate was added to the solution, and then the reaction mixture was extracted twice with chloroform. The organic layer was dried over anhydrous sodium sulfate, and the solvent was evaporated under reduced pressure. The resulting residue was purified by silica gel column chromatography (eluent: chloroform-methanol; gradient: 100:0-90:10) to give 5-(4-chlorophenyl)-3-[4-[(1-methylpiperidin-4-yl)oxycarbonylamino]piperidino]-1,2,4-triazine (95 mg) as a yellow solid.

MS (APCI) 431/433 [M+H]$^+$

Example 250

[Chemical formula 104]

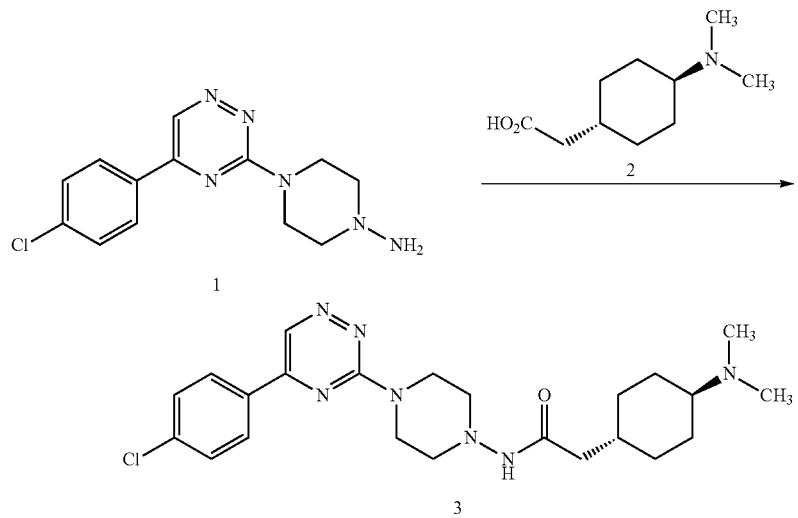

The compound 1 (40 mg) and the compound 2 (40 mg) were dissolved in DMF (1.5 mL). Diisopropylethylamine (96 µL) and O-(7-azabenzotriazol-1-yl)-N,N,N',N'-tetramethyluroniumhexafluorophosphate (79 mg) were added to the solution, and the reaction mixture was stirred at room temperature for 1 hour. The reaction mixture was diluted with a saturated aqueous solution of sodium bicarbonate, and extracted twice with chloroform. The organic layer was dried over anhydrous sodium sulfate, and the solvent was evaporated under reduced pressure. The solvent was evaporated under reduced pressure, and the resulting residue was purified by NH-silica gel column chromatography (eluent: ethyl acetate-methanol 92:8) to give 5-(4-chlorophenyl)-3-[4-[1-[trans-4-(dimethylamino)cyclohexyl]acetylamino]piperazin-1-yl]-1,2,4-triazine (48 mg) as a yellow solid.

MS (ESI) 458 [M+H]$^+$

Example 251

[Chemical formula 105]

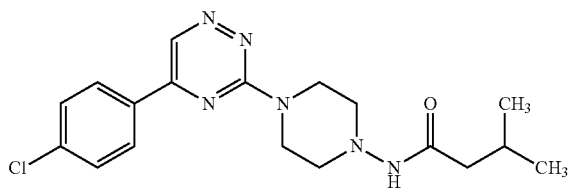

The corresponding starting compound was treated in a similar manner as that of the above Example 250 to give 5-(4-chlorophenyl)-3-[4-[(3-methylbutanoyl)amino]piperazin-1-yl]-1,2,4-triazine.

MS (ESI) 375/377 [M+H]$^+$

Example 252

[Chemical formula 106]

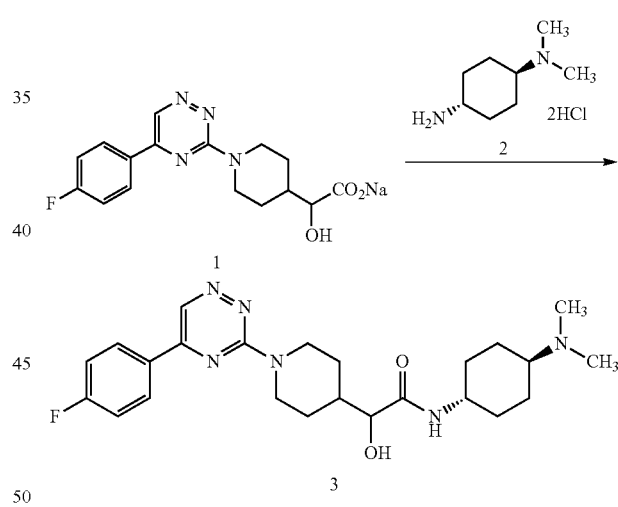

The compound 1 (120 mg) and the compound 2 (109 mg) were dissolved in DMF (3.4 mL). Diisopropylethylamine (266 µL) and O-(7-azabenzotriazol-1-yl)-N,N,N',N'-tetramethyluroniumhexafluorophosphate (193 mg) were added to the solution, and the reaction mixture was stirred at room temperature for 16.5 hours. The reaction mixture was diluted with water, an aqueous solution of potassium carbonate was added thereto, and the reaction mixture was extracted 3 times with chloroform. The organic layer was dried over anhydrous sodium sulfate, and the solvent was evaporated under reduced pressure. The resulting residue was purified by NH-silica gel column chromatography (eluent: chloroform-methanol; gradient: 100:0-97:3) to give 3-[4-[[[trans-4-(dimethylamino)cyclohexyl]carbamoyl]hydroxymethyl]piperidino]-5-(4-fluorophenyl)-1,2,4-triazine (110 mg) as a yellow solid.

MS (ESI) 457 [M+H]$^+$

Example 253

[Chemical formula 107]

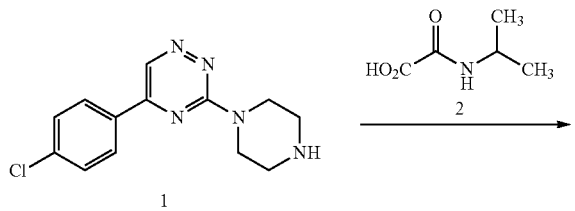

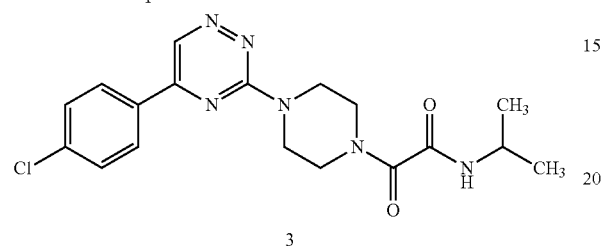

The compound 1 (200 mg) and the compound 2 (114 mg) were dissolved in DMF (7 mL). Diisopropylethylamine (500 µL) and O-(7-azabenzotriazol-1-yl)-N,N,N',N'-tetramethyl-uroniumhexafluorophosphate (303 mg) were added to the solution, and the reaction mixture was stirred for 40 minutes at room temperature. The reaction mixture was diluted with a saturated aqueous solution of sodium bicarbonate, and extracted 3 times with chloroform. The organic layer was washed with brine, and dried over anhydrous sodium sulfate. The solvent was evaporated under reduced pressure, and the resulting residue was purified by silica gel column chromatography (eluent: chloroform-methanol; gradient: 100:0-97:3) to give 5-(4-chlorophenyl)-3-[4-[(isopropylamino)oxalyl]piperazin-1-yl]-1,2,4-triazine (267 mg) as a yellow solid.
MS (APCI) 389 [M+H]$^+$

Example 254

[Chemical formula 108]

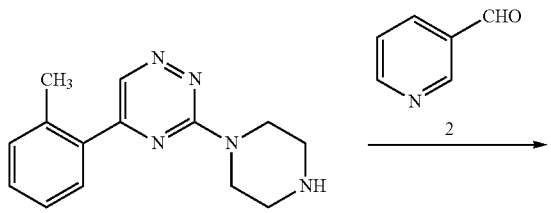

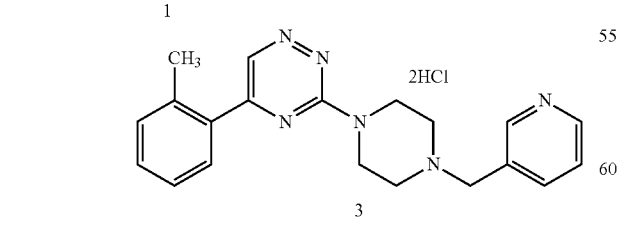

To a solution of the compound 1 (100 mg) in dichloromethane (4 mL) were added the compound 2 (50 mg), acetic acid (2 drops) and sodium triacetoxyborohydride (120 mg), and the reaction mixture was stirred for 18 hours at room temperature. The reaction mixture was diluted with water, and then extracted with chloroform. The resulting organic layer was washed with brine, dried over sodium sulfate, and the solvent was evaporated. The resulting residue was purified by silica gel column chromatography (eluent: chloroform-methanol; gradient: 100:0-95:5), and the resulting residue was treated with a solution of 4 mol/L HCl in ethyl acetate to give 3-[4-(3-pyridylmethyl) piperazin-1-yl]-5-(o-tolyl)-1,2,4-triazine dihydrochloride (120 mg) as a yellow powder.
MS (ESI) 347 [M+H]$^+$

Example 255

[Chemical formula 109]

To a solution of the compound 1 (100 mg) in anhydrous THF (3.6 mL) was added cyclopentyl isocyanate (51 µL), and the reaction mixture was stirred for 3 hours at 80° C. Then, to the reaction mixture was added copper chloride (I) (36 mg), and the reaction mixture was stirred for 17.5 hours at the same temperature, and further, cyclopentyl isocyanate (25 µL) was added thereto, followed by stirring of the reaction mixture for 4.5 hours. The reaction mixture was cooled to room temperature, diluted with conc. ammonia water which has been diluted to 3 times, and extracted twice with chloroform. The resulting organic layer was dried over anhydrous sodium sulfate, and the solvent was evaporated under reduced pressure. The resulting residue was purified by silica gel column chromatography (eluent: hexane-ethyl acetate; gradient: 70:30-40:60) to give 3-[4-(N-cyclopentyl-carbamoyloxy) piperidino]-5-(4-fluorophenyl)-1,2,4-triazine (66 mg) as a yellow solid.
MS (ESI) 386 [M+H]$^+$

Example 256

[Chemical formula 110]

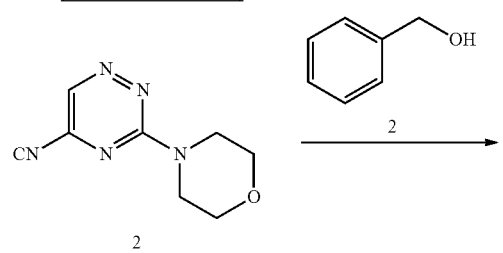

-continued

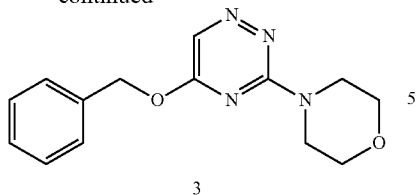

5

3

To a suspension of sodium hydride (20 mg) in anhydrous THF (2 mL) was added the compound 2 (62 µL) under argon atmosphere, and the suspension was stirred for 30 minutes at room temperature. To the reaction mixture was added the compound 1 (100 mg), and the reaction mixture was stirred for 35 minutes at room temperature. To the reaction mixture was slowly added water, the reaction mixture was extracted twice with chloroform, and the organic layer was dried over anhydrous sodium sulfate. The solvent was evaporated under reduced pressure, and the resulting residue was purified by silica gel column chromatography (eluent: hexane-ethyl acetate; gradient: 80:20-50:50) to give 5-benzyloxy-3-morpholino-1,2,4-triazine (127 mg) as a colorless solid.

MS (APCI) 273 [M+H]⁺

Example 257

[Chemical formula 111]

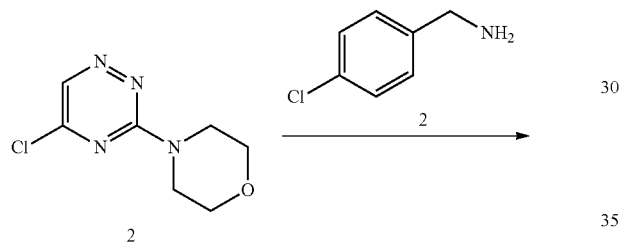

-continued

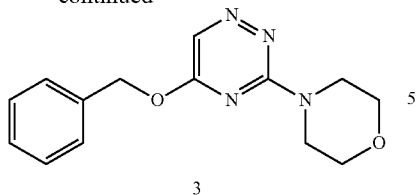

3

To a solution of the compound 1 (50 mg) in anhydrous THF (1.2 mL) were added diisopropylethylamine (65 µL) and the compound 2 (36 µL), and the reaction mixture was stirred for 50 minutes at room temperature, and then stirred for additional 18 hours at 50° C. The reaction mixture was cooled to room temperature, diluted with water, and then extracted twice with chloroform, and the organic layer was dried over anhydrous sodium sulfate. The solvent was evaporated under reduced pressure, and the resulting residue was purified by NH-silica gel column chromatography (eluent: chloroform-ethyl acetate 80:20) to give 5-(4-chlorobenzyl)amino-3-morpholino-1,2,4-triazine (42 mg) as a pale brown solid.

MS (APCI) 306/308 [M+H]⁺

Example 258-262

The corresponding starting compound was treated in a similar manner as that of the above Example 2 to give the compounds described in the following Table 31.

TABLE 31

[Chemical formula 112]

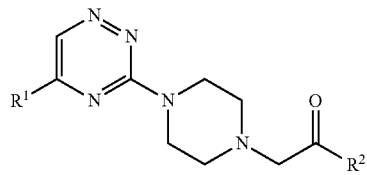

| Example | R¹ | R² | MS[M + H]⁺ |
|---|---|---|---|
| 258 | 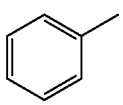 | 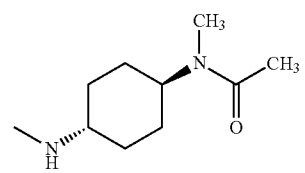 | 471 (APCI) |
| 259 | | | 452 (APCI) |

TABLE 31-continued

[Chemical formula 112]

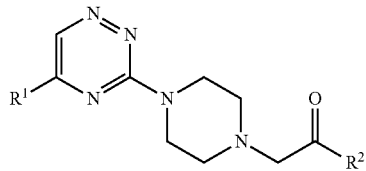

| Example | R¹ | R² | MS[M + H]⁺ |
|---|---|---|---|
| 260 | 4-methyl-2-(trifluoromethyl)phenyl (F₃C, F on ring) | pyrazole-NHCH₃ amide with NH-CH₃ | 504 (APCI) |
| 261 | 4-methyl-2-(trifluoromethyl)phenyl | cyclohexyl bearing NHCH₃ and NHC(O)CH₃ | 506 (APCI) |
| 262 | 4-chlorophenyl | piperidinyl (NHCH₃) with CH₂CH₂SO₂CH₃ | 522/524 (APCI) |

Example 263a and 263b

[Chemical formula 113]

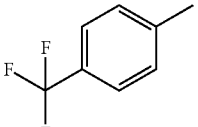

(In the above scheme, the stereochemistry for a substituent of the carbon atom labelled by "*" means trans configuration, and does not specify their absolute configuration.)

The compound 1 (200 mg), the compound 2 (74 mg) and 1-hydroxybenzotriazole (101 mg) were suspended in DMF (4 mL). 1-(3-Dimethylaminopropyl)-3-ethylcarbodiimide hydrochloride (165 mg) was added to the suspension, and the reaction mixture was stirred for 15.5 hours at room temperature. The reaction mixture was diluted with water, and then extracted 3 times with chloroform. The organic layer was washed with a saturated aqueous solution of sodium bicarbonate and brine, dried over anhydrous magnesium sulfate, and the solvent was evaporated under reduced pressure. The resulting residue was purified by silica gel column chromatography (eluent: chloroform-methanol; gradient: 100:0-95:5) to give a racemate of the compound 3 (224 mg) as a yellow solid.

MS (APCI) 447/449 [M+H]⁺

Then, two isomers having different steric configuration at a carbon atom labelled by "*" in the compound 3 (206 mg) which was a diastereomixture were isolated by recycle HPLC (Chiralpak IF (30×250), methyl-tert-butyl ether/methanol/diethylamine=80/20/0.1, flow rate: 20 mL/min), the fraction containing each of the isomers was concentrated under reduced pressure to give 5-(4-chlorophenyl)-3-[(3R)-4-[(trans-3-hydroxytetrahydropyran-4-yl)carbamoylmethyl]-3-methylpiperazin-1-yl]-1,2,4-triazine as a yellow solid (Example 263a, yellow solid, 86 mg and Example 263b, yellow solid, 83 mg).

Example 263a

Retention time: 11.28 minutes (Chiralpak IF-3 (4.6×150), methyl-tert-butyl ether/methanol/diethylamine=80/20/0.1, flow rate 0.5 mL/min)
Optical purity >99.8% ee
MS (APCI) 447/449 [M+H]

Example 263b (a Diastereomer of Example 263a)

Retention time: 13.14 minutes
Optical purity 99.73% ee
MS (APCI) 447/449 [M+H]+

For preparing the compounds of the above Examples, any commercially available reagents or any compounds which have been made through chemical modification of the reagents using conventional methods and other methods based thereon can be used as a starting material and an intermediate. In addition, they can be prepared by the methods described in the following Reference Examples.

Reference Example 1

[Chemical formula 114]

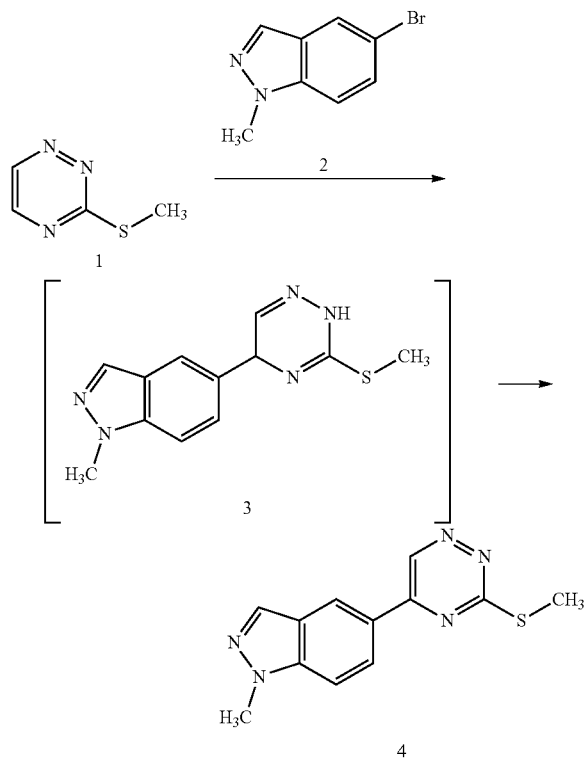

A solution of the compound 2 (2.9 g) in anhydrous THF (25 mL) was cooled to −78° C. under argon atmosphere, a solution of 1.64 mol/L n-butyllithium in hexane (8.6 mL) was added dropwise to the solution, and the reaction mixture was stirred for 1 hour at the same temperature. Then, to the reaction mixture was added dropwise a solution of the compound 1 (1.3 g) in THF (15 mL), and the reaction mixture was stirred for 1 hour at −78° C. An aqueous solution of 10% ammonium chloride was slowly added to the solution for quenching the reaction, and then a temperature of the reaction mixture was raised to room temperature, and the reaction mixture was diluted with ethyl acetate, washed with water and brine, and dried over anhydrous magnesium sulfate. The solvent was evaporated under reduced pressure, the resulting residue (the crude product 3) was dissolved in toluene (35 mL)-dioxane (35 mL), and 2,3-dichloro-5,6-dicyano-p-benzoquinone (2.8 g) was added portionwise to the solution. After stirring for 30 minutes at room temperature, the reaction mixture was diluted with ethyl acetate, and then washed with a mixed solution of aqueous solutions of 2 mol/L sodium hydroxide and sodium thiosulfate, water and brine, and dried over anhydrous magnesium sulfate. The solvent was evaporated under reduced pressure, and the resulting crystalline residue was suspended and washed in a mixed solvent of ethyl acetate-hexane (2:1), taken by filtration, and dried to give the compound 4 (2.3 g) as a brown solid.

MS (APCI) 258 [M+H]+

Reference Example 2-10

The corresponding starting compound was treated in a similar manner as that of the above Reference Example 1 to give the compounds described in the following Table 32.

TABLE 32

[Chemical formula 115]

| Reference Example | R | Ms |
|---|---|---|
| 2 | 4-(trifluoromethyl)benzyl | APCI 272 [M + H]+ |
| 3 | 4-(methoxymethyl)benzyl | APCI 248 [M + H]+ |
| 4 | 2-naphthylmethyl | APCI 254 [M + H]+ |
| 5 | (3-methyl-2-naphthyl)methyl | APCI 268 [M + H]+ |
| 6 | (2,3-dihydrobenzofuran-5-yl)methyl | APCI 246 [M + H]+ |
| 7 | (2,3-dihydrobenzofuran-7-yl)methyl | APCI 246 [M + H]+ |
| 8 | (isochroman-8-yl)methyl | APCI 260 [M + H]+ |

TABLE 32-continued

[Chemical formula 115]

| Reference Example | R | Ms |
|---|---|---|
| 9 | 2-fluoro-4-methylphenyl | APCI 236 [M + H]+ |
| 10 | 2,3-dichloro-6-methylphenyl | APCI 272/274 [M + H]+ |

Reference Example 11

[Chemical formula 116]

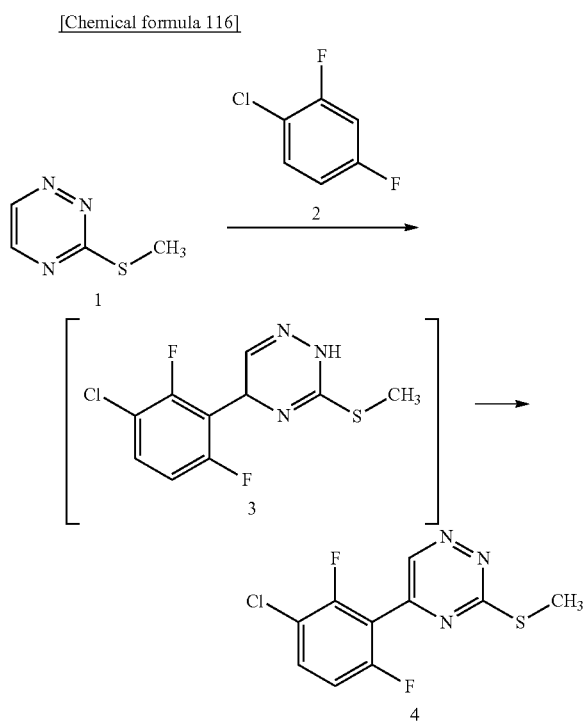

A solution of the compound 2 (5.3 mL) in anhydrous THF (60 mL) was cooled to −78° C. under argon atmosphere, a solution of 1.65 mol/L n-butyllithium in hexane (29 mL) was added dropwise to the solution, and the reaction mixture was stirred for 1 hour at the same temperature. Then, to the reaction mixture was added dropwise a solution of the compound 1 (4.0 g) in THF (20 mL), and the reaction mixture was stirred for 1 hour at −78° C. An aqueous solution of 10% ammonium chloride was slowly added to the solution for quenching the reaction, and then a temperature of the reaction mixture was raised to room temperature. The reaction mixture was diluted with ethyl acetate, washed with water and brine, and dried over anhydrous sodium sulfate. The solvent was evaporated under reduced pressure, and the resulting residue (the crude product 3) was dissolved in toluene (160 mL), and 2,3-dichloro-5,6-dicyano-p-benzoquinone (8.6 g) was added portionwise to the solution. After stirring for 20 hours at room temperature, the reaction mixture was diluted with ethyl acetate, and then washed with a mixed solution of aqueous solutions of 2 mol/L sodium hydroxide and sodium thiosulfate, water, and brine, and dried over anhydrous magnesium sulfate. The solvent was evaporated under reduced pressure, and the resulting crystalline residue was suspended and washed in diisopropylether, taken by filtration, and dried to give the compound 4 (7.5 g) as a yellow solid.

MS (APCI) 274/276 [M+H]+

Reference Example 12

[Chemical formula 117]

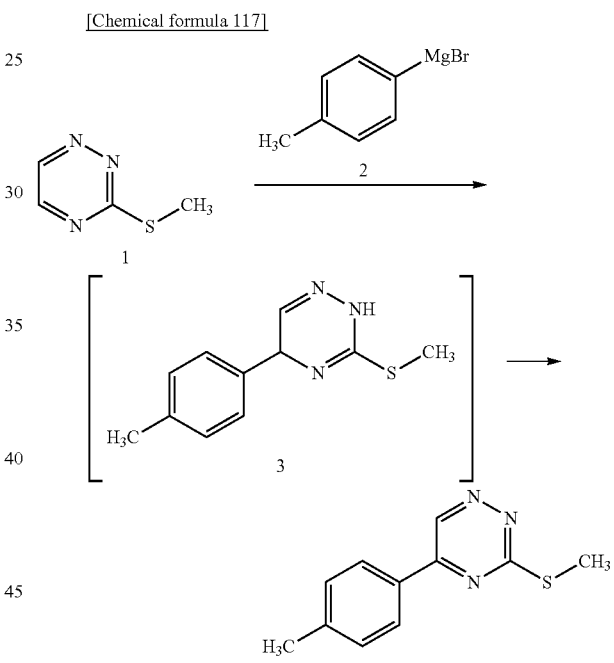

To a solution of the compound 1 (3.0 g) in anhydrous THF (250 mL) was added dropwise a solution of 0.5 mol/L of the compound 2 in THF (52 mL) with ice-cooling under argon atmosphere. A temperature of the reaction mixture was slowly raised to room temperature, the reaction mixture was stirred for 15 hours, and then diluted hydrochloric acid was slowly added under ice-cooling. The reaction mixture was adjusted to neutral pH with a saturated aqueous solution of sodium bicarbonate, and then the solution was diluted with ethyl acetate, washed with brine, and dried over anhydrous sodium sulfate. The solvent was evaporated under reduced pressure. The resulting crude product 3 was dissolved in toluene (250 mL), and 2,3-dichloro-5,6-dicyano-p-benzoquinone (6.4 g) was added portionwise to the solution. After stirring for 40 minutes at room temperature, the reaction mixture was diluted with ethyl acetate, and then washed with a mixed solution of aqueous solutions of 2 mol/L sodium hydroxide and sodium thiosulfate, water, and brine, and dried over anhydrous magnesium sulfate. The solvent was evaporated under reduced pressure, and the resulting residue was suspended and washed in a mixed solvent of ethyl acetate-hexane (1:2), taken by filtration, and dried to give the compound 4 (3.3 g) as a yellow solid.

MS (APCI) 218 [M+H]$^+$

Reference Example 13-17

The corresponding starting compound was treated in a similar manner as that of the above Reference Example 12 to give the compounds described in the following Table 33.

TABLE 33

[Chemical formula 118]

| Reference Example | R | Ms |
|---|---|---|
| 13 | 4-fluorophenyl | APCI 222 [M + H]+ |
| 14 | 4-chlorophenyl | APCI 238/240 [M + H]+ |
| 15 | 2-methylphenyl (CH$_3$) | APCI 218 [M + H]+ |
| 16 | 2-methoxyphenyl (OCH$_3$) | APCI 234 [M + H]+ |
| 17 | 3-methylthiophen-2-yl (H$_3$C) | ESI 224 [M + H]+ |

Reference Example 18

[Chemical formula 119]

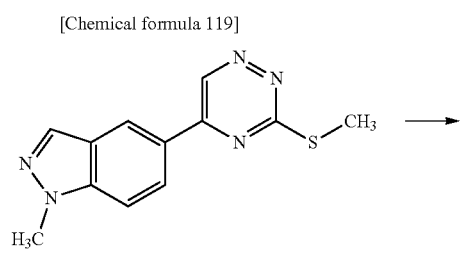

To a solution of the compound 1 (2.3 g) in dichloromethane (45 mL) was added a suspension of hydrous 25% m-chloroperbenzoic acid (4.7 g) in dichloromethane (45 mL), and the reaction mixture was stirred for 17 hours at room temperature. The reaction mixture was treated with an aqueous solution of sodium thiosulfate, and then a mixed solution of a saturated aqueous solution of sodium bicarbonate and water (about 1:1) was added thereto, and the reaction mixture was stirred. The reaction mixture was filtered, and the resulting crystals were washed with water and dichloromethane. The filtrate was extracted with chloroform, washed with water and brine, and then dried over anhydrous magnesium sulfate, and the solvent was evaporated under reduced pressure. The resulting crystalline residue was combined to the previously obtained crystals, and the combined substance was suspended and washed in a mixed solvent of ethyl acetate-hexane, taken by filtration, and dried under reduced pressure to give the compound 2 (2.4 g) as a yellow solid.

MS (APCI) 290 [M+H]$^+$

Reference Example 19-32

The corresponding starting compound was treated in a similar manner as that of the above Reference Example 18 to give the compounds described in the following Tables 34 and 35.

TABLE 34

[Chemical formula 120]

| Reference Example | R | Ms |
|---|---|---|
| 19 | 4-(trifluoromethyl)phenyl (F$_3$C) | APCI 304 [M + H]+ |
| 20 | 4-(methoxymethyl)phenyl (H$_3$C-O-) | APCI 280 [M + H]+ |
| 21 | naphthalen-2-yl | APCI 286 [M + H]+ |
| 22 | 2,3-dihydrobenzofuran-5-yl | APCI 278 [M + H]+ |

TABLE 34-continued

[Chemical formula 120]

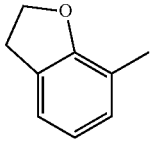

| Reference Example | R | Ms |
|---|---|---|
| 23 | 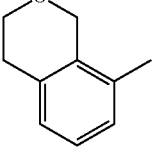 | APCI 278 [M + H]+ |
| 24 | 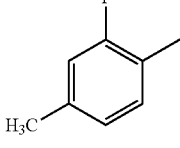 | APCI 292 [M + H]+ |
| 25 | 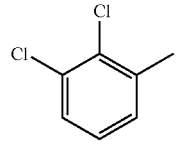 | APCI 268 [M + H]+ |
| 26 | 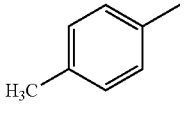 | APCI 304/306 [M + H]+ |
| 27 | 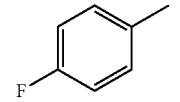 | APCI 250 [M + H]+ |
| 28 | 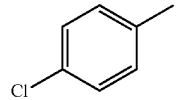 | APCI 254 [M + H]+ |
| 29 | 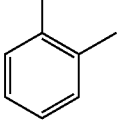 | APCI 270/272 [M + H]+ |

TABLE 35

[Chemical formula 121]

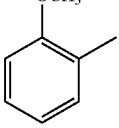

| Reference Example | R | Ms |
|---|---|---|
| 30 | 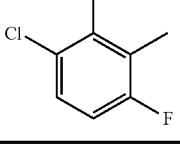 | APCI 250 [M + H]+ |
| 31 | 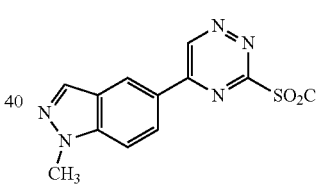 | APCI 266 [M + H]+ |
| 32 |  | |

Reference Example 33

[Chemical formula 122]

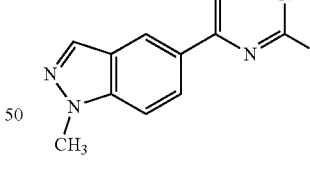

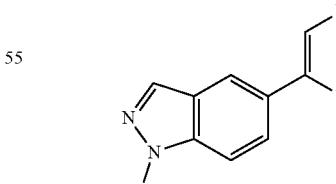

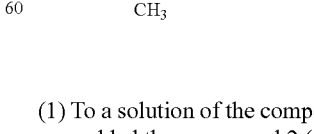

(1) To a solution of the compound 1 (1.2 g) in DMF (40 mL) was added the compound 2 (1.8 g), and the reaction mixture was stirred for 3 days at room temperature under argon atmosphere. After concentrating under reduced pressure, the reaction mixture was diluted with ethyl acetate, and then washed with water, a saturated aqueous solution of sodium bicarbonate and brine, and dried over anhydrous magnesium sulfate. The solvent was evaporated under reduced pressure, and the resulting residue was purified by silica gel column chromatography (eluent: ethyl acetate-methanol; gradient: 100:0-90:10). The resulting crystalline residue was suspended and washed in a mixed solvent of ethyl acetate-hexane (1:1), taken by filtration, and dried to give the compound 3 (1.3 g) as a yellow solid.

MS (APCI) 382 [M+H]$^+$ (2) The compound 3 (1.3 g) was dissolved in ethanol (15 mL)-THF (15 mL), an aqueous solution of 1 mol/L of sodium hydroxide (7 mL) was added to the solution, and the reaction mixture was stirred for 2 hours at room temperature. The reaction mixture was concentrated under reduced pressure, the residue was dissolved in water, and then an aqueous solution of 1 mol/L hydrochloric acid was added to the solution with ice-cooling to adjust a pH of the solution to pH 4-5. The precipitate was taken by filtration, washed, and dried to give the compound 4 (1.3 g) as a yellow solid.

MS (APCI) 354 [M+H]$^+$

Reference Example 34-39

The corresponding starting compound was treated in a similar manner as that of the above Reference Example 33 to give the compounds described in the following Table 36.

TABLE 36

[Chemical formula 123]

| Reference Example | R | Ms |
|---|---|---|
| 34 | 4-methylbenzyl methyl ether group (H$_3$C-O-CH$_2$-C$_6$H$_4$-CH$_3$) | 344 [M + H]+ ESI |
| 35 | naphthalen-2-yl | 350 [M + H]+ APCI |
| 36 | 2,3-dichlorophenyl | 368/370 [M + H]+ APCI |
| 37 | 2-methylphenyl | 314 [M + H]+ APCI |

TABLE 36-continued

[Chemical formula 123]

| Reference Example | R | Ms |
|---|---|---|
| 38 | 2-methoxyphenyl (OCH$_3$) | 330 [M + H]+ APCI |
| 39 | 3-chloro-2,6-difluorophenyl | 370/372 [M + H]+ APCI |

Reference Example 40

[Chemical formula 124]

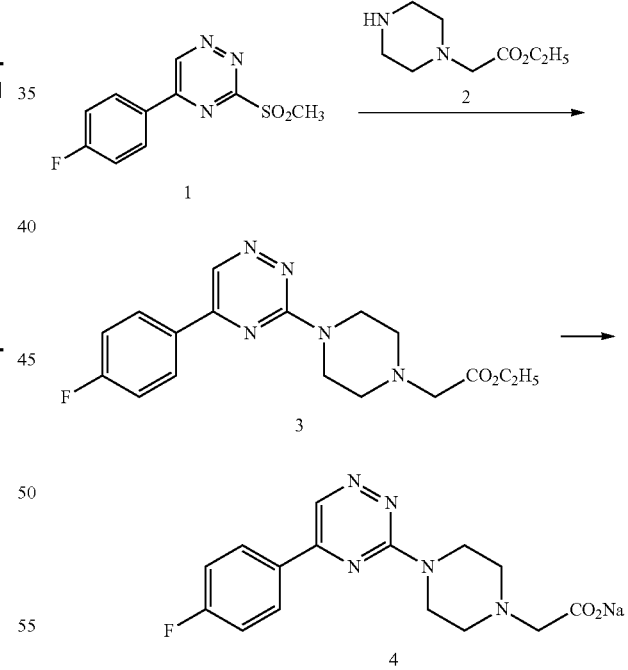

(1) To a solution of the compound 1 (10 g) in acetonitrile (200 mL) was added the compound 2 (13.5 mL), and the reaction mixture was stirred for 7.5 hours at room temperature under argon atmosphere. The reaction mixture was diluted with water, and then extracted twice with chloroform, and the resulting organic layer was dried over anhydrous sodium sulfate. The solvent was evaporated under reduced pressure, and the resulting residue was purified by silica gel column chromatography (eluent: hexane-ethyl acetate; gradient: 50:50-0:100). The resulting crystalline residue was suspended and washed in diethyl ether, taken by filtration, and dried to give the compound 3 (10.2 g) as a yellow solid.

MS (APCI) 346 [M+H]⁺

(2) The compound 3 (10.2 g) was dissolved in ethanol (80 mL)-THF (10 mL), an aqueous solution of 2 mol/L of sodium hydroxide (22 mL) was added to the solution, and the reaction mixture was stirred for 16 hours at room temperature. The reaction mixture was stirred for 10 minutes under ice-cooling, and then the precipitate was taken by filtration, washed with a mixed solvent of THF:ethanol (1:1), and dried to give the compound 4 (10 g) as a yellow solid.

MS (ESI) 316 [M−Na]−

Reference Example 41-45

The corresponding starting compound was treated in a similar manner as that of the above Reference Example 40 to give the compounds described in the following Table 37.

TABLE 37

[Chemical formula 125]

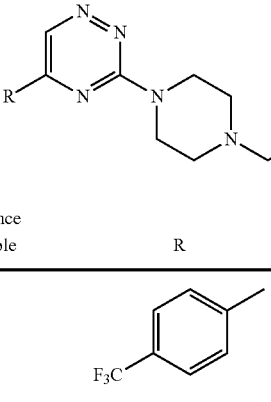

| Reference Example | R | Ms |
|---|---|---|
| 41 | 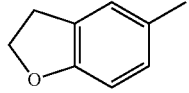 | 366 [M − Na]− ESI |
| 42 | 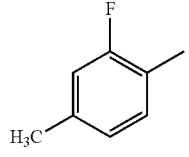 | 340 [M − Na]− ESI |
| 43 | 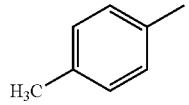 | 330 [M − Na]− ESI |
| 44 | 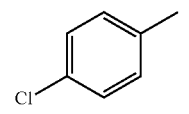 | 312 [M − Na]− ESI |
| 45 | | 332/334 [M − Na]− ESI |

Reference Example 46

[Chemical formula 126]

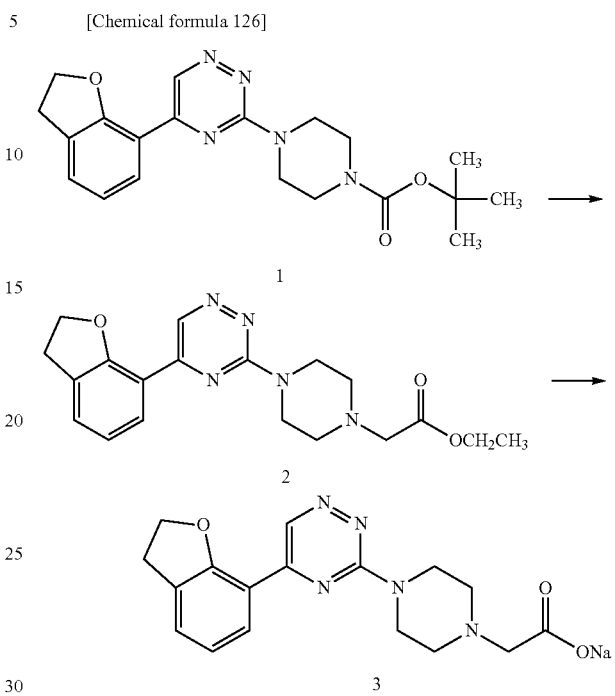

(1) To a solution of the compound 1 (1240 mg) in chloroform (6 mL) was added trifluoroacetic acid (6 mL), and the reaction mixture was stirred for 2 hours at room temperature. The reaction mixture was diluted with chloroform, and then an aqueous solution of potassium carbonate was added under ice-cooling, and the reaction mixture was extracted twice with chloroform. The resulting organic layer was dried over potassium carbonate, and the solvent was concentrated under reduced pressure. The resulting residue was dissolved in acetonitrile (32 mL), then ethyl chloroacetate (420 µL) and sodium carbonate (1030 mg) were added to the solution, and the reaction mixture was stirred for 20 hours at 65° C. The reaction mixture was cooled to room temperature, and then diluted with ethyl acetate, washed with water and brine, and dried over anhydrous sodium sulfate. The solvent was evaporated under reduced pressure, and the resulting residue was purified by NH-silica gel column chromatography (eluent: hexane-ethyl acetate; gradient: 70:30-50:50) to give the compound 2 (672 mg) as a yellow solid.

MS (APCI) 370 [M+H]⁺

(2) The compound 2 (672 mg) was dissolved in ethanol (10 mL)-THF (10 mL). An aqueous solution of 1 mol/L of sodium hydroxide (1.8 mL) was added to the solution, and the reaction mixture was stirred for 4 hours at room temperature. The precipitate was taken by filtration, and dried to give the compound 3 (582 mg) as a yellow solid.

MS (ESI) 340 [M−Na]⁺

Reference Example 47-48

The corresponding starting compound was treated in a similar manner as that of the above Reference Example 46 to give the compounds described in the following Table 38.

TABLE 38

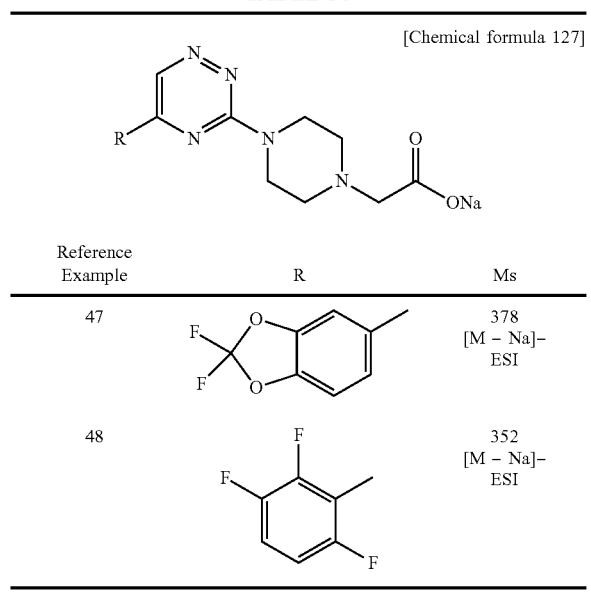

[Chemical formula 127]

| Reference Example | R | Ms |
|---|---|---|
| 47 | (2,2-difluoro-benzo[d][1,3]dioxol-5-yl)methyl group | 378 [M − Na]− ESI |
| 48 | (2,3,6-trifluoro-phenyl)methyl group | 352 [M − Na]− ESI |

Reference Example 49

[Chemical formula 128]

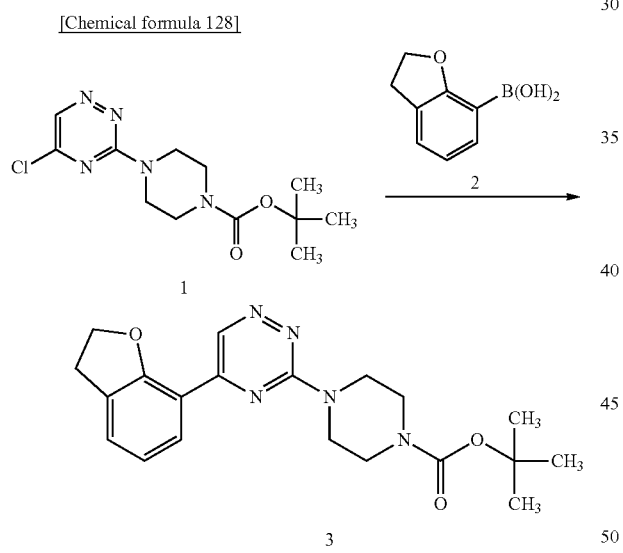

To a mixed solution of the compound 1 (100 mg), the compound 2 (109 mg), and dichlorobis(triphenylphosphine)palladium (12 mg) in dioxane (3.3 mL) was added an aqueous solution of 2 mol/L sodium carbonate (0.7 mL), the reaction mixture was stirred for 15 minutes at 150° C. in a microwave reactor (Initiator, Biotage). The reaction mixture was cooled to room temperature, diluted with ethyl acetate, and then washed with water and brine, dried over anhydrous sodium sulfate, and filtered. The solvent was evaporated under reduced pressure, and the resulting residue was purified by silica gel column chromatography (eluent: hexane-ethyl acetate; gradient: 85:15-50:50) to give the compound 3 (97 mg) as a yellow solid.

MS (APCI) 384 [M+H]+

Reference Example 50-62

The corresponding starting compound was treated in a similar manner as that of the above Reference Example 49 to give the compounds described in the following Tables 39 and 40.

TABLE 39

[Chemical formula 129]

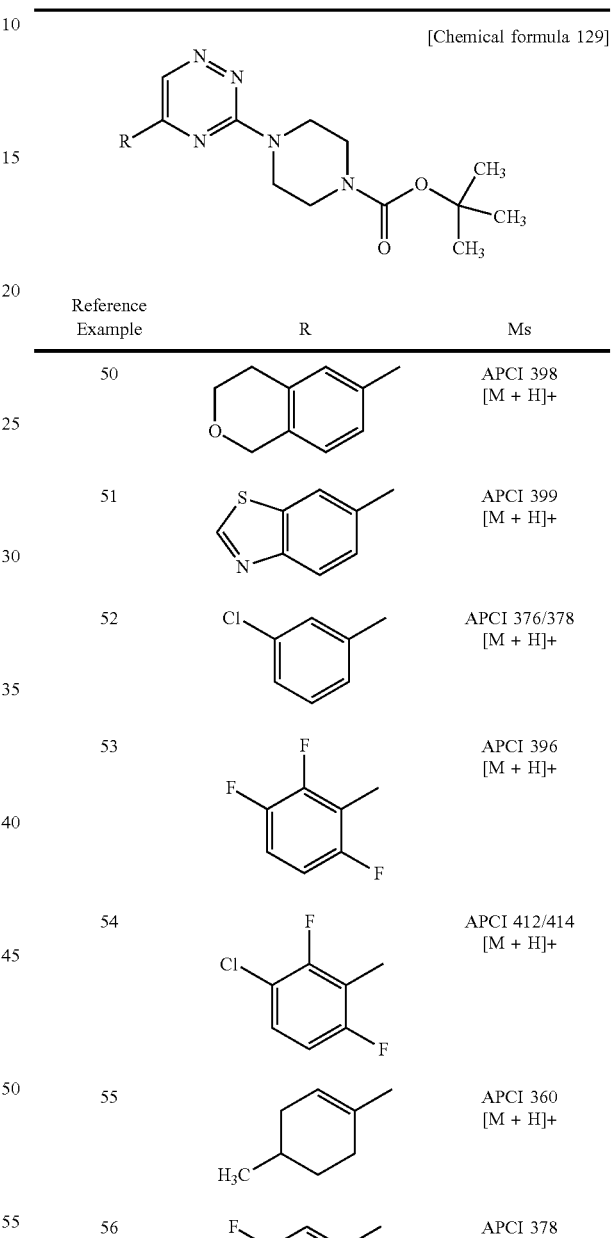

| Reference Example | R | Ms |
|---|---|---|
| 50 | isochroman-6-yl | APCI 398 [M + H]+ |
| 51 | benzothiazol-5-yl | APCI 399 [M + H]+ |
| 52 | 3-chlorophenyl | APCI 376/378 [M + H]+ |
| 53 | 2,3,6-trifluoro-phenyl | APCI 396 [M + H]+ |
| 54 | 3-chloro-2,6-difluorophenyl | APCI 412/414 [M + H]+ |
| 55 | 4-methylcyclohex-1-enyl | APCI 360 [M + H]+ |
| 56 | 2,4-difluorophenyl | APCI 378 [M + H]+ |
| 57 | 1,7-dimethyl-1H-indazol-4-yl | APCI 396 [M + H]+ |

TABLE 39-continued

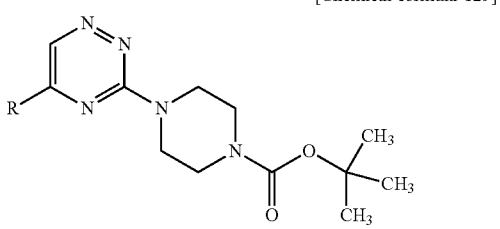

[Chemical formula 129]

| Reference Example | R | Ms |
|---|---|---|
| 58 | (3,4-dihydronaphthalen-2-yl, methyl-substituted) | APCI 394 [M + H]+ |
| 59 | (styryl) | APCI 368 [M + H]+ |

TABLE 40

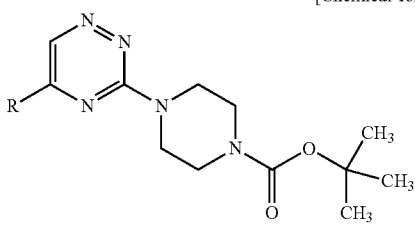

[Chemical formula 130]

| Reference Example | R | Ms |
|---|---|---|
| 60 | (4-trifluoromethylphenyl, methyl) | 3136226 APCI 410 [M + H]+ |
| 61 | (2,3-dihydrobenzofuran-5-yl, methyl) | 3098814 APCI 384 [M + H]+ |
| 62 | (isochroman-8-yl, methyl) | 3096558 APCI 398 [M + H]+ |

Reference Example 63

[Chemical formula 131]

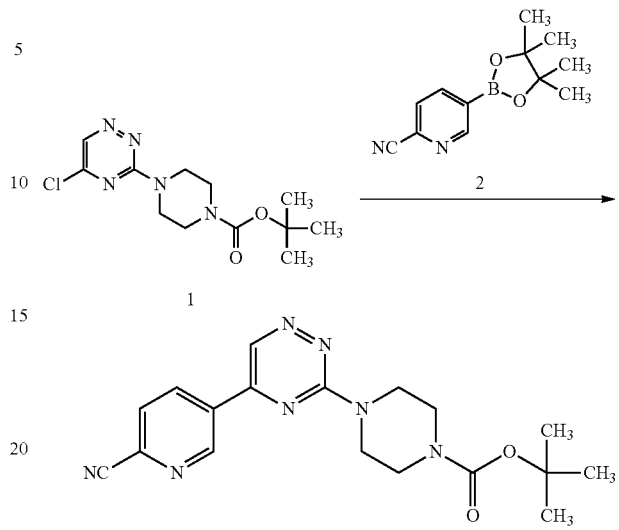

A mixed solution of the compound 1 (200 mg), the compound 2 (169 mg), tris(dibenzylideneacetone)dipalladium (31 mg), a solution of 1 mol/L tri-t-butylphosphine toluene (66 µL), and cesium carbonate (870 mg) in THF (12 mL) was degassed under reduced pressure, and then back-filled with argon. The reaction mixture was stirred for 2 hours with heating to reflux, and then cooled to room temperature, diluted with ethyl acetate, and then the reaction mixture was washed with water and brine, and dried over anhydrous magnesium sulfate.

The solvent was evaporated under reduced pressure, and the resulting crystalline residue was suspended and washed in a mixed solvent of ethyl acetate-hexane, taken by filtration, and dried to give the compound 3 (157 mg) as a yellow solid.

MS (APCI) 368 [M+H]$^+$

Reference Example 64

The corresponding starting compound was treated in a similar manner as that of the above Reference Example 63 to give the compound described in the following Table 41.

TABLE 41

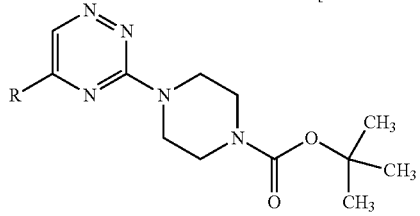

[Chemical formula 132]

| Reference Example | R | Ms |
|---|---|---|
| 64 | (1-methyl-1H-indazol-5-yl) | APCI 396 [M + H]+ |

Reference Example 65

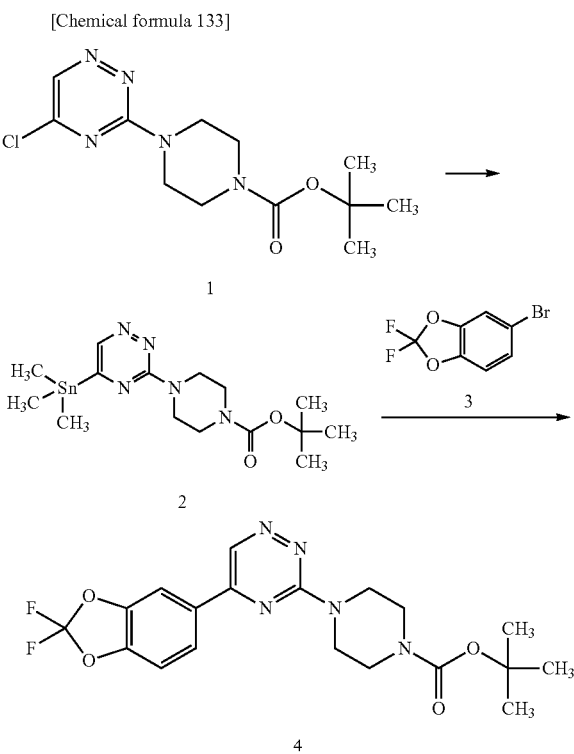

(1) A solution of the compound 1 (2.0 g) in dioxane (6 mL) was degassed under reduced pressure, and then back-filled with argon. To the reaction mixture were added hexamethylditin (2.5 mL) and tetrakis(triphenylphosphine) palladium (233 mg), the reaction mixture was again degassed under reduced pressure, and then back-filled with argon, and the reaction mixture was stirred for 1.3 hours with heating to reflux. The reaction mixture was cooled to room temperature, and concentrated under reduced pressure. The resulting residue was purified by NH-silica gel column chromatography (eluent: hexane-ethyl acetate; gradient: 95:5-75:25-50:50), and the resulting crude product was again purified by silica gel column chromatography (eluent: hexane-ethyl acetate; gradient: 95:5-70:30-34:66) to give the compound 2 (1.3 g) as a yellow solid.

MS (APCI) 426/428/430 $[M+H]^+$ (2) A solution of the compound 2 (250 mg) and the compound 3 (138 mg) in dioxane (6 mL) was degassed under reduced pressure, and then back-filled with argon. To the reaction mixture was added tetrakis(triphenylphosphine) palladium (850 mg), and the reaction mixture was again degassed under reduced pressure, and then back-filled with argon, stirred for 17.5 hours with heating to reflux. The reaction mixture was cooled to room temperature, and an aqueous solution of 10% potassium fluoride was added thereto. The reaction mixture was stirred for 30 minutes at room temperature, and then extracted with ethyl acetate. The organic layer was washed with brine, and dried over anhydrous magnesium sulfate. The solvent was evaporated under reduced pressure, and the resulting residue was purified by silica gel column chromatography (eluent: hexane-ethyl acetate; gradient: 80:20-50:50) to give the compound 4 (192 mg) as a yellow solid.

MS (APCI) 422 $[M+H]^+$

Reference Example 66

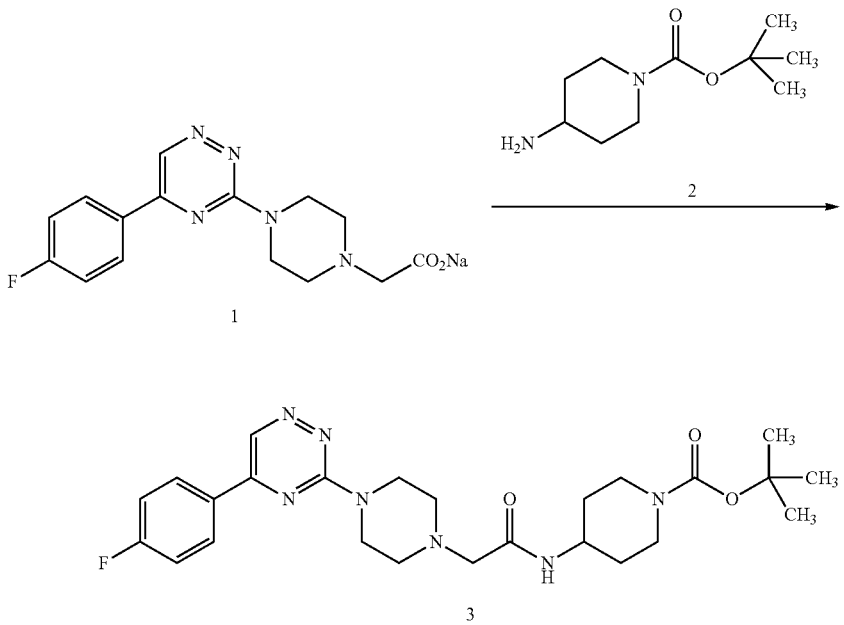

The compound 1 (1.0 g) and the compound 2 (885 mg) were suspended in DMF (20 mL). Diisopropylethylamine (1.0 mL), 1-hydroxybenzotriazole (598 mg) and 1-(3-dimethylaminopropyl)-3-ethylcarbodiimide hydrochloride (848 mg) were added to the suspension, and the reaction mixture was stirred for 18 hours at room temperature. The reaction mixture was diluted with a saturated aqueous solution of sodium bicarbonate, and extracted twice with ethyl acetate. The organic layer was washed with brine, dried over anhydrous sodium sulfate, and the solvent was evaporated under reduced pressure. The resulting residue was purified by silica gel column chromatography (eluent: chloroform-methanol; gradient: 100:0-95:5) to give the compound 3 (1.6 g) as yellow powder.

MS (APCI) 500 [M+H]

Reference Example 67-75

The corresponding starting compound was treated in a similar manner as that of the above Reference Example 66 to give the compounds described in the following Table 42.

TABLE 42

[Chemical formula 135]

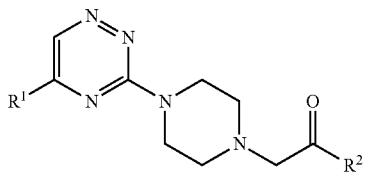

| Reference Example | $R^1$ | $R^2$ | Ms |
|---|---|---|---|
| 67 | 4-Cl-phenyl | N-Boc-piperidin-4-yl-NH- | 516/518 APCI [M + H]+ |
| 68 | 4-F-phenyl | N-Boc-azetidin-3-yl-NH- | 472 APCI [M + H]+ |
| 69 | 4-F-phenyl | (S)-N-Boc-pyrrolidin-3-yl-NH- | 486 APCI [M + H]+ |
| 70 | 4-Cl-phenyl | trans-3-F-N-Boc-piperidin-4-yl-NH- | 534/536 APCI [M + H]+ |
| 71 | 4-F-phenyl | trans-3-F-N-Boc-piperidin-4-yl-NH- | 518 APCI [M + H]+ |

TABLE 42-continued

[Chemical formula 135]

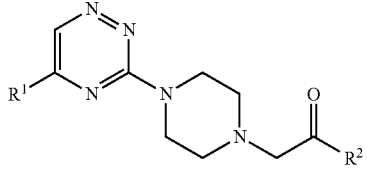

| Reference Example | R¹ | R² | Ms |
|---|---|---|---|
| 72 | 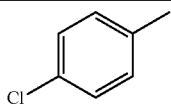 | 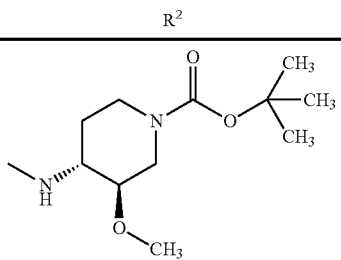 | 546/548 APCI [M + H]+ |
| 73 | 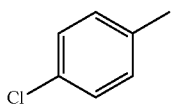 | 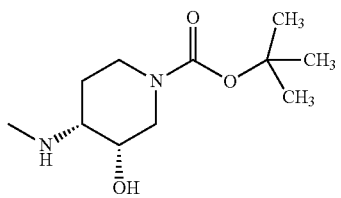 | 532/534 [M + H]+ APCI |
| 74 | 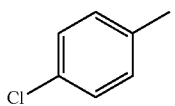 | 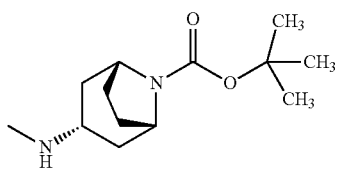 | 542/544 ESI [M + H]+ |
| 75 | 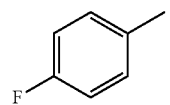 | 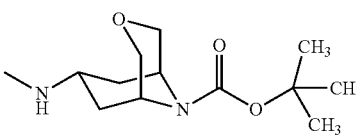 | 542 ESI [M + H]+ |

Reference Example 76

[Chemical formula 136]

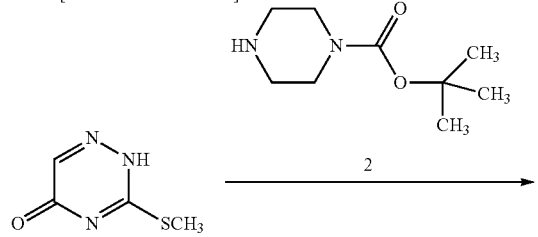

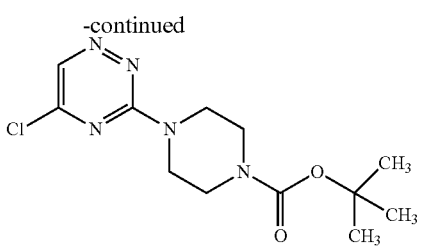

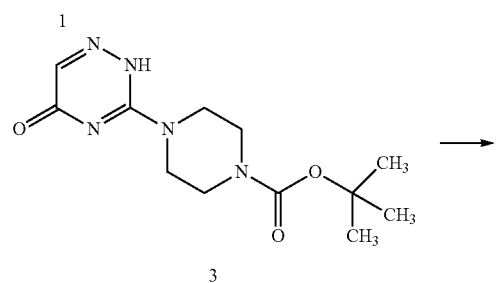

(1) The compound 1 (5.0 g) and the compound 2 (19.5 g) were suspended in THF (175 mL), and the suspension was stirred for 18 hours with heating to reflux. The reaction mixture was cooled to room temperature, the precipitate was taken by filtration, washed with ethyl acetate, and dried to give the compound 3 (6.5 g) as a colorless solid.

MS (APCI) 282 [M+H]$^+$ (2) To a solution of triphenylphosphine (699 mg) in dioxane (22 mL) was added N-chlorosuccinimide (356 mg), and the reaction mixture was stirred for 30 minutes at room temperature. Then, to the reaction mixture was added the compound 3 (150 mg), and the reaction mixture was stirred for 40 minutes with heating to reflux. The reaction mixture was cooled to room temperature, and concentrated under reduced pressure. The resulting residue was diluted with ethyl acetate, and triethylamine (296 µL) and water were added to the solution, followed by filtration to remove an insoluble substance, and washed with ethyl acetate. The filtrate was washed with water and brine, and dried over anhydrous magnesium sulfate. The solvent was evaporated under reduced pressure, and the resulting residue was immediately purified by silica gel column chromatography (eluent: hexane-ethyl acetate 80:20) to give the compound 4 (146 mg) as a red solid.

MS (APCI) 300/302 [M+H]$^+$

Reference Example 77

[Chemical formula 137]

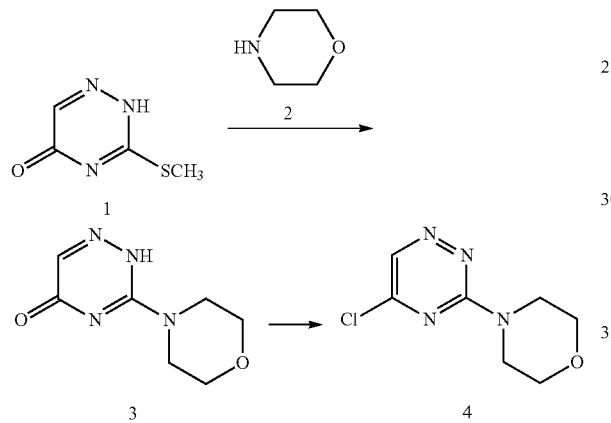

(1) The compound 1 (5.0 g) and the compound 2 (9.1 g) were suspended in THF (180 mL), and the suspension was stirred for 20 hours with heating to reflux. The reaction mixture was cooled to room temperature, the precipitate was taken by filtration, washed with ethyl acetate, and dried to give the compound 3 (5.8 g) as a pale yellow solid.

MS (APCI) 183 [M+H]$^+$ (2) To a solution of triphenylphosphine (13.0 g) in dioxane (550 mL) was added N-chlorosuccinimide (6.7 g), and the reaction mixture was stirred for 30 minutes at room temperature. Then, to the reaction mixture was added the compound 3 (3.0 g), and the reaction mixture was stirred for 1 hour with heating to reflux. The reaction mixture was cooled in ice bath, triethylamine (5.1 mL) was added thereto, and the reaction mixture was stirred for 1 hour. An insoluble substance was removed by filtration, washed with dioxane, and then the resulting filtrate was concentrated under reduced pressure. The resulting residue was immediately purified by silica gel column chromatography (eluent: hexane-ethyl acetate; gradient: 95:5-75:25) to give the compound 4 (2.5 g) as an orange solid.

MS (APCI) 201/203 [M+H]$^+$

Reference Example 78

[Chemical formula 138]

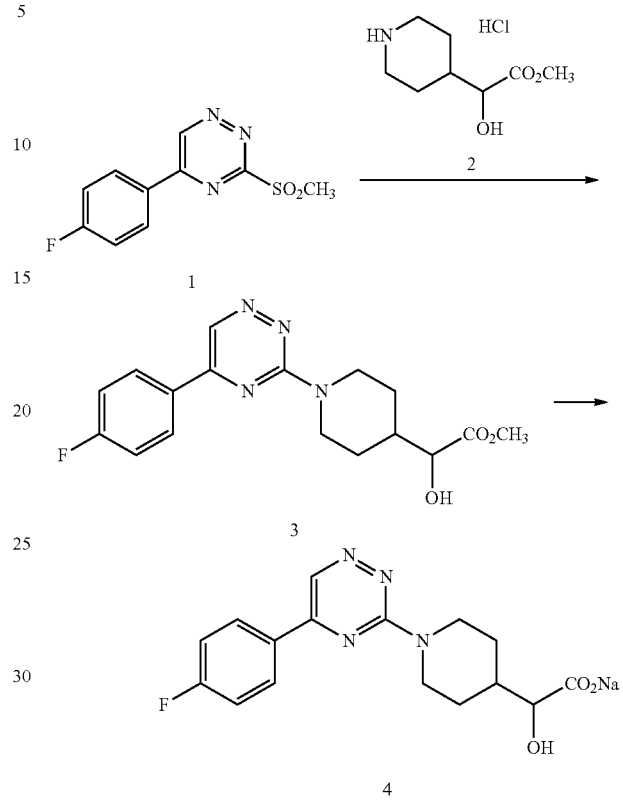

(1) To a suspension of the compound 1 (500 mg) and the compound 2 (624 mg) in acetonitrile (6 mL) was added diisopropylethylamine (1040 µL), and the suspension was stirred for 14 hours at room temperature. The reaction mixture was diluted with water, and then extracted 3 times with chloroform, and the resulting organic layer was dried over anhydrous sodium sulfate. The solvent was evaporated under reduced pressure, and the resulting residue was purified by silica gel column chromatography (eluent: chloroform-ethyl acetate 67:33) to give the compound 3 (409 mg) as a yellow solid.

MS (APCI) 347 [M+H]$^+$ (2) The compound 3 (400 mg) was dissolved in methanol (2.3 mL), an aqueous solution of 2 mol/L of sodium hydroxide (1.2 mL) was added to the solution, and the reaction mixture was stirred for 18 hours at room temperature. The precipitate was filtered, and dried to give the compound 4 (184 mg) as a yellow solid.

MS (ESI) 331 [M−Na]−

Reference Example 79

[Chemical formula 139]

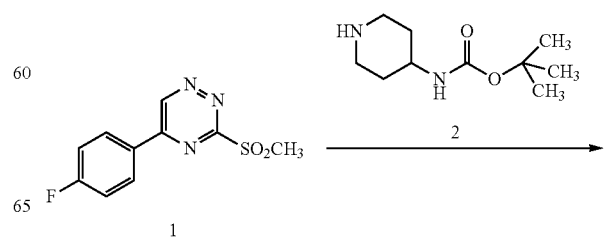

-continued

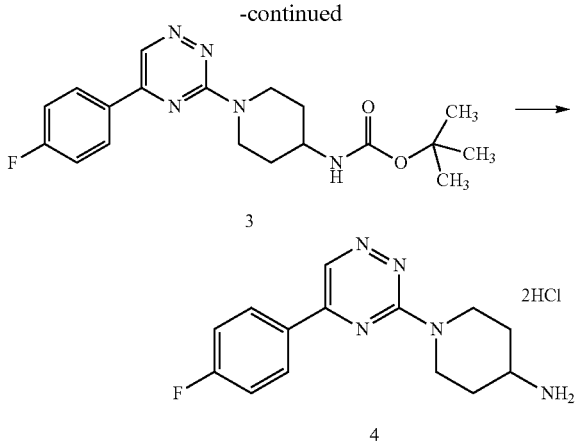

(1) To a solution of the compound 1 (3.0 g) and the compound 2 (2.37 g) in THF (300 mL) was added triethylamine (3.3 mL), and the reaction mixture was stirred for 14 hours at room temperature. To the reaction mixture was added DMF (100 mL), and the reaction mixture was stirred for additional 7 hours at room temperature, and then diluted with water. The reaction mixture was extracted with ethyl acetate, and the resulting organic layer was washed with water, a saturated aqueous solution of sodium bicarbonate and brine, and then dried over anhydrous magnesium sulfate. The solvent was evaporated under reduced pressure, and the resulting residue was purified by silica gel column chromatography (eluent: hexane-ethyl acetate; gradient: 65:35-50:50) to give the compound 3 (3.29 g) as a yellow solid.

MS (APCI) 374 [M+H]$^+$ (2) To a solution of the compound 3 (664 mg) in THF (20 mL) was added a solution of 4 mol/L HCl in ethyl acetate (10 mL), and the reaction mixture was stirred for 1 day at room temperature. The reaction mixture was concentrated under reduced pressure, and the resulting residue was suspended and washed in ethyl acetate, taken by filtration, and dried to give the compound 4 (599 mg) as a pale yellow powder.

MS (APCI) 274 [M+H]$^+$

Reference Example 80

[Chemical formula 140]

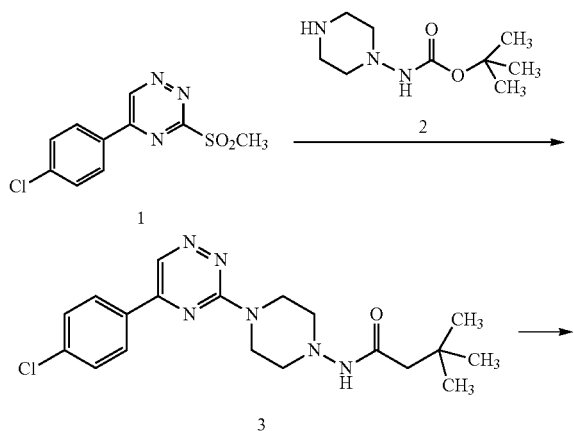

-continued

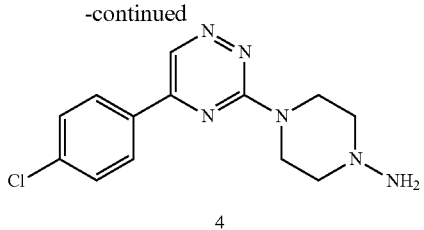

(1) To a solution of the compound 1 (450 mg) in acetonitrile (16 mL) were added the compound 2 (403 mg) and diisopropylethylamine (580μ), and the reaction mixture was stirred for 1 hour at room temperature under argon atmosphere, and then stirred for additional 4 hours at 60° C. The reaction mixture was cooled to room temperature, and then diluted with a saturated aqueous solution of sodium bicarbonate, and extracted twice with chloroform. The organic layer was dried over anhydrous sodium sulfate, and the solvent was evaporated under reduced pressure. The resulting residue was purified by NH-silica gel column chromatography (eluent: hexane-ethyl acetate; gradient: 70:30-50:50) to give the compound 3 (390 mg) as a yellow solid.

MS (ESI) 391/393 [M+H]$^+$ (2) To a solution of the compound 3 (390 mg) in chloroform (2 mL) was added trifluoroacetic acid (2 mL), and the reaction mixture was stirred for 1.5 hours at room temperature. The reaction mixture was diluted with methanol, then treated with packed strong cation exchange resin (PoraPak Rxn Cx, eluent: a solution of 1 mol/L NH$_3$ in methanol), and the eluate was concentrated under reduced pressure to give the compound 4 (296 mg) as a yellow solid.

MS (ESI) 291/293 [M+H]$^+$

Reference Example 81

[Chemical formula 141]

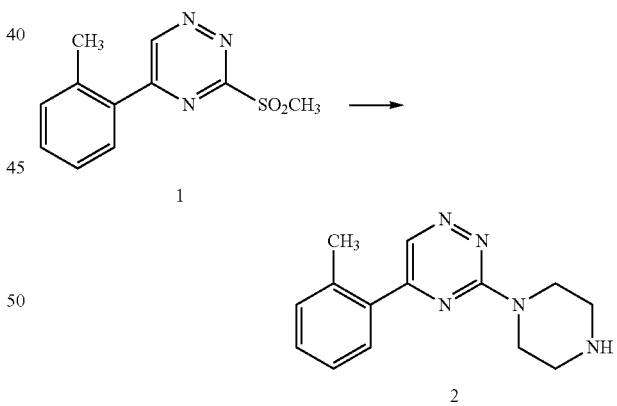

To a solution of the compound 1 (750 mg) in THF (30 mL) was added piperazine (1.3 g), and the reaction mixture was stirred for 20 minutes at room temperature under argon atmosphere. The reaction mixture was diluted with ethyl acetate, and then washed with an aqueous solution of 20% potassium carbonate, and the organic layer was dried over anhydrous magnesium sulfate. The solvent was evaporated under reduced pressure, and the resulting residue was purified by silica gel column chromatography (eluent: chloroform-10% aqueous ammonia/methanol; gradient: 97:3-90:10) to give the compound 2 (524 mg) as a yellow viscous substance.

MS (APCI) 256 [M+H]$^+$

Reference Example 82-83

The corresponding starting compound was treated in a similar manner as that of the above Reference Example 79 or Reference Example 80 to give the compounds described in the following Table 43.

TABLE 43

| Reference Example | Structure | MS [M + H]+ | Salt | Method |
|---|---|---|---|---|
| 82 | ![structure] | 290/292 APCI | 2HCl | Similar method as Reference Example 79 |
| 83 | ![structure] | 276/278 APCI | | Similar method as Reference Example 80 |

Reference Example 84

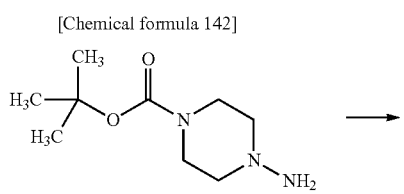

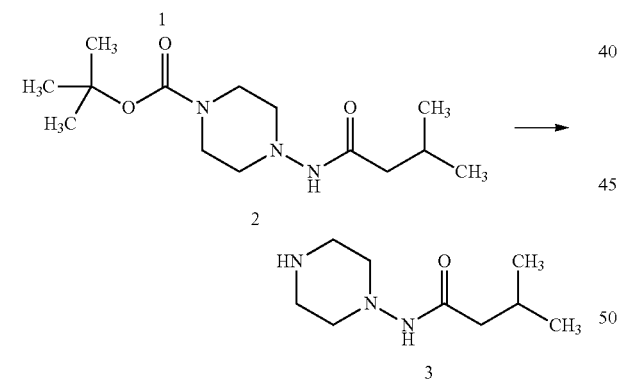

(1) The compound 1 (100 mg) and diisopropylethylamine (240 μL) were dissolved in chloroform, isovaleryl chloride (217 μL) was added to the solution, and the reaction mixture was stirred for 3 hours at room temperature. The reaction mixture was diluted with a saturated aqueous solution of sodium bicarbonate, and extracted twice with chloroform. The organic layer was dried over anhydrous sodium sulfate, and the solvent was evaporated under reduced pressure. The resulting residue was suspended and washed in a mixed solution of ethyl acetate-hexane, taken by filtration, and dried to give the compound 2 (120 mg) as a colorless solid.
MS (APCI) 286 [M+H]+

(2) To a solution of the compound 2 (120 mg) in chloroform (1 mL) was added trifluoroacetic acid (1 mL), and the reaction mixture was stirred for 4 hours at room temperature. The reaction mixture was diluted with methanol, treated with packed strong cation exchange resin (PoraPak Rxn Cx, eluent: a solution of 1 mol/L NH3 in methanol), and the eluate was concentrated under reduced pressure to give the compound 3 (74 mg) as a colorless solid.

MS (ESI) 186 [M+H]+

Reference Example 85

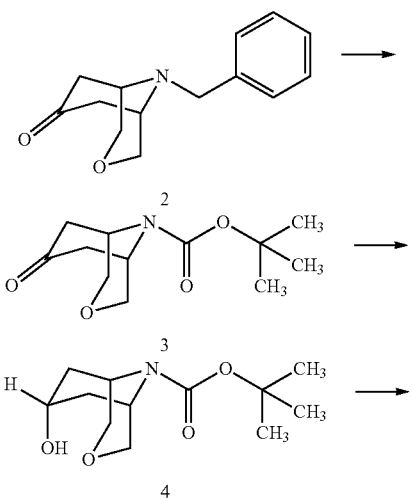

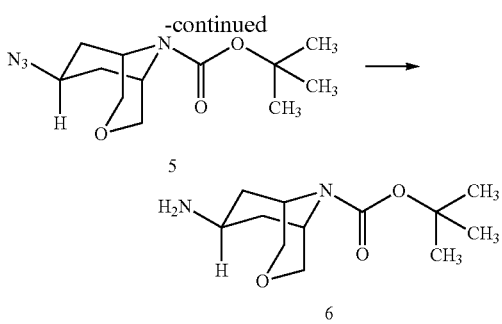

(1) To a solution of the compound 1 (10 mL) in water (120 mL) was added sodium periodate (13 g), and the reaction mixture was stirred for 18 hours at room temperature. To the reaction mixture was added acetonitrile (180 mL), and the precipitate was removed by filtration. The filtrate was concentrated under reduced pressure, acetonitrile (180 mL) was added to the resulting residue, and an insoluble substance was removed by filtration. The filtrate was concentrated under reduced pressure, and the resulting residue was dissolved in water, and then acetone-1,3-dicarboxylic acid (17.8 g) and conc. hydrochloric acid (6.6 mL) were added to the solution. Then, to the reaction mixture was added dropwise benzylamine at room temperature over 1 hour, and the reaction mixture was stirred for 2.5 hours after heating to 50° C. The reaction mixture was cooled to room temperature, and then an aqueous solution of 1 mol/L of sodium hydroxide was added thereto, a pH of the reaction mixture was adjusted to 9-10, and the reaction mixture was extracted with chloroform. The organic layer was dried over potassium carbonate, and the solvent was evaporated under reduced pressure. The resulting residue was suspended and washed in a mixed solution of ethyl acetate-hexane, taken by filtration, and dried to give the compound 2 (9.9 g) as a colorless solid.

MS (ESI) 232 [M+H]$^+$ (2) The compound 2 (3.0 g) was dissolved in methanol (40 mL). Hydrous 20% palladium hydroxide on carbon (900 mg) and di-t-butyl dicarbonate (3.1 g) were added to the solution, and the reaction mixture was stirred for 6 hours at room temperature under hydrogen atmosphere. The reaction mixture was back-filled with argon, and then di-t-butyl dicarbonate (1.0 g) was added thereto, and the reaction mixture was stirred for 20 hours at room temperature. Palladium hydroxide on carbon was removed by filtration, and then washed with methanol. The filtrate was concentrated under reduced pressure, and the resulting residue was suspended and washed in hexane, taken by filtration, and dried to give the compound 3 (2.6 g) as a colorless solid.

(3) The compound 3 (1.0 g) was dissolved in methanol (10 mL). Sodium borohydride (157 mg) was added to the solution under ice-cooling, and the reaction mixture was stirred for 1 hour at the same temperature, and then stirred for additional 17 hours at room temperature. To the reaction mixture was again added sodium borohydride (157 mg), and the reaction mixture was stirred for additional 1 day at room temperature. The reaction mixture was diluted with a saturated aqueous solution of sodium bicarbonate, and extracted with chloroform. The organic layer was dried over anhydrous sodium sulfate, the solvent was evaporated under reduced pressure to give the compound 4 (917 mg) as a colorless solid.

MS (APCI) 244 [M+H]

(4) The compound 4 (400 mg) was dissolved in THF (16 mL).

Diphenylphosphoryl azide (1360 mg), triphenylphosphine (1280 mg) and a solution of 2.2 mol/L diethyl azodicarboxylate/toluene (2.3 mL) were added to the solution under ice-cooling, and a temperature of the reaction mixture was raised to room temperature, followed by stirring of the reaction mixture for 18 hours. The reaction mixture was diluted with water, and then extracted with ethyl acetate. The organic layer was dried over anhydrous sodium sulfate, and the solvent was evaporated under reduced pressure. The resulting residue was purified by silica gel column chromatography (eluent: hexane-ethyl acetate; gradient: 100:0-80:20) to give the compound 5 (320 mg) as a colorless viscous substance.

MS (APCI) 269 [M+H]$^+$ (5) The compound 5 (320 mg) was dissolved in methanol (10 mL). Hydrous 10% palladium on carbon (160 mg) was added to the solution, and the reaction mixture was stirred for 2 hours under hydrogen atmosphere. Palladium on carbon was removed by filtration, and then washed with methanol. The filtrate was concentrated under reduced pressure, and the resulting residue was suspended and washed in a mixed solution of ethyl acetate-hexane, taken by filtration, and dried to give the compound 6 (280 mg) as a colorless solid.

MS (APCI) 243 [M+H]$^+$

Reference Example 86

[Chemical formula 144]

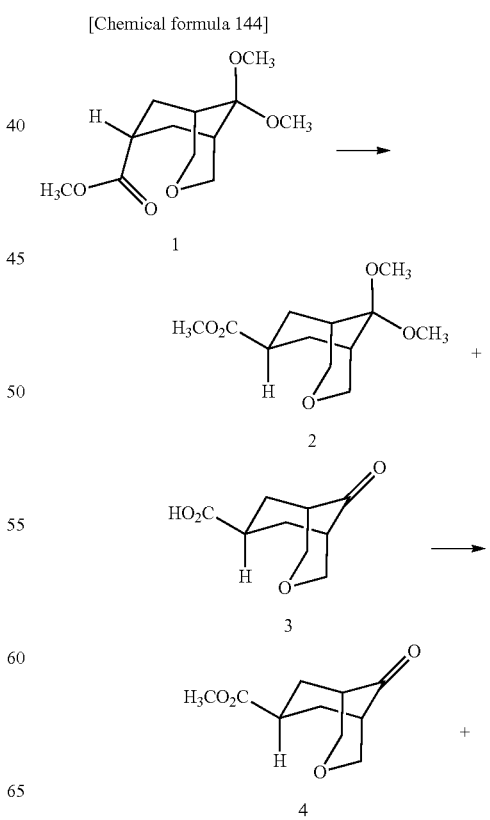

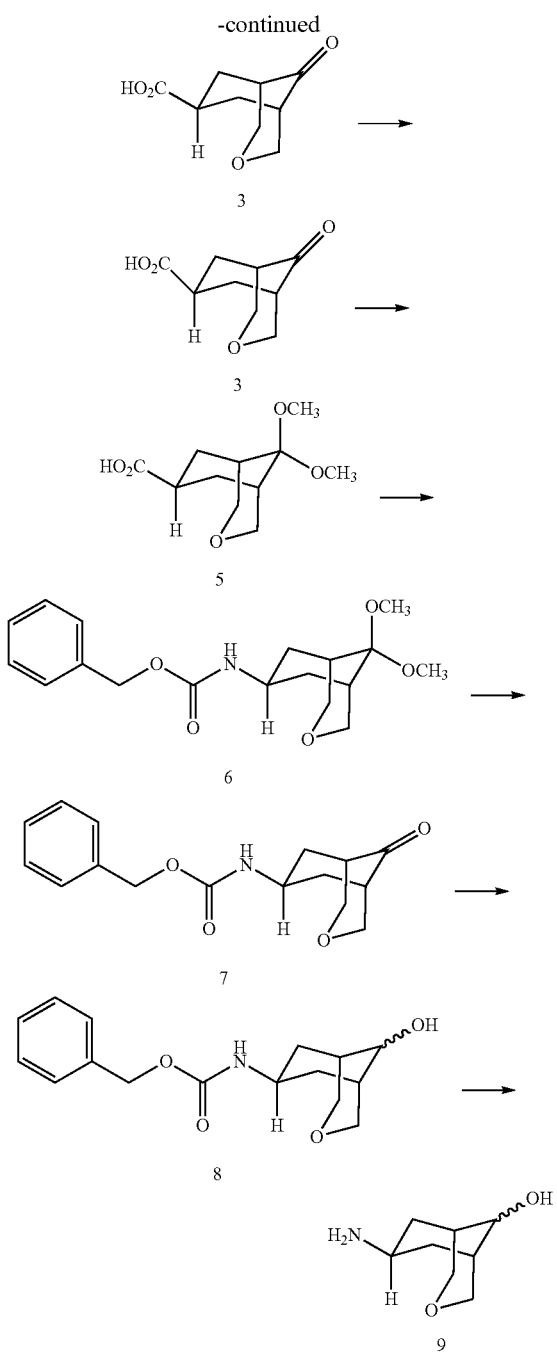

(1) The compound 1 (13.6 g) prepared according to a method described in Bioorganic and Medicinal Chemistry Letters, Vol. 16 (2006) page 5408 was dissolved in methanol (80 mL). A solution of 5 mol/L sodium methoxide in methanol (16.7 mL) was added to the solution, and the reaction mixture was stirred for 16 hours at 80° C. The reaction mixture was cooled to room temperature, and then diluted with diethyl ether, 0.5 mol/L hydrochloric acid was added to the solution, and the solution was extracted with ethyl acetate. The organic layer was dried over anhydrous sodium sulfate, and the solvent was evaporated to give a mixture of the compound 2 and the compound 3.

The resulting mixture was dissolved in acetone (80 mL). Amberlyst 15 (Aldrich, 1.4 g) was added to the solution, and the reaction mixture was stirred for 3 hours at 65° C. The reaction mixture was cooled to room temperature, and then filtered, and the filtrate was concentrated under reduced pressure to give a mixture of the compound 3 and the compound 4. Then, the resulting mixture was dissolved in methanol (120 mL), and an aqueous solution of 1 mol/L of sodium hydroxide (120 mL) was added to the solution, followed by stirring of the reaction mixture for 1 hour at room temperature. The reaction mixture was neutralized by 1 mol/L hydrochloric acid, and then methanol was evaporated, and the solution was extracted with ethyl acetate. The organic layer washed with brine, and then dried over anhydrous sodium sulfate. The solvent was evaporated under reduced pressure, and the resulting residue was suspended and washed in diethyl ether, taken by filtration, and dried to give the compound 3 (5.0 g) as a colorless solid.

MS (APCI) 185 [M+H]$^+$ (2) The compound 3 (2.0 g) was dissolved in methanol (24 mL), methyl orthoformate (8.0 mL) and Amberlyst 15 (Aldrich, 200 mg) were added to the solution, and the reaction mixture was stirred for 3.5 hours at 80° C. The reaction mixture was cooled to room temperature, and then filtered, and the filtrate was concentrated under reduced pressure. The resulting residue was suspended and washed in a mixed solution of ethyl acetate-hexane, taken by filtration, and dried to give the compound 5 (1040 mg) as a colorless solid.

The compound 5 (1040 mg) was dissolved in toluene (25 mL). Diphenylphosphoryl azide (1490 mg) and triethylamine (750 μL) were added to the solution, and the reaction mixture was stirred for 1 hour at 80° C. Then, benzyl alcohol (4.6 mL) was added thereto, and the reaction mixture was stirred for 17 hours at 80° C. The reaction mixture was cooled to room temperature, diluted with water and a saturated aqueous solution of sodium bicarbonate, and then extracted with ethyl acetate. The organic layer was washed with brine, and dried over anhydrous sodium sulfate, and then the solvent was evaporated. The resulting residue was purified by silica gel column chromatography (eluent: hexane-ethyl acetate; gradient: 70:30-50:50) to give the compound 6 (954 mg) as a colorless solid.

MS (APCI) 336 [M+H]$^+$ (3) The compound 6 (954 mg) was dissolved in acetone (15 mL). Amberlyst 15 (Aldrich, 280 mg) was added to the solution, and the reaction mixture was stirred for 1.5 hours at 65° C. The reaction mixture was cooled to room temperature, and then filtered, and the filtrate was concentrated under reduced pressure to give the compound 7 (833 mg) as a colorless solid.

MS (APCI) 290 [M+H]$^+$ (4) The compound 7 (350 mg) was dissolved in methanol (12 mL), and sodium borohydride (92 mg) was added to the solution at room temperature, followed by stirring of the reaction mixture for 2 hours. To the reaction mixture was added an aqueous solution of ammonium chloride, and methanol was evaporated under reduced pressure, and then the solution was extracted with ethyl acetate. The organic layer was dried over anhydrous sodium sulfate, and the solvent was evaporated under reduced pressure to give the compound 8 (colorless solid, 362 mg) as a cis:trans (1:1) mixture.

MS (APCI) 292 [M+H]$^+$ (5) The compound 8 (352 mg) was dissolved in ethanol (12 mL), hydrous 5% palladium on carbon (100 mg) was added to the solution, the reaction mixture was stirred for 4.5 hours under hydrogen atmosphere. Palladium on carbon was removed by filtration, and then washed with ethanol. The filtrate was concentrated under reduced pressure, and the resulting residue was dried to give the compound 9 (colorless solid, 180 mg) as a cis:trans (1:1) mixture.

MS (APCI) 158 [M+H]$^+$

Reference Example 87

[Chemical formula 145]

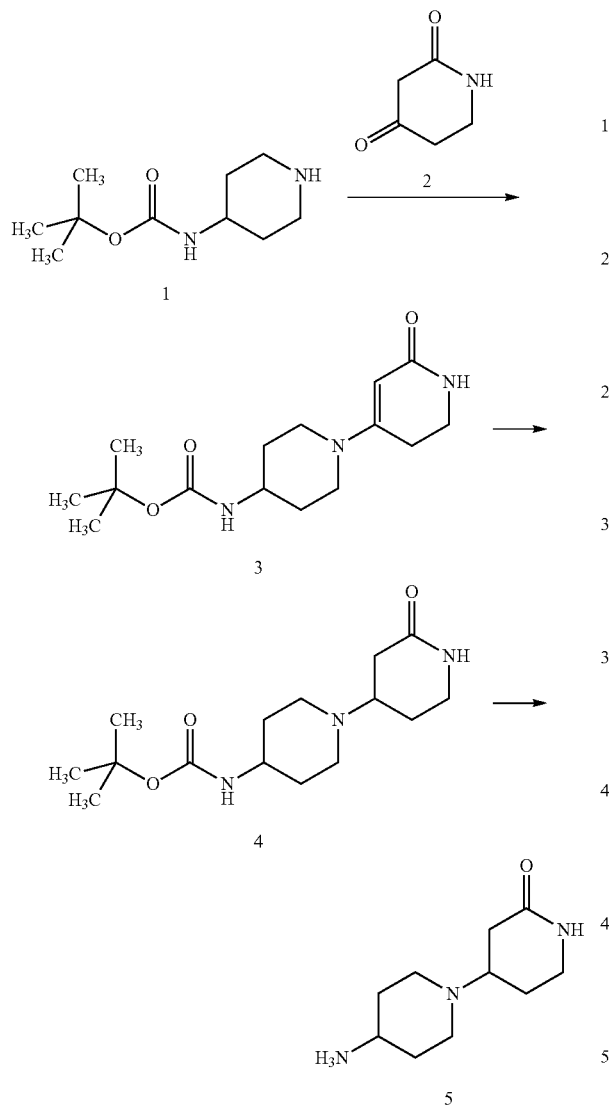

(1) To a solution of the compound 1 (2.0 g) in chloroform (5 mL) were added the compound 2 (1.24 g) and acetic acid (0.63 mL), and the reaction mixture was stirred for 1 hour at room temperature. The reaction mixture was diluted with a saturated aqueous solution of sodium bicarbonate, and then extracted 3 times with chloroform. The resulting organic layer was dried over anhydrous sodium sulfate, and the solvent was evaporated under reduced pressure. The resulting residue was purified by silica gel column chromatography (eluent: chloroform-methanol; gradient: 100:0-95:5), and dried to give the compound 3 (900 mg) as a brown solid.

MS (APCI) 296 [M+H]$^+$ (2) The compound 3 (900 mg) was dissolved in methanol (15 mL), sodium borohydride (340 mg) was added to the solution in three parts under ice-cooling, and a temperature of the reaction mixture was raised to room temperature. The reaction mixture was diluted with a saturated aqueous solution of sodium bicarbonate, and extracted 3 times with chloroform. The organic layer was dried over anhydrous sodium sulfate, and the solvent was evaporated under reduced pressure. The resulting residue was purified by silica gel column chromatography (eluent: chloroform-methanol; gradient: 100:0-90:10), and dried to give the compound 4 (390 mg) as a colorless solid.

MS (APCI) 298 [M+H]$^+$ (3) To a solution of the compound 4 (390 mg) in chloroform (6.5 mL) was added trifluoroacetic acid (6.5 mL) under ice-cooling, and the reaction mixture was stirred for 30 minutes at room temperature. The reaction mixture was diluted with methanol, and then treated with packed strong cation exchange resin (PoraPak Rxn Cx, eluent: a solution of 1 mol/L NH$_3$ in methanol). The eluate was concentrated under reduced pressure to give the compound 5 (201 mg) as a colorless solid.

MS (APCI) 198 [M+H]$^+$

Reference Example 88

[Chemical formula 146]

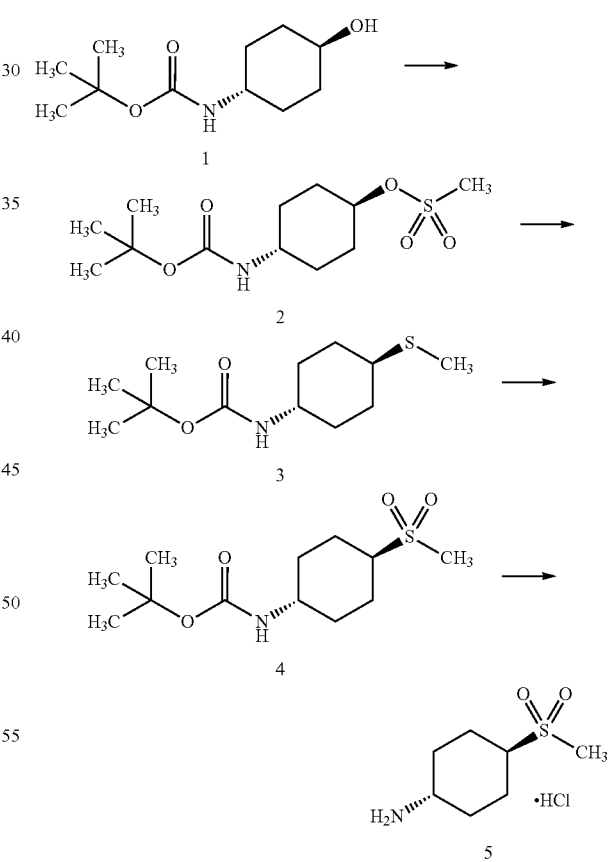

(1) The compound 1 (999.5 mg) was dissolved in chloroform (10 mL), triethylamine (650 μL) and anhydrous methanesulfonic acid were added to the solution under ice-water bath cooling, and the solution was stirred for 17 hours at room temperature. The reaction mixture was diluted with chloroform, washed with water and a saturated aqueous solution of sodium bicarbonate, and then dried over anhydrous sodium sulfate, followed by evaporation of the solvent.

The resulting residue was suspended and washed in a mixed solvent of normal-hexane and ethyl acetate, and then taken by filtration, and dried in vacuo to give the compound 2 (1056.1 mg) as a colorless solid.

MS (APCI) 311 [M+NH$_4$]$^+$ (2) The compound 2 (501.0 mg) was dissolved in dimethylformamide (5.5 mL), sodium methanethiolate (237.9 mg) was added to the solution at room temperature, and the reaction mixture was stirred for 15.5 hours. To the reaction mixture was added an aqueous solution of 1 mol/L of sodium hydroxide, and the reaction mixture was extracted with ethyl acetate. The organic layer was washed with water, and then dried over anhydrous sodium sulfate, followed by evaporation of the solvent. The resulting residue was purified by silica gel column chromatography (eluent: hexane-ethyl acetate; gradient: 93:7-80:20) to give the compound 3 (77.5 mg) as a colorless solid.

MS (APCI) 146 [M−C$_5$H$_8$O$_2$+H]$^+$ (3) The compound 3 (70.0 mg) was dissolved in chloroform (3 mL). Hydrous 30% m-chloroperbenzoic acid (168.1 mg) was added to the solution at room temperature, and the reaction mixture was stirred for 17 hours. The reaction mixture was diluted with chloroform, washed with an aqueous solution of 1 mol/L sodium hydroxide, and then dried over anhydrous sodium sulfate, followed by evaporation of the solvent. The resulting residue was dried in vacuo to give the compound 4 (80.0 mg) as a colorless solid.

MS (APCI) 295 [M+NH$_4$]$^+$ (4) The compound 4 (78.0 mg) was suspended in methanol (3 mL), a solution of 4 mol/L hydrogen chloride in ethyl acetate (705 μL) was added to the suspension at room temperature, and the reaction mixture was stirred for 22 hours. The reaction mixture was concentrated under reduced pressure, and the resulting residue was dried in vacuo to give the compound 5 (61.2 mg) as a slightly yellow solid.

MS (APCI) 178 [M+H]$^+$

Reference Example 89

[Chemical formula 147]

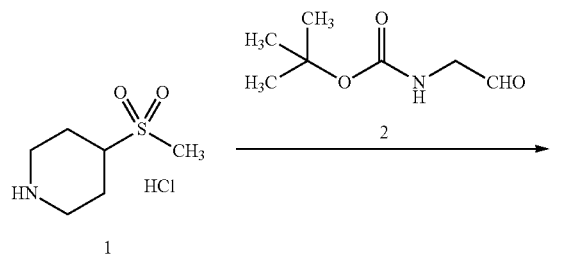

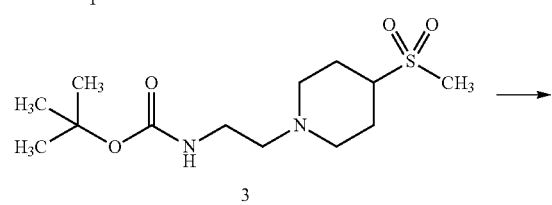

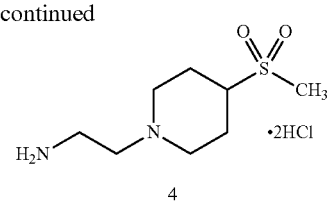

(1) The compound 1 (900.0 mg) was suspended in chloroform (9 mL). Acetic acid (258 μL), the compound 2 (1594.4 mg), triethylamine (628 μL), and sodium triacetoxyborohydride (1432.8 mg) were added to the suspension at room temperature, and the reaction mixture was stirred for 25 hours. To the reaction mixture was added a saturated aqueous solution of sodium bicarbonate, and the reaction mixture was stirred for 10 minutes at room temperature, and then extracted with chloroform, and the organic layer was dried over anhydrous sodium sulfate, followed by evaporation of the solvent. The resulting residue was purified by silica gel column chromatography (eluent: ethyl acetate-methanol; gradient: 100:0-92:8) to give the compound 3 (1265.3 mg) as a colorless solid.

MS (APCI) 307 [M+H]$^+$ (2) The compound 3 (1255.1 mg) was dissolved in chloroform (13 mL). Trifluoroacetic acid (13 mL) was added to the solution at room temperature, and the reaction mixture was stirred for 16 hours. The solvent was evaporated, and the resulting residue was suspended in methanol (15 mL), and then a solution of 4 mol/L hydrogen chloride in 1,4-dioxane (10 mL) was added to the suspension, followed by evaporation of the solvent. The resulting residue was dried in vacuo to give the compound 4 (1059.7 mg) as a pale brown solid.

MS (APCI) 207 [M+H]$^+$

Reference Example 90

[Chemical formula 148]

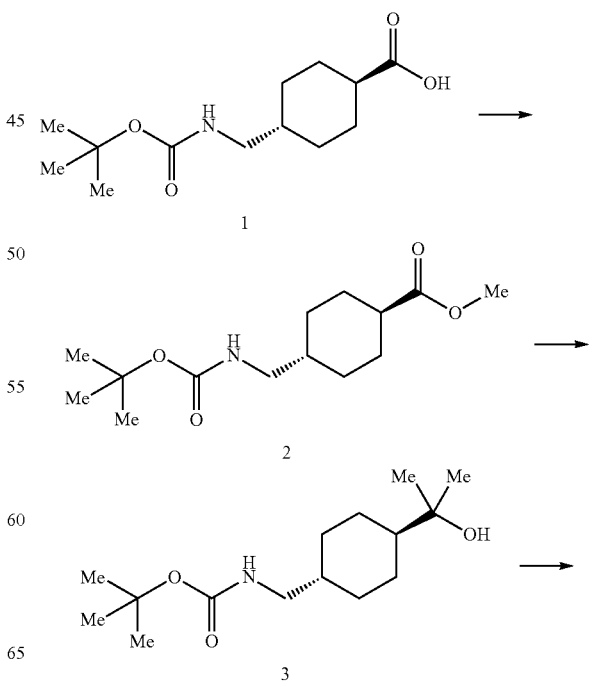

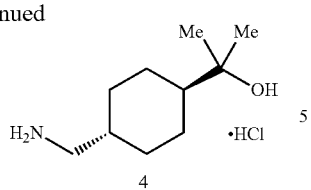

(1) The compound 1 (5.90 g) was dissolved in methanol (20 mL), and a solution of 2 mol/L trimethylsilyldiazomethane in hexane (12.6 mL) was added to the solution under nitrogen atmosphere and ice-water bath cooling. After several hours, a solution of 2 mol/L trimethylsilyldiazomethane in hexane (20 mL) was added to the solution, upon confirming that yellow coloring was no longer disappeared in the reaction solution, the solvent was evaporated. The resulting residue was left to crystallize at room temperature, suspended and washed in hexane, and then taken by filtration, and dried in vacuo to give the compound 2 (6.50 g) as a pale yellow solid.

MS (ESI) 272 [M+H]$^+$ (2) The compound 2 (5.43 g) was dissolved in tetrahydrofuran (50 mL), a solution of 3 mol/L methylmagnesium bromide in diethyl ether (28 mL) was added dropwise to the solution under nitrogen atmosphere and ice-water bath cooling. After completion of the dropwise addition, the reaction mixture was stirred for 1 hour at room temperature. To the reaction mixture were added sodium chloride and a saturated aqueous solution of ammonium chloride, and the reaction mixture was extracted with ethyl acetate. The organic layer was washed with a saturated aqueous solution of sodium chloride, dried over magnesium sulfate, and then the solvent was evaporated. The resulting residue was purified by silica gel column chromatography (eluent: hexane-ethyl acetate; gradient: 75:25-50:50) to give the compound 3 (2.75 g) as a colorless solid.

MS (ESI) 272 [M+H]$^+$ (3) To the compound 3 (2.71 g) was added trifluoroacetic acid (11.56 mL), and the reaction mixture was stirred for 10 minutes at room temperature. The reaction mixture was concentrated under reduced pressure, conc. hydrochloric acid and methanol were added thereto, and the reaction mixture was stirred for 2 minutes.

After concentration under reduced pressure, ethanol and diethylether were added to the concentrate, and the reaction mixture was stirred overnight. The solvent was ditilled off, and dried in vacuo to give the compound 4 (3.43 g) as a pale yellow solid.

MS (APCI) 172 [M+H]$^+$

Reference Example 91

[Chemical formula 149]

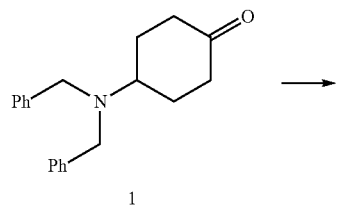

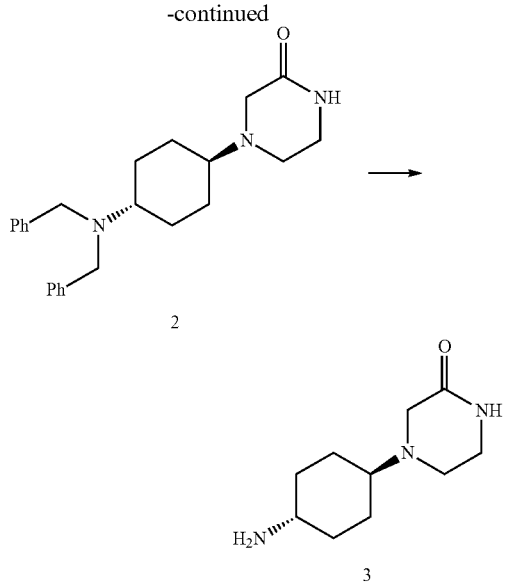

(1) The compound 1 (10.0 g) was suspended in 1,2-dichloroethane (60 mL). The compound 2 (3.75 g), tetrahydrofuran (40 mL), and acetic acid (2.93 mL) were added to the suspension, and then 1,2-dichloroethane (40 mL), tetrahydrofuran (60 mL), and sodium triacetoxyborohydride (8.67 g) were added thereto, and the reaction mixture was stirred for 14 hours at room temperature. To the reaction mixture was added a saturated aqueous solution of sodium bicarbonate, and the reaction mixture was stirred for 4 hours at room temperature, and then extracted with chloroform. The organic layer was washed with water, and then dried over magnesium sulfate, followed by evaporation of the solvent. The resulting residue was purified by silica gel column chromatography (eluent: chloroform-methanol 95:5) to give the compound 2 (5.335 g) as a colorless solid.

MS (APCI) 378 [M+H]$^+$ (2) The compound 2 (2.50 g) was dissolved in a mixed solvent of methanol (80 mL) and tetrahydrofuran (40 mL). 10% Palladium on carbon (0.80 g) was added to the solution, and the reaction mixture was stirred for 21 hours at room temperature under ordinary pressure and hydrogen atmosphere. The reaction mixture was filtrated, and the solvent was evaporated. The resulting residue was suspended and washed in hexane, and then taken by filtration, and dried to give the compound 3 (1.213 g) as a colorless solid.

MS (APCI) 198 [M+H]$^+$

Reference Example 92

[Chemical formula 150]

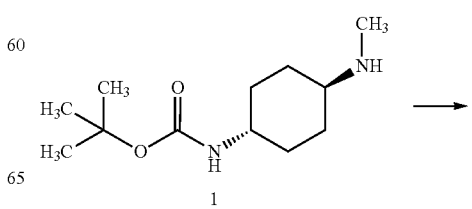

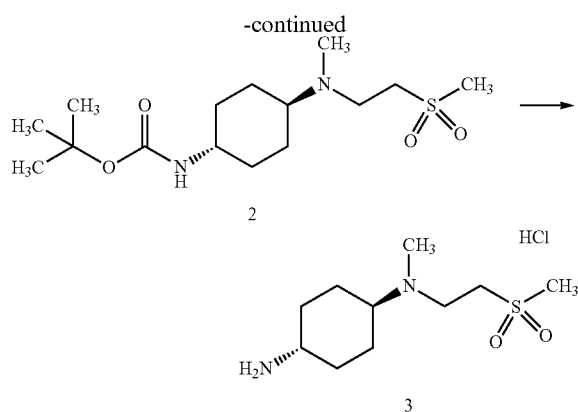

(1) To a solution of the compound 1 (400 mg) in methanol (15 mL) was added vinyl sulfone (380 μL), and the reaction mixture was stirred for 30 minutes at room temperature. The reaction mixture was concentrated under reduced pressure, and the resulting residue was suspended and washed in diisopropylether, taken by filtration, and dried to give the compound 2 (516 mg) as a colorless solid.

MS (APCI) 335 [M+H]$^+$ (2) The compound 2 (516 mg) was dissolved in a mixed solvent of ethyl acetate (1.5 mL)/methanol (1.5 mL), a solution of 4 mol/L HCl in ethyl acetate (3 mL) was add to the solution, and the reaction mixture was stirred for 3 hours at room temperature. The reaction mixture was concentrated under reduced pressure, and the resulting residue was suspended and washed in ethyl acetate, taken by filtration, and dried to give the compound 3 (357 mg) as a colorless solid.

MS (APCI) 235 [M+H]$^+$

Reference Example 93

[Chemical formula 151]

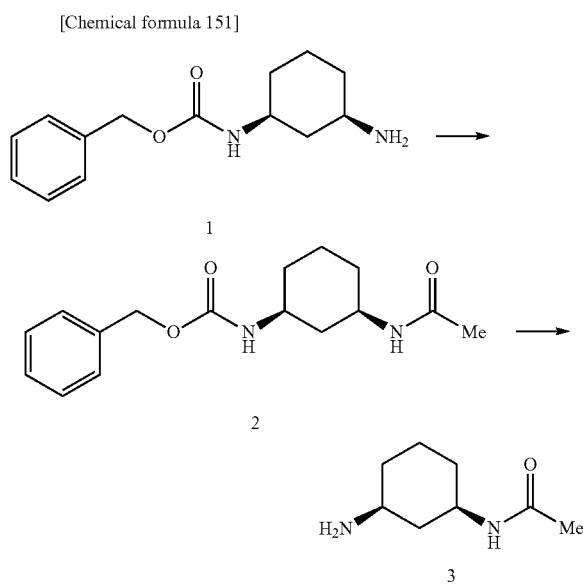

(1) To a suspension of the compound 1 (350 mg) in chloroform (14 mL) were added triethylamine (294 μL) and acetyl chloride (120 μL) under ice-cooling, and the reaction mixture was kept in stirring for 1 hour. To the reaction mixture were added water and a saturated aqueous solution of sodium bicarbonate, and then the reaction mixture was extracted with chloroform. The organic layer was dried over anhydrous sodium sulfate, and then the solvent was evaporated under reduced pressure. The resulting residue was suspended and washed in a mixed solution of diisopropylether/ethyl acetate, taken by filtration, and dried to give the compound 2 (328 mg) as a colorless solid.

MS (APCI) 291 [M+H]$^+$ (2) The compound 2 (328 mg) was dissolved in methanol (10 mL). Wet 5% palladium on carbon (65 mg) was added to the solution, and the reaction mixture was stirred for 3 hours under hydrogen atmosphere. The palladium on carbon was removed by filtration, and then washed with methanol. The filtrate was concentrated under reduced pressure, and the resulting residue was dried to give the compound 3 (172 mg) as a colorless solid.

MS (APCI) 157 [M+H]$^+$

Reference Example 94

[Chemical formula 152]

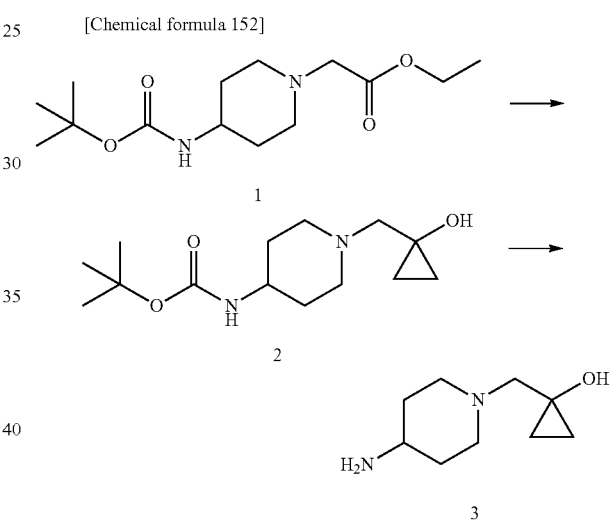

To a solution of the compound 1 (2 g) in THF (14 mL) were added tetraisopropyl orthotitanate (2.3 mL) and a solution of 1 mol/L ethylmagnesium bromide in THF (35 mL) at room temperature, and then the reaction mixture was stirred for 1 hour. To the reaction mixture were added water and a saturated aqueous solution of ammonium chloride, and then the reaction mixture was extracted with ethyl acetate. The organic layer was dried over anhydrous sodium sulfate, and then the solvent was evaporated under reduced pressure. The resulting residue was purified by silica gel column chromatography (eluent: chloroform-10% aqueous ammonia/methanol; gradient: 100:0-90:10) to give the compound 2 (545 mg) as a colorless solid. The compound 2 (545 mg) was dissolved in chloroform (4 mL), trifluoroacetic acid (4 mL) was added to the solution, and the reaction mixture was stirred for 30 minutes at room temperature. The reaction mixture was diluted with methanol, and then treated with packed strong cation exchange resin (PoraPak Rxn Cx, eluent: a solution of 1 mol/L NH$_3$ in methanol). The eluate was concentrated under reduced pressure to give the compound 3 (88 mg) as a colorless viscous substance.

MS (ESI) 171 [M+H]$^+$

Reference Example 95

[Chemical formula 153]

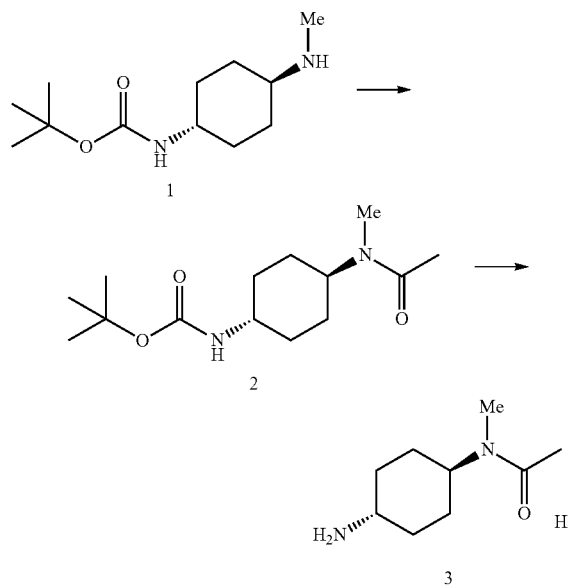

(1) The compound 1 (500 mg) was dissolved in pyridine (2 mL) and acetic anhydride (1 mL), and the reaction mixture was stirred for 1.5 hours at room temperature. The reaction mixture was concentrated under reduced pressure, and the resulting residue was suspended and washed in a mixed solvent of ethyl acetate/hexane, taken by filtration, and dried to give the compound 2 (410 mg) as a colorless solid.

MS (APCI) 271 [M+H]$^+$ (2) The compound 2 (410 mg) was dissolved in dioxane (4 mL), a solution of 4 mol/L HCl in dioxane (4 mL) was added to the solution, and the reaction mixture was stirred for 1 hour at room temperature. The reaction mixture was concentrated under reduced pressure to give the compound 3 (360 mg) as a colorless solid.

MS (APCI) 171 [M+H]$^+$

Reference Example 96

[Chemical formula 154]

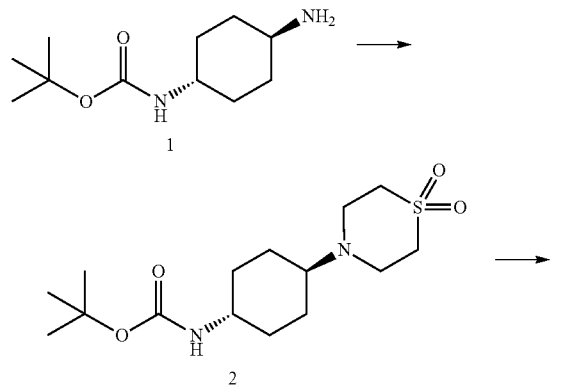

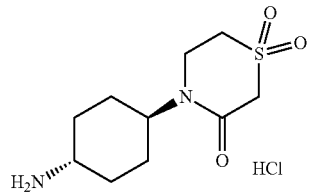

(1) The compound 1 (195 mg) was dissolved in dimethylacetoamide (4 mL). Sodium carbonate (190 mg), sodium iodide (290 mg), and bis(2-chloroethyl)sulfone (190 mg) were added to the solution at room temperature, and then the reaction mixture was heated to 80° C. After stirring for 3 hours at the same temperature, the reaction mixture was cooled to room temperature, and water and an aqueous solution of potassium carbonate were added thereto. The organic layer extracted with ethyl acetate, dried over anhydrous sodium sulfate, and then the solvent was evaporated under reduced pressure. The resulting residue was suspended and washed in a mixed solvent of ethyl acetate/hexane, taken by filtration, and dried to give the compound 2 (233 mg) as a colorless solid.

MS (APCI) 333 [M+H]$^+$ (2) The compound 2 (233 mg) was dissolved in dioxane (1.5 mL), a solution of 4 mol/L HCl in dioxane (1.5 mL) was added to the solution, and the reaction mixture was stirred for 2 hours at room temperature. The reaction mixture was concentrated under reduced pressure to give the compound 3 (170 mg) as a colorless solid.

$^1$H NMR (400 MHz, DMSO-d6) δ7.99 (3H, brs), 3.39-3.92 (8H, m), 2.95 (1H, m), 2.25 (2H, brs), 2.03 (2H, d, J=12.4 Hz), 1.56 (2H, brs), 1.37 (2H, m)

Reference Example 97

[Chemical formula 155]

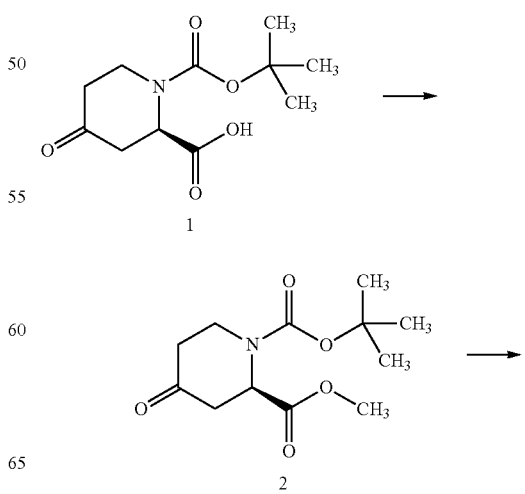

-continued

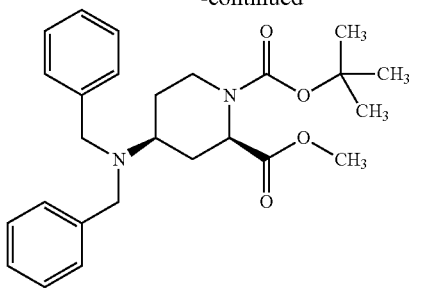

3

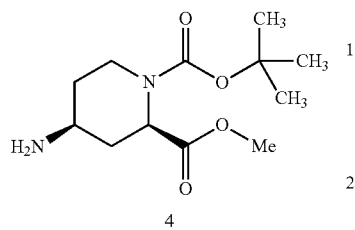

4

(1) The compound 1 (1 g) was dissolved in a mixed solvent of toluene (15 mL)/methanol (5 mL), a solution of 2 mol/L trimethylsilyldiazomethane in hexane (3.5 mL) was added to the solution, and the reaction mixture was stirred for 1 hour at room temperature. To the reaction mixture was added acetic acid (1 mL), and then the reaction mixture was concentrated under reduced pressure to give the compound 2 (1.06 g) as a colorless viscous substance.

MS (APCI) 258 [M+H]$^+$ (2) The compound 2 (1.06 g) was dissolved in THF (21 mL). Dibenzylamine (1.2 mL), acetic acid (235 μL), and sodium triacetoxyborohydride (2.62 g) were added to the solution, and the reaction mixture was stirred for 18 hours at room temperature. To the reaction mixture was added water and a saturated aqueous solution of sodium bicarbonate, and then the reaction mixture was extracted with ethyl acetate. The organic layer was dried over anhydrous sodium sulfate, and then the solvent was evaporated under reduced pressure. The resulting residue was purified by silica gel column chromatography (eluent: hexane-ethyl acetate; gradient: 90:10-80:20) to give the compound 3 (354 mg) as a colorless solid. The compound 3 (353 mg) was dissolved in methanol (10 mL), hydrous 5% palladium hydroxide on carbon (176 mg) was added to the solution, and the reaction mixture was stirred for 3 hours under hydrogen atmosphere. The palladium hydroxide on carbon was removed by filtration, and then washed with methanol. The filtrate was concentrated under reduced pressure, and the resulting residue was purified by silica gel column chromatography (eluent: chloroform-methanol; gradient: 100:0-90:10) to give the compound 4 (70 mg) as a colorless viscous substance.

MS (APCI) 259 [M+H]$^+$

Reference Example 98

[Chemical formula 156]

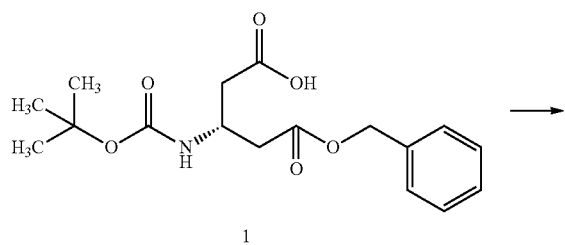

1

-continued

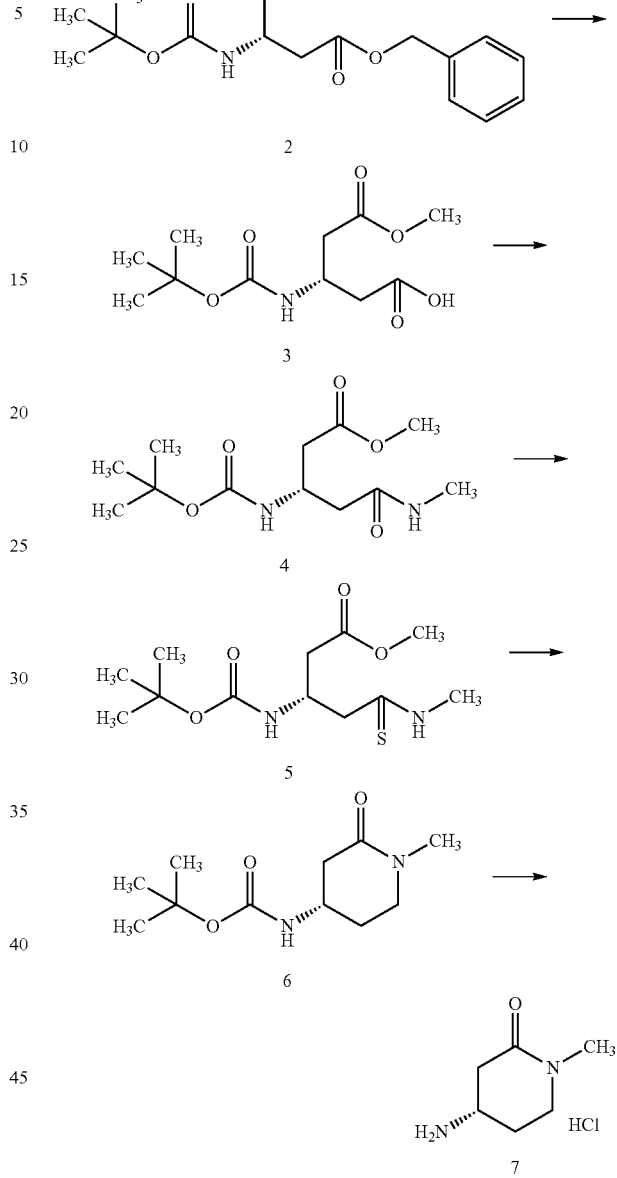

(1) The compound 1 (3.2 g) was dissolved in a mixed solvent of toluene (36 mL)/methanol (12 mL), a solution of 2 mol/L trimethylsilyldiazomethane in hexane (11 mL) was added to the solution, and the reaction mixture was stirred for 40 minutes at room temperature. Acetic acid (2.5 mL) was added to the reaction mixture, and then the solvent was evaporated under reduced pressure to give the compound 2 (3.3 g) as a colorless viscous substance.

MS (APCI) 352 [M+H]$^+$ (2) The compound 2 (3.3 g) was dissolved in methanol (50 mL), hydrous 5% palladium on carbon (1.0 g) was added to the solution, and the reaction mixture was stirred for 2 hours under hydrogen atmosphere. The palladium on carbon was removed by filtration, and then washed with methanol. The filtrate was concentrated under reduced pressure to give the compound 3 (2.5 g) as a colorless viscous substance.

MS (APCI) 262 [M+H]

(3) The compound 3 (2.48 g) was dissolved in dimethylformamide (50 mL). Methylamine hydrochloride (955 mg), diisopropylethylamine (6.6 mL), and O-(7-azabenzotriazol-1-yl)-N,N,N',N'-tetramethyluroniumhexafluorophosphate (5.4 g) were added to the solution, and the reaction mixture was stirred for 30 minutes at room temperature. The solvent was concentrated under reduced pressure, and then water and a saturated aqueous solution of sodium bicarbonate were added to the residue, and the aqueous solution was extracted with chloroform. The organic layer was dried over anhydrous sodium sulfate, and then the solvent was evaporated under reduced pressure. The resulting residue was suspended and washed in a mixed solvent of ethyl acetate/hexane, taken by filtration, and dried to give the compound 4 (1.7 g) as a colorless solid.

MS (APCI) 275 [M+H]$^+$ (4) The compound 4 (2.4 g) was dissolved in THF (45 mL), Lawesson's reagent (4.0 g) was added to the solution, and the reaction mixture was stirred for 12 hours at room temperature. To the reaction mixture were added water and a saturated aqueous solution of sodium bicarbonate, and the reaction mixture was extracted with ethyl acetate. The organic layer was dried over anhydrous sodium sulfate, and then the solvent was evaporated under reduced pressure. The resulting residue was purified by silica gel column chromatography (eluent: hexane-ethyl acetate; gradient: 30:70-50:50) to give the compound 5 (1.7 g) as a colorless solid.

MS (APCI) 291 [M+H]$^+$ (5) The compound 5 (1.9 g) was dissolved in a mixed solvent of THF (15 mL)/methanol (45 mL). Nickel chloride (II) hexahydrate (5.5 g) and sodium borohydride (2.5 g) were added to the solution under ice-cooling, and then the reaction mixture was stirred for 6 hours at room temperature. To the reaction mixture were added water and a saturated aqueous solution of sodium bicarbonate, and the reaction mixture was extracted with ethyl acetate. The organic layer was dried over anhydrous sodium sulfate, and then the solvent was evaporated under reduced pressure. The resulting residue was suspended and washed in a mixed solvent of ethyl acetate/hexane, taken by filtration, and dried to give the compound 6 (982 mg) as a colorless solid.

MS (APCI) 229 [M+H]$^+$ (6) The compound 6 (1.0 g) was dissolved in dioxane (10 mL), a solution of 4 mol/L HCl in dioxane (4.6 mL) was added to the solution, and the reaction mixture was stirred for 1.5 hours at room temperature. The reaction mixture was concentrated under reduced pressure to give the compound 7 (770 mg) as a colorless solid.

MS (APCI) 129 [M+H]$^+$

Reference Example 99

[Chemical formula 157]

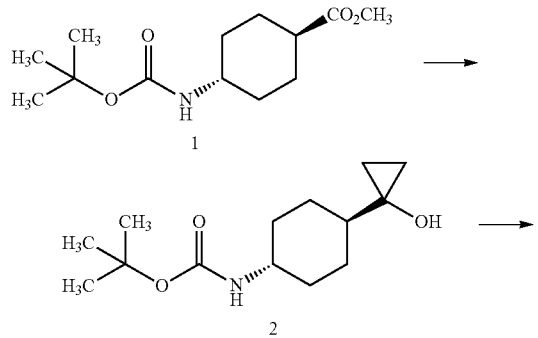

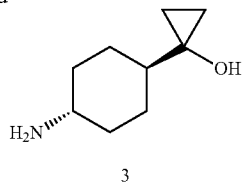

(1) To a solution of the compound 1 (3.0 g) in THF (30 mL) was added a solution of 1 mol/L methylmagnesium bromide in THF (47 mL) under argon atmosphere and ice-cooling, and then a temperature of the reaction mixture was raised to room temperature, and the reaction mixture was stirred for 1.5 hours. The reaction mixture was cooled under ice-cooling, water and a saturated aqueous solution of sodium chloride were added thereto, and then the reaction mixture was extracted with ethyl acetate. The organic layer was washed with a saturated aqueous solution of sodium bicarbonate and brine, dried over anhydrous magnesium sulfate. The solvent was evaporated under reduced pressure, and the resulting residue was purified by silica gel column chromatography (eluent: hexane-ethyl acetate; gradient: 75:25-50:50) to give the compound 2 (545 mg) as a colorless solid.

MS (APCI) 256 [M+H]$^+$ (2) The compound 2 (300 mg) was dissolved in chloroform (2 mL), trifluoroacetic acid (1 mL) was added to the solution, and the reaction mixture was stirred for 1 hour at room temperature. The reaction mixture was diluted with methanol, and then treated with packed strong cation exchange resin (PoraPak Rxn Cx, eluent: a solution of 1 mol/L NH$_3$ in methanol). The eluate was concentrated under reduced pressure to give the compound 3 (165 mg) as a colorless solid.

MS (APCI) 156 [M+H]$^+$

Reference Example 100

[Chemical formula 158]

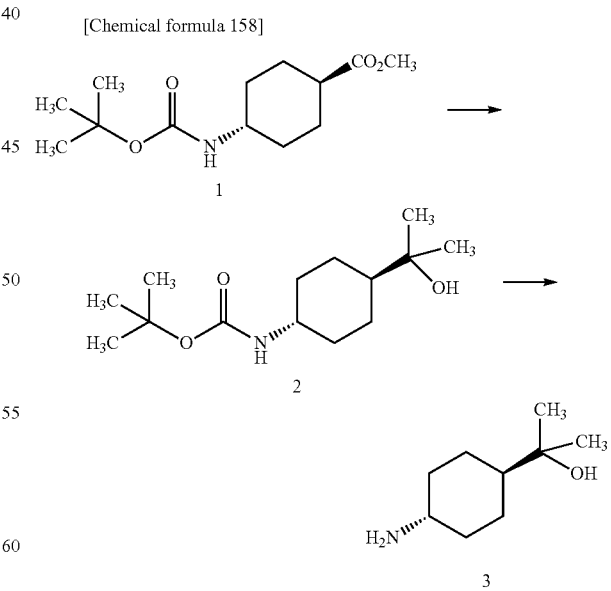

(1) To a solution of the compound 1 (1.5 g) in THF (35 mL) were added tetraisopropyl orthotitanate (1.9 mL) and a solution of 1 mol/L ethylmagnesium bromide in THF (29 mL) at room temperature, and then the reaction mixture was stirred for 50 minutes. The reaction mixture was cooled under ice-cooling, water was added thereto, and then the reaction mixture was extracted with ethyl acetate. The organic layer was washed with water, a saturated aqueous solution of sodium bicarbonate, and brine, and dried over anhydrous magnesium sulfate.

The solvent was evaporated under reduced pressure, and the resulting residue was purified by silica gel column chromatography (eluent: hexane-ethyl acetate; gradient: 65:35-50:50) to give the compound 2 (1.93 g) as a colorless solid.

MS (APCI) 258 $[M+H]^+$ (2) The compound 2 (1.85 g) was dissolved in dichloromethane (20 mL), trifluoroacetic acid (10 mL) was added to the solution, and the reaction mixture was stirred for 40 minutes at room temperature. The reaction mixture was diluted with methanol, and then treated with packed strong cation exchange resin (PoraPak Rxn Cx, eluent: a solution of 1 mol/L $NH_3$ in methanol). The eluate was concentrated under reduced pressure to give the compound 3 (225 mg) as a colorless solid.

MS (APCI) 158 $[M+H]^+$

Reference Example 101

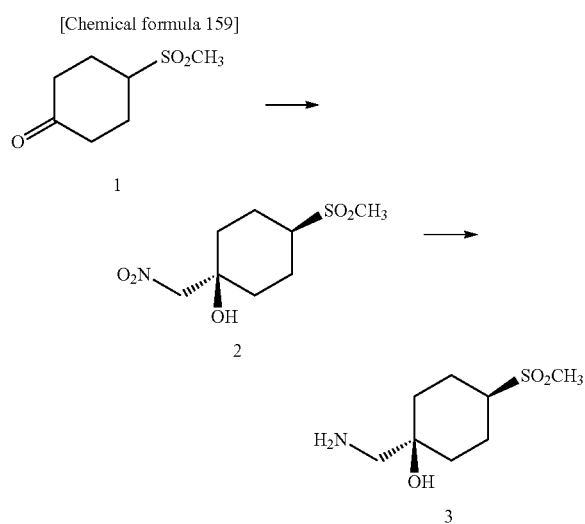

(1) To a solution of the compound 1 (400 mg) and sodium ethoxide (8 mg) in ethanol (1 mL) was added a solution of nitromethane (182 µL) in ethanol (1 mL) under ice-cooling. A temperature of the reaction mixture was raised to room temperature, and the reaction mixture was stirred for 23 hours. The reaction mixture was diluted with water, and extracted 4 times with chloroform. In addition, sodium chloride was added to the aqueous layer, and the reaction mixture was extracted twice with chloroform. The organic layer was dried over anhydrous magnesium sulfate, and the solvent was evaporated under reduced pressure. The resulting residue was suspended and washed in a mixed solvent of ethyl acetate-diisopropylether, taken by filtration, and dried to give the compound 2 (286 mg) as a colorless solid.

MS (APCI) 255 $[M+NH_4]^+$ (2) A suspension of the compound 2 (150 mg) and hydrous 20% palladium hydroxide on carbon (75 mg) in methanol (6 mL) was stirred for 18 hours under hydrogen atmosphere. The palladium on carbon was removed by filtration, and then washed with methanol. The filtrate was concentrated under reduced pressure, the resulting residue was suspended and washed in ethyl acetate, taken by filtration, and dried to give the compound 3 (81 mg) as a colorless solid.

MS (APCI) 208 $[M+H]^+$

Reference Example 102

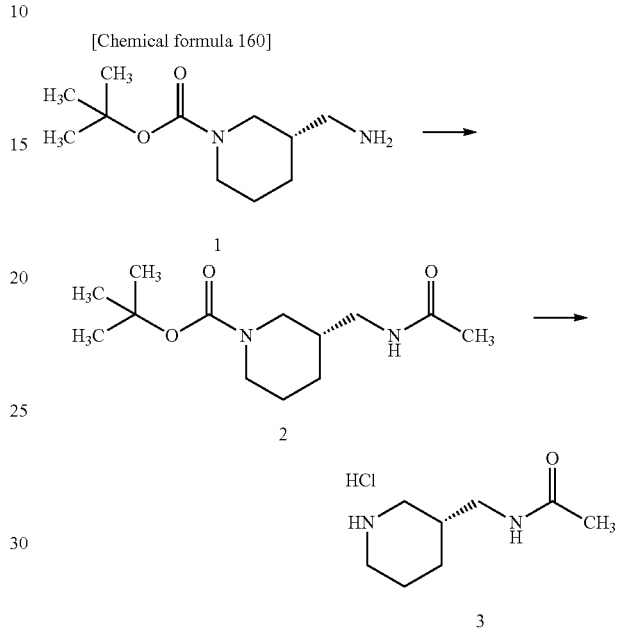

(1) To a suspension of the compound 1 (857 mg) in chloroform (15 mL) were added triethylamine (832 µL) and acetic anhydride (454 µL) under ice-cooling, and the reaction mixture was kept in stirring for 1 hour. To the reaction mixture was added a saturated aqueous solution of sodium bicarbonate, and then extracted with chloroform. The organic layer was dried, and then the solvent was evaporated under reduced pressure, and the resulting residue was purified by silica gel column chromatography (eluent: ethyl acetate-methanol; gradient: 100:0-95:5) to give the compound 2 (1.03 g) as a colorless viscous substance.

MS (APCI) 257 $[M+H]^+$ (2) The compound 2 (1.0 g) was dissolved in ethyl acetate (10 mL), a solution of 4 mol/L HCl in ethyl acetate (10 mL) was added to the solution, and the solution was stirred for 2 hours at room temperature. The precipitate was taken by filtration, dried under reduced pressure to give the compound 3 (830 mg) as a colorless powder.

MS (APCI) 157 $[M+H]^+$

Reference Example 103

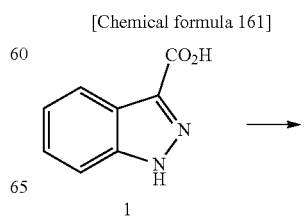

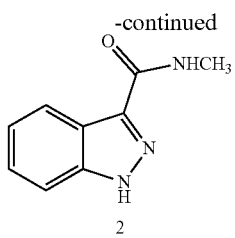

2

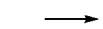

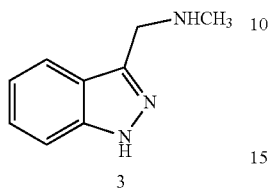

3

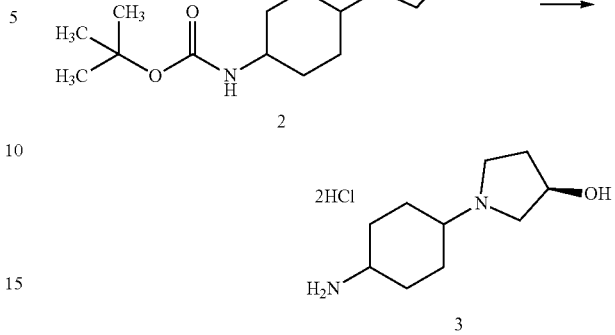

(1) To the compound 1 (2.5 g) was added thionyl chloride (15.4 mL), and the reaction mixture was stirred for 3 hours with heating to reflux. The reaction mixture was cooled to room temperature, and then concentrated under reduced pressure. The resulting residue was suspended in THF (18.5 mL), and the suspension was added dropwise to a mixed solution of an aqueous solution of 40% methylamine (18.5 mL) and chloroform (37 mL) over 5 minutes under ice-cooling. A temperature of the reaction mixture was raised to room temperature, and the reaction mixture was stirred for 2 hours, and then extracted 3 times with chloroform. The organic layer was dried over anhydrous sodium sulfate, and then the solvent was evaporated under reduced pressure. The resulting residue was suspended and washed in a mixed solvent of chloroform-diisopropylether, taken by filtration, and dried to give the compound 2 (2.56 g) as a colorless solid.

MS (APCI) 176 [M+H]$^+$ (2) Lithium aluminum hydride (2.22 g) was suspended in THF (128 mL), the compound 2 (2.56 g) was added portionwise to the suspension over 5 minutes at 65° C., and a temperature of the suspension was raised to 80° C., and then the suspension was stirred for 5 hours. The reaction mixture was cooled slowly under ice-cooling, and then water (2.22 mL) was added slowly thereto. Then, an aqueous solution of 15% sodium hydroxide (2.22 mL) and water (6.66 mL) was added sequentially to the solution, and the reaction mixture was stirred for 18 hours at room temperature. To the reaction mixture was added anhydrous sodium sulfate, and then an insoluble substance was removed by filtration, and washed with a mixed solvent of methanol-chloroform-ethyl acetate. The filtrate was concentrated under reduced pressure, and the resulting residue was purified by NH-silica gel column chromatography (eluent: ethyl acetate-methanol; gradient: 100:0-95:5) to give the compound 3 (2.09 g) as a colorless solid.

MS (APCI) 162 [M+H]$^+$

Reference Example 104

[Chemical formula 162]

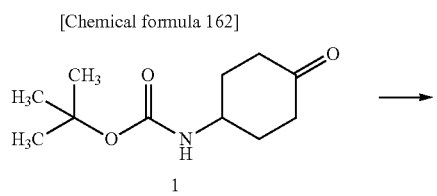

1

(1) To a solution of the compound 1 (1.0 g) in chloroform (20 mL) were added (R)-3-hydroxypyrrolidine (545 mg), acetic acid (270 μL), and sodium triacetoxyborohydride (1.29 g), and the reaction mixture was stirred for 20 hours at room temperature. The reaction mixture was diluted with a saturated aqueous solution of sodium bicarbonate, and then the reaction mixture was extracted twice with chloroform. The organic layer was washed with brine, and then dried over anhydrous sodium sulfate, and the solvent was evaporated under reduced pressure. The resulting residue was purified by NH-silica gel column chromatography (eluent: chloroform-methanol 97:3) to give the compound 2 (pale brown viscous substance, 1.06 g) as a mixture of cis-isomer and trans-isomer.

MS (APCI) 285 [M+H]$^+$ (2) The compound 2 (1.05 g) was dissolved in ethyl acetate (10 mL), a solution of 4 mol/L HCl in ethyl acetate (3.7 mL) was added to the solution, and the reaction mixture was stirred for 17 hours at room temperature. To the reaction mixture was added ethyl acetate (20 mL), and then the precipitate was taken by filtration, and dried under reduced pressure to give the compound 3 (pale brown powder, 834 mg) as a mixture of cis-isomer and trans-isomer.

MS (APCI) 185 [M+H]$^+$

Reference Example 105

[Chemical formula 163]

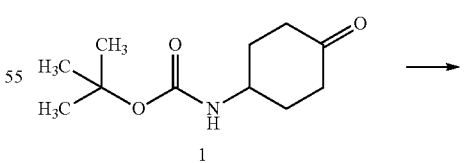

1

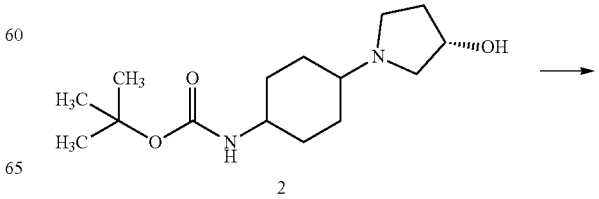

2

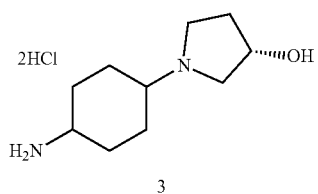

3

(1) To a solution of the compound 1 (1.0 g) in chloroform (20 mL) were added (S)-3-hydroxypyrrolidine (537 mg), acetic acid (270 µL), and sodium triacetoxyborohydride (1.29 g), and the reaction mixture was stirred for 20 hours at room temperature. The reaction mixture was diluted with a saturated aqueous solution of sodium bicarbonate, and then the reaction mixture was extracted twice with chloroform. The organic layer was washed with brine, and then dried over anhydrous sodium sulfate, and the solvent was evaporated under reduced pressure. The resulting residue was purified by NH-silica gel column chromatography (eluent: chloroform-methanol 97:3) to give the compound 2 (pale brown viscous substance, 1.02 g) as a mixture of cis-isomer and trans-isomer.

MS (APCI) 285 [M+H]$^+$ (2) The compound 2 (1.01 g) was dissolved in ethyl acetate (10 mL), a solution of 4 mol/L HCl in ethyl acetate (3.6 mL) was added to the solution, and the reaction mixture was stirred for 17 hours at room temperature. To the reaction mixture was added ethyl acetate (20 mL), and then the precipitate was taken by filtration, and dried under reduced pressure to give the compound 3 (pale brown powder, 796 mg) as a mixture of cis-isomer and trans-isomer.

MS (APCI) 185 [M+H]$^+$

Reference Example 106

[Chemical formula 164]

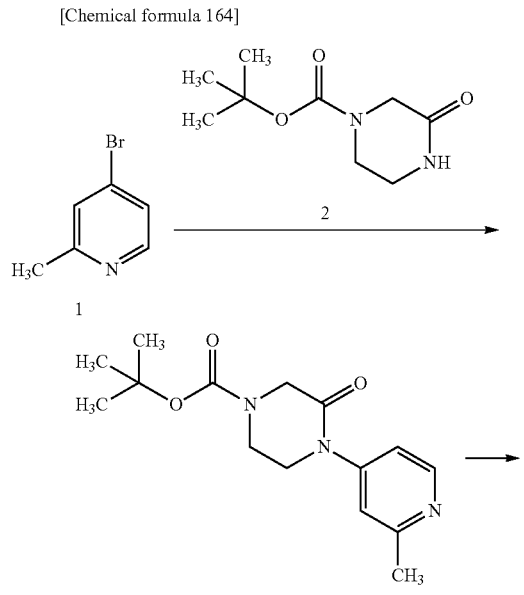

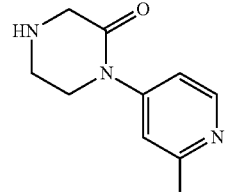

4

(1) To a solution of the compound 1 (200 mg) in THF (3 mL) was added dropwise a solution of 1 mol/L triethylborane in THF (2.3 mL) at room temperature under argon atmosphere. The reaction mixture was stirred for 4 hours, the solvent was evaporated under reduced pressure, and the residue was dissolved in toluene (2.5 mL). To the reaction mixture were added the compound 2 (559 mg), bis(dibenzylideneacetone) palladium (27 mg), 4,5-bis(diphenylphosphino)-9,9-dimethylxanthene(xantphos, 27 mg), and potassium phosphate (592 mg), and the reaction mixture was stirred for 22 hours with heating to reflux. The reaction mixture was cooled to room temperature, and diluted with ethyl acetate. The solution was washed with water and brine, and dried over anhydrous magnesium sulfate. The solvent was evaporated under reduced pressure, and the resulting residue was purified by silica gel column chromatography (eluent: chloroform-methanol; gradient: 98:2-95:5) to give the compound 3 (450 mg) as a yellow solid.

MS (APCI) 292 [M+H]$^+$ (2) The compound 3 (126 mg) was dissolved in dichloromethane (1 mL), trifluoroacetic acid (1 mL) was added to the solution, and the reaction mixture was stirred for 2.5 hours at room temperature. The reaction mixture was concentrated under reduced pressure, and the resulting residue was purified by silica gel column chromatography (eluent: chloroform-methanol-conc. ammonia water; gradient: 100:0:0-80:18:2) to give the compound 4 (66 mg) as a pale yellow solid.

MS (APCI) 192 [M+H]$^+$

Reference Example 107

[Chemical formula 165]

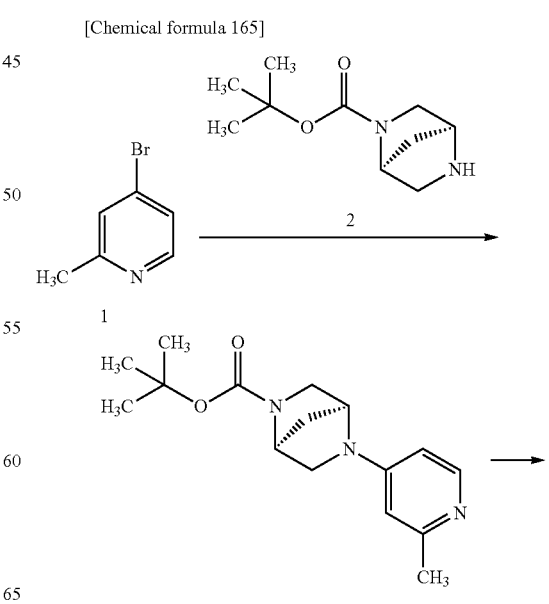

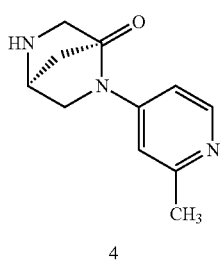

4

(1) A mixture of the compound 1 (344 mg), the compound 2 (397 mg), bis(dibenzylideneacetone)palladium (45 mg), 2-(dicyclohexylphosphino)-2'-(dimethylamino) biphenyl (DavePhos, 157 mg), and sodium-t-butoxide (288 mg) in dioxane (10 mL) was stirred for 2.5 hours with heating to reflux. The reaction mixture was cooled to room temperature, diluted with ethyl acetate, and then an insoluble substance was removed by filtration. The filtrate was concentrated under reduced pressure, and the resulting residue was purified by silica gel column chromatography (eluent: chloroform-methanol; gradient: 98:2-92:8) to give the compound 3 (364 mg) as a pale yellow solid.

MS (APCI) 290 [M+H]⁺

(2) The compound 3 (126 mg) was dissolved in chloroform (3 mL)-methanol (3 mL), a solution of 4 mol/L HCl in ethyl acetate (4.7 mL) was added to the solution, and the reaction mixture was stirred for 18 hours at room temperature. The reaction mixture was concentrated under reduced pressure, an aqueous solution of 40% potassium carbonate was added to the resulting residue, and the solution was extracted twice with ethyl acetate. The organic layer was dried over sodium sulfate, and the solvent was evaporated under reduced pressure to give the compound 4 (211 mg) as a yellow solid.

MS (APCI) 190 [M+H]⁺

Reference Example 108

[Chemical formula 166]

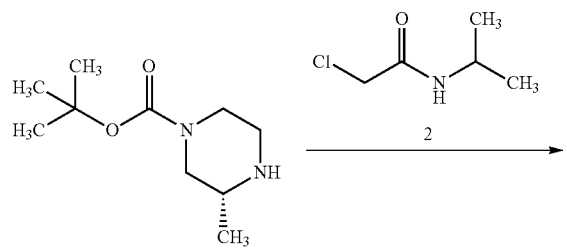

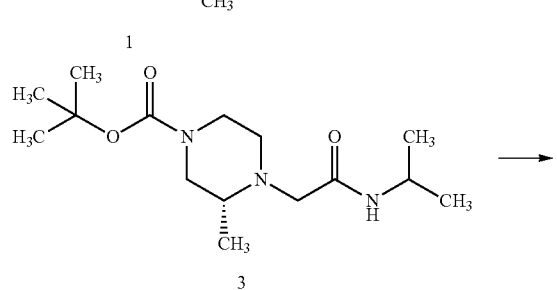

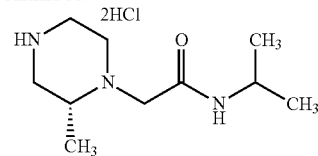

4

(1) The compound 1 (500 mg), the compound 2 (677 mg) and sodium carbonate (529 mg) were suspended in acetonitrile (10 mL), and the reaction mixture was stirred for 18 hours at 60° C. The reaction mixture was cooled to room temperature, and then diluted with ethyl acetate, washed with water and brine, and dried over anhydrous sodium sulfate. The solvent was evaporated under reduced pressure, and the resulting residue was purified by silica gel column chromatography (eluent: ethyl acetate-methanol; gradient: 100:0-95:5) to give the compound 3 (711 mg) as a colorless solid.

MS (APCI) 300 [M+H]

(2) The compound 3 (690 mg) was dissolved in ethyl acetate (15 mL)-methanol (2 mL), a solution of 4 mol/L HCl in ethyl acetate (12 mL) was added to the solution, and the reaction mixture was stirred for 15 hours at room temperature. The reaction mixture was concentrated under reduced pressure, the residue was suspended and washed in ethyl acetate, taken by filtration, and dried to give the compound 4 (608 mg) as a colorless powder.

MS (APCI) 200 [M+H]⁺

Reference Example 109

[Chemical formula 167]

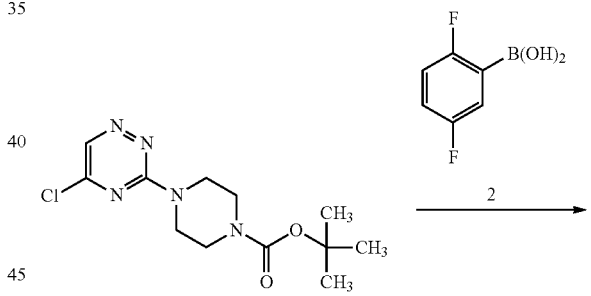

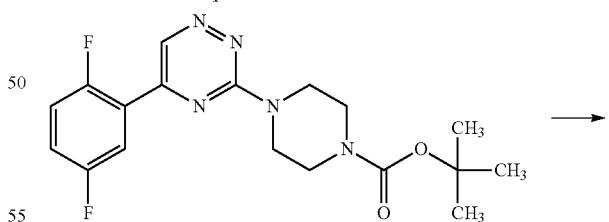

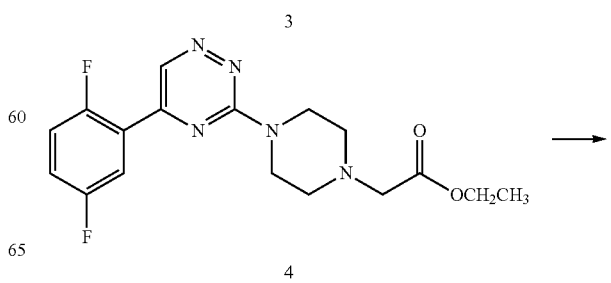

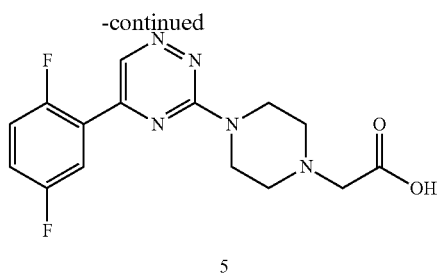

(1) A mixed solution of the compound 1 (300 mg), the compound 2 (316 mg), tris(dibenzylideneacetone)dipalladium (92 mg), a solution of 1 mol/L tri-t-butylphosphine in toluene (200 μL), and potassium fluoride (232 mg) in THF-water (10:1) (4 mL) was degassed under reduced pressure, and then back-filled with argon. The reaction mixture was stirred for 15 minutes at 150° C. in a microwave reactor (Initiator, Biotage). The reaction mixture was cooled to room temperature, diluted with ethyl acetate, and then the solution was washed with water and brine, dried over anhydrous sodium sulfate, and filtered. The solvent was evaporated under reduced pressure, and the resulting residue was purified by silica gel column chromatography (eluent: hexane-ethyl acetate; gradient: 80: 20-65:35) to give the compound 3 (367 mg) as a yellow solid.

MS (APCI) 378 [M+H]$^+$ (2) To a solution of the compound 3 (360 mg) in chloroform (4 mL) was added trifluoroacetic acid (3.6 mL), and the reaction mixture was stirred for 30 minutes at room temperature. The reaction mixture was diluted with methanol, treated with packed strong cation exchange resin (PoraPak Rxn Cx, eluent: a solution of 1 mol/L $NH_3$ in methanol), and the eluate was concentrated under reduced pressure. The resulting residue was dissolved in acetonitrile (8 mL), ethyl chloroacetate (123 μL) and sodium carbonate (202 mg) were added to the solution, and the reaction mixture was stirred for 2.5 hours at 60° C. The reaction mixture was cooled to room temperature, and then diluted with ethyl acetate, washed with water, dried over anhydrous sodium sulfate, and filtered. The solvent was evaporated under reduced pressure, and the resulting residue was purified by silica gel column chromatography (eluent: hexane-ethyl acetate; gradient: 50:50-20:80) to give the compound 4 (315 mg) as a yellow solid.

MS (APCI) 364 [M+H]$^+$ (3) The compound 4 (309 mg) was dissolved in ethanol (3 mL)-THF (2 mL), an aqueous solution of 1 mol/L of sodium hydroxide (1.7 mL) was added to the solution, and the reaction mixture was stirred for 1 hour at room temperature. The reaction mixture was concentrated under reduced pressure, the residue was dissolved in water, and then an aqueous solution of 1 mol/L hydrochloric acid was added to the solution under ice-cooling, and a pH of the solution was adjusted to 3-4. The precipitate was taken by filtration, washed with water, and dried to give the compound 5 (266 mg) as a yellow solid.

MS (APCI) 336 [M+H]$^+$

Experimental Example 1 (Inhibitory Effect on hCYP11B2)

Experimental Method

The pcDNA3. 1-human CYP11B2 plasmid was transfected into a Chinese hamster lung fibroblast V79 cell line to produce a cell line stably expressing human CYP11B2 gene.

The cells were cultured and grown in the Dulbecco's modified Eagle's/Ham's medium supplemented with 10% fetal bovine serum and 1% G418 disulfate solution under the environment of 37° C., 95% air, and 5% $CO_2$, and the grown cells were harvested.

Then, the cells were fractionated to obtain mitochondria by reference to a method described in Chabre et al. JCE & M 85 (11) 4060-68, 2000. In particular, the cells suspended in a 5 mmol/L Tris-HCl buffer (pH 7.4) containing 250 mmol/L sucrose were homogenized in a Teflon (Registered Trademark) Potter Elvehjem homogenizer, and then the suspension was centrifuged (800×g, 15 min.). The supernatant was separated and again centrifuged (10000×g, 15 min.) to obtain a pellet (mitochondrial fraction).

The mitochondrial fraction diluted with a buffer containing 10 mmol/L $KH_2PO_4$, 10 mmol/L Tris, 20 mmol/L KCl, 25 mmol/L sucrose, 5 mmol/L $MgCl_2$, and 0.05% bovine serum albumin was dispensed to a 96-well plate. 0.5 μmol/L Deoxycorticosterone, 150 μmol/L NADPH and a compound of each concentration were added to each well, and incubated for 1.5-2 hours at room temperature to produce aldosterone. An amount of the produced aldosterone in the incubated solution was determined by using HTRF (Homogeneous Time Resolved Fluorescence) method.

IC 50 (nmol/L) was calculated by analyzing the aldosterone production inhibition rate (%) of each concentration of compounds by non-linear regression to a logistic curve.

<Experimental Results>

TABLE 44

| Example No. | hCYP11B2 $IC_{50}$ (nmol/L) |
|---|---|
| 12 | 6.9 |
| 16 | 16 |
| 18 | 7.9 |
| 19 | 17 |
| 22 | 17 |
| 26 | 8.5 |
| 27 | 13 |
| 28 | 8.4 |
| 29 | 18 |
| 38 | 14 |
| 40 | 4.9 |
| 44 | 17 |
| 47 | 11 |
| 48 | 9.0 |
| 50 | 6.3 |
| 54 | 7.2 |
| 55 | 8.7 |
| 59 | 19 |
| 62 | 10 |
| 64 | 19 |
| 71 | 6.1 |
| 75 | 7.6 |
| 76 | 4.5 |
| 79 | 4.5 |
| 80 | 4.5 |
| 81 | 2.7 |
| 82 | 12 |
| 83 | 7.6 |
| 84 | 25 |
| 85 | 9.9 |
| 86 | 0.5 |
| 115 | 6.3 |
| 124 | 16 |
| 135 | 12 |
| 141 | 11 |
| 147 | 18 |
| 151 | 16 |
| 153 | 18 |
| 154 | 1.1 |
| 157a | 14 |
| 159a | 7.7 |
| 160 | 13 |

TABLE 44-continued

| Example No. | hCYP11B2 IC$_{50}$ (nmol/L) |
|---|---|
| 161 | 6.1 |
| 164a | 16 |
| 166a | 5.6 |
| 167a | 11 |
| 170 | 23 |
| 178 | 5.0 |
| 180 | 6.1 |
| 183 | 0.7 |
| 188 | 6.0 |
| 192 | 38 |
| 196 | 67 |
| 199 | 12 |
| 211 | 2.4 |
| 215 | 29 |
| 218 | 9.8 |
| 219 | 3.1 |
| 220 | 20 |
| 221 | 2.4 |
| 222 | 26 |
| 233 | 20 |
| 236 | 23 |
| 244 | 11 |
| 251 | 7.5 |
| 252 | 15 |
| 256 | 26 |
| 257 | 13 |

INDUSTRIAL APPLICABILITY

A compound [I] of the present invention or a pharmacologically acceptable salt thereof has an inhibitory activity against aldosterone synthetase, and therefore, it is useful as a medicament for preventing or treating various diseases and/or disease states evoked by an increased level of aldosterone and/or overproduction of aldosterone, such as hypertension, primary aldosteronism, or for improving prognosis of these diseases.

The invention claimed is:

1. A method for treating heart failure, nephropathy, and sleep apnea syndrome, comprising administering a therapeutically effective amount of a compound of the following formula [I]:

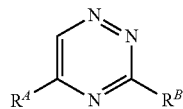

[I]

wherein
R$^A$ is
a group of the following formula (A-1):

(A-1)

wherein ring A$^1$ represents an aryl group which may be partially hydrogenated and may be substituted, wherein
a substituent of an aryl group which may be partially hydrogenated and may be substituted represented by ring A$^1$ in the above formula (A-1) is 1-3 groups selected independently from the group consisting of a halogen atom, a cyano group, an alkyl group, a haloalkyl group, an alkoxyalkyl group, an alkoxy group, and an alkylenedioxy group which may be substituted with 1-2 halogen atoms,
an aryl moiety in the aryl group which may be partially hydrogenated and may be substituted is 6- to 10-membered monocyclic or bicyclic aryl,
R$^B$ is
a group of the following formula (B-4):

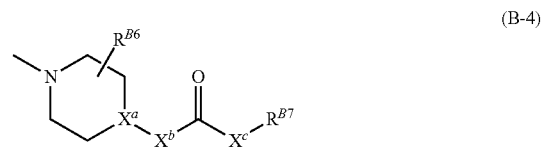

(B-4)

wherein X$^a$ represents CR$^{3a}$ or N,
(i) when X$^a$ represents CR$^{3a}$,
X$^b$ represents CHR$^{3b}$, X$^c$ represents O or NR$^{4c}$,
X$^b$ represents O, X$^c$ represents NR$^{4c}$, or
X$^b$ represents NR$^{4b}$, X$^a$ represents O, NR$^{4c}$, or CHR$^{3c}$,
(ii) when X$^a$ represents N,
X$^b$ represents CHR$^{3b}$ or C(=O), X$^c$ represents NR$^{4c}$, or
X$^b$ represents NR$^{4b}$, X$^c$ represents CHR$^{3c}$;
R$^{3a}$ represents a hydrogen atom, a hydroxyl group, an alkyl group, or an amino group,
each of R$^{3b}$ and R$^{3c}$ represents a group selected independently from the group consisting of a hydrogen atom, a hydroxyl group, and an alkyl group,
each of R$^{3b}$ and R$^{4c}$ represents a group selected independently from the group consisting of a hydrogen atom, an alkyl group, and a cycloalkyl group;
R$^{B6}$ represents a hydrogen atom or an alkyl group;
R$^{B7}$ represents
(i) a cycloalkyl group which may be substituted,
(ii) an aliphatic heterocyclic group which may be substituted,
(iii) a heteroaryl group which may be partially hydrogenated and may be substituted, or
when X$^c$ represents NR$^{4c}$, R$^{B7}$ and R$^{4c}$ are bound to each other at their terminus to form an aliphatic heterocyclic group, which may be substituted with an alkyl group which may be substituted, together with a nitrogen atom to which they are bound,
wherein
a substituent of (i) the cycloalkyl group which may be substituted, (ii) the aliphatic heterocyclic group which may be substituted, and (iii) the heteroaryl group which may be partially hydrogenated and may be substituted represented by R$^{B7}$ is 1-4 groups selected independently from the group consisting of a halogen atom; a hydroxyl group; an oxo group; an alkyl group which may be substituted with 1-3 groups selected independently from the group consisting of a hydroxyl group, an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, an aliphatic heterocyclic carbonyl group, and a heteroaryl group which may be substituted with an alkyl group and may be partially hydrogenated; a cycloalkyl group which may be substituted with 1-2 groups selected independently from the group consisting of a hydroxyl group and an alkylsulfonyl group; an aryl group; a heteroaryl group which may be partially hydrogenated; an alkanoyl group which may be substituted with 1-3 groups selected independently from the group consisting of a halogen atom and a hydroxyl group; a cycloalkylcarbonyl group which may be substituted with a hydroxyl group; an aliphatic heterocyclic carbonyl group which may be substituted with an alkyl group; an amino group which may be substituted with 1-2 groups selected independently from the group consisting of an alkyl group which may be substituted with an alkylsulfonyl group, an alkanoyl group, and an alkoxycarbonyl group; a carbamoyl group which may be substituted with 1-2 alkyl groups; an alkylsulfonyl group; an alkoxy group which may be substituted with a carbamoyl group which may be substituted with 1-2 alkyl groups; and an aliphatic heterocyclic group which may be substituted with 1-3 groups selected independently from the group consisting of a hydroxyl group, an oxo group, an alkyl group, an alkanoyl group, and an alkylsulfonyl group, or when $R^{B7}$ is (i) a cycloalkyl group which may be substituted, or (ii) an aliphatic heterocyclic group which may be substituted, two substituents on the same ring-constituting carbon atom may be bound to each other at the terminus thereof to form an alkylene group which may be substituted (wherein a substituent of the alkylene group is an oxo group or an alkyl group, and the alkylene group may contain 1-3 heteroatoms selected independently from a sulfur atom, an oxygen atom, and a nitrogen atom), in $R^{B7}$, aryl is 6- to 10-membered monocyclic or bicyclic aryl, heteroaryl is 5- to 10-membered monocyclic or bicyclic heteroaryl which contains 1-4 heteroatoms selected independently from the group consisting of a sulfur atom, an oxygen atom, and a nitrogen atom, an aliphatic heterocyclic ring is a 4- to 9-membered aliphatic heterocyclic ring which contains 1-2 heteroatoms selected independently from the group consisting of an oxygen atom and a nitrogen atom, or when $X^c$ is $NR^{4c}$, and $R^{B7}$ and $R^{4c}$ are bound to each other at their terminus to form an aliphatic heterocyclic group which may be substituted with an alkyl group which may be substituted, together with a nitrogen atom to which they are bound, a substituent of the alkyl group which may be substituted is a hydroxyl group, and the aliphatic heterocyclic group is a 4-to 9-membered aliphatic heterocyclic ring which may further contain 1 heteroatom selected independently from the group consisting of a sulfur atom, an oxygen atom and a nitrogen atom other than the nitrogen atom to which $R^{B7}$ and $R^{4c}$ are bound, or a pharmaceutically acceptable salt thereof to a patient in need thereof.

2. The method according to claim 1, wherein in a group represented by the above formula (A-1), ring $A^1$ is an aryl group which may be partially hydrogenated and may be substituted, wherein a substituent of the aryl group which may be partially hydrogenated and may be substituted is 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, an aryl moiety of the aryl group which may be partially hydrogenated and may be substituted is phenyl or naphthyl, in a group of the above formula (B-4), $R^{B7}$ is (i) a cycloalkyl group which may be substituted, (ii) an aliphatic heterocyclic group which may be substituted, or (iii) a heteroaryl group which may be partially hydrogenated and may be substituted, or when $X^c$ is $NR^{4c}$, $R^{B7}$ and $R^{4c}$ may be bound to each other at their terminus to form an aliphatic heterocyclic group which may be substituted with an alkyl group which may be substituted with a hydroxyl group, together with a nitrogen atom to which they are bound, wherein (i) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), (ii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of a hydroxyl group, an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, an aliphatic heterocyclic carbonyl group, and a heteroaryl group which may be substituted with an alkyl group and may be partially hydrogenated; an alkanoyl group which may be substituted with 1-3 groups selected independently from the group consisting of a halogen atom and a hydroxyl group; a cycloalkylcarbonyl group which may be substituted with a hydroxyl group; an aliphatic heterocyclic carbonyl group which may be substituted with an alkyl group; an alkoxy group; a carbamoyl group which may be substituted with 1-2 alkyl groups; an aliphatic heterocyclic group which may be substituted with an oxo group; and a heteroaryl group, (iii) a substituent of the heteroaryl group which may be partially hydrogenated and may be substituted is 1-2 groups selected independently from the group consisting of an aliphatic heterocyclic group; and an alkyl group which may be substituted with 1-2 groups selected independently from the group consisting of a carbamoyl group which may be substituted with 1-2 alkyl groups, alkylsulfonyl group, and a heteroaryl group, in the above items (i)-(iii), the aliphatic heterocyclic ring is selected from azetidinyl, oxetanyl, pyrrolidinyl, tetrahydrothiophenyl, tetrahydrofuranyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, the aliphatic heterocyclic ring in the aliphatic heterocyclic carbonyl is selected from azetidinyl, oxetanyl, pyrrolidinyl, tetrahydrothiophenyl, tetrahydrofuranyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, the heteroaryl is selected from pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl, the heteroaryl group which may be partially hydrogenated is selected from a pyrrolyl group, a furanyl group, a thienyl group, an imidazolyl group, an imidazolinyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, or a dihydrobenzopyranyl group, or when $X^c$ is $NR^{4c}$, and $R^{B7}$ and $R^{4c}$ are bound to each other at their terminus to form an aliphatic heterocyclic group which may be substituted with an alkyl group which may be substituted with a hydroxyl group, together with a nitrogen atom to which they are bound, an aliphatic heterocyclic group is a group selected from azetidinyl, pyrrolidinyl, piperidinyl, piperazinyl, morpholinyl, thiomorpholinyl, or homomorpholinyl.

3. The method according to claim 1, wherein
$R^A$ is
(1) a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms, or (2) a naphthyl group which may be partially hydrogenated and may be substituted with an alkyl group, $R^B$ is a group represented by the above formula (B-4), $R^{B7}$ is (i) a cycloalkyl group which may be substituted, (ii) an aliphatic heterocyclic group which may be substituted, or (iii) a heteroaryl group which may be partially hydrogenated and may be substituted, or, when $X^c$ is $NR^{4c}$, $R^{B7}$ and $R^{4c}$ are bound to each other at their terminus to form an aliphatic heterocyclic group which may be substituted with an alkyl group (wherein the alkyl group may be substituted with a hydroxyl group), together with a nitrogen atom to which they are bound, wherein (i) a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom), wherein the aliphatic heterocyclic group is pyrrolidinyl, piperidinyl, piperazinyl, morpholinyl, or thiomorpholinyl, and a cycloalkyl moiety of (i) the cycloalkyl group which may be substituted is cyclobutyl, cyclopentyl, cyclohexyl, bicyclo[2.2.2]octyl, or adamantyl, (ii) a substituent of the aliphatic heterocyclic group which may be substituted is 1-3 groups selected independently from the group consisting of a halogen atom; a hydroxyl group; an oxo group; an alkyl group which may be substituted with 1-3 groups selected independently from the group consisting of an alkoxy group, an alkylsulfonyl group, an amino group which may be substituted with 1-2 groups selected independently from the group consisting of an alkoxycarbonyl group and an alkylsulfonyl group, a carbamoyl group which may be substituted with 1-2 alkyl groups, a cycloalkyl group which may be substituted with a hydroxyl group, a morpholinylcarbonyl group, and a heteroaryl group which may be substituted with an alkyl group and may be partially hydrogenated (wherein the heteroaryl which may be partially hydrogenated is imidazolyl, imidazolinyl, oxazolyl, triazolyl, or pyridyl); an alkanoyl group which may be substituted with 1-3 groups selected independently from the group consisting of an a halogen atom and a hydroxyl group; a cycloalkylcarbonyl group which may be substituted with a hydroxyl group; an oxetanylcarbonyl group which may be substituted with an alkyl group; an alkoxy group; a carbamoyl group which may be substituted with 1-2 alkyl groups; an aliphatic heterocyclic group which may be substituted with an oxo group (wherein the aliphatic heterocyclic group is piperidinyl or tetrahydropyranyl); and a pyrimidinyl group, wherein an aliphatic heterocyclic moiety of (ii) the aliphatic heterocyclic group which may be substituted is azetidinyl, pyrrolidinyl, piperidinyl, tetrahydrothiophenyl, tetrahydrothiopyranyl, tetrahydrofuranyl, tetrahydropyranyl, 1-azabicyclo[2.2.2]octyl, 8-azabicyclo[3.2.1]octyl, homomorpholinyl, 3-oxabicyclo[3.3.1]nonyl, or 3-oxo-9-azabicyclo[3.3.1]nonyl, (iii) a substituent of the heteroaryl group which may be partially hydrogenated and may be substituted is 1-2 groups selected independently from the group consisting of a tetrahydropyranyl group; and an alkyl group which may be substituted with 1-2 groups selected independently from the group consisting of a carbamoyl group which may be substituted with 1-2 alkyl groups, an alkylsulfonyl group, and pyridazinyl group, wherein a heteroaryl moiety of (iii) the heteroaryl group which may be partially hydrogenated and may be substituted is pyrazolyl, pyridyl, or imidazopyridinyl, an aliphatic heterocyclic moiety of the aliphatic heterocyclic group which may be substituted with an alkyl group which may be substituted with a hydroxyl group is piperazinyl or pyrrolidinyl (wherein the aliphatic heterocyclic group is formed from $R^{B7}$ and $R^{4c}$ being bound to each other at their terminus, together with a nitrogen atom to which they are bound, when $X^c$ is $NR^{4c}$).

4. The method according to claim 3,
wherein
$R^A$ is
(1) a phenyl group which may be substituted with 1-3 groups selected independently from the group consisting of a halogen atom, an alkyl group, a haloalkyl group, an alkoxyalkyl group, an alkoxy group, and a methylenedioxy group which may be substituted with 1-2 halogen atoms,
(2) a naphthyl group which may be substituted with an alkyl group, or
(3) a tetrahydronaphthyl group,
$R^{B7}$ is
(i) a cycloalkyl group which may be substituted (wherein the cycloalkyl group is a cyclopentyl group, a cyclohexyl group, a bicyclo[2.2.2]octyl group, or an adamantyl group), wherein a substituent of the cycloalkyl group is 1-2 groups selected independently from the group consisting of a hydroxyl group; an aliphatic heterocyclic group which may be substituted with 1-2 groups selected independently from the group consisting of a hydroxyl group and an oxo group (wherein the aliphatic heterocyclic group is selected from a thiomorpholinyl group, a piperidinyl group, a piperazinyl group, or a morpholinyl group); an amino group which may be substituted with 1-2 groups selected independently from the group consisting of an alkyl group and an alkanoyl group; an alkyl group which may be substituted with a hydroxyl group; an alkoxy group which may be substituted with a carbamoyl group which may be substituted with 1-2 alkyl groups; and an alkylsulfonyl group, (ii) an aliphatic heterocyclic group which may be substituted (wherein the aliphatic heterocyclic group is selected from an azetidinyl group, a tetrahydrofuranyl group, a pyrrolidinyl group, a tetrahydropyranyl group, a piperidinyl group, a tetrahydrothiopyranyl group, or 3-oxabicyclo[3.3.1]nonyl), wherein a substituent of the aliphatic heterocyclic group is 1-3 groups selected independently from the group consisting of a halogen atom; a hydroxyl group; an oxo group; an alkyl group which may be substituted with 1-3 groups selected independently from the group consisting of a hydroxyl group, a cycloalkyl group which may be substituted with a hydroxyl group, an alkoxy group, an alkylsulfonyl group, an alkylsulfonylamino group, a carbamoyl group which may be substituted with 1-2 alkyl groups, morpholinylcarbonyl group, and a heteroaryl group which may be substituted with an alkyl group and may be partially hydrogenated (wherein the heteroaryl which may be partially hydrogenated is pyridyl, imidazolyl, imidazolinyl, oxazolyl, or triazolyl); an alkanoyl group which may be substituted with a hydroxyl group; a pyrimidinyl group; and a cycloalkylcarbonyl group which may be substituted with a hydroxyl group, or (iii) a pyrazolyl group which may be substituted with an alkyl group which may be substituted with a carbamoyl group which may be substituted with 1-2 alkyl groups.

5. The method according to claim 3,
wherein
$R^A$ is
(1) a phenyl group which may be substituted with 1-3 groups selected independently from the group consisting of a halogen atom, an alkyl group, and a haloalkyl group,
$R^B$ is a group of the above formula (B-4):
wherein $X^a$ represents N,
$X^b$ represents $CH_2$, and $X^c$ represents NH, or
$X^b$ represents NH, and $X^c$ represents $CH_2$,
$R^{B6}$ represents a hydrogen atom,
$R^{B7}$ is
(i) a cyclohexyl group which may be substituted, wherein a substituent of the cyclohexyl group is 1-2 groups selected independently from the group consisting of a piperidinyl group which may be substituted with a hydroxyl group; an amino group which may be substituted with 1-2 groups selected independently from the group consisting of an alkyl group and an alkanoyl group; and an alkoxy group which may be substituted with a carbamoyl group which may be substituted with 1-2 alkyl groups,
(ii) an aliphatic heterocyclic group which may be substituted (wherein the aliphatic heterocyclic group is selected from an azetidinyl group, a tetrahydrofuranyl group, a pyrrolidinyl group, a tetrahydropyranyl group, a piperidinyl group, a tetrahydrothiopyranyl group, or 3-oxabicyclo[3.3.1]nonyl), wherein a substituent of the aliphatic heterocyclic group is 1-3 groups selected independently from the group consisting of a hydroxyl group; an alkyl group which may be substituted with 1-3 groups selected independently from the group consisting of an amino group which may be substituted with an alkylsulfonyl group, a carbamoyl group which may be substituted with 1-2 alkyl groups, an imidazolinyl group which may be substituted with an alkyl group; an alkanoyl group which may be substituted with a hydroxyl group; and a cycloalkylcarbonyl group which may be substituted with a hydroxyl group, or (iii) a pyrazolyl group which may be substituted with an alkyl group which may be substituted with a carbamoyl group which may be substituted with 1-2 alkyl groups.

6. The method according to claim 3, wherein
$R^A$ is a phenyl group which may be substituted with an alkyl group or a haloalkyl group,
$R^B$ is a group of the above formula (B-4): wherein
$X^a$ is $CR^{3a}$,
$X^b$ is $CHR^{3b}$,
$R^{3a}$ is a hydrogen atom,
$R^{3b}$ is a hydrogen atom or a hydroxyl group,
$X^c$ is $NR^{4c}$,
$R^{4c}$ is a hydrogen atom or an alkyl group,
$R^{B6}$ is a hydrogen atom, and
$R^{B7}$ is a cycloalkyl group which may be substituted with an alkyl group or an amino group which may be substituted with 1-2 alkyl groups.

7. The method according to claim 3, wherein
$R^B$ is a group of the above formula (B-4): wherein
$X^a$ is N,
$X^b$ is $CHR^{3b}$, and $X^c$ is $NR^{4c}$, or
$X^b$ is $NR^{4b}$, and $X^c$ is $CHR^{3c}$,
$R^{3b}$ and $R^{3c}$ is a hydrogen atom,
$R^{3b}$ and $R^{4c}$ is a hydrogen atom, and
$R^{B6}$ is a hydrogen atom.

8. The method according to claim 3, wherein
$X^a$ is N, $X^b$ is $CHR^{3b}$ or C(=O), $X^c$ is $NR^{4c}$,
$R^{3b}$ is a hydrogen atom or an alkyl group, and
$R^{4c}$ is a hydrogen atom, an alkyl group, or a cycloalkyl group.

9. The method according to claim 3, wherein
$X^a$ is N, $X^b$ is $CH_2$, $X^c$ is NH, and
$R^{B6}$ is a hydrogen atom.

10. The method according to claim 3, wherein
$R^A$ is a phenyl group which may be substituted with 1-3 groups selected independently from the group consisting of a halogen atom, an alkyl group, a haloalkyl group, an alkoxyalkyl group, an alkoxy group, and an alkylenedioxy group which may be substituted with 1-2 halogen atoms.

11. The method according to claim 3, wherein
$R^{B7}$ is a cycloalkyl group which may be substituted, wherein a substituent of the cycloalkyl group which may be substituted is 1-2 groups selected independently from the group consisting of a hydroxyl group; an aliphatic heterocyclic group which may be substituted with 1-3 groups selected independently from the group consisting of a hydroxyl group and an oxo group; an amino group which may be substituted with 1-2 groups selected independently from the group consisting of an alkyl group which may be substituted with an alkylsulfonyl group, and an alkanoyl group; an alkyl group which may be substituted with a hydroxyl group; a carbamoyl group which may be substituted with 1-2 alkyl groups; an alkoxy group which may be substituted with a carbamoyl group which may be substituted with 1-2 alkyl groups; a cycloalkyl group which may be substituted with a hydroxyl group; and an alkylsulfonyl group, or two substituents on the same carbon atom in the above cycloalkyl group which may be substituted are bound to each other at the terminus thereof to form an alkylene group which may be substituted with 1-3 groups selected independently from the group consisting of an alkyl group and an oxo group (wherein the alkylene group may contain, in the alkylene chain, 1-2 heteroatoms selected independently from a nitrogen atom, an oxygen atom, and a sulfur atom),
wherein the aliphatic heterocyclic group is pyrrolidinyl, piperidinyl, piperazinyl, morpholinyl, or thiomorpholinyl, and
a cycloalkyl moiety of the above cycloalkyl group which may be substituted is cyclobutyl, cyclopentyl, cyclohexyl, bicyclo[2.2.2]octyl, or adamantyl.

12. A method for treating heart failure, nephropathy, and sleep apnea syndrome, comprising administering a therapeutically effective amount of a compound selected from the group consisting of:

3-[4-[(cis-3-hydroxytetrahydrofuran-4-yl)carbamoylmethyl]piperazin-1-yl]-5-(4-trifluoromethylphenyl)-1,2,4-triazine, 5-(4-fluorophenyl)-3-[4-[[trans-4-(N-methylcarbamoylmethyloxy)cyclohexyl]carbamoylmethyl]piperazin-1-yl]-1,2,4-triazine, 3-[4-[[(1-acetyl-4-hydroxypiperidin-4-yl)methyl]carbamoylmethyl]piperazin-1-yl]-5-(4-chlorophenyl)-1,2,4-triazine, 3-[4-[[(7-exo-9-endo)-9-hydroxy-3-oxabicyclo[3.3.1]nonan-7-yl]carbamoylmethyl]piperazin-1-yl]-5-(4-trifluoromethylphenyl)-1,2,4-triazine, 5-(4-fluorophenyl)-3-[4-[[1-[2-(methylsulfonylamino)ethyl]piperidin-4-yl]carbamoylmethyl]piperazin-1-yl]-1,2,4-triazine, 5-(2-cyano-5-pyridyl)-3-[4-[[1-[(1-hydroxycyclopropyl)carbonyl]piperidin-4-yl]carbamoylmethyl]piperazin-1-yl]-1,2,4-triazine, 5-(4-fluorophenyl)-3-[4-[[trans-4-(4-hydroxypiperidino)cyclohexyl]carbamoylmethyl]piperazin-1-yl]-1,2,4-triazine, 5-(4-fluorophenyl)-3-[4-[[1-((R)-2-hydroxybutanoyl)piperidin-4-yl]carbamoylmethyl]piperazin-1-yl]-1,2,4-triazine, 5-(4-fluorophenyl)-3-[4-[(3S)-1-[(1-hydroxycyclopropyl)carbonyl]pyrrolidin-3-yl]carbamoylmethyl]piperazin-1-yl]-1,2,4-triazine, 3-[4-[[cis-3-(dimethylamino)cyclohexyl]carbamoylmethyl]piperazin-1-yl]-5-(4-fluorophenyl)-1,2,4-triazine, 3-[4-[[1-[(4,5-dihydro-1H-imidazol-2-yl)methyl]piperidin-4-yl]carbamoylmethyl]piperazin-1-yl]-5-(4-fluorophenyl)-1,2,4-triazine, 3-[4-[[trans-4-(acetoamino)cyclohexyl]carbamoylmethyl]piperazin-1-yl]-5-(p-tolyl)-1,2,4-triazine, 3-[4-[[1-(N,N-dimethylcarbamoylmethyl)-1H-pyrazol-4-yl]carbamoylmethyl]piperazin-1-yl]-5-(4-fluorophenyl)-1,2,4-triazine, 5-(4-fluorophenyl)-3-[4-[1-[(1-hydroxycyclopropyl)carbonyl]azetidin-3-yl]carbamoylmethyl]piperazin-1-yl]-1,2,4-triazine, 3-[4-[[trans-4-(N-methylcarbamoylmethyloxy)cyclohexyl]carbamoylmethyl]piperazin-1-yl]-5-(4-trifluoromethylphenyl)-1,2,4-triazine, 3-[4-[[cis-3-(acetoamino)cyclohexyl]carbamoylmethyl]piperazin-1-yl]-5-(4-fluorophenyl)-1,2,4-triazine, 5-(4-chlorophenyl)-3-[(3S,4S)-4-[(cis-3-hydroxytetrahydropyran-4-yl)carbamoylmethyl]piperazin-1-yl]-1,2,4-triazine, 3-[4-[[1-(N,N-dimethylcarbamoylmethyl)-1H-pyrazol-4-yl]carbamoylmethyl]piperazin-1-yl]-5-(p-tolyl)-1,2,4-triazine, 5-(4-chlorophenyl)-3-[4-[[1-(N,N-dimethylcarbamoylmethyl)-1H-pyrazol-4-yl]carbamoylmethyl]piperazin-1-yl]-1,2,4-triazine, 5-(4-chlorophenyl)-3-[4-[(trans-3-hydroxytetrahydropyran-4-yl)carbamoylmethyl]piperazin-1-yl]-1,2,4-triazine, 3-[4-[[1-(N-methylcarbamoylmethyl)-1H-pyrazol-4-yl]carbamoylmethyl]piperazin-1-yl]-5-(p-tolyl)-1,2,4-triazine, 5-(4-fluorophenyl)-3-[4-[[1-(N-methylcarbamoylmethyl)-1H-pyrazol-4-yl]carbamoylmethyl]piperazin-1-yl]-1,2,4-triazine, 5-(4-chlorophenyl)-3-[4-[[1-(N-methylcarbamoylmethyl)-1H-pyrazol-4-yl]carbamoylmethyl]piperazin-1-yl]-1,2,4-triazine, 5-(4-chlorophenyl)-3-[4-[(3-methylbutanoyl)amino]piperazin-1-yl]-1,2,4-triazine, 5-(4-fluorophenyl)-3-[4-[[((2R)-4-methylmorpholyn-2-yl)methyl]carbamoylmethyl]piperazin-1-yl]-1,2,4-triazine, 3-[4-[[1-(N-methylcarbamoylmethyl) piperidin-4-yl]carbamoylmethyl]piperazin-1-yl]-5-(p-tolyl)-1,2,4-triazine, 3-[4-[[2-(1,1-dioxothiomorholino)ethyl]carbamoylmethyl]piperazin-1-yl]-5-(4-fluorophenyl)-1,2,4-triazine, 3-[4-[[trans-4-(dimethylamino)cyclohexyl]carbamoylmethyl]piperazin-1-yl]-5-(4-fluorophenyl)-1,2,4-triazine, 5-(4-fluorophenyl)-3-[4-[(piperazin-1-yl)carbamoylmethyl]piperazin-1-yl]-1,2,4-triazine, 5-(dihydrobenzopyran-5-yl)-3-[4-(isopropylcarbamoylmethyl) piperazin-1-yl]-1,2,4-triazine, 3-[4-(4-fluorophenyl) piperazin-1-yl]-5-(o-tolyl)-1,2,4-triazine, and 5-(2-cyano-5-pyridyl)-3-[4-(isopropylcarbamoylmethyl) piperazin-1-yl]-1,2,4-triazine, or a pharmaceutically acceptable salt thereof to a patient in need thereof.

13. The method according to claim 1, wherein nephropathy is diabetic nephropathy.

14. The method according to claim 12, wherein nephropathy is diabetic nephropathy.

\* \* \* \* \*